United States Patent
Dransfield et al.

(10) Patent No.: US 7,514,534 B2
(45) Date of Patent: Apr. 7, 2009

(54) METALLOPROTEINASE-BINDING PROTEINS

(75) Inventors: Daniel T. Dransfield, Hanson, MA (US);
Kristin Rookey, Revere, MA (US);
Robert C. Ladner, Ijamsville, MD (US)

(73) Assignee: DYAX Corp., Cambridge, MA (US)

( * ) Notice: Subject to any disclaimer, the term of this patent is extended or adjusted under 35 U.S.C. 154(b) by 16 days.

(21) Appl. No.: 10/993,543

(22) Filed: Nov. 19, 2004

(65) Prior Publication Data

US 2006/0036076 A1 Feb. 16, 2006

Related U.S. Application Data

(60) Provisional application No. 60/523,745, filed on Nov. 19, 2003.

(51) Int. Cl.
*C07K 14/725* (2006.01)
*C07K 16/46* (2006.01)
*A61K 39/00* (2006.01)

(52) U.S. Cl. .................. 530/350; 530/387.3; 424/133.1

(58) Field of Classification Search .............. 424/133.1; 530/350, 387.3
See application file for complete search history.

(56) References Cited

U.S. PATENT DOCUMENTS 7,034,134 B2 * 4/2006 Wu et al. .................... 536/23.2

OTHER PUBLICATIONS

ATCC search output for hybridomas a01, c01, c08, d04, d08, D6-orig, a11, c12, A1-orig and H6-orig, MMP-26, MPP26, matrilysin-2, endometase and matrixin (pp. 1-16).*
Fundamental Immunology 242 (William E. Paul, M.D. ed., 3d ed. 1993).*
Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987).*
Lin et al Biochemistry USA vol. 14:1559-1563 (1975).*
Rudikoff et al (Proc Natl Acad Sci USA 1982 vol. 79 p. 1979).*
Marchenko et al. (Biochem J 356:705-718 (2001)).*
C6C monoclonal datasheets from ABR-Affinity BioReagents (pp. 1-2) and Abnova (pp. 1-3).*
172307 monoclonal datasheet from R & D (pp. 1-2).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
MacCallum et al. (J. Mol. Biol. (1996) 262:732-745).*
De Pascalis et al. The Journal of Immunology (2002) 169, 3076-3084.*
Casset et al. (2003) BBRC 307, 198-205.*
Vajdos et al. (2002) J. Mol. Biol. 320, 415-428.*
Holm et al (2007) Mol. Immunol. 44: 1075-1084.*
Chen et al. J. Mol. Bio. (1999) 293, 865-881.*
Wu et al. J. Mol. Biol. (1999) 294, 151-162.*
Benincosa et al. "Pharmacokinetics and Pharmacodynamics of a Humanized Monoclonal Antibody to Factor IX in Cynomolgus Monkeys." *The Journal of Pharmacology and Experimental Therapeutics*, vol. 292, No. 2:pp. 810-816 (2000).
de Coignac AB, et al. "Cloning of MMP-26. A novel matrilysin-like proteinase." Eur J Biochem. Jun. 2000;267(11):3323-9.
Haas et al. "Matrix metalloproteinase activity is required for activity-induced angiogenesis in rat skeletal muscle" *Am J Physiol Heart Circ Physiol*, vol. 279:H1540-H1547 (2000).
Park et al. "Peptide Substrate Specificities and Protein Cleavage Sites of Human Endometase/Matrilysin-2/Matrix Metalloproteinase-26", *The Journal of Biological Chemistry*, vol. 277, No. 38:pp. 35168-35175 (2002).
Uria et al. "Matrilysin-2, a new matrix metalloproteinase expressed in human tumors and showing the minimal domain organization required for secretion, latency, and activity" (2000) Cancer Res.; 60(17):4745-51.
Zhao et al. "Activation of Pro-gelatinase B by Endometase/Matrilysin-2 Promotes Invasion of Human Prostate Cancer Cells" *The Journal of Biological Chemistry*, vol. 278, No. 17:pp. 15056-15064 (2003).
MM26_Human (Q9NRE1), Swiss Prot Entry, Sequence entered Oct. 2001, Annotations modified in Feb. 2003, Printed Oct. 2003.
Ahrens, et al., "Receptor-mediated endocytosis of iron-oxide particles provides efficient labeling of dendritic cells for in vivo MR imaging," *Magn. Reson. Med*. 49(6):1006-13, Jun. 2003.

* cited by examiner

Primary Examiner—David J. Blanchard
Assistant Examiner—Lynn Bristol
(74) *Attorney, Agent, or Firm*—Lowrie, Lando & Anastasi, LLP

(57) ABSTRACT

Disclosed are antibodies that interact with a matrix metalloproteases such as MMP-26. Exemplary antibodies inhibit MMP-26 activity. These antibodies can be used, e.g., to treat or prevent metastatic disorders, hyperproliferative disorders, disorders which are characterized by excessive extracellular matrix degradation, and inflammatory disorders.

13 Claims, No Drawings

METALLOPROTEINASE-BINDING PROTEINS

CROSS-REFERENCE TO RELATED APPLICATIONS

This application claims priority to U.S. Application Ser. No. 60/523,745, filed on 19 Nov. 2003, the contents of which are hereby incorporated by reference in its entirety.

SUBMISSIONS ON COMPACT DISC

This application incorporates by reference ASCII text file identified by the name 10280-088001.txt, containing 187 KB of data, and created on Sep. 29, 2005, filed in computer-readable format (CRF) and encoded on the CD-ROM, mailed 29 Sep. 2005.

BACKGROUND

Matrix metalloproteinases (MMPs) are endopeptidases which, in their typical homeostatic role, digest unneeded matrix proteins including tissue components such as collagens, fibronectin, and proteoglycans. Matrix metalloproteinase-26 (MMP-26) is one member of this class of proteins. In certain cancers, these proteins are overexpressed, thus causing increased hydrolytic activity and digestion of extracellular matrix components. This process facilitates the metastatic spread of these cells.

SUMMARY

In one aspect, the invention features an antibody that interacts with a matrix metalloproteases such as MMP-26, e.g., human MMP-26. The antibody can include one or more human regions, e.g., one or more human complementarity determining regions (CDRs), one or more human frameworks (e.g., germline or somatically-mutated human FR), or one or more human constant regions, or effectively human regions of the same. In one embodiment, the antibody inhibits MMP-26 activity.

In certain implementations, the antibody is used to prevent metastatic spread of certain cancers by inhibiting MMP-26-induced cleavage of extracellular matrix proteins. In certain implementations, the antibody also decreases the hyperproliferative properties of a neoplastic cell by modulating the availability of a MMP-26 cleavage product, e.g., a growth factor, e.g., an Insulin-like Growth Factor (IGF) or an alpha-1-anti-trypsin ($\alpha$1AT). Other disorders which are characterized by excessive extracellular matrix degradation include periodontitis, rheumatoid arthritis, and osteoarthritis. In certain implementations, the antibody also modulates (e.g., decreases) inflammation, and accordingly can be used to treat an inflammatory disorder.

In one aspect, the invention features an antibody that interacts with a matrix metalloproteases such as MMP-26, e.g., human MMP-26. The antibody can include one or more human regions, e.g., one or more human CDRs, one or more human frameworks (e.g., germline or somatically mutated human FR), or one or more human constant regions, or effectively human regions of the same. In one embodiment, the antibody inhibits MMP-26 activity.

In certain implementations, the antibody is used to prevent metastatic spread of certain cancers by inhibiting MMP-26-induced cleavage of extracellular matrix proteins. In certain implementations, the antibody also decreases the hyperproliferative properties of a neoplastic cell by modulating the availability of a MMP-26 cleavage product, e.g., a growth factor, e.g., an IGF or an $\alpha$1AT. Other disorders which are characterized by excessive extracellular matrix degradation include periodontitis, rheumatoid arthritis, and osteoarthritis. In certain implementations, the antibody also modulates (e.g., decreases) inflammation, and accordingly can be used to treat an inflammatory disorder.

In another aspect, the invention features a protein including a heavy chain immunoglobulin variable domain sequence and a light chain immunoglobulin variable domain sequence. The protein binds to MMP-26. For example, the protein binds to MMP-26 with a $K_D$ of less than $1 \times 10^{-7}$ M, $3 \times 10^{-8}$, $1 \times 10^{-8}$, $3 \times 10^{-9}$, $1 \times 10^{-9}$, $3 \times 10^{-10}$, $1 \times 10^{-10}$, $3 \times 10^{-11}$, $1 \times 10^{-11}$, or $1 \times 10^{-12}$ M. In one embodiment, the protein includes at least one human CDR or at least one human framework.

In one embodiment, the protein inhibits MMP-26 proteolytic activity.

In one embodiment, the heavy chain variable domain sequence includes (a) a CDR1 that includes
X-Y-X-M-M (SEQ ID NO:236)("X" as defined herein refers to any amino acid, for example, any of all twenty natural amino acids or any of the nineteen non-cysteine residues),
(A/S/M/Y/W/F/E/Q)-Y-(A/W/F/N/Q)-M-(A/S/M/W/F) (SEQ ID NO:237)(as used herein, amino acids in parentheses refer to amino acids that are used in the alternative at a particular position);

(b) a CDR2 that includes

```
                                        (SEQ ID NO:185)
R-I-X-(S/P)-S-G-G-X-T-X-Y-A-D-S-V-K-G,,
or
                                        (SEQ ID NO:186)
(G/S/V/W/R)-I-(G/S/V/Y)-(S/P)-S-G-G-(S/I/F/K/D/H)-
T-(L/M/K/D/P)-Y-A-D-S-V-K-G,;
and/or
```

(c) a CDR3 that includes F-D-I.

In one embodiment, the heavy chain variable domain sequence includes a CDR1 that includes a sequence of which at least 3 of 5 amino acids are identical to a reference sequence from column 1, a CDR2 that includes a sequence of which at least 13 of 16 amino acids are identical to a reference sequence from column 2, and a CDR3 of which at least 70, 80, 85, 87, 90, 92, 94, 96, 97, or 98% of the amino acids are identical to a reference sequence from column 3 of Table 7.

In one embodiment, the heavy chain variable domain sequence includes a CDR1 that includes a sequence of which at least 3 of 5 amino acids are identical to a reference sequence from column 1 in a particular row (or two or three particular rows), a CDR2 that includes a sequence of which at least 13 of 16 amino acids are identical to a reference sequence from column 2 in the particular row (or two or three particular rows), and a CDR3 of which at least 70, 80, 85, 87, 90, 92, 94, 96, 97, or 98% of the amino acids are identical to a reference sequence from column 3 in the particular row (or two or three particular rows), the columns being from Table 7.

In one embodiment, at least 30, 50, 60, 70, 80, 90 or 100% of the CDR amino acid residues that are not identical to residues in the reference sequences from Table 7 are identical to residues at corresponding positions in a human germline sequence (e.g., a human germline sequence described herein, e.g., the human germline sequence that is associated with the respective CDR in an example described herein).

In one embodiment, the heavy chain variable domain sequence includes a CDR1 that includes a sequence from column 1, a CDR2 that includes a sequence from column 2, and a CDR3 from that includes a sequence from column 3 of Table 7.

In one embodiment, the light chain variable domain sequence is a κ light chain and includes (a) a CDR1 that includes

```
                                         (SEQ ID NO:187)
R-(AT)-S-Q-(GSI)-(IV)-(SDN)-(STR)-Y-L-(AN)-X,;

(SEQ ID NO:188)
R-(AT)-S-Q-(GSIN)-(IV)-(GSRDN)-(STRKDN)-(STYW)-
(LVY)-(ALN)-A,;

(SEQ ID NO:189)
R-A-S-Q-(GS)-I-(SD)-(ST)-Y-L-(AN)-X,;

(SEQ ID NO:190)
R-A-S-Q-X-I-X-X-Y-L-N-X,,
or (SEQ ID NO:191)
R-A-S-Q-(GSI)-(IV)-(GSRD)-(STRKDN)-(STYW)-(LVY)-
(ALN)-A,;
```

(b) a CDR2 that includes

```
                                         (SEQ ID NO:238)
(AG)-A-S-(STIK)-L-(EQ)-(GSD),, (SEQ ID NO:239)
(AGTQ)-(AT)-(STF)-(STIK)-(LVR)-(AEQ)-(GSTDN),
or (SEQ ID NO:192)
A-A-S-X-L-(EDNQ),;
andor
```

(c) a CDR3 that includes

```
                                         (SEQ ID NO:193)
Q-Q-(STY)-(YN)-S-(ST)-P-(GLP)-(TI)-T,,;
or (SEQ ID NO:194)
Q-(REQ)-(ASTY)-(GYN)-(STID)-(STIYFP)-(SP)-
(GLYFRP)-(TIFE)-(TV)-T,.
```

In one embodiment, the light chain variable domain sequence is a λ light chain and includes:

(a) a CDR1 that includes

```
                                         (SEQ ID NO:195)
S-G-X-S-S-X-X-G-S,;
or (SEQ ID NO:196)
T-G-T-(SN)-S-D-(IV)-G-(AG)-Y-N-Y-V-S,;
```

(b) a CDR2 that includes

```
                                         (SEQ ID NO:240)
(RDNE)-(VDN)-(GSTDN)-(KDNEQ)-R-P-S,,
or (SEQ ID NO:241)
(RE)-(VDN)-(TDN)-(KQ)-R-P-S,;
andor
```

(c) a CDR3 that includes

```
                                         (SEQ ID NO:242)
(AQ)-(STV)-(YW)-(AD)-(GSD)-(SN)-(LVN)-(SN)-(GL)-
P-V,,
or (SEQ ID NO:197)
W-D-X-S-X-X-X-X-V,.
```

In one embodiment, the light chain variable domain sequence includes a CDR1 that includes a sequence of which at least 9 of 11 amino acids are identical to a reference sequence from column 1, a CDR2 that includes a sequence of which at least 7 of 9 amino acids are identical to a reference sequence from column 2, and a CDR3 of which at least 70, 80, 85, 87, 90, 92, 94, 96, 97, or 98% of the amino acids are identical to a reference sequence from column 3 of Table 8.

In one embodiment, the light chain variable domain sequence includes a CDR1 that includes a sequence of which at least 9 of 11 amino acids are identical to a reference sequence from column 1 in a particular row (or two or three particular rows), a CDR2 that includes a sequence of which at least 7 of 9 amino acids are identical to a reference sequence from column 2 in the particular row (or two or three particular rows), and a CDR3 of which at least 70, 80, 85, 87, 90, 92, 94, 96, 97, or 98% of the amino acids are identical to a reference sequence from column 3 in the particular row (or two or three particular rows), the columns being from Table 8.

In one embodiment, at least 30, 50, 60, 70, 80, 90 or 100% of the CDR amino acid residues that are not identical to residues in the reference sequences from Table 8 are identical to residues at corresponding positions in a human germline sequence (e.g., a human germline sequence described herein, e.g., the human germline sequence that is associated with the respective CDR in an example described herein).

In one embodiment, the light chain variable domain sequence includes a CDR1 that includes a sequence from column 1, a CDR2 that includes a sequence from column 2, and a CDR3 from that includes a sequence from column 3 of Table 8.

In one embodiment, CDR2 of the heavy chain variable domain sequence includes: serine at position 4, and lysine at position 10, and CDR3 of the heavy chain variable domain sequence includes: A-F-D-I (SEQ ID NO:253).

In one embodiment, CDR2 of the heavy chain variable domain sequence includes: R or S at position 1, and P at position 4, and CDR3 of the heavy chain variable domain sequence includes: F-D-Y.

In one embodiment, CDR3 of the heavy chain variable domain sequence further includes a dityrosine sequence.

In one embodiment, CDR1 of the light chain variable domain sequence includes S-G-S-S-S-N-I-G-S-X-Y-V, (SEQ ID NO:198), wherein X is any amino acid. In one embodiment, CDR2 of the light chain variable domain sequence includes R-N-X-Q-R-P-S, (SEQ ID NO:250) wherein X is any amino acid. In one embodiment, CDR3 includes W-T-D-D-S (SEQ ID NO:251).

In one embodiment, CDR2 of the heavy chain variable domain sequence includes: P at position 4 and M, F, or R at position 10, and CDR1 of the light chain variable domain sequence includes: R-(A/T)-S-Q-X-(V/I)-X-X-(Y/W)-(L/V), (SEQ ID NO:199).

In one embodiment, CDR3 of the light chain variable domain sequence includes Q-Q-X-(Y/N)-(S/T)-X-(P/S) (SEQ ID NO:254).

In one embodiment, CDR2 of the heavy chain variable domain sequence includes: Y at position 3 and F at position 10, CDR1 of the light chain variable domain sequence includes: T-G-T-(S/N)-S-D-(V/I)-G-G-Y-N-Y-V-S, (SEQ ID NO:200), and CDR2 of the light chain variable domain sequence includes: E-V-X-X-R-P-S, (SEQ ID NO:201).

The protein can also bind to MMP-26, e.g., and not substantially inhibit its enzymatic activity.

In one embodiment, the heavy chain variable domain sequence includes (a) a CDR1 that includes P-Y-F-M-F,, (SEQ ID NO:202)
or
(ALVEP)-Y-(SMWFD)-M-(YFKDNP),; (SEQ ID NO:255)
andor (b) a CDR2 that includes (SV)-I-Y-(SP)-S-G-G-X-T-X-Y-A-D-S-V-K-G,, (SEQ ID NO:203)
or
(GSVY)-I-(GSVYW)-(SP)-S-G-G-(SIYFD)-T-(SLRNQ)-Y-A-D-S-V-K-G,. (SEQ ID NO:204)

In one embodiment, the heavy chain variable domain sequence includes a CDR1 that includes a sequence of which at least 3 of 5 amino acids are identical to a sequence from column 1, a CDR2 that includes a sequence of which at least 13 of 16 amino acids are identical to a sequence from column 2, and a CDR3 of which at least 70, 80, 85, 87, 90, 92, 94, 96, 97, or 98% of the amino acids are identical to a sequence from column 3 of Table 9.

In one embodiment, at least 30, 50, 60, 70, 80, 90 or 100% of the CDR amino acid residues that are not identical to residues in the reference sequences from Table 9 are identical to residues at corresponding positions in a human germline sequence (e.g., a human germline sequence described herein, e.g., the human germline sequence that is associated with the respective CDR in an example described herein).

In one embodiment, the heavy chain variable domain sequence includes a CDR1 that includes a sequence from column 1, a CDR2 that includes a sequence from column 2, and a CDR3 from that includes a sequence from column 3 of Table 9.

In one embodiment, the light chain variable domain sequence is a κ light chain and includes (a) a CDR1 that includes (SEQ ID NO:205)
R-A-S-Q-S-(IV)-S-(SN)-(SY)-(LY)-(ALN)-A,;

(SEQ ID NO:206)
R-A-S-Q-(GS)-(IV)-S-(STN)-(SY)-(LY)-(ALN)-A,;

(SEQ ID NO:207)
R-A-S-Q-S-(IV)-S-S-Y-L,;
or (SEQ ID NO:208)
R-A-S-Q,;

(b) a CDR2 that includes (SEQ ID NO:256)
(AGDP)-(AN)-S-(STIKDN)-(LR)-(AEPQ)-(STRDN),;

(SEQ ID NO:257)
(AGD)-A-S-(STN)-(LR)-(AEQ)-(ST),;

(SEQ ID NO:258)
(AGD)-A-S-(STN)-(LR)-(AQ)-(ST),;

(SEQ ID NO:259)
(AGD)-A-S-S-(LR)-(AQ)-(ST),;

(SEQ ID NO:244)
D-(AD)-S-X-(LR)-(AP)-(ST),;

(SEQ ID NO:245)
(AD)-(ADN)-S-(SKDNQ)-(LR)-(APQ)-(ST),;
or (SEQ ID NO:246)
(AGRD)-(ADN)-(SYN)-(SKDNQ)-(LR)-(APQ)-(ST),.

In one embodiment, the light chain variable domain sequence is a λ light chain and includes (a) a CDR1 that includes (SEQ ID NO:209)
S-G-X-S-S-N-I-G-S-N-X-V-X-X,;

(SEQ ID NO:260)
(GST)-G-(GSTN)-(SN)-(SI)-(GDN)-(TIV)-(GK)-(GS)-(VYN)-(YFNH)-(VY)-(VY)-S,;

(SEQ ID NO:210)
(ST)-G-(GST)-S-S-(DN)-(IV)-G-(GS)-(YN)-(YFN)-(VY)-(VY)-S,;

(SEQ ID NO:234)
G-G-(SN)-(SN)-(ID)-(GI)-(GT)-(SK)-(SYN)-V-H,;
or (SEQ ID NO:235)
G-(GST)-(SN)-(SN)-(IDN)-(GIV)-(GST)-(SKN)-(SYN)-(VFN)-(VYH),;

(b) a CDR2 that includes (SEQ ID NO:261)
D-(AD)-S-X-(LR)-(AP)-(ST),;

(SEQ ID NO:262)
(AD)-(ADN)-S-(SKDNQ)-(LR)-(APQ)-(ST),;

(SEQ ID NO:263)
(AGRD)-(ADN)-(SYN)-(SKDNQ)-(LR)-(APQ)-(ST),;

(SEQ ID NO:211)
D-(DN)-S-(DQ)-R-P-S-X,;
or (SEQ ID NO:247)
(RDNE)-(VDN)-(SYN)-(KDQ)-R-P-S-X,;
andor (c) a CDR3 that includes (SEQ ID NO:212)
A-A-W-D-D-(SN)-(LV),;

(SEQ ID NO:248)
(QA)-X-W-D-(SDT)-(GSN),;
or

-continued (SEQ ID NO:249)
(AQ)-(ASV)-(YW)-(AD)-(GSID)-(GSN)-(STLVN)-(GSDN)-
(GSLVH)-(VQ)-V,.

In one embodiment, the light chain variable domain sequence includes a CDR1 that includes a sequence of which at least 9 of 11 amino acids are identical to a sequence from column 1, a CDR2 that includes a sequence of which at least 7 of 9 amino acids are identical to a sequence from column 2, and a CDR3 of which at least 70, 80, 85, 87, 90, 92, 94, 96, 97, or 98% of the amino acids are identical to a sequence from column 3 of Table 10.

In one embodiment, at least 30, 50, 60, 70, 80, 90 or 100% of the CDR amino acid residues that are not identical to residues in the reference sequences from Table 10 are identical to residues at corresponding positions in a human germline sequence (e.g., a human germline sequence described herein, e.g., the human germline sequence that is associated with the respective CDR in an example described herein).

In one embodiment, the light chain variable domain sequence includes a CDR1 that includes a sequence from column 1, a CDR2 that includes a sequence from column 2, and a CDR3 from that includes a sequence from column 3 of Table 10.

In one embodiment, the framework regions of the heavy and/or light chain variable domain are at least 70, 80, 90, 92, 95, 97, 98, or 99% identical to a corresponding heavy or light FR sequence, e.g., of a known FR sequence or a FR sequence described herein.

In one embodiment, the framework regions of the heavy and/or light chain variable domain are at least 70, 80, 90, 92, 95, 97, 98, or 99% identical to a corresponding framework region of a human germline sequence (e.g., the human germline sequence with which the CDRs of the protein are associated herein).

In one embodiment, the heavy and/or light chain variable domain are at least 70, 80, 90, 92, 95, 97, or 98% identical to a human germline sequence (e.g., the human germline sequence with which the CDRs of the protein are associated herein).

In one embodiment, the H1 and H2 hypervariable loops have the same canonical structure as an antibody described herein. In one embodiment, the L1 and L2 hypervariable loops have the same canonical structure as an antibody described herein.

In one embodiment, the protein binds MMP-26 with a $K_D$ that is at least 2, 4, 5, 10, 20, 50, or 100 better than its $K_D$ for another metalloproteinase, e.g., MMP-1, MMP-2, MMP-3, MMP-7, MMP-9, MMP-12, or MMP-14. In another embodiment, the protein binds MMP-26 with a $K_D$ that is at least 2, 4, 5, 10, 20, 50, or 100 better than its $K_D$ for MMP-1, MMP-2, MMP-3, MMP-7, MMP-9, MMP-12, or MMP-14.

In one embodiment, the protein inhibits MMP-26 with a $K_i$ of less than $1\times10^{-7}$ M, $3\times10^{-8}$, $1\times10^{-8}$, $3\times10^{-9}$, $1\times10^{-9}$, $3\times10^{-10}$, $1\times10^{-10}$, $3\times10^{-11}$, $1\times10^{-11}$, or $1\times10^{-12}$ M. In an embodiment, the protein inhibits MMP-26 with a $K_i$ that is at least 2, 4, 5, 10, 20, 50, or 100 better than its $K_i$ for another metalloproteinase, e.g., MMP-1, MMP-2, MMP-3, MMP-7, MMP-9, MMP-12, or MMP-14.

In one embodiment, the protein reduces cell metastasis in vivo.

In one embodiment, the protein includes two independent polypeptide chains, a first chain including the light chain variable domain sequence and the second chain including the heavy chain variable domain sequence, and each chain including a constant immunoglobulin domain. In an embodiment, the protein is composed of a single polypeptide chain that includes the light chain variable domain sequence and the heavy chain variable domain sequence.

In one embodiment, the protein further includes a label, a cytotoxic or cytostatic agent, or a serum-residence prolonging moiety. The protein can include additional features described herein.

In another aspect, the invention features a protein that includes a heavy chain immunoglobulin variable domain sequence and a light chain immunoglobulin variable domain sequence, wherein the protein binds to the MMP-26 catalytic domain and one of the immunoglobulin variable domains is at least 70, 75, 80, 85, 87, 90, 92, 94, 95, 96, 97, 98, 99, or 100% identical to a variable domain sequence of a variable domain described herein, e.g., a variable domain of a01, b04, b06, b10, c01, c08, d02, d04, d06, d08, D6-orig, a04, a11, c05, c04, c11, c12, d07, A1-orig, H6-orig, a02, a03, a05, a06, a07, a08, a09, a10, a12, b01, b02, b03, b05, b07, b08, b09, b11, b12, c02, c03, c06, c07, c09, c10, d01, d03, d05, or d09. The protein can include additional features described herein.

In another aspect, the invention features a protein that includes a heavy chain immunoglobulin variable domain sequence and a light chain immunoglobulin variable domain sequence, wherein the protein binds to MMP-26. At least one of the variable domains is related to a reference antibody selected from the group consisting of a01, b04, b06, b10, c01, c08, d02, d04, d06, d08, D6-orig, a04, all, c05, c04, c11, c12, d07, A1-orig, H6-orig, a02, a03, a05, a06, a07, a08, a09, a10, a12, b01, b02, b03, b05, b07, b08, b09, b11, b12, c02, c03, c06, c07, c09, c10, d01, d03, d05, and d09. The relationship is such that at least 75, 80, 82, 84, 87, 90, 92, 94, 95, 96, 97, 98, 99, or 100% of the amino acid residues in the variable domain are either (i) identical to a corresponding residue in the reference antibody, (ii) identical to a corresponding residue in a human germline sequence, or both. In one embodiment, the human germline sequence is the human germline sequence with which the reference antibody is associated in an example described herein.

In one embodiment, all of the amino acids residues in the variable domain are (i) identical to a corresponding residue in the reference antibody, or (ii) identical to a corresponding residue in the human germline sequence, e.g., with which the reference antibody is associated in an example described herein, or both.

In one embodiment, at least 1, 2, 3, 4, or 5 of the amino acid residues in the variable domain differ from a corresponding residue in the reference antibody, but are identical to a corresponding residue in the human germline sequence, e.g., with which the reference antibody is associated in an example described herein.

In one embodiment, in the framework regions, at least 90, 92, 94, 96, 97, 98, or 99% or all of the amino acid residues are identical to a corresponding residue in the human germline sequence, e.g., with which the reference antibody is associated in an example described herein.

In one embodiment, at least 1, 2, or 3 of the amino acid residues in the CDR regions of the variable domain differ from a corresponding residue in the reference antibody, but are identical to a corresponding residue in the human germline sequence, e.g., with which the reference antibody is associated in an example described herein.

In one embodiment, amino acid residues that are not identical are conserved substitutions relative to a corresponding residue in the reference antibody, or a human germline sequence with which the reference antibody is associated in an example described herein.

The protein can include additional features described herein.

In another aspect, the invention features a protein that includes an antigen binding fragment that binds to MMP-26, wherein the protein binds to a MMP-26 epitope that overlaps with an epitope bound by an antibody described herein. The protein can include additional features described herein.

In another aspect, the invention features a protein that includes an antigen binding fragment that binds to MMP-26, wherein the protein competes with an antibody described herein for binding to MMP-26. The protein can include additional features described herein.

An MMP-26-binding antibody is typically monospecific, e.g., a monoclonal antibody, or antigen-binding fragment thereof. The MMP-26-binding antibodies can be full-length (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')$_2$, Fv, or scFv fragment). The antibody, or antigen-binding fragment thereof, can include two heavy chain immunoglobulins and two light chain immunoglobulins, or can be a single chain antibody. The antibodies can, optionally, include a constant region chosen from a kappa, lambda, alpha, gamma, delta, epsilon or a mu constant region gene. An MMP-26-binding antibody can include a heavy and light chain constant region, e.g. a constant region substantially from a human antibody, e.g., a human IgG1, IgG2, IgG3, or IgG4, or a portion thereof.

In one embodiment, the antibody (or fragment thereof) is a recombinant or modified antibody, e.g., a chimeric, a humanized, a deimmunized, or an in vitro generated antibody. The term "recombinant" or "modified" antibody, as used herein, is intended to include all antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such recombinant antibodies include human, humanized, CDR grafted, chimeric, deimmunized, in vitro generated antibodies, and may optionally include framework and/or constant regions derived from human germline immunoglobulin-encoding nucleic acid sequences.

In one embodiment, the antibody binds to an epitope distinct from an epitope bound by known antibodies that bind to MMP-26. In other embodiments, the antibody does not compete with known antibodies that bind to MMP-26. In still other embodiments, the antibody does not compete with an antibody described herein.

In one embodiment, the antibody binds to overlapping epitopes of, or competitively inhibits, the binding of an antibody disclosed herein to MMP-26. In one embodiment, the antibody binds to an epitope that includes an amino acid that is within at least 12, 10, 8, 6, 5, or 3 amino acids of one or more of amino acid 208, 209, 212, or 218. In one embodiment, the antibody binds to an epitope that includes an amino acid between residues 200-230, e.g., between 205-220. In one embodiment, the antibody includes an antigen binding site structure that includes one or more side chains that are positioned within 12, 10, 8, 6 or 4 Angstroms of amino acid residues 200-230, e.g., between 205-220, e.g., 208, 209, 212, or 218.

Further, any combination of MMP-26-binding antibodies is within the scope of the invention, e.g., two or more antibodies that bind to different regions of MMP-26, e.g., antibodies that bind to two different epitopes on MMP-26, e.g., a bispecific antibody.

In one embodiment, the MMP-26-binding antibody includes at least one light or heavy chain immunoglobulin (or two light chain immunoglobulins and two heavy chain immunoglobulins). Preferably, each immunoglobulin includes a light or a heavy chain variable region having at least one, two and, preferably, three CDR's substantially identical to a CDR from an anti-MMP-26 light or heavy chain variable region, respectively, e.g., from a variable region of an antibody described herein.

In one aspect, the invention features an isolated nucleic acid including a coding sequence that encodes a polypeptide including a variable domain sequence of a protein described herein, e.g., a protein described above. The nucleic acid can further include a second coding sequence that encodes a polypeptide including a second immunoglobulin variable domain, e.g., thereby providing two sequences that respectively encode a heavy and light chain variable domain.

In one aspect, the invention features a host cell that produces a protein described herein. The cell can include a first nucleic acid encoding a polypeptide including a heavy chain variable domain sequence of the protein and a second nucleic acid encoding a polypeptide including a light chain domain sequence of the protein.

For example, the host cell contains a first nucleic acid encoding a polypeptide including a heavy chain variable region and a second nucleic acid encoding a polypeptide including a light chain variable region. The heavy chain variable region includes an amino acid sequence at least 70, 80, 90, 92, 95, 97, 98, or 99% identical to an amino acid sequence of a heavy chain immunoglobulin variable domain sequence described herein, and the light chain variable region includes an amino acid sequence at least 70, 80, 90, 92, 95, 97, 98, or 99% identical to a light chain immunoglobulin variable domain sequence described herein.

In another aspect, the invention features a nucleic acid that includes a coding sequence that encodes a polypeptide comprising an immunoglobulin heavy chain variable domain that binds to MMP-26, e.g., an immunoglobulin heavy chain variable domain described herein. For example, the immunoglobulin heavy chain variable domain can include: a CDR motif or CDR described herein. The immunoglobulin heavy chain variable domain can include a framework region described herein. In one example, the variable domain is a heavy chain variable domain is at least 75, 80, 85, 90, 95, 96, 97, 98, or 99% identical to an amino acid sequence described herein or a variable domain sequence thereof.

In another aspect, the invention features a nucleic acid that includes a coding sequence that encodes a polypeptide comprising an immunoglobulin light chain variable domain that binds to MMP-26, e.g., an immunoglobulin light chain variable domain described herein. For example, the immunoglobulin light chain variable domain can include: a CDR motif or CDR described herein. The immunoglobulin light chain variable domain can include a framework region described herein. In one example, the variable domain is a light chain variable domain is at least 75, 80, 85, 90, 95, 96, 97, 98, or 99% identical to an amino acid sequence described herein or a variable domain sequence thereof.

A nucleic acid described herein can further include a promoter operably linked to the coding sequence. A nucleic acid can include a first and second coding sequence, e.g., wherein the first coding sequence encodes a polypeptide that includes an immunoglobulin heavy chain variable domain and the second coding sequence encodes a polypeptide that includes an immunoglobulin light chain variable domain.

In another aspect, the invention features a host cell that contains a first nucleic acid encoding a polypeptide comprising a heavy chain variable region and a second nucleic acid encoding a polypeptide comprising a light chain variable region. The heavy chain variable region and the light chain variable region can associate to form a MMP-26 binding protein. These variable regions can have one or more properties described herein, e.g., at least 75, 80, 85, 90, 95, 96, 97, 98, or 99% identity to a sequence described herein, e.g., the sequence of a variable domain from an isolated antibody described herein or a human germline sequence described herein. The invention also includes a method of providing an MMP-26-binding antibody. The method can include providing a host cell described herein; and expressing said first and second nucleic acids in the host cell under conditions that allow assembly of said light and heavy chain variable regions to form an antigen-binding protein that interacts with MMP-26.

In another aspect, the invention features a protein ligand that includes a human or effectively human heavy chain immunoglobulin variable domain and a human or effectively human light chain immunoglobulin variable domain, wherein the protein ligand binds to human MMP-26 catalytic domain. The protein can bind to MMP-26 with a $K_d$ of less than $1 \times 10^{-7}$ M, $3 \times 10^{-8}$, $1 \times 10^{-8}$, $3 \times 10^{-9}$, $1 \times 10^{-9}$, $3 \times 10^{-10}$, $1 \times 10^{-10}$, $3 \times 10^{-11}$, $1 \times 10^{-11}$, or $1 \times 10^{-12}$ M. In one embodiment, the protein inhibits MMP-26 proteolytic activity. The protein can include one or more additional features described herein.

In another aspect, the invention provides compositions, e.g., pharmaceutical compositions, which include a pharmaceutically acceptable carrier, excipient or stabilizer, and at least one of the MMP-26-binding proteins (e.g., antibodies or fragments thereof) described herein. In one embodiment, the compositions, e.g., the pharmaceutical compositions, include a combination of two or more of the aforesaid MMP-26-binding proteins.

In another aspect, the invention features a kit that includes an MMP-26-binding antibody (or fragment thereof), e.g., an MMP-26-binding antibody (or fragment thereof) as described herein, for use alone or in combination with other therapeutic modalities, e.g., a cytotoxic or labeling agent, e.g., a cytotoxic or labeling agent as described herein, along with instructions on how to use the MMP-26 antibody or the combination of such agents to treat, prevent or detect a neoplastic disorder, an inflammatory disorder, or a disorder characterized by excessive MMP-26 activity.

In another aspect, the invention features a method of identifying a protein that specifically binds to MMP-26. In one embodiment, the method includes: providing a MMP-26 antigen; providing a library of proteins (e.g., a display library, e.g., a phage display library); and identifying a member that specifically binds to the MMP-26 antigen, e.g., the catalytic domain of MMP-26.

In another aspect, the invention features a method of identifying a protein that specifically binds to MMP-26. The method includes: providing an MMP-26 antigen; immunizing a mouse with the MMP-26 antigen; producing hybridoma cells from the spleen of the immunized mouse; and identifying individual hybridoma cell lines expressing an antibody that specifically binds to the MMP-26 antigen.

In one embodiment, the MMP-26 antigen is of human origin and includes, e.g., the extracellular domain of human MMP-26 or some fragment thereof, e.g., the catalytic domain of MMP-26. The MMP-26 antigen can be a recombinant polypeptide optionally fused to another polypeptide, e.g., a purification handle.

In preferred embodiments, the methods further include isolating a nucleic acid molecule from the identified phage or hybridoma, wherein the nucleic acid molecule encodes the polypeptide or antibody that specifically binds to the MMP-26 antigen. The isolated nucleic acid molecules can be used to produce therapeutic agents, as described herein.

In another aspect, the invention features nucleic acids that encode proteins identified by the methods described herein. In preferred embodiments, the nucleic acids include sequences encoding a heavy and light chain immunoglobulin or immunoglobulin fragment described herein. For example, the invention features, a first and second nucleic acid encoding a heavy and light chain variable region, respectively, of an MMP-26-binding antibody molecule as described herein. Sequences encoding a heavy and light chain that function together can be present on separate nucleic acid molecules or on the same nucleic acid molecule. In another aspect, the invention features host cells and vectors containing a nucleic acid described herein.

In yet another aspect, the invention features a method of producing an MMP-26-binding antibody, or antigen-binding fragment thereof. The method includes: providing a host cell that contains a first nucleic acid encoding a polypeptide comprising a heavy chain variable region, e.g., a heavy chain variable region as described herein; providing a second nucleic acid encoding a polypeptide comprising a light chain variable region, e.g., a light chain variable region as described herein; and expressing said first and second nucleic acids in the host cell under conditions that allow assembly of said light and heavy chain variable regions to form an antigen binding protein that interacts with MMP-26. The first and second nucleic acids can be linked or unlinked, e.g., expressed on the same or different vector, respectively. The first and second nucleic acids can be components of the same molecule or can reside on different molecules (e.g., different chromosomes or plasmids).

The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NSO), Chinese hamster ovary cells (CHO), Human Embryonic Kidney cells (HEK293, HEK293T), COS cells, oocyte cells, and cells from a transgenic animal, e.g., mammary epithelial cell. For example, nucleic acids encoding the antibodies described herein can be expressed in a transgenic animal. In one embodiment, the nucleic acids are placed under the control of a tissue-specific promoter (e.g., a mammary specific promoter) and the antibody is produced in the transgenic animal. For example, the antibody molecule is secreted into the milk of the transgenic animal, such as a transgenic cow, pig, horse, sheep, goat or rodent. To produce a single chain antibody, the nucleic acid is configured to encode a single polypeptide that comprises both the heavy and light chain variable domains.

In another aspect, the invention features a method that includes: providing a host cell, e.g., as described herein, that contains nucleic acids for expressing an antigen binding protein that interacts with MMP-26; and expressing said first and second nucleic acids in the host cell under conditions that allow assembly of said light and heavy chain variable regions to form an antigen binding protein that interacts with MMP-26. The protein can include additional features described herein.

In another aspect, the invention features a method of treating or preventing a neoplastic disorder. The method includes: administering an MMP-26 binding protein described herein to a subject in an amount effective to treat or prevent a neoplastic disorder in the subject. In one embodiment, the subject has, is predisposed to, or is diagnosed with a malignant cancer or metastatic disorder. For example, the neoplastic disorder is associated with epithelial carcinomas, breast cancer, prostate cancer, endometrial, esophageal squamous cell carcinoma, colon cancer, squamous cell carcinoma (SCC) of the oral cavity, verrucous carcinoma of the oral cavity, or lung cancer. For example, a patient having breast, prostate, endometrial, or esophageal, or lung cancer can be treated by administration of one or more injections of an IgG which binds and inhibits MMP-26.

In another aspect of the invention, an IgG antibody that binds to MMP-26 is administered to a patient (e.g., injected into the patient), e.g., a patient having a disease chacterized by excess MMP-26 activity. In one embodiment, the antibody clears MMP-26 from the patient. The antibody can bind MMP-26 with high affinity, e.g. a $K_d$ of less than $1 \times 10^{-7}$ M, $3 \times 10^{-8}$, $1 \times 10^{-8}$, $3 \times 10^{-9}$, $1 \times 10^{-9}$, $3 \times 10^{-10}$, $1 \times 10^{-10}$, $3 \times 10^{-11}$, $1 \times 10^{-11}$, or $1 \times 10^{-12}$ M. The antibody can be an antibody described herein.

The method can further include, prior to, during, or after the administering, evaluating cells of the subject for MMP-26 protein, mRNA, or activity.

The method can further include monitoring the subject for a metastatis.

In one embodiment, the administering includes administering a plurality of doses of the protein. For example, the doses are administered at regular intervals. The method can include other features described herein.

In another aspect, the invention features a method of treating or preventing an inflammatory disorder. The method includes: administering an MMP-26 binding protein described herein to a subject in an amount effective to treat or prevent an inflammatory disorder in the subject. In one embodiment, the inflammatory disorder is rheumatoid arthritis, lupus, restenosis, graft v. host response, or multiple sclerosis. In one embodiment, the administering includes administering a plurality of doses of the protein. For example, the doses are administered at regular intervals. The method can include other features described herein.

In another aspect, the invention features a method of treating or preventing a disorder characterized by excessive or undesired MMP-26 activity. The method includes: administering an MMP-26 binding protein to a subject in an amount effective to treat or prevent a disorder characterized by excessive or undesired MMP-26 activity in the subject. For example, the disorder is periodontitis, rheumatoid arthritis, or osteoarthritis. In one embodiment, the administering includes administering a plurality of doses of the protein. For example, the doses are administered at regular intervals. The method can include other features described herein.

In another aspect, the invention features a method of modulating MMP-26 activity. The method includes: providing an MMP-26-binding protein described herein; and contacting the protein to MMP-26, in an amount sufficient to modulate MMP-26 activity. In one embodiment, the modulated activity is MMP-26 proteolytic activity. For example, the contacting is in vitro or in vivo. In one embodiment, the protein is contacted to MMP-26 in the vicinity of a neoplastic cell (e.g., a cell found in laryngeal, epidermal, pulmonary, breast, renal, urothelial, colonic, prostatic, or hepatic cancer and/or metastasis). The method can include other features described herein.

In another aspect, the invention features a method for detecting the presence of a MMP-26 protein, e.g., in a sample, in vitro. The method includes: (i) contacting the sample (and optionally, a reference, e.g., control, sample) with an MMP-26-binding protein described herien, under conditions that allow interaction of the MMP-26-binding protein and the MMP-26 protein to occur; and (ii) detecting interaction between the MMP-26-binding protein, and the sample (and optionally, the reference, e.g., control, sample). In one embodiment, at least one of the MMP-26 binding protein or the MMP-26 is immobilized.

In another aspect, the invention features a method for detecting the presence of MMP-26 (e.g., activated MMP-26), e.g., in vivo. The method includes: (i) administering to a subject (and optionally a control subject) an MMP-26-binding protein, under conditions that allow interaction of the MMP-26-binding protein and the MMP-26 protein to occur; and (ii) detecting location of the MMP-26-binding protein in the subject or formation of a complex between the MMP-26-binding protein and MMP-26 in the subject. For example, the subject is a human subject. In one embodiment, the detecting includes imaging the subject. In one embodiment, the MMP-26-binding protein is labeled with an MRI detectable label.

With respect to any administration method, an MMP-26-binding protein described herein can be used alone, e.g., can be administered to a subject or used in vitro in non-derivatized or unconjugated forms. In other embodiments, the MMP-26-binding protein can be derivatized, modified or linked to another functional molecule, e.g., another polypeptide, protein, isotope, cell, or insoluble support. For example, the MMP-26-binding protein can be functionally-linked (e.g., by chemical coupling, genetic fusion, non-covalent association or otherwise) to one or more other molecular entities, such as an antibody (e.g., if the ligand is an antibody to form a bispecific or a multispecific antibody), a toxin, a radioisotope, a serum-residence prolonging moiety (e.g. PEG), a therapeutic (e.g., a cytotoxic or cytostatic) agent or moiety, among others. The method can include other features described herein.

In another aspect, the invention features a method of inhibiting metalloproteinase activity in a subject. The method includes administering an MMP-26-binding protein described herein in an amount effective to inhibit metalloproteinase activity in a subject. The reduced metalloproteinase activity can alter proteolysis, e.g., in the vicinity of a cancer cell, e.g., a metastatic cancer cell, in placental tissue, or in a tumor, e.g., a metastatic tumor. The method can include other features described herein.

In another aspect, the invention features a method of inhibiting metastasis in a subject. The method includes administering an MMP-26-binding protein described herein in an amount effective to inhibit metastasis in a subject. The protein can be delivered systemically or locally. For example, the protein can be targeted to a tumor. The protein can modulate the integrity of an extracellular matrix, e.g., by preventing degradation of an MMP-26 substrate that is an extracellular matrix component. The method can include other features described herein.

In another aspect, the invention features a method of treating or preventing a neoplastic disorder in a subject. The method includes providing an MMP-26-binding protein, e.g. a protein described herein, and contacting the subject with the protein, in an amount sufficient to modulate or prevent a neoplastic disorder. The method can include contacting a neoplastic cell, e.g., a benign or hyperplastic cell (e.g., a cell found in laryngeal, epidermal, pulmonary, breast, renal, endometrial, ovarian, urothelial, colonic, prostatic, or hepatic cancer and/or metastasis). The protein can include a cytotoxic entity. The method can include other features described herein.

In another aspect, the invention features a method of treating or preventing a an inflammatory disorder in a subject. The method includes providing an MMP-26-binding protein, e.g. a protein described herein, and contacting the subject with the protein, in an amount sufficient to modulate or prevent the inflammatory disorder. The method can include identifying a subject as having or being at risk for having an inflammatory disorder. The method can further include monitoring at least one indicator of inflammation, e.g., local temperature, swelling (e.g., as measured), redness, local or systemic white blood cell count, presence or absence of neutrophils, cytokine levels, elastase activity, and so forth. The method can include other features described herein.

In another aspect, the invention features a method of reducing MMP-26 activity in vivo. The method includes administering an MMP-26 binding protein (e.g., an MMP-26 binding protein described herein) to a subject. The protein can be administered in an amount sufficient to cause MMP-26 (mature MMP-26 or MMP-26 in a pro-form or other immature form) to be cleared from the subject. For example, in cases in which the MMP-26 binding protein is an IgG antibody, binding of the binding protein to endogenous MMP-26 can result in improved clearance of MMP-26 from the subject. In one embodiment, the subject has a disorder chacterized by excess MMP-26 activity. The method can include other features described herein.

In another aspect, the invention features a method of inhibiting MMP-26 activity in vitro. The method includes contacting an MMP-26-binding protein that inhibits MMP-26 to a composition that include the MMP-26 catalytic domain.

The method can be used to treat or prevent cancerous disorders, e.g., including but are not limited to, solid tumors, soft tissue tumors, and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), and genitourinary tract (e.g., renal, urothelial cells), pharynx, as well as adenocarcinomas which include malignancies such as most colon cancers, rectal cancer, renal-cell carcinoma, endometrial and ovarian cancers, liver cancer, non-small cell carcinoma of the lung, cancer of the small intestine and cancer of the esophagus. In particular, metastatic lesions of the aforementioned cancers can also be treated or prevented using the methods and compositions described herein.

The subject can be a mammal, e.g., a primate, preferably a higher primate, e.g., a human (e.g., a patient having, or at risk of, a disorder described herein, e.g., cancer).

The MMP-26-binding protein can be administered to the subject systemically (e.g., orally, parenterally, subcutaneously, intravenously, intramuscularly, intraperitoneally, intranasally, transdermally, or by inhalation), topically, or by application to mucous membranes, such as the nose, throat and bronchial tubes.

The methods can further include the step of monitoring the subject, e.g., for a reduction in one or more of: a reduction in tumor size; reduction in cancer markers (e.g., levels of cancer specific antigen or in MMP-26 protein levels or activity); reduction in the appearance of new lesions, e.g., in a bone scan; a reduction in the appearance of new disease-related symptoms; or decreased or stabilization of size of soft tissue mass; or any parameter related to improvement in clinical outcome. The subject can be monitored in one or more of the following periods: prior to beginning of treatment; during the treatment; or after one or more elements of the treatment have been administered. Monitoring can be used to evaluate the need for further treatment with the same MMP-26-binding protein or for additional treatment with additional agents. Generally, a decrease in one or more of the parameters described above is indicative of the improved condition of the subject. Information about the monitoring can be recorded, e.g., in electronic or digital form.

The MMP-26-binding protein can be used alone in unconjugated form to thereby inhibit adhesion, migration, or extravasation or the MMP-26-expressing cells, or ablate or kill the MMP-26-expressing cells. If the protein is an antibody, the ablation or killing can be mediated, e.g., by an antibody-dependent cell killing mechanisms such as complement-mediated cell lysis and/or effector cell-mediated cell killing. In other embodiments, the MMP-26-binding protein can be bound to a substance, e.g., a cytotoxic agent or moiety, effective to kill or ablate the MMP-26-expressing cells. For example, the MMP-26-binding protein can be coupled to a radioactive ion (e.g., an $\alpha$-, $\gamma$-, or $\beta$-emitter), e.g., iodine ($^{131}$I or $^{125}$I, yttrium ($^{90}$Y), lutetium ($^{177}$Lu), actinium ($^{225}$Ac), or bismuth ($^{213}$Bi). The methods and compositions described herein can be used in combination with other therapeutic modalities. In one embodiment, the method includes administering to the subject an MMP-26-binding protein, e.g., an MMP-26-binding antibody or fragment thereof, in combination with a cytotoxic agent, in an amount effective to treat or prevent said disorder. The ligand and the cytotoxic agent can be administered simultaneously or sequentially. In other embodiments, the methods and compositions described herein are used in combination with surgical and/or radiation procedures.

The subject methods also can be used on cells in culture, e.g. in vitro or ex vivo. The cultured cells can be MMP-26-producing cells, e.g., tumor cells or placental cells. For example, the cells can be cultured in vitro in culture medium and the contacting step can be effected by adding the MMP-26-binding protein to the culture medium. The method can be performed on cells (e.g., cancerous or metastatic cells) present in a subject, as part of an in vivo (e.g., therapeutic or prophylactic) protocol.

In another aspect, the invention features methods for detecting the presence of a MMP-26 protein, in a sample, in vitro (e.g., a biological sample, a tissue biopsy, e.g., a cancerous lesion). The subject method can be used to evaluate, e.g., diagnose or stage a disorder described herein, e.g., a cancerous disorder. The method includes: (i) contacting the sample (and optionally, a reference, e.g., control, sample) with an MMP-26-binding protein, as described herein, under conditions that allow interaction of the MMP-26-binding protein and the MMP-26 protein to occur; and (ii) detecting MMP-26, e.g., by detecting formation of a complex between the MMP-26-binding protein or by detecting an interaction between the MMP-26-binding protein and MMP-26, in the sample (and optionally, the reference, e.g., control, sample). Formation of the complex can be indicative of the presence of MMP-26 protein (e.g., activated MMP-26 protein), and can indicate the suitability or need for a treatment described herein. For example, a statistically significant change in the formation of the complex in the sample relative to the reference sample, e.g., the control sample, is indicative of the presence of MMP-26 (e.g., activated MMP-26) in the sample.

In yet another aspect, the invention provides a method for detecting the presence of MMP-26 (e.g., activated MMP-26) in vivo (e.g., in vivo imaging in a subject). The subject method can be used to evaluate, e.g., diagnose, localize, or stage a disorder described herein, e.g., a cancerous disorder. The method includes: (i) administering to a subject (and optionally a control subject) an MMP-26-binding protein (e.g., an antibody or antigen binding fragment thereof), under conditions that allow interaction of the MMP-26-binding protein and the MMP-26 protein to occur; and (ii) detecting formation of a complex between the ligand and MMP-26, wherein a statistically significant change in the formation of the complex in the subject relative to the reference, e.g., the control subject or subject's baseline, is indicative of the presence of the MMP-26. The presence of activated MMP-26 in particular locations within a subject can be indicative of cancer, e.g., metastatic cancer.

In other embodiments, a method of diagnosing or staging, a disorder as described herein (e.g., an inflammatory or cancerous disorder), is provided. The method includes: (i) identifying a subject having, or at risk of having, the disorder; (ii) obtaining a sample of a tissue or cell affected with the disorder; (iii) contacting said sample or a control sample with an MMP-26-binding protein, under conditions that allow interaction of the binding agent and the MMP-26 protein to occur, and (iv) detecting formation of a complex. A statistically significant increase in the formation of the complex between the ligand with respect to a reference sample, e.g., a control sample, is indicative of the disorder or the stage of the disorder. For example, the finding of activated MMP-26 on tumor cells located in a solid tumor can indicate that the tumor is progressing into a metastatic tumor.

Preferably, the MMP-26-binding protein used in the in vivo and in vitro diagnostic methods is directly or indirectly labeled with a detectable substance to facilitate detection of the bound or unbound binding agent. Suitable detectable substances include various enzymes, prosthetic groups, fluorescent materials, luminescent materials and radioactive materials. In one embodiment, the MMP-26-binding protein is coupled to a radioactive ion, e.g., indium ($^{111}$In), iodine ($^{131}$I or $^{125}$I), yttrium ($^{90}$Y), actinium ($^{225}$Ac), bismuth ($^{213}$Bi), sulfur ($^{35}$S), carbon ($^{14}$C), tritium ($^{3}$H), rhodium ($^{188}$Rh), or phosphorous ($^{32}$P). In another embodiment, the ligand is labeled with an NMR contrast agent.

The invention also provides polypeptides and nucleic acids that encompass a range of amino acid and nucleic acid sequences. In addition, the invention features a host cell that includes a nucleic acid described herein. The cell can express a protein described herein, e.g., on its surface.

MMP-26 is an ideal target for therapeutic intervention, particularly in the several cancers in which it is upregulated. Because MMP-26 is normally expressed in very limited areas of normal adult tissues (uterus and placenta), a protein that binds MMP-26 can be used to specifically target cancer cells. The limited expression of MMP-26 in normal adults also makes this molecule useful for detecting cancer cells in a subject.

As used herein, the term "antibody" refers to a protein comprising at least one immunoglobulin variable domain. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917). Kabat definitions are used herein.

Each VH and VL is composed of three CDR's and four FR's, arranged from amino-terminus to carboxy-terminus in the following order: FR1, CDR1, FR2, CDR2, FR3, CDR3, FR4. The canonical structures of hypervariable loops of an immunoglobulin variable can be inferred from its sequence, as described in Chothia et al. (1992) *J. Mol. Biol.* 227:799-817; Tomlinson et al. (1992) *J. Mol. Biol.* 227:776-798); and Tomlinson et al. (1995) *EMBO J.* 14(18):4628-38.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may omit one, two or more N- or C-terminal amino acids, internal amino acids, or may include other alterations. In one embodiment, a polypeptide that includes immunoglobulin variable domain sequence can associate with another immunoglobulin variable domain sequence to form an MMP-26-binding structure.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoeitic cell. In one embodiment, the human sequences are germline sequences, e.g., encoded by a germline nucleic acid. One or more of the constant regions can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the N-terminus (about 110 amino acids) and a kappa or lambda constant region gene at the C-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

The term "antigen-binding fragment" refers to a protein that includes an immunoglobulin light chain variable domain sequence and an immunoglobulin heavy chain variable domain sequence, the protein being able to specifically bind to an antigen, e.g., MMP-26. In one embodiment, an antigen-binding fragment is a fragment of a full-length antibody (or simply "antibody portion," or "fragment") that retain the ability to specifically bind to MMP-26 (e.g., human MMP-26). Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated CDR that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) *Science* 242:423-426; and Huston et al. (1988) *Proc. Natl. Acad. Sci. USA* 85:5879-5883. The term "antibody" encompasses antigen-binding fragments of antibodies (e.g., single chain antibodies, Fab fragments, F(ab')$_2$, a Fd fragment, a Fv fragments, and dAb fragments) as well as complete antibodies. Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition. As used herein, "isotype" refers to the antibody class (e.g., IgM or IgG1) that is encoded by heavy chain constant region genes.

An "effectively human" immunoglobulin variable region is an immunoglobulin variable region that includes a sufficient number of human amino acid positions (e.g., framework positions and/or CDR positions) such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified to include a sufficient number of human framework amino acid positions such that the immunoglobulin variable region does not elicit an immunogenic response in a normal human. Descriptions of "humanized" immunoglobulins include, for example, U.S. Pat. No. 6,407,213 and U.S. Pat. No. 5,693,762.

As used herein, "binding affinity" refers to the apparent association constant or Ka. The Ka is the reciprocal of the dissociation constant (Kd). A ligand may, for example, have a binding affinity of at least $10^{-5}$, $10^{-6}$, $10^{-7}$ or $10^{-8}$ M for a particular target molecule. Higher affinity binding of a ligand to a first target relative to a second target can be indicated by a higher Ka (or a smaller numerical value Kd) for binding the first target than the Ka (or numerical value Kd) for binding the second target. In such cases the ligand has specificity for the first target relative to the second target. Differences in binding affinity (e.g., for specificity or other comparisons) can be at least 1.5, 2, 5, 10, 50, 100, or 1000-fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in PBS (phosphate buffered saline) at pH 7.2 at 30° C. These techniques can be used to measure the concentration of bound and free ligand as a function of ligand (or target) concentration. The concentration of bound ligand ([Bound]) is related to the concentration of free ligand ([Free]) and the concentration of binding sites for the ligand on the target where (N) is the number of binding sites per target molecule by the following equation:

$$[\text{Bound}] = N \cdot [\text{Free}]/((1/Ka) + [\text{Free}]).$$

It is not always necessary to make an exact determination of Ka, though, since sometimes it is sufficient to obtain a quantitative measurement of affinity, e.g., determined using a method such as ELISA or FACS analysis, is proportional to Ka, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interests is at least 5, 10, 25, 50, 75, 80, 90, 92, 95, 98, or 99% pure on a weight-weight basis.

An "epitope" refers to the site on a target compound that is bound by a ligand, e.g., a polypeptide ligand or an antigen-binding ligand (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. For example, the reference sequence may be the length of the immunoglobulin variable domain sequence.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6.

As used herein, the term "substantially identical" (or "substantially homologous") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity relative to the same antigen.

Sequences similar or homologous (e.g., at least about 85% sequence identity) to the sequences disclosed herein are also part of this application. In some embodiment, the sequence identity can be about 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., highly stringent hybridization conditions), to the complement of the strand. The nucleic acids may be present in whole cells, in a cell lysate, or in a partially purified or substantially pure form.

As used herein, the term "homologous" is synonymous with "similarity" and means that a sequence of interest differs from a reference sequence by the presence of one or more amino acid substitutions (although modest amino acid insertions or deletions) may also be present. In addition to the GAP program described above, a variety of means of calculating degrees of homology or similarity to a reference sequence are available. One method uses the BLAST algorithms (available from the National Center of Biotechnology Information (NCBI), National Institutes of Health, Bethesda Md.), in each case, using the algorithm default or recommended parameters for determining significance of calculated sequence relatedness. The percent identity between two amino acid or nucleotide sequences can also be determined using the algorithm of E. Meyers and W. Miller ((1989) *CABIOS,* 4:11-17) which has been incorporated into the ALIGN program (version 2.0), using a PAM120 weight residue table, a gap length penalty of 12 and a gap penalty of 4.

As used herein, the term "hybridizes under low stringency, medium stringency, high stringency, or very high stringency conditions" describes conditions for hybridization and washing. Guidance for performing hybridization reactions can be found in *Current Protocols in Molecular Biology,* John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. The invention includes nucleic acids that hybridize with low, medium, high, or very high stringency to a nucleic acid described herein or to a complement thereof. The nucleic acids can be the same length or within 30, 20, or 10% of the length of the reference nucleic acid.

It is understood that a MMP-26-binding protein may have mutations relative to a ligand described herein (e.g., a conservative or non-essential amino acid substitutions), which do not have a substantial effect on the polypeptide functions. Whether or not a particular substitution will be tolerated, i.e., will not adversely affect desired biological properties, such as binding activity can be determined as described in Bowie, et al. (1990) *Science* 247:1306-1310. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). It is possible for many framework and CDR amino acid residues to include one or more conservative substitutions.

A "non-essential" amino acid residue is a residue that can be altered from the wild-type sequence of the binding agent, e.g., the antibody, without abolishing or more preferably, without substantially altering a biological activity, whereas an "essential" amino acid residue results in such a change.

The terms "polypeptide" or "peptide" (which may be used interchangeably) refer to a polymer of three or more amino acids linked by a peptide bond, e.g., between 3 and 30, 12 and 60, or 30 and 300, or over 300 amino acids in length. The polypeptide may include one or more unnatural amino acids. Typically, the polypeptide includes only natural amino acids. A "protein" can include one or more polypeptide chains. Accordingly, the term "protein" encompasses polypeptides. A protein or polypeptide also can include one or more modifications, e.g., a glycosylation, amidation, phosphorylation, and so forth. The term "small peptide" can be used to describe a polypeptide that is between 3 and 30 amino acids in length, e.g., between 8 and 24 amino acids in length. The term "ligand" refers to a protein that can interact with a target molecule, e.g., MMP-26. A "specific ligand" refers to a protein that specifically interacts with the target molecule.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. Particular ligands may show a difference, e.g., in specificity or binding, that are statistically significant (e.g., P value <0.05 or 0.02).

Other features and advantages of the instant invention will become more apparent from the following detailed description and claims. Embodiments of the invention can include any combination of features described herein. The contents of all references, pending patent applications and published patents, cited throughout this application are hereby expressly incorporated by reference.

DETAILED DESCRIPTION

The invention provides, inter alia, proteins (e.g., antibodies) that bind to matrix metalloproteinase-26 (MMP-26). In one embodiment, the proteins inhibit MMP-26. Other names for MMP-26 include Matrilysin-2 and endometase. An exemplary human MMP-26 amino acid sequence is as follows (as provided by SWISSPROT entry Q9NRE1):

```
                                                  (SEQ ID NO:213)
MQLVILRVTIFLPWCFAVPVPPAADHKGWDFVEGYFHQFFLTKKESPLLT

QETQTQLLQQFHRNGTDLLDMQMHALLHQPHCGVPDGSDTSISPGRCKWN

KHTLTYRIINYPHDMKPSAVKDSIYNAVSIWSNVTPLIFQQVQNGDADIK

VSFWQWAHEDGWPFDGPGGILGHAFLPNSGNPGVVHFDKNEHWSASDTGY

NLFLVATHETGHSLGLQHSGNQSSIMYPTYWYHDPRTFQLSADDIQRIQH

LYGEKCSSDTP
```

TABLE 1

MMP-26 Features

| From | To | Length | Description |
|---|---|---|---|
| 1 | 17 | 17 | Signal Sequence |
| 18 | 89 | 72 | Propeptide |
| 90 | 261 | 172 | mature protein chain |
| 82 | 82 | | potential cysteine switch (potential). |
| 208 | 208 | | catalytic zinc - interacting resdiue |
| 209 | 209 | | Active Site |
| 212 | 212 | | catalytic zinc - interacting resdiue |
| 218 | 218 | | catalytic zinc - interacting resdiue |

After removal of the signal sequence and the prodomain, the amino acid sequence of the mature MMP-26 protein can be as follows:

```
                                                  (SEQ ID NO:214)
TSISPGRCKWNKHTLTYRIINYPHDMKPSAVKDSIYNAVSTWSNVTPLTF

QQVQNGDADIKVSFWQWAHEDGWPFDGPGGTLGHAFLPNSGNPGVVHFDK

NEHWSASDTGYNLFLVATHEIGHSLGLQHSGNQSSIMYPTYWYHDPRTFQ

LSADDIQRIQHLYGEKCSSDIP
```

Typically, MMP-26 is specifically expressed in human placenta and uterine tissue. MMP-26 is expressed by endometrial tumors and other tumors of epithelial origin, including carcinomas of the breast, lung and prostate. In addition, a variety of breast, lung and prostate cancer cell lines express this MMP. Accordingly, MMP-26 may participate in tissue remodeling events associated with tumor progression and metastasis as well as embryo implantation.

MMP-26 cleaves a variety of substrates, including type I gelatin, serpin alpha-1-anti-trypsin ($\alpha$1AT), fibronectin, vitronectin, denatured collagen and pro-gelatinase B (pro-MMP-9) (thereby activating the zymogen). MMP-26 does not substantially cleave non-denatured collagens, laminin, elastin, and plasminogen. In addition, MMP-26 cleaves insulin-like growth factor binding protein-1 (IGFBP-1). Cleavage of this binding protein can increase local concentrations of insulin-like growth factor-1 (IGF-1) and may similarly effect IGF-2. Insulin-like growth factors have been linked to proliferation of a variety of cancer cells. Accordingly, an inhibitor of MMP-26 (e.g., an inhibitory antibody described herein) can be used to reduce insulin-like growth factor activity (e.g., levels or presence of IGF-1 or IGF-2).

MMP-26-mediated $\alpha$1AT hydrolysis inactivates this regulator of serine proteases resulting in enhanced protease activity and further destruction of the extracellular matrix. MMP-26 protease activity previously has been associated with invasiveness by breast cancer cells.

Identification of MMP-26 Binding Proteins

A number of methods can be used to identify proteins that bind to MMP-26. To identify antibodies, it is possible to immunize a non-human animal with the target molecule. Spleen cells can be isolated from the immunized animal and used to produce hybridoma cells using standard methods. In one embodiment, the non-human animal includes one or more human immunoglobulin genes. One method for identifying proteins that bind to MMP-26 includes: providing a library and selecting from the library one or more members that encode a protein that binds to the MMP-26 antigen. The selection can be performed in a number of ways. For example, the library can be a display library.

The MMP-26 can be tagged and recombinantly expressed. The MMP-26 is purified and attached to a support, e.g., to affinity beads, or paramagnetic beads or other magnetically responsive particles.

The MMP-26 can also be expressed on the surface of a cell. Members of the display library that specifically bind to the cell, e.g., only if the MMP-26 is activated, can be selected.

Display Libraries

In one embodiment, a display library is used to identify proteins that bind to MMP-26. A display library is a collection of entities; each entity includes an accessible protein component (e.g., a Fab or scFv) and a recoverable component (e.g., a nucleic acid) that encodes or identifies the protein component. The protein component can be of any length, e.g. from three amino acids to over 300 amino acids. In a selection, the protein component of each member of the library is probed with MMP-26 protein and if the protein component binds to MMP-26, the display library member is identified, e.g., by retention on a support. The protein component can include one or more immunoglobulin variable domains or variants of another domain. Methods using immunoglobulin domains for display are described below (see, e.g., "Antibody Display Libraries").

Retained display library members are recovered from the support and analyzed. The analysis can include amplification and a subsequent selection under similar or dissimilar conditions. For example, positive and negative selections can be alternated. The analysis also can include determining the amino acid sequence of the protein component and purification of the protein component for detailed characterization.

A variety of formats can be used for display libraries. Examples include the following.

Phage Display. One format utilizes viruses, particularly bacteriophages. This format is termed "phage display." The protein component is typically covalently linked to a bacteriophage coat protein. The linkage results form translation of a nucleic acid encoding the protein component fused to the coat protein. The linkage can include a flexible peptide linker, a protease site, or an amino acid incorporated as a result of suppression of a stop codon. Phage display is described, for example, in Ladner et al., U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J.* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Rebar et al. (1996) *Methods Enzymol.* 267:129-49; Hoogenboom et al. (1991) *Nuc Acid Res* 19:4133-4137; and Barbas et al. (1991) *PNAS* 88:7978-7982.

Phage display systems have been developed for filamentous phage (phage fl, fd, and M13) as well as other bacteriophage (e.g., T7 bacteriophage and lambdoid phages; see, e.g., Santini (1998) *J. Mol. Biol.* 282:125-135; Rosenberg et al. (1996) *Innovations* 6:1-6; Houshmet al. (1999) *Anal Biochem* 268:363-370). The filamentous phage display systems typically use fusions to a minor coat protein, such as gene III protein, and gene VIII protein, a major coat protein, but fusions to other coat proteins such as gene VI protein, gene VII protein, gene IX protein, or domains thereof also can be used (see, e.g., WO 00/71694). In one embodiment, the fusion is to a domain of the gene III protein, e.g., the anchor domain or "stump," (see, e.g., U.S. Pat. No. 5,658,727 for a description of the gene III protein anchor domain). It also is possible to physically associate the protein being displayed to the coat using a non-peptide linkage, e.g., a non-covalent bond or a non-peptide covalent bond. For example, a disulfide bond and/or c-fos and c-jun coiled-coils can be used for physical associations (see, e.g., Crameri et al. (1993) *Gene* 137:69 and WO 01/05950).

Bacteriophage displaying the protein component can be grown and harvested using standard phage preparatory methods, e.g. PEG precipitation from growth media. After selection of individual display phages, the nucleic acid encoding the selected protein components, by infecting cells using the selected phages. Individual colonies or plaques can be picked, the nucleic acid isolated and sequenced.

Cell-based Display. In still another format the library is a cell-display library. Proteins are displayed on the surface of a cell, e.g., a eukaryotic or prokaryotic cell. Exemplary prokaryotic cells include *E. coli* cells, *B. subtilis* cells, and spores (see, e.g., Lu et al. (1995) *Biotechnology* 13:366). Exemplary eukaryotic cells include yeast (e.g., *Saccharomyces cerevisiae, Schizosaccharomyces pombe, Hanseula,* or *Pichia pastoris*). Yeast surface display is described, e.g., in Boder and Wittrup (1997) *Nat. Biotechnol.* 15:553-557 and WO 03/029456, which describes a yeast display system that can be used to display immunoglobulin proteins such as Fab fragments and the use of mating to generate combinations of heavy and light chains.

In one embodiment, diverse nucleic acid sequences are cloned into a vector for yeast display. The cloning joins the variegated sequence with a domain (or complete) yeast cell surface protein, e.g., Aga2, Aga1, Flo1, or Gas1. A domain of these proteins can anchor the polypeptide encoded by the variegated nucleic acid sequence by a transmembrane domain (e.g., Flo1) or by covalent linkage to the phospholipid bilayer (e.g., Gas1). The vector can be configured to express two polypeptide chains on the cell surface such that one of the chains is linked to the yeast cell surface protein. For example, the two chains can be immunoglobulin chains.

In one embodiment, nucleic acids encoding immunoglobulin heavy chains that have been mutagenized based on an initial MMP-26-binding immunoglobulin are introduced into yeast cells of one cell type, and nucleic acids encoding immunoglobulin light chains that have been mutagenized based on an initial MMP-26-binding immunoglobulin are introduced into yeast cells of the other cell type. These two populations of cells can be combined to form diploid yeast that each express an immunoglobulin heavy and light chain. The yeast cells can be selected and/or screened for cells that bind to MMP-26, e.g., bind with improved affinity.

Ribosome Display. RNA and the polypeptide encoded by the RNA can be physically associated by stabilizing ribosomes that are translating the RNA and have the nascent polypeptide still attached. Typically, high divalent $Mg^{2+}$ concentrations and low temperature are used. See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30; and Schaffitzel et al. (1999) *J Immunol Methods.* 231(1-2):119-35.

Polypeptide-Nucleic Acid Fusions. Another format utilizes polypeptide-nucleic acid fusions. Polypeptide-nucleic acid fusions can be generated by the in vitro translation of mRNA that include a covalently attached puromycin group, e.g., as described in Roberts and Szostak (1997) *Proc. Natl. Acad. Sci. USA* 94:12297-12302, and U.S. Pat. No. 6,207,446. The mRNA can then be reverse transcribed into DNA and crosslinked to the polypeptide.

Other Display Formats. Yet another display format is a non-biological display in which the protein component is attached to a non-nucleic acid tag that identifies the polypeptide. For example, the tag can be a chemical tag attached to a bead that displays the polypeptide or a radiofrequency tag (see, e.g., U.S. Pat. No. 5,874,214).

Epitope Specific Ligands. Display technology also can be used to obtain ligands, e.g., antibody ligands, that bind to particular epitopes of a target. Epitopes can be classified as "conformational" or "sequential". Conformational epitopes involve amino-acid residues that have a defined relative orientation in a properly folded target even though the amino acids may be substantially separated in the sequence (e.g., separated by at least one, two, four, six, eight or ten amino acids). Sequential epitopes involve short portions of the polypeptide chain that bind an antibody whatever the folding state of the protein (e.g., native or unfolded). Ligands for conformational epitopes can be identified, for example, by using competing non-target molecules that lack the particular epitope or are mutated within the epitope, e.g., with alanine. Such non-target molecules can be used in a negative selection procedure as described below, as competing molecules when binding a display library to the target, or as a pre-elution agent, e.g., to capture in a wash solution dissociating display library members that are not specific to the target. In another implementation, epitope specific ligands are identified by eluting display library members with a competing ligand that binds to the epitope of interest on the target molecule. Ligands that bind sequential epitopes can be selected, for example, using short peptides that have amino-acid sequences found in a target protein. Often ligands that bind to conformational epitopes also bind weakly to one or another peptide that contains some of the amino acids involved in the conformational epitope. Thus, one can select for binding to a peptide at very low stringency and then select for binding to the folded target protein.

Affinity Maturation. In one embodiment, a ligand that binds to a target is modified, e.g., by mutagenesis, to provide a pool of modified ligands. The modified ligands are then evaluated to identify one or more altered ligands which have altered functional properties (e.g., improved binding, improved stability, lengthened stability in vivo). In one implementation, display library technology is used to select or screen the pool of modified ligands. Higher affinity ligands are then identified from the second library, e.g., by using higher stringency or more competitive binding and washing conditions. Other screening techniques also can be used.

In one example of affinity maturation the methods described herein are used to first identify a protein ligand from a display library that binds a MMP-26 with at least a minimal binding specificity for a target or a minimal activity, e.g., an equilibrium dissociation constant for binding of less than 1 nM, 10 nM, or 100 nM. The nucleic acid sequence encoding the initial identified protein ligand are used as a template nucleic acid for the introduction of variations, e.g., to identify a second protein ligand that has enhanced properties (e.g., binding affinity, kinetics, or stability) relative to the initial protein ligand. Alternatively, the amino-acid sequence of one or more CDRs can be used as a guide for design of a nucleic acid library that includes nucleic acids encoding the isolated sequence and many neighboring sequences. Such diversified nucleic acids can be introduced into a display vector containing the initial isolate and improved variants are selected from the library.

In some implementations, the mutagenesis is targeted to regions known or likely to be at the binding interface. If, for example, the identified ligands are antibodies, then mutagenesis can be directed to the CDR regions of the heavy or light chains as described herein. Further, mutagenesis can be directed to framework regions near or adjacent to the CDRs, e.g., framework regions, particular within ten, five, or three amino acids of a CDR junction. In the case of antibodies, mutagenesis also can be limited to one or a few of the CDRs, e.g., to make step-wise improvements.

Some exemplary mutagenesis techniques include: error-prone PCR (Leung et al. (1989) *Technique* 1:11-15), recombination (see, e.g., U.S. Ser. No. 10/279,633), DNA shuffling using random cleavage (Stemmer (1994) *Nature* 389-391; termed "nucleic acid shuffling"), RACHITT™ (Coco et al. (2001) *Nature Biotech.* 19:354), site-directed mutagenesis (Zoller et al. (1987) *Nucl Acids Res* 10:6487-6504), cassette mutagenesis (Reidhaar-Olson (1991) *Methods Enzymol.* 208: 564-586) and incorporation of degenerate oligonucleotides (Griffiths et al. (1994) *EMBO J* 13:3245).

In one embodiment, mutagenesis is used to make an antibody more similar to one or more germline sequences. One exemplary germlining method can include: identifying one or more germline sequences that are similar (e.g., most similar in a particular database) to the sequence of the isolated antibody. Then mutations (at the amino acid level) can be made in the isolated antibody, either incrementally, in combination, or both. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a CDR region. For example, the germline CDR residue can be from a germline sequence that is similar (e.g., most similar) to the variable region being modified. After mutagenesis, activity (e.g., binding or other functional activity) of the antibody can be evaluated to determine if the germline residue or residues are tolerated. Similar mutagenesis can be performed in the framework regions.

Accordingly, it is possible to isolate an antibody which has similar activity to a given antibody of interest, but is more similar to one or more germline sequences. For example, an antibody can be at least 90, 91, 92, 93, 94, 95, 96, 97, 98, 99, 99.5% identical to a germline sequence in a region outside the CDRs (e.g., framework regions). Further an antibody can include at least 1, 2, 3, 4, or 5 germline residues in a CDR region, the germline residue being from a germline sequence of similar (e.g., most similar) to the variable region being modified. Germline sequences of primary interest are human germline sequences. The activity of the antibody (e.g., the binding activity) can be within a factor or 100, 10, 5, 2, 0.5, 0.1, and 0.001 of the original antibody.

Off-Rate Selection. Since a slow dissociation rate can be predictive of high affinity, particularly with respect to interactions between polypeptides and their targets, the methods described herein can be used to isolate ligands with a desired kinetic dissociation rate (i.e. reduced) for a binding interaction to a target.

To select for slow dissociating ligands from a display library, the library is contacted to an immobilized target. The immobilized target is then washed with a first solution that removes non-specifically or weakly bound biomolecules. Then the immobilized target is eluted with a second solution that includes a saturation amount of free target, i.e., replicates of the target that are not attached to the particle. The free target binds to biomolecules that dissociate from the target. Rebinding is effectively prevented by the saturating amount of free target relative to the much lower concentration of immobilized target.

The second solution can have solution conditions that are substantially physiological or that are stringent. Typically, the solution conditions of the second solution are identical to the solution conditions of the first solution. Fractions of the second solution are collected in temporal order to distinguish early from late fractions. Later fractions include biomolecules that dissociate at a slower rate from the target than biomolecules in the early fractions.

Further, it also is possible to recover display library members that remain bound to the target even after extended incubation. These can either be dissociated using chaotropic conditions or can be amplified while attached to the target. For example, phage bound to the target can be contacted to bacterial cells.

Selecting and Screening for Specificity. "Selection", in the context of a display library, refers to a process in which many members of a display library are allowed to contact the target and those that bind are recovered and propagated. The selection can be from a library having numerous members, e.g., more than $10^{10}$ members. "Screening", in the context of a display library, refers to a process in which isolated members of the library are tested singly for binding to the target.

Through automation, thousands of candidates may be screened in a highly parallel process. The display library selection methods described herein can include a selection process that discards display library members that bind to a non-target molecule. Examples of non-target molecules include, e.g., metalloproteinases other than MMP-26, e.g., a matrix metalloproteinase other than MMP-26, e.g., MMP-12, MMP-3 (stromelysin-1), MMP-9 (gelatinase), and so on. In one implementation, a so-called "negative selection" step is used to discriminate between the target and related non-target molecule and a related, but distinct non-target molecules. The display library or a pool thereof is contacted to the non-target molecule. Members of the sample that do not bind the non-target are collected and used in subsequent selections for binding to the target molecule or even for subsequent negative selections. The negative selection step can be prior to or after selecting library members that bind to the target molecule.

In another implementation, a screening step is used. After display library members are isolated for binding to the target molecule, each isolated library member is tested for its ability to bind to a non-target molecule (e.g., a non-target listed above). For example, a high-throughput ELISA screen can be used to obtain this data. The ELISA screen can also be used to obtain quantitative data for binding of each library member to the target. The non-target and target binding data are compared (e.g., using a computer and software) to identify library members that specifically bind to MMP-26.

The display library selection and screening methods described herein can include a selection or screening process that selects for display library members that bind to specific sites on the target molecule. For example, elution with high concentration of an antibody described herein selects for phage that bind to the epitope bound by such an antibody. One can screen for a phage that binds to a particular epitope of MMP-26 by performing ELISAs with and without a competing antibody that recognizes the epitope in the buffer.

Selection and Screening for MMP-26-binding Antibodies:

The following provides one exemplary method for identifying antibodies that bind to MMP-26 using a phagemid Fab library. For example, three rounds of selection can be performed with decreasing amounts of target protein (e.g., 500 to 50 nM for first to third rounds, respectively). The target is immobilized on streptavidin-coated magnetic beads (Dynal). The library is depleted against streptavidin-coated magnetic beads prior to each round of selection and optionally against an unrelated protein which may include a common purification handle. For example, if the target is produced as a fusion to an Fc domain, the library can be depleted against soluble Trail-Fc (a commercially available Fc fusion protein). The depletion process removes Fc binders.

Each round of selection can include, e.g., two cycles of streptavidin magnetic bead depletion, a cycle of binding of phage to MMP-26-coated beads, ten cycles of washes, elution of bound phage, and propagation of enriched phage for the next round. Phage bound to MMP-26-coated beads after ten washes can be directly amplified or eluted before amplification. After three rounds of selection, individual clones may be grown in 96-well microtiter plates and individually screened for MMP-26 binding activity by phage ELISA. ELISAs can include evaluations of binding to MMP-26, specificity controls, and unrelated controls. Isolates can be DNA fingerprinted to determine the diversity emerging from the selection process. For example, positive isolates can be PCR amplified with the oligonucleotide primers M13-reverse and gene III-forward (see, e.g., Marks et al. (1991), *J. Mol. Biol.* 222:581).

The products can be analyzed by BstNI fingerprinting.

An exemplary method for performing ELISA's with phage that display a ligand is as follows. Individual clones can be grown and rescued as described previously (Marks et al. (1991), *J. Mol. Biol.* 222:581). For ELISAs, 96-well Immulon 2 HB plates (Thermo Labsystems) are coated with 1 µg/well ImmunoPure™ streptavidin (Pierce) in PBS and incubated overnight at 4° C. After three washes with PBS, 100 µL of biotinylated MMP-26 protein is allowed to bind to the immobilized streptavidin for 30-60 minutes at room temperature. Then, MMP-26-coated wells are blocked with 300 µL of 2% milk/1×PBS/0.05% Tween (2% MPBST) for two hours at 37° C. The wells are incubated with 100 µL of phage culture supernatant that had been blocked with 2% MPBST for one hour at room temperature. The wells are washed five times with 1×PBS/Tween 0.1% (PBST), and incubated with 100 µL of anti-M13-HRP secondary antibody at a 1:5,000 dilution for one hour at room temperature. The wells are washed five times with PBST before developing with TMB-solution and read at 630 nm.

For the cell ELISAs, cells are washed once in PBS and resuspended at a concentration of $1 \times 10^6$ to $2 \times 10^6$ cells/mL of PBS. A final concentration of $1-2 \times 10^5$ cells per well of a 96-well tissue culture plate (Falcon, VWR) can be used. The cells are fixed by adding an equal volume of 0.2% glutaraldehyde (Sigma-Aldrich) and incubating at 37° C. for 12 minutes. They are then washed three times with PBS using an automated plate washer (Bio-Tek Instruments, Inc.) and blocked with 200 µL of 2% MPBST for one hour at room temperature. The rest of the ELISA procedure can be performed as described above except that 1×PBS/Tween 0.05% is used for the washes and incubations.

Diversity

Display libraries and other libraries include variation at one or more positions in the displayed polypeptide. The variation at a given position can be synthetic or natural. For some libraries, both synthetic and natural diversity are included.

Synthetic Diversity. Libraries can include regions of diverse nucleic acid sequence that originate from artificially synthesized sequences. Typically, these are formed from degenerate oligonucleotide populations that include a distribution of nucleotides at each given position. The inclusion of a given sequence is random with respect to the distribution. One example of a degenerate source of synthetic diversity is an oligonucleotide that includes NNN wherein N is any of the four nucleotides in equal proportion.

Synthetic diversity can also be more constrained, e.g., to limit the number of codons in a nucleic acid sequence at a given trinucleotide to a distribution that is smaller than NNN. For example, such a distribution can be constructed using less than four nucleotides at some positions of the codon. In addition, trinucleotide addition technology can be used to further constrain the distribution.

So-called "trinucleotide addition technology" is described, e.g., in Wells et al. (1985) *Gene* 34:315-323, U.S. Pat. Nos. 4,760,025 and 5,869,644. Oligonucleotides are synthesized on a solid phase support, one codon (i.e., trinucleotide) at a time. The support includes many functional groups for synthesis such that many oligonucleotides are synthesized in parallel. The support is first exposed to a solution containing a mixture of the set of codons for the first position. The unit is protected so additional units are not added. The solution containing the first mixture is washed away and the solid support is deprotected so a second mixture containing a set of codons for a second position can be added to the attached first unit. The process is iterated to sequentially assemble multiple codons. Trinucleotide addition technology enables the synthesis of a nucleic acid that at a given position can encode a number of amino acids. The frequency of these amino acids can be regulated by the proportion of codons in the mixture. Further the choice of amino acids at the given position is not restricted to quadrants of the codon table as is the case if mixtures of single nucleotides are added during the synthesis. Synthetic oligonucleotides including randomized or spiked codons can be also be used for producing a library for an affinity maturation selection.

Natural Diversity. Libraries can include regions of diverse nucleic acid sequence that originate (or are synthesized based on) from different naturally-occurring sequences. An example of natural diversity that can be included in a display library is the sequence diversity present in immune cells (see also below). Nucleic acids are prepared from these immune cells and are manipulated into a format for polypeptide display.

Antibody Display Libraries

In one embodiment, the display library presents a diverse pool of proteins, each of which includes an immunoglobulin domain, e.g., an immunoglobulin variable domain. Display libraries are particular useful, for example, for identifying human or effectively human antibodies that recognize human antigens. Such antibodies can be used as therapeutics to treat human disorders such as cancer, e.g., metastatic cancer. Since the constant and framework regions of the antibody are human, these therapeutic antibodies may avoid themselves being recognized and targeted as antigens. The constant regions are also optimized to recruit effector functions of the human immune system. The in vitro display selection process surmounts the inability of a normal human immune system to generate antibodies against self-antigens.

A typical antibody display library displays a polypeptide that includes a VH domain and a VL domain. An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay 1988 *Ann. Rev Immunol.* 6:381-405). The display library can display the antibody as a Fab fragment (e.g., using two polypeptide chains) or a single chain Fv (e.g., using a single polypeptide chain). Other formats can also be used.

As in the case of the Fab and other formats, the displayed antibody can include a constant region as part of a light or heavy chain. In one embodiment, each chain includes one constant region, e.g., as in the case of a Fab. In other embodiments, additional constant regions are displayed.

Antibody libraries can be constructed by a number of processes (see, e.g., de Haard et al. (1999) *J. Biol. Chem* 274: 18218-30; Hoogenboom et al. (1998) Immunotechnology 4:1-20. and Hoogenboom et al. (2000) *Immunol Today* 21:371-8). Further, elements of each process can be combined with those of other processes. The processes can be used such that variation is introduced into a single immunoglobulin domain (e.g., VH or VL) or into multiple immunoglobulin domains (e.g., VH and VL). The variation can be introduced into an immunoglobulin variable domain, e.g., in the region of one or more of CDR1, CDR2, CDR3, FR1, FR2, FR3, and FR4, referring to such regions of either and both of heavy and light chain variable domains. In one embodiment, variation is introduced into all three CDRs of a given variable domain. In another preferred embodiment, the variation is introduced into CDR1 and CDR2, e.g., of a heavy chain variable domain. Any combination is feasible. In one process, antibody libraries are constructed by inserting diverse oligonucleotides that encode CDRs into the corresponding regions of the nucleic acid. The oligonucleotides can be synthesized using a variety of subunits, e.g., monomeric nucleotides or trinucleotides. For example, Knappik et al. (2000) *J. Mol. Biol.* 296:57-86 describe a method for constructing CDR encoding oligonucleotides using trinucleotide synthesis and a template with engineered restriction sites for accepting the oligonucleotides.

In another process, an animal, e.g., a rodent, is immunized with the MMP-26. The animal is optionally boosted with the antigen to further stimulate the response. Then spleen cells are isolated from the animal, and nucleic acid encoding VH and/or VL domains is amplified and cloned for expression in the display library.

In yet another process, antibody libraries are constructed from nucleic acid amplified from naïve germline immunoglobulin genes (e.g., human genes). The amplified nucleic acid includes nucleic acid encoding the VH and/or VL domain. Sources of immunoglobulin-encoding nucleic acids are described below. Amplification can include PCR, e.g., with primers that anneal to the conserved constant region, or another amplification method.

Nucleic acid encoding immunoglobulin domains or fragments thereof can be obtained from the immune cells of, e.g., a human, a primate, mouse, rabbit, camel, or rodent. In one example, the cells are selected for a particular property. B cells at various stages of maturity can be selected. In another example, the B cells are naïve.

In one embodiment, fluorescent-activated cell sorting (FACS) is used to sort B cells that express surface-bound IgM, IgD, or IgG molecules. Further, B cells expressing different isotypes of IgG can be isolated. In another preferred embodiment, the B or T cell is cultured in vitro. The cells can be stimulated in vitro, e.g., by culturing with feeder cells or by adding mitogens or other modulatory reagents, such as antibodies to CD40, CD40 ligand or CD20, phorbol myristate acetate, bacterial lipopolysaccharide, concanavalin A, phytohemagglutinin or pokeweed mitogen.

In still another embodiment, the cells are isolated from a subject that has an immunological disorder, e.g., systemic lupus erythematosus (SLE), rheumatoid arthritis, vasculitis, Sjogren syndrome, systemic sclerosis, or anti-phospholipid syndrome. The subject can be a human, or an animal, e.g., an animal model for the human disease, or an animal having an analogous disorder. In yet another embodiment, the cells are isolated from a transgenic non-human animal that includes a human immunoglobulin locus.

In one preferred embodiment, the cells have activated a program of somatic hypermutation. Cells can be stimulated to undergo somatic mutagenesis of immunoglobulin genes, for example, by treatment with anti-immunoglobulin, anti-CD40, and anti-CD38 antibodies (see, e.g., Bergthorsdottir et al. (2001) *J Immunol.* 166:2228). In another embodiment, the cells are naïve.

The nucleic acid encoding an immunoglobulin variable domain can be isolated from a natural repertoire by the following exemplary method. First, RNA is isolated from the immune cell. Full length (i.e., capped) mRNAs are separated (e.g. by dephosphorylating uncapped RNAs with calf intestinal phosphatase). The cap is then removed with tobacco acid pyrophosphatase and reverse transcription is used to produce the cDNAs.

The reverse transcription of the first (antisense) strand can be done in any manner with any suitable primer. See, e.g., de Haard et al. (1999) *J. Biol. Chem* 274:18218-30. The primer binding region can be constant among different immunoglobulins, e.g., in order to reverse transcribe different isotypes of immunoglobulin. The primer binding region can also be specific to a particular isotype of immunoglobulin. Typically, the primer is specific for a region that is 3' to a sequence encoding at least one CDR. In another embodiment, poly-dT primers may be used (and may be preferred for the heavy-chain genes).

A synthetic sequence can be ligated to the 3' end of the reverse transcribed strand. The synthetic sequence can be used as a primer binding site for binding of the forward primer during PCR amplification after reverse transcription. The use of the synthetic sequence can obviate the need to use a pool of different forward primers to fully capture the available diversity.

The variable domain-encoding gene is then amplified, e.g., using one or more rounds. If multiple rounds are used, nested primers can be used for increased fidelity. The amplified nucleic acid is then cloned into a display library vector.

Any method for amplifying nucleic acid sequences may be used for amplification. Methods that maximize and do not bias diversity are preferred. A variety of techniques can be used for nucleic acid amplification. The polymerase chain reaction (PCR; U.S. Pat. Nos. 4,683,195 and 4,683,202, Saiki, et al. (1985) *Science* 230, 1350-1354) utilizes cycles of varying temperature to drive rounds of nucleic acid synthesis. Transcription-based methods utilize RNA synthesis by RNA polymerases to amplify nucleic acid (U.S. Pat. Nos. 6,066, 457; 6,132,997; 5,716,785; Sarkar et. al., *Science* (1989) 244: 331-34; Stofler et al., *Science* (1988) 239: 491). NASBA (U.S. Pat. Nos. 5,130,238; 5,409,818; and 5,554,517) utilizes cycles of transcription, reverse-transcription, and RNaseH-based degradation to amplify a DNA sample. Still other amplification methods include rolling circle amplification (RCA; U.S. Pat. Nos. 5,854,033 and 6,143,495) and strand displacement amplification (SDA; U.S. Pat. Nos. 5,455,166 and 5,624,825).

Exemplary MMP-26 Inhibition Assays

Methods for evaluating MMP-26 enzymatic activity are known. See, e.g., Park et al. (2002) *J. Biol. Chem.* 277:35168-35175. In addition, MMP-26 assay may be monitored by measuring the cleavage of MMP-26-catalyzable substrates including vitronectin and collagen with subsequent detection of the cleaved substrates by standard SDS-PAGE techniques.

Inhibitory dissociation constants can be determined using 1 μM of the peptide substrate: Mca-Pro-Leu-Gly-Leu-Dpa-Ala-Arg-NH$_2$ (SEQ ID NO:215). The protein being evaluated can be tested at a range of concentrations, e.g., five to ten different concentrations. Kinetic parameters can be monitored by evaluating fluorescence of 3-methoxycoumarin, by excitation at 328 nm and by monitoring emission at 393 nm. The K$_i$ can be calculating by fitting data to an equation. Kinetic experiments can be performed in 50 mM HEPES pH 7.5, 10 mM CaCl$_2$, 0.2 M NaCl and 0.01% Brij-35. Additional substrates include Mca-Lys-Pro-Ile-Ser(P1)-Leu-Dpa-Ala-Arg-NH$_2$ (SEQ ID NO:216), or Mca-Pro-Ile-Ser(P1)-Leu-Dpa-Ala-Arg-NH$_2$ (SEQ ID NO:217). See, e.g., Park et al. (2002) J Biol Chem. 277(38):35168-75.

Additional assays for inhibtion can monitor ability to inhibit MMP-26 mediated activation of MMP-9. Activation is monitored by MMP-9 cleavage of gelatin (Molecular Probes E-12055) or cleavage of an MMP-9 specific peptide (Calbiochem 444221). MMP-26, e.g., at a concentration of 100 nM, is incubated with the candidate inhibitors at varying concentrations for one hour. The proMMP-9, at a concentration of 10 nM, is then added to the mixture followed by fluorescently labeled gelatin or a fluorescently labeled peptide substrate. MMP-9 activity is monitored using a fluorimeter (Molecular Devices) and is observed as an increase in signal.

In one embodiment, a protein (e.g., an antibody described herein) has a K$_i$ of less than $10^{-7}$, $10^{-8}$, $10^{-9}$, $10^{-10}$, or $10^{-11}$ M in an assay described herein.

Exemplary Biological Assays

Potential MMP-26 binding protein can also be evaluated for their activity in vivo. For example, to evaluate the activity of a protein (e.g., an antibody described herein) to reduce tumor growth through binding and/or inhibition of MMP-26, the procedures described by Jankun et al., *Canc. Res.*, 57: 559-563 (1997) to evaluate PAI-1 can be employed. Briefly, the ATCC cell lines DU145 and LNCaP are injected into SCID mice. After tumors are established, the mice are administered the test protein. Tumor volume measurements are taken twice a week for about five weeks. A binding protein can be deemed active in this assay if an animal to which the protein was administered exhibited decreased tumor volume and/or decreased metastatic spread of the tumor, as compared to animals receiving appropriate control compounds (e.g., antibody molecules specific to other proteins, particularly proteins unrelated to tumor growth and metastatic activity, or the formulation without the protein).

To evaluate the ability of a protein (e.g., an antibody described herein) to reduce the occurrence of, or inhibit, metastasis, the procedures described by Kobayashi et al., *Int. J. Canc.*, 57: 727-733d (1994) can be employed. Briefly, a murine xenograft selected for high lung colonization protential in injected into C57B1/6 mice i.v. (experimental metastasis) or s.c. into the abdominal wall (spontaneous metastasis). Various concentrations of the compound to be tested can be admixed with the tumor cells in MATRIGEL™ basement membrane matrix prior to injection. Daily i.p. injections of the test compound are made either on days 1-6 or days 7-13 after tumer inoculation. The animals are sacrificed about three or four weeks after tumor Inoculation, and the lung tumor colonies are counted. Evaluation of the resulting data permits a determination as to efficacy of the test compound, optimal dosing and route of administration.

The activity of the proteins toward decreasing tumor volume and metastasis can be evaluated in model described in Rabbani et al., *Int. J Cancer* 63: 840-845 (1995). See also Xing et al., *Canc. Res.*, 57: 3585-3593 (1997). There, Mat LyLu tumor cells were injected into the flank of Copenhagen rats. The animals were implanted with osmotic minipumps to continuously administer various doses of test compound for up to three weeks. The tumor mass and volume of experimental and control animals were evaluated during the experiment, as were metastatic growths. Evaluation of the resulting data permits a determination as to efficacy of the test compound, optimal dosing, and route of administration. Xing et al., *Canc. Res.*, 57: 3585-3593 (1997) describes a related protocol.

A protein (e.g., an antibody described herein) can also be evaluated in culture or in an animal for ability to modulate inflammation or an inflammatory disorder. For example, US 20030161810 provides a non-human animal model for an inflammatory disorder (including rheumatoid arthritis), the animal includes human synovial fluid. US 20030176389 describes a dextran sodium sulfate-induced mouse model of colitis. In another example, cell culture is used to monitor adhesion of leukocytes. For example, a compound can be immobilized on a solid surface and adhesion of cells expressing an adhesion molecule can be evaluated for interaction with the surface. Cells suitable for this assay include any leukocytes, such as T cells, B cells, monocytes, eosinophils, and basophils. Exemplary leukocyte cell lines include Jurkat and U937 cells.

In one embodiment, a protein (e.g., an antibody described herein) has a statistically significant effect in an assay described herein.

Secondary Screening Methods

After selecting candidate display library members that bind to a target or any candidate MMP-26-binding protein, each candidate protein can be further analyzed, e.g., to further characterize its binding properties for the target. Each candidate display library member can be subjected to one or more secondary screening assays. The assay can be for a binding property, a catalytic property, a physiological property (e.g., cytotoxicity, renal clearance, immunogenicity), a structural property (e.g., stability, conformation, oligomerization state) or another functional property. The same assay can be used repeatedly, but with varying conditions, e.g., to determine pH, ionic, or thermal sensitivities.

As appropriate, the assays can use the display library member directly, a recombinant polypeptide produced from the nucleic acid encoding a displayed polypeptide, a synthetic peptide synthesized based on the sequence of a displayed polypeptide. In the case of a candidate MMP-26 binding protein from any source, the protein can be obtained, e.g., from such a source or by recombinant production. Exemplary assays for binding properties include the following.

ELISA. Proteins encoded by a display library can also be screened for a binding property using an ELISA assay. For example, each protein is contacted to a microtitre plate whose bottom surface has been coated with the target, e.g., a limiting amount of the target. The plate is washed with buffer to remove non-specifically bound polypeptides. Then the amount of the protein bound to the plate is determined by probing the plate with an antibody that can recognize the polypeptide, e.g., a tag or constant portion of the polypeptide. The antibody is linked to an enzyme such as alkaline phosphatase, which produces a colorimetric product when appropriate substrates are provided. The protein can be purified from cells or assayed in a display library format, e.g., as a fusion to a filamentous bacteriophage coat. Alternatively, cells (e.g., live or fixed) that express the target molecule, e.g., MMP-26, can be plated in a microtitre plate and used to test the affinity of the peptides/antibodies present in the display library or obtained by selection from the display library.

In another version of the ELISA assay, each polypeptide of a diversity strand library is used to coat a different well of a microtitre plate. The ELISA then proceeds using a constant target molecule to query each well.

Homogeneous Binding Assays. The binding interaction of candidate protein with a target can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means well known in the art (e.g., using a fluorimeter). By titrating the amount of the first or second binding molecule, a binding curve can be generated to estimate the equilibrium binding constant.

Another example of a homogenous assay is Alpha Screen (Packard Bioscience, Meriden Conn.). Alpha Screen uses two labeled beads. One bead generates singlet oxygen when excited by a laser. The other bead generates a light signal when singlet oxygen diffuses from the first bead and collides with it. The signal is only generated when the two beads are in proximity. One bead can be attached to the display library member, the other to the target. Signals are measured to determine the extent of binding.

The homogenous assays can be performed while the candidate protein is attached to the display library vehicle, e.g., a bacteriophage or using a candidate protein as free molecule.

Surface Plasmon Resonance (SPR). The binding interaction of a molecule isolated from a display library and a target can be analyzed using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether (1988) *Surface Plasmons* Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden).

Information from SPR can be used to provide an accurate and quantitative measure of the equilibrium dissociation constant ($K_d$), and kinetic parameters, including $K_{on}$ and $K_{off}$, for the binding of a biomolecule to a target. Such data can be used to compare different biomolecules. For example, proteins encoded by nucleic acid selected from a library of diversity strands can be compared to identify individuals that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $K_{off}$. This information can be combined with structural modeling (e.g., using homology modeling, energy minimization, or structure determination by crystallography or NMR). As a result, an understanding of the physical interaction between the protein and its target can be formulated and used to guide other design processes.

Protein Arrays. Polypeptides identified from the display library can be immobilized on a solid support, for example, on a bead or an array. For a protein array, each of the polypeptides is immobilized at a unique address on a support. Typically, the address is a two-dimensional address. Protein arrays are described below (see, e.g., Diagnostics).

Cellular Assays. Candidate polypeptides can be selected from a library by transforming the library into a host cell; the library could have been previousy identified from a display library. For example, the library can include vector nucleic acid sequences that include segments that encode the polypeptides and that direct expression, e.g., such that the polypeptides are produced within the cell, secreted from the cell, or attached to the cell surface. The cells can be screened or selected for polypeptides that bind to the MMP-26, e.g., as dectected by a change in a cellular phenotype or a cell-mediated activity. For exmple, in the case of an antibody that binds to MMP-26, the activity may be an in vitro assay for cell invasion. In one embodiment, the antibody is contacted to an invasive mammalian cell, e.g., a carcinoma cell e.g., JEG-3 (choriocarcinoma) cell. The ability of the cell to invade a matrix is evaluated. The matrix can be an artificial matrix e.g., MATRIGEL™ basement membrane matrix, gelatin, etc., or a natural matrix, e.g., extracellular matrix of a tissue sample., or a combination thereof. For example, the matrix can be produced in vitro by a layer of cells.

Protein Production

Standard recombinant nucleic acid methods can be used to express a MMP-26 binding protein. See, for example, the techniques described in Sambrook & Russell, *Molecular Cloning: A Laboratory Manual*, 3$^{rd}$ Edition, Cold Spring Harbor Laboratory, N.Y. (2001) and Ausubel et al., Current Protocols in Molecular Biology (Greene Publishing Associates and Wiley Interscience, N.Y. (1989). Generally, a nucleic acid sequence encoding the protein of interest is cloned into a nucleic acid expression vector. If the protein includes multiple polypeptide chains, each chain can be cloned into an expression vector, e.g., the same or different vectors, that are expressed in the same or different cells. Methods for producing antibodies also are provided below.

The expression vector for expressing the protein can include, in addition to the segment encoding the protein or fragment thereof, regulatory sequences, including for example, a promoter, operably linked to the nucleic acid(s) of interest. Vectors are typically tailored for the intended expression system. Large numbers of suitable vectors and promoters are known to those of skill in the art and are commercially available for generating the recombinant constructs.

Methods well known to those skilled in the art can be used to construct vectors containing a polynucleotide encoding a ligand and appropriate regulatory signals (e.g., transcriptional/translational control signals). These methods include in vitro recombinant DNA techniques, synthetic techniques and in vivo recombination/genetic recombination. See, for example, the techniques described in Sambrook & Russell, *Molecular Cloning: A Laboratory Manual*, 3$^{rd}$ Edition, Cold Spring Harbor Laboratory, N.Y. (2001) and Ausubel et al., Current Protocols in Molecular Biology (Greene Publishing Associates and Wiley Interscience, N.Y. (1989). Promoter regions can be selected from any desired gene using CAT (chloramphenicol transferase) vectors or other vectors with selectable markers.

Generally, recombinant expression vectors will include origins of replication and selectable markers permitting transformation of the host cell, e.g., an antibiotic resistance gene for a bacterial cell, and a promoter derived from a highly expressed gene to direct transcription of a downstream structural sequence. The polynucleotide is assembled in appropriate phase with translation initiation and termination sequences, and preferably, a leader sequence capable of directing secretion of translated protein into the periplasmic space or extracellular medium. Optionally, the polynucleotide can encode a fusion protein including an identification sequence (e.g., a terminus, e.g., N- or C-terminal) imparting desired characteristics, e.g., stabilization or simplified purification of expressed recombinant product.

Prokaryotic Expression. Useful expression vectors for bacteria are constructed by inserting a polynucleotide encoding a ligand together with suitable translation initiation and termination signals, optionally in operable reading phase with a functional promoter. The vector can include one or more phenotypic selectable markers and an origin of replication to ensure maintenance of the vector and to, if desirable, provide amplification within the host. Suitable prokaryotic hosts for transformation include, e.g., *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacteria can include a selectable marker (e.g., an antibiotic resistance gene) and bacterial origin of replication derived from commercially available plasmids including genetic elements of the well known cloning vector pBR322 (ATCC 37017). Exemplary prokaryotic vectors include, for example, pKK223-3 (Pharmacia Fine Chemicals, Uppsala, Sweden) and pGEM1 (Promega, Madison, Wis., USA), pBS, phagescript, PsiX174, pBluescript SK, pBs KS, pNH8a, pNH16a, pNH18a, pNH46a (Stratagene); pTrc99A, pKK223-3, pKK233-3, pDR540, and pRIT5 (Pharmacia), as well as phage and phagemid vectors. Exemplary bacterial promoters include lacI, lacZ, T3, T7, gpt, lambda P, and trc. Vectors can be introduced into bacterial cells, e.g., by chemical transformation (e.g., the Hanahan protocol), electroporation, or bacteriophage infection.

If the protein is made in bacteria (or some yeast), it may be necessary to modify the protein produced therein, for example, by glycosylation of the appropriate sites, in order to obtain the functional protein. Such covalent attachments may be accomplished using known chemical or enzymatic methods.

It also is possible to produce host cells containing a vector that can express a ligand that binds to MMP-26. The vector can be introduced into the host cell, e.g., using known transformation, transfection or infection methods. For example, the host cells can include members of a library constructed from the diversity strand. The host cell can be a eukaryotic host cell, such as a mammalian cell, a lower eukaryotic host cell, such as a yeast cell, or the host cell can be a prokaryotic cell, such as a bacterial cell.

Yeast Expression Systems. The host cell for producing a protein ligand (e.g., antibody) also may be a yeast (e.g., *Pichia, Hanseula, Saccharomyces cerevisiae, Schizosaccharomyces pombe, Kluyveromyces* strains, or *Candida*) or other fungus. In yeast, a number of vectors containing constitutive or inducible promoters may be used. Exemplary yeast promoters include the promoters of genes encoding glycolytic enzymes such as 3-phosphoglycerate kinase (PGK), a-factor, acid phosphatase, and heat shock proteins, the PHO5 promoter, and GAL promoter, among others. A yeast vector can include a selectable marker, e.g., a drug resistance gene, or an auxotrophic marker (such as the URA3, LEU2, HIS3, and TRP1 genes). It is possible to maintain yeast vectors as extrachromosomal elements in high or low copy and to integrate the vectors into yeast chromosomes (e.g., endogenous or artificial).

For a review of yeast expression systems, see, e.g., Current Protocols in Molecular Biology, Vol. 2, Ed. Ausubel et al., Greene Publish. Assoc. & Wiley Interscience, Ch. 13 (1988); Grant et al., Expression and Secretion Vectors for Yeast, in *Methods in Enzymology*, Ed. Wu & Grossman, Acad. Press, N.Y. 153:516-544 (1987); Glover, DNA Cloning, Vol. II, IRL Press, Wash., D.C., Ch. 3 (1986); Bitter, Heterologous Gene Expression in Yeast, in *Methods in Enzymology*, Eds. Berger & Kimmel, Acad. Press, N.Y. 152:673-684 (1987); Powers et al. (2001) *J Immunol Methods*. 251:123-35; and *The Molecular Biology of the Yeast Saccharomyces*, Eds. Strathem et al., Cold Spring Harbor Press, Vols. I and 11 (1982).

Mammalian Expression. Various mammalian cell culture systems can also be employed to express a protein ligand, e.g., an antibody. Examples of mammalian expression systems include the COS-7 lines of monkey kidney fibroblasts (described by Gluzman, Cell 23:175 (1981)), the C127, 3T3, CHO, HeLa and BHK cell lines. Mammalian host cells include, for example, monkey COS cells, Chinese Hamster Ovary (CHO) cells, human embryonic kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK and Jurkat cells. Mammalian expression vectors can include an origin of replication, a suitable promoter and also any necessary ribosome-binding sites, polyadenylation site, splice donor and acceptor sites, transcriptional termination sequences, and 5' flanking non-transcribed sequences.

Exemplary eukaryotic vectors include: pWLneo, pSV2cat, pOG44, PXTI, pSG (Stratagene) pSVK3, pBPV, pMSG, and pSVL (Pharmacia). Exemplary eukaryotic promoters include CMV immediate early, HSV thymidine kinase, early and late SV40, LTRs from retrovirus, mouse metallothionein-I, and various art-known tissue specific promoters. In one example, DNA sequences derived from the SV40 viral genome, for example, SV40 origin, early promoter, enhancer, splice, and polyadenylation sites may be used to provide the required non-transcribed genetic elements. Introduction of the recombinant construct into a mammalian host cell can be effected, for example, by calcium phosphate transfection, DEAE, dextran mediated transfection, electroporation (Davis, L. et al., Basic Methods in Molecular Biology (1986)), or viral infection.

In another embodiment, cells and tissues may be engineered to express an endogenous gene that encodes a protein ligand described herein or a protein target. The method includes using homologous recombination to replace regulatory sequences of the endogenous gene with heterologous regulatory sequences, e.g., inducible regulatory elements. Such regulatory sequences may include promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals. Messenger RNA stability elements, splice sites, leader sequences for enhancing or modifying transport or secretion properties of the protein, or other sequences which alter or improve the function or stability of protein or RNA molecules.

Purification. Protein ligands can be purified from cells or from media surrounding cells. Cells expressing the proteins can be disrupted by any convenient method, including freeze-thaw cycling, sonication, mechanical disruption, or use of cell lysing agents. Recombinant polypeptides and proteins produced in culture are usually isolated by initial extraction from cell pellets, followed by one or more salting-out, aqueous ion exchange or size exclusion chromatography steps. In some embodiments, the protein also includes a polypeptide tag, e.g., penta- or hexa-histidine. The recombinant polypeptides can then be purified using affinity chromatography. Scopes (1994) *Protein Purification: Principles and Practice*, New York: Springer-Verlag provides a number of general methods for purifying recombinant (and non-recombinant) proteins. The methods include, e.g., ion-exchange chromatography, size-exclusion chromatography, affinity chromatography, selective precipitation, dialysis, and hydrophobic interaction chromatography. These methods can be adapted for devising a purification strategy for the MMP-26-binding protein. For ligands that include an Fc domain, one type of affinity chromatography uses immobilized protein A or protein G.

Antibody Production. Some antibodies, e.g., Fabs, can be produced in bacterial cells, e.g., *E. coli* cells. For example, if the Fab is encoded by sequences in a phage display vector that includes a suppressible stop codon between the display entity and a bacteriophage protein (or fragment thereof), the vector nucleic acid can be shuffled into a bacterial cell that cannot suppress a stop codon. In this case, the Fab is not fused to the gene III protein and is secreted into the media.

Antibodies can also be produced in eukaryotic cells. In one embodiment, the antibodies (e.g., scFv's) are expressed in a yeast cell such as Pichia (see, e.g., Powers et al. (2001) *J Immunol Methods*. 251:123-35), *Hanseula*, or *Saccharomyces*.

In one embodiment, antibodies are produced in mammalian cells. Preferred mammalian host cells for expressing the clone antibodies or antigen-binding fragments thereof include Chinese Hamster Ovary (CHO cells) (including dhfr-CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NSO myeloma cells and SP2 cells, COS cells, and a cell from a transgenic animal, e.g., a transgenic mammal. For example, the cell is a mammary epithelial cell.

In addition to the nucleic acid sequence encoding the immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

In an exemplary system for recombinant expression of an antibody (e.g., a full length antibody or an antigen-binding portion thereof), a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G.

For antibodies that include an Fc domain, the antibody production system preferably synthesizes antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcγ receptors and complement C1q (Burton and Woof (1992) Adv. Immunol. 51:1-84; Jefferis et al. (1998) Immunol. Rev. 163:59-76). In a preferred embodiment, the Fc domain is produced in a mammalian expression system that appropriately glycosylates the residue corresponding to asparagine 297. The Fc domain can also include other eukaryotic post-translational modifications.

Antibodies also can be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

It also is possible to produce antibodies that bind to MMP-26 by immunization, e.g., using an animal, e.g., with natural, human, or partially human immunoglobulin loci. Non-human antibodies also can be modified to include substitutions for human immunoglobulin sequences, e.g., consensus human amino acid residues at particular positions, e.g., at one or more of the following positions (preferably at least five, ten, twelve, or all): (in the FR of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the FR of the variable domain of the heavy chain) 2H, 4H, 24H, 36H, 37H, 39H, 43H, 45H, 49H, 58H, 60H, 67H, 68H, 69H, 70H, 73H, 74H, 75H, 78H, 91H, 92H, 93H, and/or 103H (according to the Kabat numbering). See, e.g., U.S. Pat. No. 6,407,213.

MMP-26 production. Method for producing a MMP-26 protein or a catalytic domain thereof are known in the art. See, e.g., the example below and Park, et al. (2000) J. Biol. Chem. 275, 20540-20544.

Biotinylation Methods. A variety of methods are available to biotinylate proteins, e.g., an immunoglobulin protein or a target protein. For example, the protein can be incubated with a 5-fold molar excess of sulfo-NHS-SS-biotin in 50 mM HEPES, pH 8.0, 100 mM NaCl overnight at 4° C. Free biotin is removed by buffer exchange into PBS, 0.01% Tween 20, e.g., using a Biomax device with a 10 kDa molecular weight cut-off membrane or by dialysis. The number of biotin molecules incorporated per mole of protein can be determined using the HABA assay as described by the manufacturer (Pierce).

Pharmaceutical Compositions

In another aspect, the invention provides compositions, e.g., pharmaceutically acceptable compositions, which include an MMP-26-binding protein, e.g., an antibody molecule, other polypeptide or peptide identified as binding to MMP-26, or described herein, formulated together with a pharmaceutically acceptable carrier. As used herein, "pharmaceutical compositions" encompass labeled ligands (e.g., for in vivo imaging) as well as therapeutic compositions.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., protein ligand may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for administration of humans with antibodies. The preferred mode of administration is parenteral (e.g., intravenous, subcutaneous, intraperitoneal, intramuscular). In a preferred embodiment, the MMP-26-binding protein is administered by intravenous infusion or injection. In another preferred embodiment, the MMP-26-binding protein is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Pharmaceutical compositions typically are sterile and stable under the conditions of manufacture and storage. A pharmaceutical composition can also be tested to insure it meets regulatory and industry standards for administration. For example, endotoxin levels in the preparation can be tested using the Limulus amebocyte lysate assay (e.g., using the kit from Bio Whittaker lot # 7L3790, sensitivity 0.125 EU/mL) according to the USP 24/NF 19 methods. Sterility of pharmaceutical compositions can be determined using thioglycollate medium according to the USP 24/NF 19 methods. For example, the preparation is used to inoculate the thioglycollate medium and incubated at 35° C. for 14 or more days. The medium is inspected periodically to detect growth of a microorganism.

The composition can be formulated as a solution, microemulsion, dispersion, liposome, or other ordered structure suitable to high drug concentration. Sterile injectable solutions can be prepared by incorporating the active compound (i.e., the ligand) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An MMP-26-binding protein can be administered by a variety of methods known in the art. For many applications, the route/mode of administration is intravenous injection or infusion. For example, for therapeutic applications, the MMP-26-binding protein can be administered by intravenous infusion at a rate of less than 30, 20, 10, 5, or 1 mg/min to reach a dose of about 1 to 100 mg/m$^2$ or 7 to 25 mg/m$^2$. The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems*, J. R. Robinson, ed., Marcel Dekker, Inc., New York, 1978.

In certain embodiments, the ligand may be orally administered, for example, with an inert diluent or an assimilable edible carrier. The compound (and other ingredients, if desired) also may be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound described herein by other than parenteral administration, it may be necessary to coat the compound with, or co-administer the compound with, a material to prevent its inactivation.

Pharmaceutical compositions can be administered with medical devices known in the art. For example, in a preferred embodiment, a pharmaceutical composition described herein can be administered with a needle-less hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Of course, many other such implants, delivery systems, and modules also are known.

In certain embodiments, the compounds described herein can be formulated to ensure proper distribution in vivo. For example, the blood-brain barrier (BBB) excludes many highly hydrophilic compounds. To ensure that a therapeutic can cross the BBB (if desired), it can be formulated, for example, in a liposome. For methods of manufacturing liposomes, see, e.g., U.S. Pat. Nos. 4,522,811; 5,374,548; and 5,399,331. The liposomes may include one or more moieties which are selectively transported into specific cells or organs, thus enhance targeted drug delivery (see, e.g., V. V. Ranade (1989) *J. Clin. Pharmacol.* 29:685).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms can be dictated by and directly dependent on (a) the unique characteristics of the active compound and the particular therapeutic effect to be achieved, and (b) the limitations inherent in compounding such an active compound for the treatment of sensitivity in individuals.

An exemplary, non-limiting range for a therapeutically or prophylactically effective amount of an antibody described herein is 0.1-20 mg/kg, more preferably 1-10 mg/kg. The MMP-26-binding antibody can be administered by intravenous infusion at a rate of less than 30, 20, 10, 5, or 1 mg/min to reach a dose of about 1 to 100 mg/m$^2$ or about 5 to 30 mg/m$^2$. For ligands smaller in molecular weight than an antibody, appropriate amounts can be proportionally less. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit.

A pharmaceutical composition may include a "therapeutically effective amount" or a "prophylactically effective amount" of an MMP-26-binding protein, e.g., a protein described herein. A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the protein to elicit a desired response in the individual. A therapeutically effective amount is also one in which any toxic or detrimental effects of the composition are outweighed by the therapeutically beneficial effects. A "therapeutically effective dosage" preferably inhibits a measurable parameter, e.g., inflammation or tumor growth rate by at least about 20%, more preferably by at least about 40%, even more preferably by at least about 60%, and still more preferably by at least about 80% relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the invention are kits including the protein ligand that binds to MMP-26 and instructions for use, e.g., treatment, prophylactic, or diagnostic use. In one embodiment, the instructions for diagnostic applications include the use of the MMP-26-binding protein (e.g., antibody or antigen-binding fragment thereof, or other polypeptide or peptide) to detect MMP-26, in vitro, e.g., in a sample, e.g., a biopsy or cells from a patient having an inflammatory disorder or a cancer or neoplastic disorder, or in vivo. In another embodiment, the instructions for therapeutic applications include suggested dosages and/or modes of administration in a patient with a cancer or neoplastic disorder. The kit can further contain a least one additional reagent, such as a diagnostic or therapeutic agent, e.g., a diagnostic or therapeutic agent as described herein, and/or one or more additional MMP-26-binding proteins, formulated as appropriate, in one or more separate pharmaceutical preparations.

Stabilization and Retention

In one embodiment, an MMP-26-binding protein (e.g., a MMP-26-binding antibody described herein) is physically associated with a moiety that improves its stabilization and/or retention in circulation, e.g., in blood, serum, lymph, or other tissues.

For example, a MMP-26-binding protein can be associated with a polymer, e.g., a substantially non-antigenic polymers, such as polyalkylene oxides or polyethylene oxides. Suitable polymers will vary substantially by weight. Polymers having molecular number average weights ranging from about 200 to about 50,000, e.g., 1,000 to 15,000, 2,000 to 12,500, or 10,000 to about 30,000 are usually selected for the purposes of the present invention.

For example, an MMP-26-binding protein can be conjugated to a water soluble polymer, e.g., hydrophilic polyvinyl polymers, e.g. polyvinylalcohol and polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon.

Other compounds can also be attached to the same polymer, e.g., a cytotoxin, a label, or another targeting agent, e.g., another MMP-26-binding protein or an unrelated ligand. Mono-activated, alkoxy-terminated polyalkylene oxides (PAO's), e.g., monomethoxy-terminated polyethylene glycols (mPEG's); $C_{1-4}$ alkyl-terminated polymers; and bis-activated polyethylene oxides (glycols) can be used for crosslinking. See, e.g., U.S. Pat. No. 5,951,974

In one embodiment, the polymer prior to cross-linking need not be, but preferably is, water soluble. Generally, after crosslinking, the product is water soluble, e.g., exhibits a water solubility of at least about 0.01 mg/ml, and more preferably at least about 0.1 mg/ml, and still more preferably at least about 1 mg/ml. In addition, the polymer should not be highly immunogenic in the conjugate form, nor should it possess viscosity that is incompatible with intravenous infusion or injection if the conjugate is intended to be administered by such routes.

In one embodiment, the polymer contains only a single group which is reactive. This helps to avoid cross-linking of protein molecules. However, it is within the scope herein to maximize reaction conditions to reduce cross-linking, or to purify the reaction products through gel filtration or ion exchange chromatography to recover substantially homogenous derivatives. In other embodiments, the polymer contains two or more reactive groups for the purpose of linking multiple ligands to the polymer backbone. Again, gel filtration or ion exchange chromatography can be used to recover the desired derivative in substantially homogeneous form.

The molecular weight of the polymer can range up to about 500,000 D, and preferably is at least about 20,000 D, or at least about 30,000 D, or at least about 40,000 D. The molecular weight chosen can depend upon the effective size of the conjugate to be achieved, the nature (e.g. structure, such as linear or branched) of the polymer, and the degree of derivatization.

The covalent crosslink can be used to attach an MMP-26-binding protein to a polymer, for example, crosslinking to the N-terminal amino group and epsilon amino groups found on lysine residues, as well as other amino, imino, carboxyl, sulfhydryl, hydroxyl or other hydrophilic groups. The polymer may be covalently bonded directly to the MMP-26-binding protein without the use of a multifunctional (ordinarily bifunctional) crosslinking agent. Covalent binding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, activated succinimidyl esters, activated dithiocarbonate PEG, 2,4,5-trichlorophenylcloroformate or P-nitrophenylcloroformate activated PEG.) Carboxyl groups can be derivatized by coupling PEG-amine using carbodiimide. Sulfhydryl groups can be derivatized by coupling to maleimido-substituted PEG (e.g. alkoxy-PEG amine plus sulfosuccinimidyl 4-(N-maleimidomethyl)cyclohexane-1-carboxylate) WO 97/10847 or PEG-maleimide commercially available from Shearwater Polymers, Inc., Huntsville, Ala.). Alternatively, free amino groups on the ligand (e.g. epsilon amino groups on lysine residues) can be thiolated with 2-imino-thiolane (Traut's reagent) and then coupled to maleimide-containing derivatives of PEG, e.g., as described in Pedley et al., Br. J. Cancer, 70: 1126-1130 (1994).

Functionalized PEG polymers that can be attached to an MMP-26-binding protein are available, e.g., from Shearwater Polymers, Inc. (Huntsville, Ala.). Such commercially available PEG derivatives include, e.g., amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG vinylsulfone, PEG-maleimide, PEG-orthopyridyl-disulfide, heterofunctional PEGs, PEG vinyl derivatives, PEG silanes, and PEG phospholides. The reaction conditions for coupling these PEG derivatives may vary depending on the MMP-26-binding protein, the desired degree of PEGylation, and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc. Specific instructions for the use of any particular derivative are available from the manufacturer.

The conjugates of an MMP-26-binding protein and a polymer can be separated from the unreacted starting materials, e.g., by gel filtration or ion exchange chromatography, e.g., HPLC. Heterologous species of the conjugates are purified from one another in the same fashion. Resolution of different species (e.g. containing one or two PEG residues) is also possible due to the difference in the ionic properties of the unreacted amino acids. See, e.g., WO 96/34015.

Treatments

Protein ligands that bind to MMP-26 (e.g., those described herein) have therapeutic and prophylactic utilities. For example, these ligands can be administered to cells in culture, e.g. in vitro or ex vivo, or in a subject, e.g., in vivo, to treat, prevent, and/or diagnose a variety of disorders, such as cancers, particularly metastatic cancers, an inflammatory disorder, and other disorders associated with increased MMP-26 activity, e.g., a disorder of the endometrium or placental.

As used herein, the term "treat" or "treatment" is defined as the application or administration of an MMP-26-binding antibody, alone or in combination with, a second agent to a subject, e.g., a patient, or application or administration of the agent to an isolated tissue or cell, e.g., cell line, from a subject, e.g., a patient, who has a disorder (e.g., a disorder as described herein), a symptom of a disorder or a predisposition toward a disorder, with the purpose to cure, heal, alleviate, relieve, alter, remedy, ameliorate, improve or affect the disorder, the symptoms of the disorder or the predisposition toward the disorder. Treating a cell refers to the inhibition of growth or activity, ablation, killing of a cell in vitro or in vivo, or otherwise reducing capacity of a cell, e.g., an aberrant cell, to mediate a disorder, e.g., a disorder as described herein (e.g., a cancerous disorder).

In one embodiment, "treating a cell" or "treating a tissue" refers to a reduction in the activity and/or proliferation of a cell, e.g., a hyperproliferative cell, or a tissue, e.g., a tumor. Such reduction includes a reduction, e.g., a statistically significant reduction, in the activity of a cell or tissue (e.g., metastatic tissue) or the number of the cell or size of the tissue. An example of a reduction in activity is a reduction in migration of the cell (e.g., migration through an extracellular matrix) or a reduction in cell differentiation. Another example is an activity that, directly or indirectly, reduces inflammation or an indicator of inflammation.

As used herein, an amount of an MMP-26-binding protein effective to treat a disorder, or a "therapeutically effective amount" refers to an amount of the ligand which is effective, upon single or multiple dose administration to a subject, in treating a cell, (e.g., a MMP-26-expressing cell or cancer cell, particularly a metastatic cell thereof), or in prolonging curing, alleviating, relieving or improving a subject with a disorder as described herein beyond that expected in the absence of such treatment. As used herein, "inhibiting the growth" of the neoplasm refers to slowing, interrupting, arresting or stopping its growth and metastases and does not necessarily indicate a total elimination of the neoplastic growth.

As used herein, an amount of an MMP-26-binding protein effective to prevent a disorder, or a "a prophylactically effective amount" of the ligand refers to an amount of an MMP-26-binding protein, e.g., an MMP-26-binding antibody described herein, which is effective, upon single- or multiple-dose administration to the subject, in preventing or delaying the occurrence of the onset or recurrence of a disorder, e.g., a metastatic disorder or a cancer.

The terms "induce", "inhibit", "potentiate", "elevate", "increase", "decrease" or the like, e.g., which denote quantitative differences between two states, refer to a difference, e.g., a statistically significant difference, between the two states. For example, "an amount effective to inhibit the proliferation of the MMP-26-expressing hyperproliferative cells" means that the rate of growth of the cells will be different, e.g., statistically significantly different, from the untreated cells.

Exemplary subjects include human and non-human animals. Preferred human animals include a human patient having a disorder characterized by abnormal cell proliferation or cell differentiation, or an inflammatory disorder, or other disorder described herein. Exemplary non-human animals include all vertebrates, e.g., non-mammals (such as chickens, amphibians, reptiles) and mammals, such as non-human primates, sheep, dog, cow, pig, etc.

In one embodiment, the subject is a human subject. Alternatively, the subject can be a mammal expressing a MMP-26-like antigen with which an antibody described herein cross-reacts. A protein ligand described herein can be administered to a human subject for therapeutic purposes (discussed further below). Moreover, an MMP-26-binding protein can be administered to a non-human mammal expressing the MMP-26-like antigen to which the ligand binds (e.g., a primate, pig or mouse) for veterinary purposes or as an animal model of human disease. Regarding the latter, such animal models may be useful for evaluating the therapeutic efficacy of the ligand (e.g., testing of dosages and time courses of administration).

In one embodiment, the invention provides a method of treating (e.g., ablating or killing) a cell (e.g., a non-cancerous cell, e.g., a normal, benign or hyperplastic cell, or a cancerous cell, e.g., a malignant cell, e.g., cell found in a solid tumor, a soft tissue tumor, or a metastatic lesion (e.g., a cell found in renal, urothelial, colonic, rectal, pulmonary, breast or hepatic, cancers and/or metastasis)). The method can include the steps of contacting the cell with an MMP-26-binding protein, e.g., an MMP-26-binding antibody described herein, in an amount sufficient to treat or prevent a disorder, e.g., a disorder caused by a cancerous cell, e.g., a metastatic cell.

The subject method can be used on cells in culture, e.g. in vitro or ex vivo. For example, cancerous or metastatic cells (e.g., renal, urothelial, colon, rectal, lung, breast, endometrial, ovarian, prostatic, or liver cancerous or metastatic cells) can be cultured in vitro in culture medium and the contacting step can be effected by adding the MMP-26-binding protein to the culture medium. The method can be performed on cells (e.g., cancerous or metastatic cells) present in a subject, as part of an in vivo (e.g., therapeutic or prophylactic) protocol. For in vivo embodiments, the contacting step is effected in a subject and includes administering the MMP-26-binding protein to the subject under conditions effective to permit both binding of the ligand to the cell and the treating, e.g., a disorder.

The method can be used to treat a cancer. As used herein, the terms "cancer", "hyperproliferative", "malignant", and "neoplastic" are used interchangeably, and refer to those cells an abnormal state or condition characterized by rapid proliferation or neoplasm. The terms include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth.

The common medical meaning of the term "neoplasia" refers to "new cell growth" that results as a loss of responsiveness to normal growth controls, e.g. to neoplastic cell growth. A "hyperplasia" refers to cells undergoing an abnormally high rate of growth. However, as used herein, the terms neoplasia and hyperplasia can be used interchangeably, as their context will reveal, referring generally to cells experiencing abnormal cell growth rates. Neoplasias and hyperplasias include "tumors," which may be benign, premalignant or malignant.

Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), and genitourinary tract (e.g., renal, urothelial cells), pharynx, prostate, ovary as well as adenocarcinomas which include malignancies such as most colon cancers, rectal cancer, renal-cell carcinoma, liver cancer, non-small cell carcinoma of the lung, cancer of the small intestine and so forth. Metastatic lesions of the aforementioned cancers also can be treated or prevented using a method or composition described herein.

The subject method can be useful in treating malignancies of the various organ systems, such as those affecting lung, breast, lymphoid, gastrointestinal (e.g., colon), and genitourinary tract, prostate, ovary, pharynx, as well as adenocarcinomas which include malignancies such as most colon cancers, renal-cell carcinoma, prostate cancer and/or testicular tumors, non-small cell carcinoma of the lung, cancer of the small intestine and cancer of the esophagus. Exemplary solid tumors that can be treated include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung carcinoma, bladder carcinoma, ovarian carcinoma, endometrial carcinoma, breast carcinoma, choriocarcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The term "carcinoma" is recognized by those skilled in the art and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include choriocarcinomas and those forming from tissue of the cervix, lung, prostate, breast, endometrium, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is recognized by those skilled in the art and refers to malignant tumors of mesenchymal derivation.

The subject method also can be used to inhibit the proliferation of hyperplastic/neoplastic cells of hematopoietic origin shown to express MMP-26, e.g., a B cells.

Methods of administering MMP-26-binding proteins are described in "Pharmaceutical Compositions". Suitable dosages of the molecules used will depend on the age and weight of the subject and the particular drug used. The ligands can be used as competitive agents to inhibit, reduce an undesirable interaction, e.g., between a natural or pathological agent and the MMP-26.

In one embodiment, the MMP-26-binding proteins are used to kill or ablate cancerous cells and normal, benign hyperplastic, and cancerous cells in vivo. The ligands can be used by themselves or conjugated to an agent, e.g., a cytotoxic drug, radioisotope. This method includes: administering the ligand alone or attached to a cytotoxic drug, to a subject requiring such treatment.

The terms "cytotoxic agent" and "cytostatic agent" and "anti-tumor agent" are used interchangeably herein and refer to agents that have the property of inhibiting the growth or proliferation (e.g., a cytostatic agent), or inducing the killing, of hyperproliferative cells, e.g., an aberrant cancer cell. In cancer therapeutic embodiment, the term "cytotoxic agent" is used interchangeably with the terms "anti-cancer" or "anti-tumor" to mean an agent, which inhibits the development or progression of a neoplasm, particularly a solid tumor, a soft tissue tumor, or a metastatic lesion.

Nonlimiting examples of anti-cancer agents include, e.g., antimicrotubule agents, topoisomerase inhibitors, antimetabolites, mitotic inhibitors, alkylating agents, intercalating agents, agents capable of interfering with a signal transduction pathway, agents that promote apoptosis, radiation, and antibodies against other tumor-associated antigens (including naked antibodies, immunotoxins and radioconjugates). Examples of the particular classes of anti-cancer agents are provided in detail as follows: antitubulin/antimicrotubule, e.g., paclitaxel, vincristine, vinblastine, vindesine, vinorelbin, taxotere; topoisomerase I inhibitors, e.g., topotecan, camptothecin, doxorubicin, etoposide, mitoxantrone, daunorubicin, idarubicin, teniposide, amsacrine, epirubicin, merbarone, piroxantrone hydrochloride; antimetabolites, e.g., 5-fluorouracil (5-FU), methotrexate, 6-mercaptopurine, 6-thioguanine, fludarabine phosphate, cytarabine/Ara-C, trimetrexate, gemcitabine, acivicin, alanosine, pyrazofurin, N-Phosphoracetyl-L-Asparate=PALA, pentostatin, 5-azacitidine, 5-Aza 2'-deoxycytidine, ara-A, cladribine, 5-fluorouridine, FUDR, tiazofurin, N-[5-[N-(3,4-dihydro-2-methyl-4-oxoquinazolin-6-ylmethyl)-N-methylamino]-2-thenoyl]-L-glutamic acid; alkylating agents, e.g., cisplatin, carboplatin, mitomycin C, BCNU=Carmustine, melphalan, thiotepa, busulfan, chlorambucil, plicamycin, dacarbazine, ifosfamide phosphate, cyclophosphamide, nitrogen mustard, uracil mustard, pipobroman, 4-ipomeanol; agents acting via other mechanisms of action, e.g., dihydrolenperone, spiromustine, and desipeptide; biological response modifiers, e.g., to enhance anti-tumor responses, such as interferon; apoptotic agents, such as actinomycin D; and anti-hormones, for example anti-estrogens such as tamoxifen or, for example antiandrogens such as 4'-cyano-3-(4-fluorophenylsulphonyl)-2-hydroxy-2-methyl-3'-(trifluoromethyl) propionanilide.

Since the MMP-26-binding proteins recognize MMP-26-expressing cancer cells, e.g., cancerous lung, liver, colon, breast, endometrium, ovarian, epidermal, laryngeal, and cartilage cells, and particularly metastatic cells thereof, any such cells to which the ligands bind are destroyed. Alternatively, the ligands bind to cells in the vicinity of the cancerous cells and kill them, thus indirectly attacking the cancerous cells which may rely on surrounding cells for nutrients, growth signals and so forth. Thus, the MMP-26-binding proteins (e.g., modified with a cytotoxin) can selectively kill or ablate cells in cancerous tissue (including the cancerous cells themselves).

The ligands may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters, as described herein.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin. Procedures for preparing enzymatically active polypeptides of the immunotoxins are described in WO84/03508 and WO85/03508, and in the appended Examples below. Examples of cytotoxic moieties that can be conjugated to the antibodies include adriamycin, chlorambucil, daunomycin, methotrexate, neocarzinostatin, and platinum.

In the case of polypeptide toxins, recombinant nucleic acid techniques can be used to construct a nucleic acid that encodes the ligand (or a protein component thereof) and the cytotoxin (or a protein component thereof) as translational fusions. The recombinant nucleic acid is then expressed, e.g., in cells and the encoded fusion polypeptide isolated.

Procedures for conjugating protein ligands (e.g., antibodies) with the cytotoxic agents have been previously described. Procedures for conjugating chlorambucil with antibodies are described by Flechner (1973) *European Journal of Cancer*, 9:741-745; Ghose et al. (1972) *British Medical Journal*, 3:495-499; and Szekerke, et al. (1972) *Neoplasma*, 19:211-215. Procedures for conjugating daunomycin and adriamycin to antibodies are described by Hurwitz, E. et al. (1975) *Cancer Research*, 35:1175-1181 and Arnon et al. (1982) *Cancer Surveys*, 1:429-449. Procedures for preparing antibody-ricin conjugates are described in U.S. Pat. No. 4,414,148 and by Osawa, T., et al. (1982) *Cancer Surveys*, 1:373-388 and the references cited therein. Coupling procedures as also described in EP 86309516.2.

To kill or ablate normal, benign hyperplastic, or cancerous cells, a first protein ligand is conjugated with a prodrug which is activated only when in close proximity with a prodrug activator. The prodrug activator is conjugated with a second protein ligand, preferably one which binds to a non-competing site on the target molecule. Whether two protein ligands bind to competing or non-competing binding sites can be determined by conventional competitive binding assays. Some suitable drug-prodrug pairs are described in Blakely et al., (1996) *Cancer Research*, 56:3287-3292.

Alternatively, the MMP-26-binding protein can be coupled to high energy radiation emitters, for example, a radioisotope, such as $^{131}I$, a γ-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy*, R. W. Baldwin et al. (eds.), pp 303-316 (Academic Press 1985). Other suitable radioisotopes include α-emitters, such as $^{212}Bi$, 213Bi, and $^{211}At$, and β-emitters, such as $^{186}Re$ and $^{90}Y$. Moreover, $Lu^{117}$ may also be used as both an imaging and cytotoxic agent.

Radioimmunotherapy (RIT) using antibodies labeled with $^{131}I$, $^{90}Y$, and $^{177}Lu$ is under intense clinical investigation. There are significant differences in the physical characteristics of these three nuclides and as a result, the choice of radionuclide is very critical in order to deliver maximum radiation dose to the tumor. The higher beta energy particles of $^{90}Y$ may be good for bulky tumors. The relatively low energy beta particles of $^{131}I$ are ideal, but in vivo dehalogenation of radioiodinated molecules is a major disadvantage for internalizing antibody. In contrast, $^{177}Lu$ has low energy beta particle with only 0.2-0.3 mm range and delivers much lower radiation dose to bone marrow compared to $^{90}Y$. In addition, due to longer physical half-life (compared to $^{90}Y$), the tumor residence times are higher. As a result, higher activities (more mCi amounts) of $^{177}Lu$ labeled agents can be administered with comparatively less radiation dose to marrow. There have been several clinical studies investigating the use of $^{177}Lu$ labeled antibodies in the treatment of various cancers. (Mulligan T et al. (1995) *Clin Cancer Res.* 1:1447-1454; Meredith R F, et al. (1996) *J Nucl Med* 37:1491-1496; Alvarez R D, et al. (1997) *Gynecologic Oncology* 65: 94-101).

The MMP-26-binding proteins can be used directly in vivo to eliminate antigen-expressing cells via natural complement-dependent cytotoxicity (CDC) or antibody-dependent cellular cytotoxicity (ADCC). In one embodiment, the protein includes a complement binding effector domain, such as an Fc portion (e.g., functional portion) from IgG1, -2, or -3 or corresponding portions of IgM which bind complement. In one embodiment, a population of target cells is ex vivo treated with a binding protein described herein and appropriate effector cells. The treatment can be supplemented by the addition of complement or serum containing complement. In another embodiment, target cells coated with the protein ligand which includes a complement binding effector domain are lysed by complement.

Also encompassed by the invention is a method of killing or ablating which involves using the MMP-26 binding proteins for prophylaxis. For example, these materials can be used to prevent or delay development or progression of cancers.

Use of the therapeutic methods of the invention to treat cancers has a number of benefits. Since the protein ligands specifically recognize MMP-26, other tissue is spared and high levels of the agent are delivered directly to the site where therapy is required. Treatment in accordance with the invention can be effectively monitored with clinical parameters. Alternatively, these parameters can be used to indicate when such treatment should be employed.

A MMP-26-binding protein described herein can be administered in combination with one or more of the existing modalities for treating cancers, including, but not limited to: surgery; radiation therapy, and chemotherapy.

An MMP-26-binding protein can be administered in combination with one or more of the existing modalities for treating an inflammatory disease or disorder. Exemplary inflammatory diseases or disorders include: acute and chronic immune and autoimmune pathologies, such as, but not limited to, rheumatoid arthritis (RA), juvenile chronic arthritis (JCA), psoriasis, graft versus host disease (GVHD), scleroderma, diabetes mellitus, allergy; asthma, acute or chronic immune disease associated with an allogenic transplantation, such as, but not limited to, renal transplantation, cardiac transplantation, bone marrow transplantation, liver transplantation, pancreatic transplantation, small intestine transplantation, lung transplantation and skin transplantation; chronic inflammatory pathologies such as, but not limited to, sarcoidosis, chronic inflammatory bowel disease, ulcerative colitis, and Crohn's pathology or disease; vascular inflammatory pathologies, such as, but not limited to, disseminated intravascular coagulation, atherosclerosis, Kawasaki's pathology and vasculitis syndromes, such as, but not limited to, polyarteritis nodosa, Wegener's granulomatosis, Henoch-Schonlein purpura, giant cell arthritis and microscopic vasculitis of the kidneys; chronic active hepatitis; Sjogren's syndrome; psoriatic arthritis; enteropathic arthritis; reactive arthritis and arthritis associated with inflammatory bowel disease; and uveitis.

Inflammatory bowel diseases (IBD) include generally chronic, relapsing intestinal inflammation. IBD refers to two distinct disorders, Crohn's disease and ulcerative colitis (UC). The clinical symptoms of IBD include intermittent rectal bleeding, crampy abdominal pain, weight loss and diarrhea. A clinical index can also be used to monitor IBD such as the Clinical Activity Index for Ulcerative Colitis. See also, e.g., Walmsley et al. *Gut*. 1998 July; 43(1):29-32 and Jowett et al. (2003) *Scand J Gastroenterol*. 38(2):164-71.

A MMP26-binding protein can be used to treat or prevent one of the foregoing diseases or disorders. For example, the protein can be administered (locally or systemically) in an amount effective to ameliorate at least one symptom of the respective disease or disorder. The protein may also ameliorate inflammation, e.g., an indicator of inflammation, e.g., such as local temperature, swelling (e.g., as measured), redness, local or systemic white blood cell count, presence or absence of neutrophils, cytokine levels, elastase activity, and so forth. It is possible to evaluate a subject, e.g., prior, during, or after administration of the protein, for one or more of indicators of inflammation, e.g., an aforementioned indicator.

Diagnostic Uses

Protein ligands that bind to MMP-26 (e.g., those described herein) also have in vitro and in vivo diagnostic, therapeutic and prophylactic utilities. In one aspect, the invention provides a diagnostic method for detecting the presence of a MMP-26, in vitro (e.g., a biological sample, such as tissue, biopsy, e.g., a cancerous tissue such as a tumor) or in vivo (e.g., in vivo imaging in a subject).

The method includes: (i) contacting a sample with MMP-26-binding protein; and (ii) detecting formation of a complex between the MMP-26-binding protein and the sample. The method can also include contacting a reference sample (e.g., a control sample) with the ligand, and determining the extent of formation of the complex between the ligand and the sample relative to the same for the reference sample. A change, e.g., a statistically significant change, in the formation of the complex in the sample or subject relative to the control sample or subject can be indicative of the presence of MMP-26 in the sample.

Another method includes: (i) administering the MMP-26-binding protein to a subject; and (ii) detecting formation of a complex between the MMP-26-binding protein, and the subject. The detecting can include determining location or time of formation of the complex. In one embodiment, the subject has, is suspected of having, or is at risk for a disorder described herein, e.g., a neoplastic disorder, an inflammatory disorder, or a disorder characterized by excessive MMP-26 activity.

The MMP-26-binding protein can be directly or indirectly labeled with a detectable substance to facilitate detection of the bound or unbound antibody. Suitable detectable substances include various enzymes, prosthetic groups, fluorescent materials, luminescent materials and radioactive materials.

Complex formation between the MMP-26-binding protein and MMP-26 can be detected by measuring or visualizing either the ligand bound to the MMP-26 or unbound ligand. Conventional detection assays can be used, e.g., an enzyme-linked immunosorbent assays (ELISA), a radioimmunoassay (RIA) or tissue immunohistochemistry. Further to labeling the MMP-26-binding protein, the presence of MMP-26 can be assayed in a sample by a competition immunoassay utilizing standards labeled with a detectable substance and an unlabeled MMP-26-binding protein. In one example of this assay, the biological sample, the labeled standards and the MMP-26 binding agent are combined and the amount of labeled standard bound to the unlabeled ligand is determined. The amount of MMP-26 in the sample is inversely proportional to the amount of labeled standard bound to the MMP-26 binding agent.

Fluorophore and chromophore labeled protein ligands can be prepared. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer (1968) *Science*, 162:526 and Brand, L. et al. (1972) *Annual Review of Biochemistry*, 41:843-868. The protein ligands can be labeled with fluorescent chromophore groups by conventional procedures such as those disclosed in U.S. Pat. Nos. 3,940,475, 4,289,747, and 4,376,110. One group of fluorescers having a number of the desirable properties described above is the xanthene dyes, which include the fluoresceins and rhodamines. Another group of fluorescent compounds are the naphthylamines. Once labeled with a fluorophore or chromophore, the protein ligand can be used to detect the presence or localization of the MMP-26 in a sample, e.g., using fluorescent microscopy (such as confocal or deconvolution microscopy).

Histological Analysis. Immunohistochemistry can be performed using the protein ligands described herein. For example, in the case of an antibody, the antibody can synthesized with a label (such as a purification or epitope tag), or can be detectably labeled, e.g., by conjugating a label or label-binding group. For example, a chelator can be attached to the antibody. The antibody is then contacted to a histological preparation, e.g., a fixed section of tissue that is on a microscope slide. After an incubation for binding, the preparation is washed to remove unbound antibody. The preparation is then analyzed, e.g., using microscopy, to identify if the antibody bound to the preparation.

Of course, the antibody (or other polypeptide or peptide) can be unlabeled at the time of binding. After binding and washing, the antibody is labeled in order to render it detectable.

Protein Arrays. The MMP-26-binding protein can also be immobilized on a protein array. The protein array can be used as a diagnostic tool, e.g., to screen medical samples (such as isolated cells, blood, sera, biopsies, and the like). Of course, the protein array can also include other ligands, e.g., that bind to MMP-26 or to other target molecules, such as hyaluronic acid.

Methods of producing polypeptide arrays are described, e.g., in De Wildt et al. (2000) Nat. Biotechnol. 18:989-994; Lueking et al. (1999) Anal. Biochem. 270:103-111; Ge (2000) Nucleic Acids Res. 28, e3, I-VII; MacBeath and Schreiber (2000) Science 289:1760-1763; WO 01/40803 and WO 99/51773A1. Polypeptides for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the protein ligands can be grown on a filter in an arrayed format. Polypeptide production is induced, and the expressed polypeptides are immobilized to the filter at the location of the cell.

A protein array can be contacted with a labeled target to determine the extent of binding of the target to each immobilized polypeptide from the diversity strand library. If the target is unlabeled, a sandwich method can be used, e.g., using a labeled probed, to detect binding of the unlabeled target.

Information about the extent of binding at each address of the array can be stored as a profile, e.g., in a computer database. The protein array can be produced in replicates and used to compare binding profiles, e.g., of a target and a non-target. Thus, protein arrays can be used to identify individual members of the diversity strand library that have desired binding properties with respect to one or more molecules.

An MMP-26-binding protein described herein can also be used to detecting binding of a MMP-26 to an insoluble support. For example, a sample can be immobilized on array, and MMP-26 can be detected on the array using the MMP-26-binding protein.

In Vivo Imaging. In still another embodiment, the invention provides a method for detecting the presence of a MMP-26-expressing cancerous tissues in vivo. The method includes (i) administering to a subject (e.g., a patient having a cancer or neoplastic disorder) an MMP-26-binding antibody, conjugated to a detectable marker; (ii) exposing the subject to a means for detecting said detectable marker to the MMP-26-expressing tissues or cells. For example, the subject is imaged, e.g., by NMR or other tomographic means.

Examples of labels useful for diagnostic imaging in accordance with the invention include radiolabels such as $^{131}$I, $^{111}$In, $^{123}$I, $^{99m}$Tc, $^{32}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes can also be employed. The protein ligand can be labeled with such reagents using known techniques. For example, see Wensel and Meares (1983) Radioimmunoimaging and Radioimmunotherapy, Elsevier, New York for techniques relating to the radiolabeling of antibodies and D. Colcher et al. (1986) Meth. Enzymol. 121: 802-816.

A radiolabeled ligand of this invention can also be used for in vitro diagnostic tests. The specific activity of an isotopically-labeled ligand depends upon the half-life, the isotopic purity of the radioactive label, and how the label is incorporated into the antibody.

Procedures for labeling polypeptides with the radioactive isotopes (such as $^{14}$C, $^{3}$H, $^{35}$S, $^{125}$I, $^{32}$P, $^{131}$I) are generally known. For example, tritium labeling procedures are described in U.S. Pat. No. 4,302,438. Iodinating, tritium labeling, and $^{35}$S labeling procedures, e.g., as adapted for murine monoclonal antibodies, are described, e.g., by Goding, J. W. (Monoclonal antibodies: principles and practice: production and application of monoclonal antibodies in cell biology, biochemistry, and immunology 2nd ed. London; Orlando: Academic Press, 1986. pp 124-126) and the references cited therein. Other procedures for iodinating polypeptides, such as antibodies, are described by Hunter and Greenwood (1962) Nature 144:945, David et al. (1974) Biochemistry 13:1014-1021, and U.S. Pat. Nos. 3,867,517 and 4,376,110. Exemplary radio-isotopes that are useful for imaging include $^{123}$I, $^{131}$I, $^{111}$In, and $^{99m}$Tc. Procedures for iodinating antibodies are described by Greenwood, F. et al. (1963) Biochem. J. 89:114-123; Marchalonis, J. (1969) Biochem. J. 113:299-305; and Morrison, M. et al. (1971) Immunochemistry 289-297. Procedures for $^{99m}$Tc-labeling are described by Rhodes, B. et al. in Burchiel, S. et al. (eds.), Tumor Imaging: The Radioimmunochemical Detection of Cancer, New York: Masson 111-123 (1982) and the references cited therein. Procedures suitable for $^{111}$In-labeling antibodies are described by Hnatowich, D. J. et al. (1983) J. Immul. Methods, 65:147-157, Hnatowich, D. et al. (1984) J. Applied Radiation, 35:554-557, and Buckley, R. G. et al. (1984) F.E.B.S. 166:202-204.

In the case of a radiolabeled ligand, the ligand is administered to the patient, is localized to the tumor bearing the antigen with which the ligand reacts, and is detected or "imaged" in vivo using known techniques such as radionuclear scanning using e.g., a gamma camera or emission tomography. See e.g., A. R. Bradwell et al., "Developments in Antibody Imaging", Monoclonal Antibodies for Cancer Detection and Therapy, R. W. Baldwin et al., (eds.), pp 65-85 (Academic Press 1985). Alternatively, a positron emission transaxial tomography scanner, such as designated Pet VI located at Brookhaven National Laboratory, can be used where the radiolabel emits positrons (e.g., $^{11}$C, $^{18}$F, $^{15}$O, and $^{13}$N).

MRI Contrast Agents. Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP-A-0 502 814. Generally, the differences related to relaxation time constants T1 and T2 of water protons in different environments are used to generate an image. However, these differences can be insufficient to provide sharp high resolution images.

The differences in these relaxation time constants can be enhanced by contrast agents. Examples of such contrast agents include a number of magnetic agents paramagnetic agents (which primarily alter T1) and ferromagnetic or superparamagnetic (which primarily alter T2 response). Chelates (e.g., EDTA, DTPA and NTA chelates) can be used to attach (and reduce toxicity) of some paramagnetic substances (e.g., $Fe^{+3}$, $Mn^{+2}$, $Gd^{+3}$). Other agents can be in the form of particles, e.g., less than 10 μm to about 10 nM in diameter). Particles can have ferromagnetic, antiferromagnetic or superparamagnetic properties. Particles can include, e.g., magnetite ($Fe_3O_4$), $\gamma$-$Fe_2O_3$, ferrites, and other magnetic mineral compounds of transition elements. Magnetic particles may include: one or more magnetic crystals with and without nonmagnetic material. The nonmagnetic material can include synthetic or natural polymers (such as sepharose, dextran, dextrin, starch and the like The MMP-26-binding proteins can also be labeled with an indicating group containing of the NMR-active $^{19}F$ atom, or a plurality of such atoms inasmuch as (i) substantially all of naturally abundant fluorine atoms are the $^{19}F$ isotope and, thus, substantially all fluorine-containing compounds are NMR-active; (ii) many chemically active polyfluorinated compounds such as trifluoracetic anhydride are commercially available at relatively low cost, and (iii) many fluorinated compounds have been found medically acceptable for use in humans such as the perfluorinated polyethers utilized to carry oxygen as hemoglobin replacements. After permitting such time for incubation, a whole body MRI is carried out using an apparatus such as one of those described by Pykett (1982) *Scientific American*, 246:78-88 to locate and image cancerous tissues.

Information obtained from evaluating an MMP-26-binding protein, e.g., a ligand described herein, can be recorded on machine-compatible media, e.g., computer readable or computer accessible media. The information can be stored as a computer representation, e.g., in a database (e.g., in the case of imaging using a ligand, a database of images for one or a plurality of subjects). The term "computer representation" refers to information which is in a form that can be manipulated by a computer. The act of storing a computer representation refers to the act of placing the information in a form suitable for manipulation by a computer.

Kits

Also within the scope of the invention are kits that include a composition described herein, e.g., a composition that contains a MMP-26-binding protein. In one embodiment, the kit includes (a) a composition that includes the MMP-26-binding protein, and, optionally, (b) informational material. The informational material can be descriptive, instructional, marketing or other material that relates to the methods described herein and/or the use of the compound for the methods described herein, e.g., a treatment, prophylactic, or diagnostic use. For example, the informational material describes methods for administering the composition to treat a disorder, e.g., a neoplastic disorder such as a metastatic disorder, an inflammatory disorder, or a disorder characterized by excessive MMP-26 activity.

In one embodiment, the informational material can include instructions to administer the compound in a suitable manner, e.g., in a suitable dose, dosage form, or mode of administration (e.g., a dose, dosage form, or mode of administration described herein). In another embodiment, the informational material can include instructions for identifying a suitable subject, e.g., a human, e.g., a human having, or at risk for a neoplastic disorder, an inflammatory disorder, or a disorder characterized by excessive MMP-26 activity. The informational material can include information about production of the compound, molecular weight of the compound, concentration, date of expiration, batch or production site information, and so forth. The informational material of the kits is not limited in its form. Information about the compound can include structural information, e.g., amino acid sequence, tradename, FDA approved name, antibody isotype, and so forth. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In another embodiment, the informational material of the kit is a link or contact information, e.g., a physical address, email address, hyperlink, website, or telephone number, where a user of the kit can obtain substantive information about the compound and/or its use in the methods described herein. The informational material can also be provided in any combination of formats.

In addition to the composition that includes the MMP-26-binding protein, the composition itself can include other ingredients, such as a solvent or buffer, a stabilizer or a preservative, and/or a second agent for treating a condition or disorder described herein, e.g. a neoplastic disorder (e.g., a metastatic disorder) or an inflammatory disorder. Alternatively, such other ingredients can be included in the kit, but in different compositions or containers than the composition that includes the MMP-26-binding protein. In such embodiments, the kit can include instructions for admixing the compound and the other ingredients, or for using the compound together with the other ingredients.

The composition that includes the MMP-26-binding protein can be provided in any form, e.g., liquid, dried or lyophilized form. It is preferred that composition be substantially pure and/or sterile. When the composition that includes the MMP-26-binding protein is provided in a liquid solution, the liquid solution preferably is an aqueous solution, with a sterile aqueous solution being preferred. When the composition that includes the MMP-26-binding protein is provided as a dried form, reconstitution generally is by the addition of a suitable solvent. The solvent, e.g., sterile water or buffer, can optionally be provided in the kit.

The kit can include one or more containers for the composition that includes the MMP-26-binding protein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the MMP-26-binding protein. For example, the kit includes a plurality of syringes, ampules, foil packets, or blister packs, each containing a single unit dose of the compound. The containers of the kits can be air tight, waterproof (e.g., impermeable to changes in moisture or evaporation), and/or light-tight.

Kits can be provided that include a MMP-26-binding antibody and instructions for diagnostic, e.g., the use of the MMP-26-binding ligand (e.g., antibody or antigen-binding fragment thereof, or other polypeptide or peptide) to detect MMP-26, in vitro, e.g., in a sample, e.g., a biopsy or cells from a patient having a cancer or neoplastic disorder, or in vivo, e.g., by imaging a subject. The kit can further contain a least one additional reagent, such as a label or additional diagnostic agent. For in vivo use the ligand can be formulated as a pharmaceutical composition.

The following invention is further illustrated by the following examples, which should not be construed as limiting.

EXAMPLES

In the following examples, 48 Fab's were isolated that bind to MMP-26. Of these Fabs, 20 had inhibitory. These 20 Fab's include 12 with κ light chains and 8 with λ light chains. The other 28 Fab's included 14 with κ light chains and 14 with λ light chains.

Cloning and Expression of MMP-26

MMP-26 is synthesized as an inactive precursor that undergoes proteolytic cleavage and release of the propeptide in order to exhibit catalytic domain-specific enzymatic activity. A clone containing the full-length MMP-26 sequence was used as template to generate a nucleic acid encoding the catalytic domain alone. A nucleic acid encoding the catalytic domain of MMP-26 was amplified using primers mat2.top.cat.NcoI and mat2.bot.HindIII:

```
Mat2.cat.top.ncoI
                                      (SEQ ID NO:218)
5'-GCCATCCATGGCGACCTCCATCTCGCCAGG Mat2.bot.HindIII:
                                      ((SEQ ID NO:219)
5'-GCAGCAAGCTTCATCATCATCATCATCATAGGTATGTCAGATGAAC
ATTTTTCTCC
```

The resulting PCR product was digested with HindIII and NcoI, ligated into a modified version of the pQE60 vector (Qiagen), and electroporated into XL1 Blue MRF' cells (Stratagene). A 200 mL culture of pQE60 containing XL1 Blue MRF' cells was induced with 2.5 mM IPTG and grown overnight at 37° C. The following day the bacteria were pelleted and sonicated. The insoluble material was collected and dissolved in 8M urea-containing buffer. MMP-26 was purified using nickel-coated magnetic beads and refolded by a standard dialysis procedures.

MMP-26 Activity Assessment

MMP-26 activity was determined by zymogram gel analysis and vitronectin digestion assays. For the zymogram gel analysis assays, 375 ng of MMP-26 was resolved on a 10% gelatin-containing zymogram gels (Invitrogen). Following electrophoresis, the gel was developed overnight at 37° C. according to the manufacturers recommended directions and subsequently stained with Coomassie blue. All fractions displayed gelatinase activity. For the vitronectin digestion assays, 250 ng of MMP-26 was incubated with 250 ng of vitronectin overnight at 37° C. The MMP-26 digested vitronectin was resolved by SDS-PAGE and visualized by Coomassie blue staining. MMP-26 activity is indicated if vitronectin is cleaved.

Identification of MMP-26-binding Fab-displaying Phage

Selections were performed using two different methods. The first method utilized three rounds of standard solution-based selections. In each round, the amount (500 nM to 50 nM) of MMP-26 catalytic domain as target protein was decreased while the input of phage was kept constant at $3 \times 10^{11}$ pfu. The second strategy utilized was the URSA (Ultra Rapid Screening of Antigens) method (which is described, inter alia, in U.S. Ser. No. 10/313,822). Three rounds of URSA selections were performed in one day.

Briefly, the MMP-26 target protein (tagged with hexa-histidine) was contacted to a Fab-displaying phage library. The mixture was then bound to nickel magnetic beads. After three washes, XL1 Blue MRF' cells were added to the target-containing beads in order to propagate MMP-26 specific-binding phage. The XL1 Blue cells were infected by phage bound on the beads and extruded replicates of these phage. These replicate phage then bound to the MMP-26 on the beads. The XL1 Blue MRF' cells were removed. The phage-target-bead complexes were washed to remove unbound phage, and fresh XL1 Blue MRF' cells were added to initiate Round Two. This cycle was repeated one more time such that three rounds were performed overall. The antibodies encoded by the Fab-displaying phage library include HC CDR3 and light chains that are obtained from human cells. HC CDR1 and HC CDR2 are encoded by sequences based on human CDR sequences.

ELISA Screening of Output Fab-displaying Phage

The output Fab-displaying phage from both rounds two and three from either of the selection campaigns were screened by ELISA to positively identify MMP-26 binding phage isolates. MMP-26 (1 μg/ml) was passively immobilized on Immulon 2 HB 96-well ELISA plates (Thermo Labsystems) overnight at 4° C. The plates were blocked for thirty minutes with phosphate buffered saline containing 3% (w/v) bovine serum albumin (BSA) and 0.05% (v/v) Tween-20. Overnight bacterial growths of Fab-displaying phage were then incubated with the target for 1 hour at room temperature. Fab-displaying phage were detected with an anti-M13 HRP-conjugated antibody. Standard solution-based selections yielded a hit rate of 23% in round 2 and a 92% hit rate for round 3. The URSA method yielded a hit rate of 69% for both rounds 2 and 3.

Reformatting of Fab Clones into Whole IgGs

Sixty eight of the Fab-displaying phage positive for MMP-26 binding were reformatted as human whole IgG antibody clones. Briefly, the Fab cassette of each positive Fab-displaying phage was PCR amplified with oligos KAPPA, LAMBDA 1, 2, 3, and 4, and CjliftNheRev:

```
KAPPA:
                                      (SEQ ID NO:220)
5'-ATATATGTGCACTCTGACATCCAGATGACCCAGTC 3',;

LAMBDA1:
                                      (SEQ ID NO:221)
5'-ATATATGTGCACTCACAGAGCGTCTTGACTC 3',;

LAMBDA2:
                                      (SEQ ID NO:222)
5'-ATATATGTGCACTCACAGAGCGCTTTGACTC 3',;

LAMBDA3:
                                      (SEQ ID NO:223)
5'-ATATATGTGCACTCAAGCTACGAATTGACTC 3',;

LAMBDA4:
                                      (SEQ ID NO:224)
5'-ATATATGTGCACTCACAGAGCGAATTGACTC 3',;

CJliftNheRev:
                                      (SEQ ID NO:225)
5'-GGAGGGTGCTAGCGGGAAGACCG 3',.
```

PCR products were restricted using ApaLI and NheI. The digested Fab clone was ligated into a mammalian expression vector containing the human IgG4 Fc region and electroporated into XL1 BLUE™ MRF' cells. The prokaryotic ribosomal binding sequence and heavy chain leader sequence were replaced with a mammalian internal ribosomal entry and heavy chain leader sequences. Reformatted antibody clones were sequenced to confirm accuracy following the cloning steps. Endotoxin-free DNA was prepared according to the manufacturer's instructions (Qiagen) and subsequently used for transient transfection studies.

Transient Transfections of MMP-26-binding IgG4s

Reformatted MMP-26 antibodies were expressed transiently in HEK293T (GenHunter) cells using Lipofectamine 2000 (Invitrogen). Briefly, $6 \times 10^6$ cells in media containing 10% (v/v) ultra low bovine IgG fetal bovine serum were seeded into 100 mm tissue culture dishes. Twenty-four hours after plating, 5 mls of fresh media was added to each dish. The transfection was then carried out exactly as described by the manufacturer (Invitrogen). Seventy two hours after transfection, the media was removed, clarified and saved, and 15 mls of fresh media was added to each dish and the cells incubated for an additional 72 hours. At the conclusion of the second 72 hour period, the media was collected, dislodged cells clarified by centrifugation and the resulting supernatant was combined with that harvested after the first 72 hour period and, if required, human antibodies were purified according to standard protein A-based chromatographic procedures.

MMP-26 Bead-based ELISA

Reformatted and expressed full-length MMP-26 binding IgG4 antibodies were tested for specificity in a bead-based ELISA. Approximately 1.25 μg of MMP-26 protein was bound to nickel-coated magnetic beads (Novagen) which had been pre-blocked with phosphate buffered saline containing 5% (w/v) nonfat dry milk and 0.05% (v/v) Tween-20. The beads were washed in phosphate buffered saline containing 0.05% (v/v) Tween-20 (PBS-T) and 100 uls of unpurified cell culture supernatant containing transiently produced MMP-26-binding antibodies was added and incubated on a rotator for sixty minutes. The beads were washed with PBS-T and MMP-26-binding antibodies were detected with an HRP-conjugated anti-human secondary antibody. Data is expressed in fold over background where background consists of beads, blocking agent, and culture supernatant containing target antibody (Table 2; in this table, Results shown as fold over background (F>B) where background consists of beads, blocking agent, and culture supernatant).

TABLE 2

Bead Based ELISA

| Clone | F > B |
|---|---|
| A1-orig | NT |
| D6-orig | NT |
| H6-orig | NT |
| A01 | 3.3 |
| A03 | 3.54 |
| A04 | 3.17 |
| A05 | 2.48 |
| A06 | 5.4 |
| A07 | 8.38 |
| A08 | 1.94 |
| A09 | 2.5 |
| A10 | 1.84 |
| A11 | 1.7 |
| A12 | 1.8 |
| B01 | 2.3 |
| B02 | 0.36 |
| B03 | 0.65 |
| B04 | 0.6 |
| B05 | NT |
| B06 | 2.1 |
| B07 | 0.5 |
| B08 | 3 |

TABLE 2-continued

Bead Based ELISA

| Clone | F > B |
|---|---|
| B10 | 2.7 |
| B11 | 3.13 |
| B12 | 2.83 |
| C01 | 2.8 |
| C02 | 0.9 |
| C03 | 4.1 |
| C04 | 2.9 |
| C05 | 3.6 |
| C06 | 2.2 |
| C07 | 3.12 |
| C08 | 3.4 |
| C09 | 3.4 |
| C10 | 3.41 |
| C11 | 2.6 |
| C12 | 1.8 |
| D01 | 3 |
| D02 | 3.3 |
| D03 | 2.4 |
| D04 | 2.6 |
| D05 | NT |
| D06 | 3.5 |
| D07 | 3.3 |
| D08 | 3 |
| D09 | 4.3 |

MMP Cross Reactivity ELISA

Twenty-one of the reformatted MMP-26 antibodies were tested for MMP cross reactivity by ELISA analysis. MMP-3, MMP-7, MMP-9, and MMP-12 were coated onto Immulon 2 HB 96-well plates at a concentration of 1 μg/ml for 1 hour at 37° C. The plates were blocked with PBS-T containing 5% (w/v) nonfat dry milk for thirty minutes and subsequently washed with PBS-T. Each antibody was tested for reactivity to all of the above mentioned MMPs at a concentration of 2 μg/ml with an incubation time of 1 hour. Bound antibody was detected with an HRP-conjugated anti-human secondary antibody (Table 3, NT=not tested.).

TABLE 3

MMP Cross Reactivity ELISA

| Clone | MMP Cross Reactivity |
|---|---|
| A1-orig | MMP-26/MMP-9 |
| D6-orig | MMP-26/MMP-9 |
| H6-orig | MMP-26 |
| A01 | MMP-26 |
| A03 | MMP-26 |
| A04 | MMP-26 |
| A05 | MMP-26 |
| A06 | MMP-26 |
| A07 | MMP-26 |
| A08 | MMP-26 |
| A09 | MMP-26 |
| A10 | MMP-26 |
| A11 | MMP-26 |
| A12 | MMP-26 |
| B01 | MMP-26 |
| B02 | MMP-26 |
| B03 | MMP-26 |
| B04 | MMP-26 |
| B05 | NT |
| B06 | MMP-26 |
| B07 | MMP-26 |
| B08 | MMP-26 |

TABLE 3-continued

MMP Cross Reactivity ELISA

| Clone | MMP Cross Reactivity |
|---|---|
| B10 | MMP-26/MMP-3 |
| B11 | MMP-26 |
| B12 | MMP-26 |
| C01 | MMP-26 |
| C02 | MMP-26/MMP-3/MMP-9 |
| C03 | MMP-26 |
| C04 | MMP-26 |
| C05 | MMP-26 |
| C06 | MMP-26 |
| C07 | MMP-26 |
| C08 | MMP-26 |
| C09 | MMP-26 |
| C10 | MMP-26 |
| C11 | MMP-26 |
| C12 | MMP-26/MMP-3 |
| D01 | MMP-26 |
| D02 | MMP-26 |
| D03 | MMP-26 |
| D04 | MMP-26 |
| D05 | NT |
| D06 | MMP-26 |
| D07 | MMP-26 |
| D08 | MMP-26 |
| D09 | MMP-26 |

In Vitro Cellular Invasion Assay

Forty-one of the expressed and purified MMP-26-binding antibodies were tested for inhibition of JEG-3 (choniocarcinoma) cell invasion through MATRIGEL™ basement membrane matrix-coated filters using the growth-factor reduced system from Becton Dickinson. JEG3 cells ($10^4$) were diluted in RPMI media containing 0.1%(v/v) fetal bovine serum and added to the unper chamber of the MATRIGEL™ basement membrane matrix-coatad well. Six hundred microliters of spent media from cultures of 3T3 fibroblasts was placed in the lower chamber as a source chemo attractants. MMP-26-binding antibodies were added to the upper chamber at concentrations of 5 μg/ml and 25 μg/ml. In the absence of an inhibitor, the JEG3 calls invaded into the lower chamber. Data is expressed as percent inhibition relative to phosphate buffered saline (set at 100% invasion). The twelve most potent antibodies were tested further at concentrations of 1 μg/ml, 25 μg/ml, and 50 μg/ml on three censecutive days. The data is shown in Table 4 (N/E=no detectable effect).

Table 4: JEG-3 cell invasion through MATRIGEL™ basement membrane matrix in vitro

TABLE 4

JEG-3 cell invasion through Matrigel ® in vitro

| | % Inhibition | | % Inhibition | | | |
|---|---|---|---|---|---|---|
| Clone | 5 μg/ml | 25 μg/ml | 1 μg/ml | 5 μg/ml | 25 μg/ml | 50 μg/ml |
| A1-orig | 40% | 66% | 53% | 58% | 64% | 74% |
| D6-orig | 41% | 52% | 42% | 55% | 70% | 35% |
| H6-orig | 24% | 50% | 49% | 52% | 57% | 39% |
| A01 | 19% | 51% | 30% | 47% | 54% | 70% |
| A04 | 6% | 27% | | | | |
| A11 | 28% | 56% | 51% | 54% | 59% | 73% |
| B04 | 36% | 14% | | | | |
| B06 | 34% | 30% | | | | |
| B10 | 48% | 26% | 6% | 5% | 11% | 22% |
| C01 | 43% | 34% | -2% | 16% | 21% | 42% |
| C04 | 35% | 36% | 1% | 11% | 18% | 32% |
| C05 | 16% | 32% | | | | |
| C08 | 45% | 49% | 34% | 42% | 49% | 62% |
| C11 | 28% | 29% | | | | |
| C12 | 49% | 38% | 36% | 35% | 49% | 27% |
| D02 | 36% | 25% | | | | |
| D04 | 38% | 34% | 47% | 34% | 45% | 52% |
| D06 | 0% | 35% | | | | |
| D07 | 21% | 36% | | | | |
| D08 | 36% | 35% | 56% | 50% | 76% | 53% |

Inhibition of MMP-26 Specific Activation of proMMP-9

Two lead antibodies (A1-orig and A11) were tested for their ability to inhibit MMP-26 activation of ProMMP-9. Activation was monitored by MMP-9 cleavage of gelatin (Molecular Probes E-12055) or cleavage of an MMP-9 specific peptide (Calbiochem 444221). MMP-26, at a concentration of 100 nM, was incubated with the above designated Ab inhibitors at varying concentrations for one hour. The proMMP-9, at a concentration of 10 nM, was then added to the mixture followed by fluorescently labeled gelatin or a fluorescently labeled peptide substrate. Activation of proMMP-9 was monitored using a fluorimeter (Molecular Devices) and was seen as an increase in signal. Inhibitory activity was thus assessed by a loss in signal. Neither A1-orig nor A11 inhibited MMP-9 activity directly.

Exemplary results obtained using the MMP-9 cleavage assay include that following percentage inhibition where the candidate inhibitor is at 125 nM: TIMP (89%), A1-orig (80%), A11 (79%), negative control compound (31%), no candidate compound (0%). These results were obtained by monitoring MMP-9 peptide cleavage in a reaction that included MMP-26 and pro-MMP-9.

The following Table provides inhibition data with the A1-orig antibody at various concentrations using a fluorescently labeled substrate:

TABLE 5

Inhibtion of MMP-26 Cleavage by A1-orig

| nM | Inhibition |
|---|---|
| 15 | 8% |
| 31 | 19% |
| 62 | 58% |
| 125 | 68% |
| 500 | 86% |
| 2000 | 89% |

Sequence Analysis of Exemplary MMP-26-binding Antibodies

MMP-26-binding antibodies were sequenced. Both nucleic and amino acid sequence of the VL and VH regions of each sequenced antibody are as follows (Table 6).

TABLE 6

Sequences of Exemplary Antibodies

| Antibody | Sequence | Identifier |
|---|---|---|
| A1-orig VLC Nucleic Acid Sequence | GGCGTGCACTCACAGAGCGTCTTGACTCAGCCACCCTC<br>AGCGTCTGGGACCCCCGGGCAGAGGGTCATCATCTCTT<br>GTTCTGGAAGCAGCTCCAACATCGGAAGTCATTATGTA<br>CACTGGTACCAACAGGTCCCAGGAACGGCCCCCAAACT<br>CCTCATTTATAGGAATGGTCAGCGGCCCTCAGGGGTCC<br>CTGACCGATTCTCTGGCTTCAAGTCTGGCACCTCAGCC<br>TCCCTGGCCATCAGTGGGCTCCGGTCCGAGGATGAGGC<br>TAATTATTACTGTGCAACATGGGATGACAGTGTCCTAT<br>TCGGCGGAGGGACCACGCTGACCGTCCTAGGTCAGCCC<br>AAGGCTGCCCCC | SEQ ID NO:1 |
| A1-orig VLC Amino Acid Sequence | GVHSQSVLTQPPSASGTPGQRVIISCSGSSSNIGSHYV<br>HWYQQVPGTAPKLLIYRNGQRPSGVPDRFSGFKSGTSA<br>SLAISGLRSEDEANYYCATWDDSVLFGGGTTLTVLGQP<br>KAAP | SEQ ID NO:2 |
| A1-orig VHC Nucleic Acid Sequence | GAAGTTCAATTGTTAGAGTCTGGTGGCGGTCTTGTTCA<br>GCCTGGTGGTTCTTTACGTCTTTCTTGCGCTGCTTCCG<br>GATTCACTTTCTCTTATTACCGTATGTCTTGGGTTCGC<br>CAAGCTCCTGGTAAAGGTTTGGAGTGGGTTTCTTCTAT<br>CGGTCCTTCTGCTGGCGATACTCTTTATGCTGACTCCG<br>TTAAAGGTCGCTTCACTATCTCTAGAGACAACTCTAAG<br>AATACTCTCTACTTGCAGATGAACAGCTTAAGGGCTGA<br>GGACACTGCAGTCTACTATTGTGCGAGATCTTTCAGCA<br>GTGGCCCGTACTACTTTGACTACTGGGGCCAGGGAACC<br>CTGGTCACCGTCTCAAGCGCCTCCACCAAGGGCCCATC<br>GGTCTTCCCGCTAGCGCCC | SEQ ID NO:3 |
| A1-orig VHC Amino Acid Sequence | EVQLLESGGGLVQPGGSLRLSCAASGFTFSYYRMSWVR<br>QAPGKGLEWVSSTGPSGGDTLYADSVKGRFTISRDNSK<br>NTLYLQMNSLPAEDTAVYYCARSFSSGPYYFDYWGQGT<br>LVTVSSASTKGPSVFPLAP | SEQ ID NO:4 |
| D6-orig VLC Nucleic Acid Sequence | GGCGTGCACTCTGACATCCAGATGACCCAGTCTCCACT<br>CTCCCTGTCTGCATCTGTGGGAGACAGAGTCGCCATCA<br>CTTGCCGCGCAAGTCAGAGCATCGACACCTATTTAAAT<br>TGGTATCAGCAGAAACCAGGGAAAGCCCCTAAACTCCT<br>GATCTATGCTGCATCCAAGTTGGAAGACGGGGTCCCAT<br>CAAGATTCAGTGGCAGTGGAACTGGGACAGATTTCACT<br>CTCACCATCAGAAGTCTGCAACCTGAAGATTTTGCAAG<br>TTATTTCTGTCAACAGAGCTACTCTAGTCCAGGGATCA<br>CTTTCGGCCCTGGGACCAAGGTGGAGATCAAACGAACT<br>GTGGCTGCACCA | SEQ ID NO:5 |
| D6-orig VLC Amino Acid Sequence | GVHSDIQMTQSPLSLSASVGDRVAITCPASQSTDTYLN<br>WYQQKPGKAPKLLIYAASKLEDGVPSRFSGSGTGTDFT<br>LTIRSLQPEDFASYFCQQSYSSPGTTFGPGTKVEIKRT<br>VAAP | SEQ ID NO:6 |
| D6-orig VHC Nucleic Acid Sequence | GAAGTTCAATTGTTAGAGTCTGGTGGCGGTCTTGTTCA<br>GCCTGGTGGTTCTTTACGTCTTTCTTGCGCTGCTTCCG<br>GATTCACTTTCTCTATGTACTCTATGCGTTGGGTTCGC<br>CAAGCTCCTGGTAAAGGTTTGGAGTGGGTTTCTTCTAT<br>CTATCCTTCTGGTGGCTCTACTGAGTATGCTGACTCCG<br>TTAAAGGTCGCTTCACTATCTCTAGAGACAACTCTAAG<br>AATACTCTCTACTTGCAGATGAACAGCTTAAGGGCTGA<br>GGACACTGCAGTCTACTATTGTGCGAGAGAGGGCGGGG<br>AGAACGACTACTGGGGCCAGGGAACCCTGGTCACCGTC<br>TCAAGCGCCTCCACCAAGGGCCCATCGGTCTTCCCGCT<br>AGCGCCC | SEQ ID NO:7 |
| D6-orig VHC Amino Acid Sequence | EVQLLESGGGLVQPGGSLRLSCAASGFTFSMYSMRWVR<br>QAPGKGLEWVSSIYPSGGSTEYADSVKGRFTISRDNSK<br>NTLYLQMNSLPAEDTAVYYCAREGGENDYWGQGTLVTV<br>SSASTKGPSVFPLAP | SEQ ID NO:8 |
| H6-orig VLC | GGCGTGCACTCACAGAGCGAATTGACTCAGCCTCCCTC<br>CGCGTCCGGGTCTCCTGGACAGTCAGTCACCATCTCCT | SEQ ID NO:9 |

TABLE 6-continued

Sequences of Exemplary Antibodies

| Antibody | Sequence | Identifier |
|---|---|---|
| Nucleic Acid Sequence | GCACTGGAACCAGCAGTGACGTTGGTGCTTATAACTAT GTCTCCTGGTACCAACAACACCCAGGCAAAGCCCCCAA ACTCATAATCTATGAAGTCAATAAGCGGCCCTCAGGGG TCCCTGATCGCTTCTCTGCCTCCAAGTCTGGCAACACG GCCTCCCTGACCGTCTCTGGGCTCCAGGCTGAAGATGA GGCTGATTATTACTGCAACTATATGCAGGCAGCAACA GTTTGATATTCGGCGGAGGGACCAAACTGACCGTCTTA GGTCAGCCCAAGGCTGCCCCC | |
| H6-orig VLC Amino Acid Sequence | GVHSQSELTQPPSASGSPGQSVTISCTGTSSDVGAYNY VSWYQQHPGKAPKLTIYEVNKRPSGVPDRFSASKSGNT ASLTVSGLQAEDEADYYCNSYAGSNSLIFGGGTKLTVL GQPKAAP | SEQ ID NO:10 |
| H6-orig VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTCAGTACTGGATGAATTGGGTTCGC CAAGCTCCTGGTAAAGGTTTGGAGTGGGTTTCTGGTAT CGGTCCTTCTGGTGGCATTACTTATTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGAGAGGTGAGGAAG ATGGCTACAATTCTGACTACTGGGGCCAGGGAACCCTG GTCACCGTCTCAAGCGCCTCCACCAAGGGCCCATCGGT CTTCCCGCTAGCGCCC | SEQ ID NO:11 |
| H6-orig VHC Amino Acid Sequence | EVQLLESGGGLVQPGGSLRLSCAASGFTFSQYWMNWVR QAPGKGLEWVSGTGPSGGITYYADSVKGRFTISRDNSK NTLYLQMNSLPAEDTAVYYCARGEEDGYNSDYWGQGTL VTVSSASTKGPSVFPLAP | SEQ ID NO:12 |
| A01 VLC Nucleic Acid Sequence | GGCGTGCACTCTGACATCCAGATGACCCAGTCTCCAGG CACCCTGTCTTTGTCTCCAGGGGAAAGAGCCACCCTCT CCTGCAGGGCCAGTCAGATTGTTCGCAGCACCTACTTA GCCTGGTATCAGCAGAAACCTGGCCAGGCTCCCAGGCT CCTCATCTATGGTACATCCAGCAGGGCCACTGGCGTCC CAGACAGGTTCAGTGGCAGTGGGTCTGGGACAGACTTC ACTCTCACCATCAGCGGACTGGAGCCTGAAGATTTTGC ACTATACTACTGTCAGCGGTATGGTGACTCACCTCCGA TCACCTTCGGCCAAGGGACACGACTGGAGATTACACGA ACTGTGGCTGCACCATCTGTC | SEQ ID NO:13 |
| A01 VLC Amino Acid Sequence | GVHSDIQMTQSPGTLSLSPGERATLSCRASQIVRSTYL AWYQQKPGQAPRLLIYGTSSRATGVPDRFSGSGSGTDF TLTISGLEPEDFALYYCQRYGDSPPITFGQGTRLEITR TVAAPSV | SEQ ID NO:14 |
| A01 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTGCTTACAATATGTTTTGGGTTCGC CAAGCTCCTGGTAAAGGTTTGGAGTGGGTTTCTGGTAT CGGTTCTTCTGGTGGCATTGCTCCTTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGAGAGCCGCGTACG AGGTGGAGAACTGGTTCGACCCCTGGGGCCAGGGAACC CTGGTCACCGTCTCAAGCGCCTCCACCAAGGGCCCATC GGTCTTCCCG | SEQ ID NO:15 |
| A01 VHC Amino Acid Sequence | EVQLLESGGGLVQPGGSLRLSCAASGFTFSAYNMFWVR QAPGKGLEWVSGIGSSGGIAPYADSVKGRFTISRDNSK NTLYLQMNSLPAEDTAVYYCARAAYEVENWFDPWGQGT LVTVSSASTKGPSVFP | SEQ ID NO:16 |
| A03 VLC Nucleic Acid Sequence | GGCGTGCACTCACAGAGCGCTTTGACTCAGCCACCCTC AGCGTCTGGGACCCCCGGGCAGAGGGTCACCATCTCTT GTTCTGGAGGCAGCTCCAACATCGGAAGTAATTTTGTT TACTGGTACCGGCAGCTCCCAGGAACGGCCCCCAAACT CCTCATCTATAGGAATTATCAGCGGCCCTCAGGGGTCC CTGACCGATTCTCGGGTTCCAAGTCTGGCACCTCAGCC TCCCTGGCCATCAGTGGGCTCCTGTCCGAAGATGAGGC TGATTATTACTGCGCAGCATGGGATGACAACGTGGGTG | SEQ ID NO:17 |

TABLE 6-continued

Sequences of Exemplary Antibodies

| Antibody | Sequence | Identifier |
|---|---|---|
| | GGGTCTTCGGATCTGGGACCAAGGTCACCGTCCTGGGT<br>CAGCCCAAGGCCAACCCCACT | |
| A03 VLC<br>Amino<br>Acid<br>Sequence | GVHSQSALTQPPSASGTPGQRVTISCSGGSSNIGSNFV<br>YWYRQLPGTAPKLLIYRNYQRPSGVPDRFSGSKSGTSA<br>SLAUSGLLSEDEADYYCAAWDDNVGGVFGSGTKVTVLG<br>QPKANPT | SEQ ID NO:18 |
| A03 VHC<br>Nucleic<br>Acid<br>Sequence | GAAGTTCAATTGTTAGAGTCTGGTGGCGGTCTTGTTCA<br>GCCTGGTGGTTCTTTACGTCTTTCTTGCGCTGCTTCCG<br>GATTCACTTTCTCTATTTACTCTATGGATTGGGTTCGC<br>CAAGCTCCTGGTAAAGGTTTGGAGTGGGTTTCTTCTAT<br>CTATTCTTCTGGTGGCGCTACTCGTTATGCTGACTCCG<br>TTAAAGGTCGCTTCACTATCTCTAGAGACAACTCTAAG<br>AATACTCTCTACTTGCAGATGAACAGCTTAAGGGCTGA<br>GGACACTGCAGTCTACTATTGTGCGAGGTGTAGCTGGC<br>TACAATTAGTACCGATGCACCCTTGGGGCCAGGGAACC<br>CTGGTCACCGTCTCAGCGCCTCCACCAAGGGCCCATC<br>GGTCTTCCCG | SEQ ID NO:19 |
| A03 VHC<br>Amino<br>Acid<br>Sequence | EVQLLESGGGLVQPGGSLRLSCAASGFTFSIYSMDWVR<br>QAPGKGLEWVSSIYSSGGATRYADSVKGRFTISRDNSK<br>NTLYLQMNSLPAEDTAVYYCARCSWLQLVPMHPWGQGT<br>LVTVSSASTKGPSVFP | SEQ ID NO:20 |
| A04 VLC<br>Nucleic<br>Acid<br>Sequence | GGCGTGCACTCACAGAGCGCTTTGACTCAGCCACCCTC<br>AGCGTCTGGGACCCCCGGGCAGAGGGTCACCATCTCTT<br>GTTCTGGAGGCTACTCCAACATGGGAAGCAATTATGCA<br>CACTGGTACCAGCAGGTCCCAGGAACGGCCCCCAAACT<br>CCTCATCTATAACAATAATCAGAGGCCCTCAGGGGTCC<br>CTGACCGATTCTCTGGCTCCAAGTCTGGCACCTCAGCC<br>TCCCTAGCCATCAGTGGGCTCCGGTCCGAGGATGAGGC<br>TGATTATTACTGTGCAGCATGGGATGAAAACCTGAGTG<br>GTCCGGTCTTCGGAACTGGGACCAAGGTCACCGTCCTA<br>GGTCAGCCCAAGGCCAACCCCACT | SEQ ID NO:21 |
| A04 VLC<br>Amino<br>Acid<br>Sequence | GVHSQSALTQPPSASGTPGQRVTISCSGGYSNMGSNYA<br>HWYQQVPGTAPKLLIYNNNQRPSGVPDRFSGSKSGTSA<br>SLAISGLRSEDEADYYCAAWDENLSGPVFGTGTKVTVL<br>GQPKANPT | SEQ ID NO:22 |
| A04 VHC<br>Nucleic<br>Acid<br>Sequence | GAAGTTCAATTGTTAGAGTCTGGTGGCGGTCTTGTTCA<br>GCCTGGTGGTTCTTTACGTCTTTCTTGCGCTGCTTCCG<br>GATTCACTTTCTCTGAGTACAATATGGCTTGGGTTCGC<br>CAAGCTCCTGGTAAAGGTTTGGAGTGGGTTTCTCGTAT<br>CGGTTCTTCTGGTGGCAAGACTAAGTATGCTGACTCCG<br>TTAAAGGTCGCTTCACTATCTCTAGAGACAACTCTAAG<br>AATACTCTCTACTTGCAGATGAACAGCTTAAGGGCTGA<br>GGACACTGCAGTCTACTATTGTGCGAGAGATGAAGCCC<br>CCGACTACGGTGACGACGCGGAAGCTTTTGATATCTGG<br>GGCCAAGGGACAATGGTCACCGTCTCAAGCGCCTCCAC<br>CAAGGGCCCATCGGTCTTCCCG | SEQ ID NO:23 |
| A04 VHC<br>Amino<br>Acid<br>Sequence | EVQLLESGGGLVQPGGSLRLSCAASGFTFSEYNMAWVR<br>QAPGKGLEWVSRIGSSGGKTKYADSVKGRFTTSRDNSK<br>NTLYLQMNSLRAEDTAVYYCARDEAPDYGDDAEAFDTW<br>GQGTMVTVSSASTKGPSVFP | SEQ ID NO:24 |
| A05 VLC<br>Nucleic<br>Acid<br>Sequence | GGCGTGCACTCTGACATCCAGATGACCCAGTCTCCATC<br>CTCCCTGTCTTTGTCTCCAGGGGAAAGAGCCACCCTCT<br>CCTGCAGGGCCAGTCAGAGTGTTAGCAGCTACTTAGCC<br>TGGTACCAACAGAAACCTGGCCAGGCTCCCAGGCTCCT<br>CATCTATGATGCATCCAACAGGGCCACTGGCATCCCAG<br>CCAGGTTCAGTGGCAGTGGGTCTGGGACAGACTTCACT<br>CTCACCATCAGCAGCCTAGAGCCTGAAGATTTTGCAGT<br>TTATTACTGTCAGCAGCGTAGCAACTGGCCTCGGACTT<br>TCGGCGGAGGGACCAAGGTGGAGATCAAACGAACTGTG<br>GCTGCACCATCTGTC | SEQ ID NO:25 |
| A05 VLC<br>Amino<br>Acid<br>Sequence | GVHSDIQMTQSPSSLSLSPGERATLSCRASQSVSSYLA<br>WYQQKPGQAPRLLIYDASNRATGIPARFSGSGSGTDFT<br>LTISSLEPEDFAVYYCQQRSNWPRTFGGGTKVEIKRTV<br>AAPSV | SEQ ID NO:26 |

TABLE 6-continued

Sequences of Exemplary Antibodies

| Antibody | Sequence | Identifier |
|---|---|---|
| A05 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTGTTTACTCTATGAATTGGGTTCGC CAAGCTCCTGGTAAAGGTTTGGAGTGGGTTTCTTATAT CGTTCCTTCTGGTGGCAATACTCCTTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCAAGAGATGGGCGG CTACGGTGGACTTAGACTACTGGGGCCAGGGAACCCTG GTCACCGTCTCAAGCGCCTCCACCAAGGGCCCATCGGT CTTCCCG | SEQ ID NO:27 |
| A05 VHC Amino Acid Sequence | EVQLLESGGGLVQPGGSLRLSCAASGPTFSVYSMNWVR QAPGKGLEWVSYIVPSGGNTPYADSVKGRFTISRDNSK NTLYLQMNSLRAEDTAVYYCARDGAATVDLDYWGQGTL VTVSSASTKGPSVFP | SEQ ID NO:28 |
| A06 VLC Nucleic Acid Sequence | GGCGTGCACTCTGACATCCAGATGACCCAGTCTCCATC CTCCCTGTCTGCATCTGTAGGAGACAGAGTCACCATCA CTTGCCGGGCAAGTCAGAGCATTAGCAGCTATTTAAAT TGGTATCAGCAGAAACCAGGGAAAGCCCCTAAGCTCCT GATCTATGCTGCATCCAGTTTGCAAAGTGGGGTCCCAT CAAGGTTCAGTGGCAGTGGATCTGGGACAGATTTCACT CTCACCATCAGCAGTCTGCAACCTGAAGATTTTGCAAC TTACTACTGTCAACAGAGTTACAGTACCCCTCCGGAGA ACACTTTTGGCCAGGGGACCAAGCTGGAGATCAAACGA ACTGTGGCTGCACCATCTGTC | SEQ ID NO:29 |
| A06 VLC Amino Acid Sequence | GVHSDIQMTQSPSSLSASVGDRVTITCPASQSISSYLN WYQQKPGKAPKLLIYAASSLQSGVPSRFSGSGSGTDFT LTISSLQPEDFATYYCQQSYSTPPENTFGQGTKLEIKR TVAAPSV | SEQ ID NO:30 |
| A06 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTCCTTACCATATGGGTTGGGTTCGC CAAGCTCCTGGTAAAGGTTTGGAGTGGGTTTCTGGTAT CTATCCTTCTGGTGGCTGGACTAATTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGAGAGATGGGTATA GCAGTGGCTGGTTCCGGTACTGGGGCCAGGGAACCCTG GTCACCGTCTCAAGCGCCTCCACCAAGGGCCCATCGGT CTTCCCG | SEQ ID NO:31 |
| A06 VHC Amino Acid Sequence | EVQLLESGGGLVQPGGSLRLSCAASGFTFSPYHMGWVR QAPGKGLEWVSGIYPSGGWTNYADSVKGRFTISRDNSK NTLYLQMNSLRAEDTAVYYCARDGYSSGWFRYWGQGTL VTVSSASTKGPSVFP | SEQ ID NO:32 |
| A07 VLC Nucleic Acid Sequence | GGCGTGCACTCACAGAGCGAATTGACTCAGCCTCCCTC CGCGTCCGGGTCTCCTGGACAGTCAGTCACCATCTCCT GCACTGGAACCAGCAGTGACGTTGGTGGTTATAACTAT GTCTCCTGGTATCAACAACACCCAGACAAAGCCCCCAA ACTCCTGATTTATGAGGTCACTCAGCGGCCCTCAGGGG TCCCTGATCGCTTCTCTGGCTCCAGGTCTGGCAACACG GCCTCCCTGACCGTCTCTGGGCTCCAGGCTGAGGATGA GGCTGATTATTACTGCAGCTCATATGCAGGCAGGAACA ATCTTTATGTCTTCGGACCTGGGACCAAGGTCACCGTC CTAGGTCAGCCCAAGGCCAACCCCACT | SEQ ID NO:33 |
| A07 VLC Amino Acid Sequence | GVHSQSELTQPPSASGSPGQSVTISCTGTSSDVGGYNY VSWYQQHPDKAPKLLTYEVTQRPSGVPDRFSGSRSGNT ASLTVSGLQAEDEADYYCSSYAGRNNLYVFGPGTKVTV LGQPKANPT | SEQ ID NO:34 |
| A07 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTGAGTACAATATGATGTGGGTTCGC CAAGCTCCTGGTAAAGGTTTGGAGTGGGTTTCTGTTAT CTCTCCTTCTGGTGGCGGTACTCTTTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGAGAGATCTAAATA | SEQ ID NO:35 |

TABLE 6-continued

Sequences of Exemplary Antibodies

| Antibody | Sequence | Identifier |
|---|---|---|
| | ACAGCTCGCCCCCGGATTCCAATGATGCTTTTGATATC<br>TGGGGCCGAGGGACAATGGTCACCGTCTCAAGCGCCTC<br>CACCAAGGGCCCATCGGTCTTCCCG | |
| A07 VHC<br>Amino<br>Acid<br>Sequence | EVQLLESGGGLVQPGGSLRLSCAASGFTFSEYNMMWVR<br>QAPGKGLEWVSVISPSGGGTLYADSVKGRFTISRDNSK<br>NTLYLQMNSLPAEDTAVYYCARDLNNSSPPDSNDAFDI<br>WGRGTMVTVSSASTKGPSVFP | SEQ ID NO:36 |
| A08 VLC<br>Nucleic<br>Acid<br>Sequence | GGCGTGCACTCACAGAGCGTCTTGACTCAGCCACCCTC<br>AGTGTCTGGGACCCCCGGACAGAGGGTCACCATCTCTT<br>GTTCTGGAGGCTACCCCAACATGGGAAGCAATTATGCA<br>CACTGGTACCAGCAACTCCCAGGAACGGCCCCCAAACT<br>CCTCATCTATAACGATAATCAGCGGCCCTCAGGGGTCC<br>CTGACCGATTCTCTGGCTCCAAGTCTGGCACCTCAGCC<br>TCCCTGGCCATCAGTGGGCTCCGGTCCGAGGATGAGGC<br>TGATTATTACTGTGCAGCATGGGATGACAGCCTGAGTG<br>GTCCGGTGTTCGGCGGAGGGACCAAGCTGACCGTCCTA<br>GGTCAGCCCAAGGCTGCCCCCTCG | SEQ ID NO:37 |
| A08 VLC<br>Amino<br>Acid<br>Sequence | GVHSQSVLTQPPSVSGTPGQRVTTSCSGGYPNMGSNYA<br>HWYQQLPGTAPKLLIYNDNQRPSGVPDRFSGSKSGTSA<br>SLAISGLRSEDEADYYCAAWDDSLSGPVFGGGTKLTVL<br>GQPKAAPS | SEQ ID NO:38 |
| A08 VHC<br>Nucleic<br>Acid<br>Sequence | GAAGTTCAATTGTTAGAGTCTGGTGGCGGTCTTGTTCA<br>GCCTGGTGGTTCTTTACGTCTTTCTTGCGCTGCTTCCG<br>GATTCACTTTCTCTGTTTACGATATGCCTTGGGTTCGC<br>CAAGCTCCTGGTAAAGGTTTGGAGTGGGTTTCTGTTAT<br>CTATCCTTCTGGTGGCTTTACTCGTTATGCTGACTCCG<br>TTAAAGGTCGCTTCACTATCTCTAGAGACAACTCTAAG<br>AATACTCTCTACTTGCAGATGAACAGCTTAAGGGCTGA<br>GGACACTGCAGTCTACTATTGTGCGGCAGATCCGACGA<br>TACAGCTATGGGCCTACTACTACGGTATGGACGTCTGG<br>GGCCAAGGGACCACGGTCACCGTCTCAAGCGCCTCCAC<br>CAAGGGCCCATCGGTCTTCCCG | SEQ ID NO:39 |
| A08 VHC<br>Amino<br>Acid<br>Sequence | EVQLLESGGGLVQPGGSLRLSCAASGFTFSVYDMPWVR<br>QAPGKGLEWVSVIYPSGGFTRYADSVKGRFTISRDNSK<br>NTLYLQMNSLRAEDTAVYYCAADPTIQLWAYYYGMDVW<br>GQGTTVTVSSASTKGPSVFP | SEQ ID NO:40 |
| A09 VLC<br>Nucleic<br>Acid<br>Sequence | GGCGTGCACTCACAGAGCGAATTGACTCAGCCACCCTC<br>AGCGTCTGGGACCCCCGGGCAGAGGGTCACCATCTCTT<br>GTTCTGGAGGCAGCTCCAACATCGGAAGTAATTTTGTT<br>TACTGGTACCGGCAGCTCCCAGGAACGGCCCCCAAACT<br>CCTCATCTATAGGAATTATCAGCGGCCCTCAGGGGTCC<br>CTGACCGATTCTCTGGGTTCCAAGTCTGGCACCTCAGCC<br>TCCCTGGCCATCAGTGGGCTCCTGTCCGAAGATGAGGC<br>TGATTATTACTGCGCAGCATGGGATGACAACGTGGGTG<br>GGGTCTTCGGATCTGGGACCAAGGTCACCGTCCTGGGT<br>CAGCCCAAGGCCAACCCCACT | SEQ ID NO:41 |
| A09 VLC<br>Amino<br>Acid<br>Sequence | GVHSQSELTQPPSASGTPGQRVTISCSGGSSNIGSNFV<br>YWYRQLPGTAPKLLIYRNYQRPSGVPDRFSGSKSGTSA<br>SLAISGLLSEDEADYYCAAWDDNVGGVFGSGTKVTVLG<br>QPKANPT | SEQ ID NO:42 |
| A09 VHC<br>Nucleic<br>Acid<br>Sequence | GAAGTTCAATTGTTAGAGTCTGGTGGCGGTCTTGTTCA<br>GCCTGGTGGTTCTTTACGTCTTTCTTGCGCTGCTTCCG<br>GATTCACTTTCTCTTGGTACGATATGTATTGGGTTCGC<br>CAAGCTCCTGGTAAAGGTTTGGAGTGGGTTTCTTCTAT<br>CTATTCTTCTGGTGGCTATACTGCTTATGCTGACTCCG<br>TTAAAGGTCGCTTCACTATCTCTAGAGACAACTCTAAG<br>AATACTCTCTACTTGCAGATGAACAGCTTAAGGGCTGA<br>GGACACTGCAGTCTACTATTGTGCGAAAGATCGTGATC<br>CTTGTAGTAGAACCACCTGCTATAACTGGTTCGACCCC<br>TGGGGCCAGGGAACCCTGGTCACCGTCTCAAGCGCCTC<br>CACCAAGGGCCCATCGGTCTTCCCG | SEQ ID NO:43 |
| A09 VHC<br>Amino<br>Acid<br>Sequence | EVQLLESGGGLVQPGGSLRLSCAASGFTFSWYDMYWVR<br>QAPGKGLEWVSSIYSSGGYTAYADSVKGRFTISRDNSK<br>NTLYLQMNSLPAEDTAVYYCAKDRDPCSRTTCYNWFDP<br>WGQGTLVTVSSASTKGPSVFP | SEQ ID NO:44 |

TABLE 6-continued

Sequences of Exemplary Antibodies

| Antibody | Sequence | Identifier |
|---|---|---|
| A10 VLC Nucleic Acid Sequence | GGCGTGCACTCACAGAGCGAATTGACTCAGCCACCCTC AGCGTCTGGGACCCCCGGGCAGAGGGTCACCATCTCTT GTTCTGGAGGCAGCTCCAACATCGGAAGTAATTATGTC TCCTGGTACCAGCAGCTCCCAGGAACGGCCCCCAAACT CCTCATCTATAATAATAATCAGCGGCCCTCAGGGGTCC CTGACCGATTCTCTGGCTCCAAGTCTGGCACCTCAGCC TCCCTGGCCATCAGTGGGCTCCGGTCCGAGGATGAGGC TGATTATTACTGTGCAGCATGGGATGACAGCCTGAGTT CTGCTGTGTTCGGAGGAGGCACCCAGCTGACCGTCCTC GGTCAGCCCAAGGCTGCCCCCTCG | SEQ ID NO:45 |
| A10 VLC Amino Acid Sequence | GVHSQSELTQPPSASGTPGQRVTISCSGGSSNTGSNYV SWYQQLPGTAPKLLIYNNNQRPSGVPDRFSGSKSGTSA SLAISGLRSEDEADYYCAAWDDSLSSAVFGGGTQLTVL GQPKAAPS | SEQ ID NO:46 |
| A10 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTGCTTACCGTATGTTTTGGGTTCGC CAAGCTCCTGGTAAAGGTTTGGAGTGGGTTTCTTCTAT CTGGCCTTCTGGTGGCACTACTTCTTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGAGAGATCGGGGCT ATGATAGTAGTGGTTATTTTGACTACTGGGGCCAGGGA ACCCTGGTCACCGTCTCAAGCGCCTCCACCAAGGGCCC ATCGGTCTTCCCG | SEQ ID NO:47 |
| A10 VHC Amino Acid Sequence | EVQLLESGGGLVQPGGSLRLSCAASGFTFSAYRMFWVR QAPGKGLEWVSSIWPSGGTTSYADSVKGRFTISRDNSK NTLYLQMNSLPAEDTAVYYCARDRGYDSSGYFDYWGQG TLVTVSSASTKGPSVFP | SEQ ID NO:48 |
| A11 VLC Nucleic Acid Sequence | GGCGTGCACTCACAGAGCGCTTTGACTCAGCCACCCTC GGTGTCACTGGCCCCAGGACAGACGGCCAGGATTACCT GTGGGGGAAACAACATTGGAACTAAAAGTGTTCACTGG TACCAGCAGAAGCCAGGCCAGGCCCCTGTGCTGGTCGT CTATGATGACAGCGACCGGCCCTCAGGGATCCCTGAGC GATTCTCTGGCTCCAATTCTGGGAACACGGCCACCCTG ACCATCAGCAGGGTCGAAGCCGGGGATGAGGCCGACTA TTATTGTCAGGTGTGGGATAGTGGTAGTGATCATCAGG TCTTCGGCGGAGGGACCAAGCTGACCGTCCTAGGTCAG CCCAAGGCTGCCCCCTCG | SEQ ID NO:49 |
| A11 VLC Amino Acid Sequence | GVHSQSALTQPPSVSLAPGQTARITCGGNNTGTKSVHW YQQKPGQAPVLVVYDDSDRPSGTPERFSGSNSGNTATL TISRVEAGDEADYYCQVWDSGSDHQVFGGGTKLTVLGQ PKAAPS | SEQ ID NO:50 |
| A11 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTTGGTACACTATGATGTGGGTTCGC CAAGCTCCTGGTAAAGGTTTGGAGTGGGTTTCTCGTAT CTCTCCTTCTGGTGGCCATACTCTTTATGCTGACTCCG TTAAAGGTCGCTTCACTATCTCTAGAGACAACTCTNAG AATACTCTCTACTTGCAGATGAACAGCTTAAGGGCTGA GGACACTGCAGTCTACTATTGTGCGAGAGACACTTGGG ACGATTACTATGATAGTAGTGGTTATTACAACGATTTT GACTACTGGGGCCAGGGAACCCTGGTCACCGTCTCAAG CGCCTCCACCAAGGGCCCATCGGTCTTCCCGCTAGCGC CCTG | SEQ ID NO:51 |
| A11 VHC Amino Acid Sequence | EVQLLESGGGLVQPGGSLRLSCAASGFTFSWYTMMWVR QAPGKGLEWVSRISPSGGHTLYADSVKGRFTISRDNSz NTLYLQMNSLRAEDTAVYYCARDTWDDYYDSSGYYNDF DYWGQGTLVTVSSASTKGPSVFPLAP | SEQ ID NO:52 |
| A12 VLC Nucleic Acid Sequence | GGCGTGCACTCTGACATCCAGATGACCCAGTCTCCAGG CACCCTGTCTTTGTCTCCAGGGGAAAGAGCCACCCTCT CCTGCAGGGCCAGTCAGAGTGTTAGTCGTAGTACTTA GGCTGGTACCAGCAGAAACCTGGCCAGGCTCCCAGGCT CCTCATCTATGGTGCATCCAACAGGGCCACTGGCATCC CAGACAGGTTCAGTGGCAGTGGGTCTGGGACAGACTTC ACTCTCACCATCAGCAGACTGGAGCCTGAAGATTTTGC AGTGTATTACTGTCAGCAGTACGGTATCTCACCCCTCA | SEQ ID NO:53 |

TABLE 6-continued

Sequences of Exemplary Antibodies

| Antibody | Sequence | Identifier |
|---|---|---|
| | CCTTCGGCCCTGGGACCAAAGTGGATATCAAACGAACT GTGGCTGCACCATCTGTC | |
| A12 VLC Amino Acid Sequence | GVHSDIQMTQSPGTLSLSPGERATLSCPASQSVSRSYL GWYQQKPGQAPRLLIYGASNRATGIPDRFSGSGSGTDF TLTISRLEPEDFAVYYCQQYGISPLTFGPGTKVDIKRT VAAPSV | SEQ ID NO:54 |
| A12 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTGCTTACTGGATGGATTGGGTTCGC CAAGCTCCTGGTAAAGGTTTGGAGTGGGTTTCTGTTAT CTATCCTTCTGGTGGCTCTACTAATTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGAGAGAGGGGATAG CCGCAGCAGCACCAATGGACGTCTGGGGCAAAGGGACC ACGGTCACCGTCTCAAGCGCCTCCACCAAGGGCCCATC GGTCTTCCCG | SEQ ID NO:55 |
| A12 VHC Amino Acid Sequence | EVQLLESGGGLVQPGGSLRLSCAASGFTFSAYWMDWVR QAPGKGLEWVSVTYPSGGSTNYADSVKGRFTISRDNSK NTLYLQMNSLRAEDTAVYYCAREGIAAAAPMDVWGKGT TVTVSSASTKGPSVFP | SEQ ID NO:56 |
| B01 VLC Nucleic Acid Sequence | GGCGTGCACTCTGACATCCAGATGACCCAGTCTCCAGG CACCCTGTCTTTGTCTCCAGGGGAAAGAGCCACCCTCT CCTGCAGGGCCAGTCAGAGTGTTAGCAGCAGCTACTTT GCCTGGTACCAGCAGAAACCTGGCCAGGCTCCCAGGCT CCTCATCTATGATGCATCCAGCAGGGCCACTGGCATCC CAGACAGGTTCAGTGGCAGTGGGTCTGGGACAGACTTC ACTCTCACCATCAGCAGACTGGAGCCTGAAGATTTTGC AGTGTATTACTGTCAGCAGTATGGTAGCTCACCTCCCA TGTACACTTTTGGCCAGGGGACCAAGCTGGAGATCAAA CGAACTGTGGCTGCACCATCTGTC | SEQ ID NO:57 |
| B01 VLC Amino Acid Sequence | GVHSDIQMTQSPGTLSLSPGERATLSCPASQSVSSSYF AWYQQKPGQAPRLLIYDASSPATGIPDRFSGSGSGTDF TLTISRLEPEDFAVYYCQQYGSSPPMYTFGQGTKLEIK RTVAAPSV | SEQ ID NO:58 |
| B01 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTACTTACGATATGCTTTGGGTTCGC CAAGCTCCTGGTAAAGGTTTGGAGTGGGTTTCTTCTAT CTCTCCTTCTGGTGGCTCTACTTCTTATGCTGACTCCG TTAAAGGTCGCTTCACTATCTCTAGAGACAACTCTAAG AATACTCTCTACTTGCAGCTGAACAGCTTAAGGGCTGA GGACACTGCAGTCTACTATTGTGCGAGAGAGAAAGCGT CGGATCTTTCGGGGACTTACTCTGAGGCCCTTGACCAC TGGGGCCAGGGAACCCTGGTCACCGTCTCAAGCGCCTC CACCAAGGGCCCATCGGTCTTCCCG | SEQ ID NO:59 |
| B01 VHC Amino Acid Sequence | EVQLLESGGGLVQPGGSLRLSCAASGFTFSTYDMLWVR QAPGKGLEWVSSTSPSGGSTSYADSVKGRFTISRDNSK NTLYLQLNSLPAEDTAVYYCAREKASDLSGTYSEALDH WGQGTLVTVSSASTKGPSVFP | SEQ ID NO:60 |
| B02 VLC Nucleic Acid Sequence | GGCGTGCACTCTGACATCCAGATGACCCAGTCTCCATC CTCCCTGTCTGCATCTGTGGGAGACAGAGTCGCCATCA CTTGCCGTGCAAGTCAGAGCATCGACACCTATTTAAAT TGGTATCAGCAGAAACCAGGGAAAGCCCCTAAACTCCT GATCTATGCTGCATCCAAGTTGGAAGACGGGGTCCCAT CAAGATTCAGTGGCAGTGGAACTGGGACAGATTTCACT CTCACCATCAGAAGTCTGCAACCTGAAGATTTTGCAAG TTATTTCTGTCAACAGAGCTACTCTAGTCCAGGGATCA CTTTCGGCCCTGGGACCAAGGTGGAGATCAAACGAACT GTGGCTGCACCATCTGTC | SEQ ID NO:61 |
| B02 VLC Amino Acid Sequence | GVHSDTQMTQSPSSLSASVGDRVAITCRASQSIDTYLN WYQQKPGKAPKLLTYAASKLEDGVPSRFSGSGTGTDFT LTIRSLQPEDFASYFCQQSYSSPGITFGPGTKVEIKRT VAAPSV | SEQ ID NO:62 |

TABLE 6-continued

Sequences of Exemplary Antibodies

| Antibody Sequence | Identifier |
|---|---|
| B02 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTGATTACTTTATGAAGTGGGTTCGC CAAGCTCCTGGTAAAGGTTTGGAGTGGGTTTCTTCTAT CTATCCTTCTGGTGGCCCTACTAAGTATGCTCACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGAGAGAGCGTAGCA GTGGCTGGTACGGTTACTACTACTACGGTATGGACGTC TGGGGCCAAGGGACCACGGTCACCGTCTCAAGCGCCTC CACCAAGGGCCCATCGGTCTTCCCG | SEQ ID NO:63 |
| B02 VHC Amino Acid Sequence | EVQLLESGGGLVQPGGSLRLSCAASGFTFSDYFMKWVR QAPGKGLEWVSSIYPSGGPTKYADSVKGRFTISRDNSK NTLYLQMNSLRAEDTAVYYCARERSSGWYGYYYYGMDV WGQGTTVTVSSASTKGPSVFP | SEQ ID NO:64 |
| B03 VLC Nucleic Acid Sequence | GGCGTGCACTCTGACATCCAGATGACCCAGTCTCCATC CTTCCTGTCTGCTTCTGTAGGGGACAGAGTCACCATCA CTTGCCGGGCCAGTCAGGGCATTAGGGATTTTTAGGC TGGTATCAACAAAAACCAGGGAAAGCCCCTAATCAACT GATCTATGCTGCATCCATTTTGCAAAGTGGGGTCCCAT CAAGGTTCAGCGGCAGTGGATCTGGGACAGATTTCACT CTCACGATCACCAGCCTGCAGCCTGAGGATTTTGCAAC TTATTTCTGTCAACAGCTTAATGGCTACCGCGCCTTCG GCCAAGGGACACGACTGGAAATAAAGCGAACTGTGGCT GCACCATCTGTC | SEQ ID NO:65 |
| B03 VLC Amino Acid Sequence | GVHSDIQMTQSPSFLSASVGDRVTITCPASQGIRDFLG WYQQKPGKAPNQLIYAASTLQSGVPSRFSGSGSGTDFT LTITSLQPEDFATYFCQQLNGYRAFGQGTRLEIKRTVA APSV | SEQ ID NO:66 |
| B03 VUC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTCCTTACGAGATGCAGTGGGTTCGC CAAGCTCCTGGTAAAGGTTTGGAGTGGGTTTCTGGTAT CGGTTCTTCTGGTGGTGACTCCGTTAAAGGTCGCTTCA CTATCTCTAGAGACAACTCTAAGAATACTCTCTACTTG CAGATGAACAGCTTAAGGGCTGAGGACACTGCAGTCTA CTATTGTGCGAGAGAGAGGGTAGATTGTAGTGGTGGTG GCTGCGGGAGCTACTTTGACTACTGGGGCCAGGGAACC CTGGTCACCGTCTCAAGCGCCTCCACCAAGGGCCCATC GGTCTTCCCG | SEQ ID NO:67 |
| B03 VHC Amino Acid Sequence | EVQLLESGGGLVQPGGSLRLSCAASGFTFSPYEMQWVR QAPGKGLEWVSGIGSSGGDSVKGRFTTSRDNSKNTLYL QMNSLPAEDTAVYYCARERVDCSGGGCGSYFDYWGQGT LVTVSSASTKGPSVFP | SEQ ID NO:68 |
| B04 VLC Nucleic Acid Sequence | GGCGTGCACTCTGACATCCAGATGACCCAGTCTCCATC TTCCGTGTCTGCATCTGTAGGAGACAGAGTCACGATCA CTTGTCGGGCGAGTCAGGGTATTAGCAAGAGCTTAGCC TGGTATCAGCAGAAACCAGGGAAAGCCCCTAAACTCCT GGTCTATGGTGCATTCAGTTTGGAAAGTGGGGTCCCAT CAAGATTCAGCGGCACTGGAGCTGGGACAGATTTCATT CTCACCATCAGCAGGCTGCAGCCTGAAGACTTTGCAAC TTATTATTGTCAACAGGCTAACAGTTTCCCGCTCACTT TCGGCGGAGGGACCAAGGTGGAGATCAAACGAACTGTG GCTGCACCATCTGTC | SEQ ID NO:69 |
| B04 VLC Amino Acid Sequence | GVHSDIQMTQSPSSVSASVGDRVTITCPASQGISKSLA WYQQKPGKAPKLLVYGAFSLESGVPSRFSGTGAGTDFI LTISRLQPEDFATYYCQQANSFPLTFGGGTKVEIKRTV AAPSV | SEQ ID NO:70 |
| B04 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTTTTACTGGATGATGTGGGTTCGC CAAGCTCCTGGTAAAGGTTTGGAGTGGGTTTCTGGTAT CTCTTCTTCTGGTGGCTTTACTAAGTATGCTGACTCCG TTAAAGGTCGCTTCACTATCTCTAGAGACAACTCCAAG AATACTCTCTACTTGCAGATGAACAGCTTAAGGGCTGA GGACACTGCAGTCTACTATTGTGCGAGGGAGACCAGCC | SEQ ID NO:71 |

TABLE 6-continued

Sequences of Exemplary Antibodies

| Antibody | Sequence | Identifier |
|---|---|---|
| | GGAGGGCTTTTGATATCTGGGGCCAAGGGACAATGGTC<br>ACCGTCTCAAGCGCCTCCACCAAGGGCCCATCGGTCTT<br>CCCG | |
| B04 VHC<br>Amino<br>Acid<br>Sequence | EVQLLESGGGLVQPGGSLRLSCAASGFTFSFYWMMWVR<br>QAPGKGLEWVSGISSSGGFTKYADSVKGRFTTSRDNSK<br>NTLYLQMNSLPAEDTAVYYCARETSRPAFDIWGQGTMV<br>TVSSASTKGPSVFP | SEQ ID NO:72 |
| B05 VLC<br>Nucleic<br>Acid<br>Sequence | GGCGTGCACTCTGACATCCAGATGACCCAGTCTCCAGG<br>CACCCTGTCTTTGTCTCCAGGGGAAAGAGCCACCCTCT<br>CCTGCAGGGCCAGTCAGAGTGTTAGCAGCAGCTACTTA<br>GCCTGGTACCAGCAGAAACCTGGCCAGGCTCCCAGGCT<br>CCTCATCTATGGTGCATCCAGCAGGGCCACTGGCATCC<br>CAGACAGGTTCAGTGGCAGTGGGTCTGGGACAGACTTC<br>ACTCTCACCATCAGCAGACTGGAGCCTGAAGATTTTGC<br>AGTGTATTACTGTCAGCAGTATGGTAGCTCACCTGAGA<br>TCACCTTCGGCCAAGGGACACGACTGGAGATTAAACGA<br>ACTGTGGCTGCACCATCTGTC | SEQ ID NO:73 |
| B05 VLC<br>Amino<br>Acid<br>Sequence | GVHSDIQMTQSPGTLSLSPGEPATLSCRASQSVSSSYL<br>AWYQQKPGQAPRLLIYGASSPATGIPDRFSGSGSGTDF<br>TLTISRLEPEDFAVYYCQQYGSSPEITFGQGTRLEIKR<br>TVAAPSV | SEQ ID NO:74 |
| B05 VHC<br>Nucleic<br>Acid<br>Sequence | GAAGTTCAATTGTTAGAGTCTGGTGGCGGTCTTGTTCA<br>GCCTGGTGGTTCTTTACGTCTTTCTTGCGCTGCTTCCG<br>GATTCACTTTCTCTGAGTACTGGATGCCTTGGGTTCGC<br>CAAGCTCCTGGTAAAGGTTTGGAGTGGGTTTCTCGTAT<br>CTATCCTTCTGGTGGCGTTACTACTTATGCTGACTCCG<br>TTAAAGGTCGCTTCACTATCTCTAGAGACAACTCTAAG<br>AATACTCTCTACTTGCAGATGAACAGCTTAAGGGCTGA<br>GGACACTGCAGTCTACTATTGTGCGAGAGGGGGGGATT<br>ACGATTTTTGGAGTGTACAATACTACTACTACTACATG<br>GACGTCTGGGGCAAAGGGACCACGGTCACCGTCTCAAG<br>CGCCTCCACCAAGGGCCCATCGGTCTTCCCG | SEQ ID NO:75 |
| B05 VHC<br>Amino<br>Acid<br>Sequence | EVQLLESGGGLVQPGGSLRLSCAASGFTFSEYWMPWVR<br>QAPGKGLEWVSRTYPSGGVTTYADSVKGRFTISRDNSK<br>NTLYLQMNSLRAEDTAVYYCARGGDYDFWSVQYYYYYM<br>DVWGKGTTVTVSSASTKGPSVFP | SEQ ID NO:76 |
| B06 VLC<br>Nucleic<br>Acid<br>Sequence | GGCGTGCACTCTGACATCCAGATGACCCAGTCTCCATC<br>CTTCCTGTCTGCATCTGTAGGAGACAGAGTCACCATCA<br>CTTGCCGGGCCAGTCAGGGCATTAGCAGTTATTTAGCC<br>TGGTATCAGCAAAAACCAGGGAAAGCCCCTAAGCTCCT<br>GATCTATGCTGCATCCACTTTGCAAAGTGGGGTCCCAT<br>CAAGGTTCAGCGGCAGTGGATCTGGAACAGATTTCACT<br>CTCACCATCAGCAGTCTGGAACCTGAAGATTTTGCAAC<br>TTACTACTGTCAAGAGAGTTACAGTACCCCCTTCTTTA<br>CTTTCGGCCCTGGGACCAAAGTGGATATCAGACGAACT<br>GTGGCTGCACCATCTGTC | SEQ ID NO:77 |
| B06 VLC<br>Amino<br>Acid<br>Sequence | GVHSDIQMTQSPSFLSASVGDRVTTTCPASQGISSYLA<br>WYQQKPGKAPKLLIYAASTLQSGVPSRFSGSGSGTDFT<br>LTTSSLEPEDFATYYCQESYSTPFFTFGPGTKVDIRRT<br>VAAPSV | SEQ ID NO:78 |
| B06 VHC<br>Nucleic<br>Acid<br>Sequence | GAAGTTCAATTGTTAGAGTCTGGTGGCGGTCTTGTTCA<br>GCCTGGTGGTTCTTTACGTCTTTCTTGCGCTGCTTCCG<br>GATTCACTTTCTCTCAGTACTTTATGAAGTGGGTTCGC<br>CAAGCTCCTGGTAAAGGTTTGGAGTGGGTTTCTTCTAT<br>CTCTCCTTCTGGTGGCCTTACTCAGTATGCTGACTCCG<br>TTAAAGGTCGCTTCACTATCTCTAGAGACAACTCTAAG<br>AATACTCTCTACTTGCAGATGAACAGCTTAAGGGCTGA<br>GGACACTGCAGTCTACTATTGTGCGAGAGGTGGTATAG<br>AAGCACCTGGGTCCCCCTCTGACTACTGGGGCCAGGGA<br>ACCCTGGTCACCGTCTCAAGCGCCTCCACCAAGGGCCC<br>ATCGGTCTTCCCG | SEQ ID NO:79 |

TABLE 6-continued

Sequences of Exemplary Antibodies

| Antibody Sequence | Identifier |
|---|---|
| B06 VHC Amino Acid Sequence | EVQLLESGGGLVQPGGSLRLSCAASGFTFSQYFMKWVR QAPGKGLEWVSSISPSGGLTQYADSVKGRFTISRDNSK NTLYLQMNSLRAEDTAVYYCARGGIEAPGSPSDYWGQG TLVTVSSASTKGPSVFP | SEQ ID NO:80 |
| B07 VLC Nucleic Acid Sequence | GGCGTGCACTCTGACATCCAGATGACCCAGTCTCCAGC CACCCTGTCTTTGTCTCCAGGGGAAAGAGCCACCCTCT CCTGCAGGGCCAGTCAGAGTGTTAGCAGCTACTTAGCC TGGTACCAACAGAAACCTGGCCAGGCTCCCAGGCTCCT CATCTATGATGCATCCAACAGGGCCACTGGCATCCCAG CCAGGTTCAGTGGCAGTGGGTCTGGGACAGACTTCACT CTCACCATCAGCAGCCTAGAGCCTGAAGATTTTGCAGT TTATTACTGTCAGCAGCGTAGCAACTGGCCTCGGACTT TCGGCGGAGGGACCAAGGTGGAGATCAAACGAACTGTG GCTGCACCATCTGTC | SEQ ID NO:81 |
| B07 VLC Amino Acid Sequence | GVHSDIQMTQSPATLSLSPGERATLSCRASQSVSSYLA WYQQKPGQAPRLLIYDASNRATGIPARFSGSGSGTDFT LTISSLEPEDFAVYYCQQRSNWPRTFGGGTKVETKRTV AAPSV | SEQ ID NO:82 |
| B07 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTCAGTACCAGATGATTTGGGTTCGC CAAGCTCCTGGTAAAGGTTTGGAGTGGGTTTCTGTTAT CGTTCCTTCTGGTGGCATTACTAATTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGAGAGGTGGGGTAG AGGCAGTGGATAGTTCGTCGCCTGACTACTGGGGCCAG GGAACCCTGGTCACCGTCTCAAGCGCCTCCACCAAGGG CCCATCGGTCTTCCCG | SEQ ID NO:83 |
| B07 VHC Amino Acid Sequence | EVQLLESGGGLVQPGGSLRLSCAASGFTFSQYQMIWVR QAPGKGLEWVSVIVPSGGITNYADSVKGRFTISRDNSK NTLYLQMNSLRAEDTAVYYCARGGVEAVDSSSPDYWGQ GTLVTVSSASTKGPSVFP | SEQ ID NO:84 |
| B08 VLC Nucleic Acid Sequence | GGCGTGCACTCACAGAGCGAATTGACTCAGCCCCACTC TGTGTCGGGGTCTCCGGGGAAGACGGTAACCATCTCCT GCACCCGCAGCAGTGGCAGCATTGCCGGCAACTATGTG CAGTGGTACCAGCAGCGCCCGGGCAGTTCCCCCACCAC TGTGATCTATGAGGATAACAAAAGACCCTCTGGGGTCC CTGATCGGTTCTCTGGCTCCATCGACAGCTCCTCCAAC TCTGCCTCCCTCATCATCTCTGGACTGAAGACTGAGGA CGAGGCTGACTACTACTGTCATTCTTATGATACCAGCA ATCAGGTATTCGGCGGAGGGACCAAACTGACCGTCCTA GGTCAGCCCAAGGCTGCCCCCTCG | SEQ ID NO:85 |
| B08 VLC Amino Acid Sequence | GVHSQSELTQPHSVSGSPGKTVTISCTRSSGSIAGNYV QWYQQRPGSSPTTVIYEDNKRPSGVPDRFSGSIDSSSN SASLIISGLKTEDEADYYCHSYDTSNQVFGGGTKLTVL GQPKAAPS | SEQ ID NO:86 |
| B08 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTCGTTACATGATGAATTGGGTTCGC CAAGCTCCTGGTAAAGGTTTGGAGTGGGTTTCTGTTAT CTGGTCTTCTGGTGGCAAGACTCTTTATGCTGACTCCG TTAAAGGTCGCTTCACTATCTCTAGAGACAACTCTAAG AATACTCTCTACTTGCAGATGAAGAGCTTAAGGGCTGA GGACACTGCAGTCTACTATTGTGCGAGGGGTGGTTACA ACAACTACTACTACTCTATGGACGTCTGGGGCCAAGGG ACCACGGTCACCGTCTCAAGCGCCTCCACCAAGGGCCC ATCGGTCTTCCCG | SEQ ID NO:87 |
| B08 VHC Amino Acid Sequence | EVQLLESGGGLVQPGGSLRLSCAASGFTFSRYMMNWVR QAPGKGLEWVSVIWSSGGKTLYADSVKGRFTISRDNSK NTLYLQMKSLPAEDTAVYYCARGGYNNYYYSMDVWGQG TTVTVSSASTKGPSVFP | SEQ ID NO:88 |
| B10 VLC Nucleic Acid | GGCGTGCACTCTGACATCCAGATGACCCAGTCTCCTTC CTCCCTGTCTGCCTCTGTAGGAGACAGAGTCACCATCG CGTGCCGGACAAGTCAGAACGTTAATAGGTACCTGAAT | SEQ ID NO:89 |

TABLE 6-continued

Sequences of Exemplary Antibodies

| Antibody | Sequence | Identifier |
|---|---|---|
| Sequence | TGGTATCAACATAAACTCGGCCAGGCCCCTAAACTCCT GATCTACGGTGCAACCATTTTGCAGAGTGGGGTCCCAT CAAGGTTCCGTGGCAGTGGATCTGGGACAGATTTCATC CTCACCATCACCAATCTGCAACCTGAAGATTTTGCAGT TTACTACTGTCAACGACTTACAGTCCCCCACTGACGT TCGGCCAAGGGACCAAGGCGGAATTTAAAGGAACTGTG GCTGCACCATCTGTC | |
| B10 VLC Amino Acid Sequence | GVHSDIQMTQSPSSLSASVGDRVTIACRTSQNVNRYLN WYQHKLGQAPKLLIYGATTLQSGVPSRFRGSGSGTDFI LTITNLQPEDFAVYYCQQTYSPPLTFGQGTKAEFKGTV AAPSV | SEQ ID NO:90 |
| B10 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTTCTTACGCTATGATGTGGGTTCGC CAAGCTCCTGGTAAAGGTTTGGAGTGGGTTTCTTGGAT CGTTCCTTCTGGTGGCACTACTTTTTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGAGAGGCCTGTACC GGTGGGGCCAGGGAACCCTGGTCACCGTCTCAAGCGCC TCCACCAAGGGCCCATCGGTCTTCCCG | SEQ ID NO:91 |
| B10 VHC Amino Acid Sequence | EVQLLESGGGLVQPGGSLRLSCAASGFTFSSYANMWVR QAPGKGLEWVSWIVPSGGTTFYADSVKGRFTISRDNSK NTLYLQMNSLPAEDTAVYYCARGLYRWGQGTLVTVSSA STKGPSVFP | SEQ ID NO:92 |
| B11 VLC Nucleic Acid Sequence | GGCGTGCACTCACAGAGCGAATTGACTCAGCCACCCTC GGTGTCACTGGCCCCAGGACAGACGGCCAGGATTACCT GTGGGGGAAACAACATTGGAACTAAAAGTGTTCACTGG TACCAGCAGAAGCCAGGCCAGGCCCCTGTGCTGGTCGT CTATGATGACAGCGACCGGCCCTCAGGGATCCCTGAGC GATTCTCTGGCTCCAATTCTGGGAACACGGCCACCCTG ACCATCAGCAGGGTCGAAGCGGGGATGAGGCCGACTA TTATTGTCAGGTGTGGGATAGTGGTAGTGATCATCAGG TCTTCGGCGGAGGGACCAAGCTGACCGTCCTAGGTCAG CCCAAGGTTGCCCCCTCG | SEQ ID NO:93 |
| B11 VLC Amino Acid Sequence | GVHSQSELTQPPSVSLAPGQTARTTCGGNNIGTKSVHW YQQKPGQAPVLVVYDDSDRPSGIPERFSGSNSGNTATL TISRVEAGDEADYYCQVWDSGSDHQVFGGGTKLTVLGQ PKVAPS | SEQ ID NO:94 |
| B11 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTCCTTACTTTATGTTTTGGGTTCGC CAAGCTCCTGGTAAAGGTTTGGAGTGGGTTTCTTCTAT CGGTTCTTCTGGTGGCGATACTTCTTATGCTGACTCCG TTAAAGGTCGCTTCACTATCTCTAGAGACAACTCTNAG AATACTCTCTACTTGCAGATGAACAGCTTAAGGGCTGA GGACACTGCAGTCTACTATTGTGCGAGAGGCCTGTACC GGTGGGGCCAGGGAACCCTGGTCACCGTCTCAAGCGCC TCCACCAAGGGCCCATCGGTCTTCCCGCTAGCGCCC | SEQ ID NO:95 |
| B11 VHC Amino Acid Sequence | EVQLLESGGGLVQPGGSLRLSCAASGFTFSPYFMFWVR QAPGKGLEWVSSIGSSGGDTSYADSVKGRFTISRDNSz NTLYLQMNSLRAEDTAVYYCARGLYRWGQGTLVTVSSA STKGPSVFPLAP | SEQ ID NO:96 |
| B12 VLC Nucleic Acid Sequence | GGCGTGCACTCACAGAGCGCTTTGACTCAGCCACCCTC GGTGTCAGTGGCCCCAGGACAGACGGCCAGGATTTCCT GTGGGGGCGACAACATTGACACTAAAAATGTACAGTGG TACCAGCAGAGGCCAGGCCAGGCCCCTGTGCTGGTCGT CTATGATAATAGCGACCGGCCCTCAGCGATCCCTGAGC GATTCTCTGGCTCCAACTCTGGGACCACGGCCACCCTG ACCATCAGCAGGGTCGAGGCCGGGGATGAGGCCGACTA TTACTGTCAGGTGTTTGATGGTAGGAGTGATCATCCGG TGTTCGGCGGAGGGACCAAGCTGACCGTTCCTGGGTCA GCCCAAGGCTGCCCCCTC | SEQ ID NO:97 |

TABLE 6-continued

Sequences of Exemplary Antibodies

| Antibody Sequence | | Identifier |
|---|---|---|
| B12 VLC Amino Acid Sequence | GVHSQSALTQPPSVSVAPGQTARISCGGDNIDTKNVQW YQQRPGQAPVLVVYDNSDRPSAIPERFSGSNSGTTATL TISRVEAGDEADYYCQVFDGRSDHPVFGGGTKLTVPGS AQGCPL | SEQ ID NO:98 |
| B12 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTCTTTACGTTATGTATTGGGTTCGC CAAGCTCCTGGTAAAGGTTTGGAGTGGGTTTCTTATAT CTCTTCTTCTGGTGGCATTACTCATTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGAGAGGCTCTATTG TAGTAGTACCAGCTGCTATACGGAGCAACAACTGGTTC GACCCCTGGGGCCAGGGAACCCTGGTCACCGTCTCAAG CGCCTCCACCAAGGGCCCATCGGTCTTCCCG | SEQ ID NO:99 |
| B12 VHC Amino Acid Sequence | EVQLLESGGGLVQPGGSLRLSCAASGFTFSLYVMYWVR QAPGKGLEWVSYTSSSGGITHYADSVKGRFTISRDNSK NTLYLQMNSLRAEDTAVYYCARGSTVVVPAAIRSNNWF DPWGQGTLVTVSSASTKGPSVFP | SEQ ID NO:100 |
| C01 VLC Nucleic Acid Sequence | GGCGTGCACTCTGACATCCAGATGACCCAGTCTCCTTC CACCCTGTCTGCATCTGTAGGAGACAGAGTCACCATCA CTTGCCGGGCCAGTCAGAGTATTGGAAACTGGTTGGCC TGGTATCAGCAGAAACCAGGGGAAGCCCCTCACCTCCT GATCTATCAGGCGTCTAGTTTAGAAGGTGGGGTCCCAT CAAGGTTCAGCGGCAGTGGGTCTGGGACAAAATTCACT CTCAACATCAGCAGCCTGCAGCCTGATGACTTTGCAAC TTATTACTGCCAACAGTATAATTCTTATCGTACACTT TTGGCCAGGGGACCAAGCTGGACATCAAACGAACTGTG GCTGCACCATCTGTC | SEQ ID NO:101 |
| C01 VLC Amino Acid Sequence | GVHSDIQMTQSPSTLSASVGDRVTITCPASQSTGNWLA WYQQKPGEAPHLLIYQASSLEGGVPSRFSGSGSGTKFT LNISSLQPDDFATYYCQQYNSYSYTFGQGTKLDIKRTV AAPSV | SEQ ID NO:102 |
| C01 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTAATTACGGTATGTCTTGGGTTCGC CAAGCTCCTGGTAAAGGTTTGGAGTGGGTTTCTGTTAT CGGTCCTTCTGGTGGCATTACTATGTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGACCGGGTCTAGCA GTGGCTGGTACCCTAACTTTGACTACTGGGGCCAGGGA ACCCTGGTCACCGTCTCAAGCGCCTCCACCAAGGGCCC ATCGGTCTTCCCG | SEQ ID NO:103 |
| C01 VHC Amino Acid Sequence | EVQLLESGGGLVQPGGSLRLSCAASGFTFSNYGMSWVR QAPGKGLEWVSVIGPSGGTTMYADSVKGRFTISRDNSK NTLYLQMNSLRAEDTAVYYCATGSSSGWYPNFDYWGQG TLVTVSSASTKGPSVFP | SEQ ID NO:104 |
| C02 VLC Nucleic Acid Sequence | TTCTATTCTCACAGTGCACAAGACATCCAGATGACCCA GTCTCCATCCTCCCTGTCTGCATCTGTAGGAGATAGAG TCACCATCACTTGCCGGGCAAGTCAGACCATTAGCACC TATTTAGTTTGGTATCAGCAGAAACCCGAGAAAGCCCC TACGCTCCTGATCTCCGGTGCATCCACTTTGCAAAGTG GGGTCCCAAACAGGTTCAGAGGCAGTGGATCTGGGACA GACTTCACTCTCGCCATCTCCAGTCTTCAACCTGAAGA TTTTGCAACTTACTACTGTCAACAGAGTTACACTTCCC CTAGAACGTTCGGCCAAGGGACCAAGGTGGAPATCAAA CGAACTGTGGCTGCACCATCTGTC | SEQ ID NO:105 |
| C02 VLC Amino Acid Sequence | FYSHSAQDIQMTQSPSSLSASVGDRVTTTCRASQTIST YLVWYQQKPEKAPTLLISGASTLQSGVPNRFRGSGSGT DFTLAISSLQPEDFATYYCQQSYTSPRTFGQGTKVEIK RTVAAPSV | SEQ ID NO:106 |
| C02 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTCATTACTCTATGCGTTGGGTTCGC | SEQ ID NO:107 |

TABLE 6-continued

Sequences of Exemplary Antibodies

| Antibody | Sequence | Identifier |
|---|---|---|
| Sequence | CAAGCTCCTGGTAAAGGTTTGGAGTGGGTTTCTTATAT CGTTCCTTCTGGTGGCTTTACTCAGTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGAGAGGCACGCACC TCCCGGGGGTTGACTACTGGGGCCAGGGAACCCTGGTC ACCGTCTCAAGCGCCTCCACCAAGGGCCCATCGGTCTT CCCG | |
| C02 VHC Amino Acid Sequence | EVQLLESGGGLVQPGGSLRLSCAASGFTFSHYSMRWVR QAPGKGLEWVSYIVPSGGFTQYADSVKGRFTISRDNSK NTLYLQMNSLRAEDTAVYYCARGTHLPGVDYWGQGTLV TVSSASTKGPSVFP | SEQ ID NO:108 |
| C03 VLC Nucleic Acid Sequence | GGCGTGCACTCACAGAGCGCTTTGACTCAGCCACCCTC AGCGTCTGGCACCCCCGGGCAGAGGGTCACCATCTCTT GTTCTGGAAGCAACTCCAACATCGGAGGTAATATTGTA ATCTGGCTCCAGCAGCTCCCAGGAACGGCCCCCAAACT CATGATTTATGATGTCAGTGATCGGCCCTCAGGGGTCC CTGACCGATTCTCTGGCTCCAAGTCTGGCACCTCAGCC TCCCTGGCCATCAGTGGGCTCCAGTCTGAGGATGAGGC CGATTATTATTGTGCAGCCTGGGATGACAGCCTGAATG GTTGGGTGTTCGGCGGAGGGACCAAGCTGACCGTCCTA AGTCAGCCCAAGGCTGCCCCCTCG | SEQ ID NO:109 |
| C03 VLC Amino Acid Sequence | GVHSQSALTQPPSASGTPGQRVTISCSGSNSNIGGNIV IWLQQLPGTAPKLMIYDVSDRPSGVPDRFSGSKSGTSA SLATSGLQSEDEADYYCAAWDDSLNGWVFGGGTKLTVL SQPKAAPS | SEQ ID NO:110 |
| C03 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTCTTTACATGATGAAGTGGGTTCGC CAAGCTCCTGGTAAAGGTTTGGAGTGGGTTTCTGTTAT CTCTTCTTCTGGTGGCTATACTCAGTATGCTGACTCCG TTAAAGGTCGCTTCACTATCTCTAGAGACAACTCTAAG AATACTCTCTACTTGCAGATGAACAACTTAAGGGCTGA GGACACTGCAGTCTACTATTGTGCGAGAGGGTGGGACG TCTGGGGCAAAGGGACCACGGTCACCGTCTCPAGCGCC TCCACCAAGGGCCCATCGGTCTTCCCG | SEQ ID NO:111 |
| C03 VHC Amino Acid Sequence | EVQLLESGGGLVQPGGSLRLSCAASGFTFSLYMMKWVR QAPGKGLEWVSVISSSGGYTQYADSVKGRFTISRDNSK NTLYLQMNNLRAEDTAVYYCARGWDVWGKGTTVTVSSA STKGPSVFP | SEQ ID NO:112 |
| C04 VLC Nucleic Acid Sequence | GGCGTGCACTCACAGAGCGCTTTGACTCAGCCACCCTC AGCGTCTGGGACCCCCGGGCAGAGGGTCACCATCTCCT GTTCTGGAACCAGCTCCAACATCGGAAGTCATTATGTA TTCTGGTATCAGCAGCTCCCAGGAACGGCCCCCA~ACT CCTCATCCATAGGAATGATGAGCGGCCCTCAGGGGTCC CTGACCGCTTCTCTGGCTCCAAGTCTGGCACCTCCGCC TCCCTGGCCATCAGTGGCCTCCAGTCTGAGGATGAGGC TGATTATTACTGTGCTACGTGGGATGACAACCTAAATG GTCCGGTATTCGGCGGAGGGACCAAGCTGACCGGCCCT GGGTCAGCCCAAGGCTGCCCCCTC | SEQ ID NO:113 |
| C04 VLC Amino Acid Sequence | GVHSQSALTQPPSASGTPGQRVTISCSGTSSNIGSHYV FWYQQLPGTAPKLLIHRNDERPSGVPDRFSGSKSGTSA SLATSGLQSEDEADYYCATWDDNLNGPVFGGGTKLTGP GSAQGCPL | SEQ ID NO:114 |
| C04 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTATGTACTTTATGGTTTGGGTTCGC CAAGCTCCTGGTAAAGGTTTGGAGTGGGTTTCTTGGAT CGGTTCTTCTGGTGGCGAGACTCCTTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTCAAGAGGGTACAGCA GTGGCTGGTATGTAATGGGAGACTACTGGGGCCAGGGA ACCCTGGTCACCGTCTCAAGCGCCTCCACCAAGGGCCC ATCGGTCTTCCCG | SEQ ID NO:115 |

TABLE 6-continued

Sequences of Exemplary Antibodies

| Antibody | Sequence | Identifier |
|---|---|---|
| C04 VHC Amino Acid Sequence | EVQLLESGGGLVQPGGSLRLSCAASGFTFSMYFMVWVR QAPGKGLEWVSWIGSSGGETPYADSVKGRFTISRDNSK NTLYLQMNSLPAEDTAVYYCARGYSSGWYVMGDYWGQG TLVTVSSASTKGPSVFP | SEQ ID NO:116 |
| C05 VLC Nucleic Acid Sequence | GGCGTGCACTCACAGAGCGAATTGACTCAGCCACCCTC AGTGTCTGGGACCCCCGGGCAGAGGGTCACCATCTCTT GTTCTGGAAGCAGTTCCAACATCGGAAGTGAGTATGTG TACTGGTTCCAGCAGCTCCCAGGAACGGCCCCCAGACT CCTCATCTATAGGAATGATCAGCGGCCCTCAGGGGTCC CTGACCGATTCTCTGGCTCCAAGTCTGGCACCTCAGCC TCCCTGGCCATCAGTGGGCTCCGGTCCGAGGATGAGAC TGATTATTACTGTACAACATGGGATGACAGCCTGAGTG GTCCGGTGTTCGGCGGAGGGACCAAGCTGACCGTCCTA GGTCAGCCCAAGGCTGCCCCCTCG | SEQ ID NO:117 |
| C05 VLC Amino Acid Sequence | GVHSQSELTQPPSVSGTPGQRVTISCSGSSSNIGSEYV YWFQQLPGTAPRLLIYRNDQRPSGVPDRFSGSKSGTSA SLAISGLRSEDETDYYCTTWDDSLSGPVFGGGTKLTVL GQPKAAPS | SEQ ID NO:118 |
| C05 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTTCTTACCAGATGGATTGGGTTCGC CAAGCTCCTGGTA~AGGTTTGGAGTGGGTTTCTCGTAT CGTTCCTTCTGGTGGCGATACTACTTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGAGACATGTCTACT ATGATAGTAGTGATTATTCCCCAACCCGTTTGACTAC TGGGGCCAGGGAACCCTGGTCACCGTCTCAAGCGCCTC CACCAAGGGCCCATCGGTCTTCCCG | SEQ ID NO:119 |
| C05 VHC Amino Acid Sequence | EVQLLESGGGLVQPGGSLRLSCAASGFTFSSYQMDWVR QAPGKGLEWVSRIVPSGGDTTYADSVKGRFTISRDNSK NTLYLQMNSLRAEDTAVYYCARHVYYDSSDYFPNPFDY WGQGTLVTVSSASTKGPSVFP | SEQ ID NO:120 |
| C06 VLC Nucleic Acid Sequence | GGCGTGCACTCTGACATCCAGATGACCCAGTCTCCATC CTCCCTGTCTGCGTCTGTAGGAGACAGAGTCACCATCA CTTGCCGGGCGAGTCAGGGCATTAGCAATTATTTAGCC TGGTATCAGCAGAAACCAGGGAAAGTTCCTAAGCTCCT GATCTATCCTGCATCCACTTTGCAAAGTGGGGTCCCAT CAAGGTTCAGCGGCAGTGGATCTGGGACAGATTTCACT CTCACCATCAGCAGCCTGCAGCCTGAAGATTTTGCAAC TTATTATTGTCAACAGGCTGACAGTTTCCCGCCCACCT TCGGCGGAGGGACCACGGTGGAGATCAGACGAACTGTG GCTGCACCATCTGTC | SEQ ID NO:121 |
| C06 VLC Amino Acid Sequence | GVHSDIQMTQSPSSLSASVGDRVTITCRASQGISNYLA WYQQKPGKVPKLLIYPASTLQSGVPSRFSGSGSGTDFT LTISSLQPEDFATYYCQQADSFPPTFGGGTTVEIRRTV AAPSV | SEQ ID NO:122 |
| C06 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTTTTTACTTTATGTTTTGGGTTCGC CAAGCTCCTGGTAAAGGTTTGGAGTGGGTTTCTTATAT CGGTCCTTCTGGTGGCCCTACTAATTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGAGACATTACCCCA GGGAGTACCAGCTGCCCGGGTCGTTCGACCCCTGGGGC CAGGGAACCCTGGTCACCGTCTCAAGCGCCTCCACCAA GGGCCCATCGGTCTTCCCG | SEQ ID NO:123 |
| C06 VHC Amino Acid Sequence | EVQLLESGGGLVQPGGSLRLSCAASGFTFSYFMFWVR QAPGKGLEWVSYIGPSGGPTNYADSVKGRFTISRDNSK NTLYLQMNSLRAEDTAVYYCARHYPREYQLPGSFDPWG QGTLVTVSSASTKGPSVFP | SEQ ID NO:124 |
| C07 VLC Nucleic Acid | GGCGTGCACTCTGACATCCAGATGACCCAGTCTCCATC TTCCCTGTCTGCATCTGTAGGAGACAGAGTCACCATCA CTTGCCGGGCAAGTCAGAGTATTAGTAACATATTTAAAT | SEQ ID NO:125 |

TABLE 6-continued

Sequences of Exemplary Antibodies

| Antibody | Sequence | Identifier |
|---|---|---|
| Sequence | TGGTATCAGCAGAGACCAGGGAAGGCCCCTAAGCTCCT GATCTATGCTGCATCCAGTTTGGAAAGAGGGGTCCCAT CAAGGTTCAGTGGCAGTGGATCTGGGACAGATTTCACT CTCACCATCAGCAGTCTGCAATCTGAAGATTTTGCAAC TTACTACTGTCAACAGAGTTACAGTCCCCCTCCTCTCA CTTTCGGCGGAGGGACCAAACTAGAGATCAAACGAACT GTGGCTGCACCATCTGTC | |
| C07 VLC Amino Acid Sequence | GVHSDIQMTQSPSSLSASVGDRVTITCRASQSISNYLN WYQQRPGKAPKLLIYAASSLERGVPSRFSGSGSGTDFT LTISSLQSEDFATYYCQQSYSPPPLTFGGGTKLETKRT VAAPSV | SEQ ID NO:126 |
| C07 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTTATTACGTTATGATGTGGGTTCGC CAAGCTCCTGGTAAAGGTTTGGAGTGGGTTTCTGTTAT CCGTCCTTCTGGTGGCATTACTACTTATGCTGACTCCG TTAAAGGTCGCTTCACTATCTCTAGAGACAACTCTAAG AATACTCTCTACTTGCAGACGAACAGCTTAAGGGCTGA GGACACTGCAGTCTACTATTGTGCGAAAATCGACTACG GTGGTAACTCGTTCTACTTTGACTACTGGGGCCAGGGA ACCCTGGTCACCGTCTCAAGCGCCTCCACCAAGGGCCC ATCGGTCTTCCCG | SEQ ID NO:127 |
| C07 VHC Amino Acid Sequence | EVQLLESGGGLVQPGGSLRLSCAASGFTFSYYVMMWVR QAPGKGLEWVSVTRPSGGITTYADSVKGRFTISRDNSK NTLYLQTNSLRAEDTAVYYCAKIDYGGNSFYFDYWGQG TLVTVSSASTKGPSVFP | SEQ ID NO:128 |
| C08 VLC Nucleic Acid Sequence | GGCGTGCACTCTGACATCCAGATGACCCAGTCTCCACC CTCCCTGTCTGCATTAGTAGGGGACAGAGTCACCATCA CTTGCCGGGCAAGTCAGAGCATAAGCAGATATGTGAAT TGGTATCAGCAGAAACCAGGGAAAGCCCCTAAGGTCCT GATCTATGCTGCATCCATAGTAGAAAATGGGGTCCCAT CTAGGTTCAGTGGCAGTGGATCTGGGACAGATTTCAGT CTCACCATCAGCAGTCTGCAACCTGAAGATTTTGCAAC TTACTACTGTCAACAAACTTACAGTACTCCGCTCACTT TCGGCGGAGGGACCAAGCTGGCGATCAAACGAACTGTG GCTGCACCATCTGTC | SEQ ID NO:129 |
| C08 VLC Amino Acid Sequence | GVHSDIQMTQSPPSLSALVGDRVTITCRASQSISRYVN WYQQKPGKAPKVLIYAASIVENGVPSRFSGSGSGTDFS LTISSLQPEDFATYYCQQTYSTPLTFGGGTKLAIKRTV AAPSV | SEQ ID NO:130 |
| C08 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTTATTACGAGATGATGTGGGTTCGC CAAGCTCCTGGTAAAGGTTTGGAGTGGGTTTCTTCTAT CTCTCCTTCTGGTGGCCCTACTATGTATGCTGACTCCG TTAAAGGTCGCTTCACTATCTCTAGAGACAACTCTAAG AATACTCTCTACTTGCAGATGAACAGCTTAAGGGCTGA GGACACTGGAGTCTACTATTGTGCGAGAAAGATGGGGC GTGTAGGATATTGTAGTAGTACCAGCTGCTATCGGGAT GACTACTACGGTATGGACGTCTGGGGCCAAGGGACCAC GGTCACCGTCTCAAGCGCCTCCACCAAGGGCCCATCGG TCTTCCCG | SEQ ID NO:131 |
| C08 VHC Amino Acid Sequence | EVQLLESGGGLVQPGGSLRLSCAASGFTFSYYEMMWVR QAPGKGLEWVSSISPSGGPTMYADSVKGRFTISRDNSK NTLYLQMNSLPAEDTGVYYCARKMGRVGYCSSTSCYRD DYYGMDVWGQGTTVTVSSASTKGPSVFP | SEQ ID NO:132 |
| C09 VLC Nucleic Acid Sequence | GGCGTGCACTCTGACATCCAGATGACCCAGTCTCCAGG CACCCTGTCTTTGTCTCCAGGGGAAAGAGCAACCCTCT CCTGCAGGGCCAGTCAGAGTGTTAGCAGCACCTATTTA GCCTGGTACCAGCAGAAACCTGGCCAGGCTCCCAGGCT CCTCATCTCTGGTGCATCCAGCAGGGCCACTGGCATCC CAGACAGGTTCAGTGGCAGTGGGTCTGGGACAGACTTC ACTCTCACCATCAGCAGACTGGAGCCTGAAGATTTTGC AGTGTATTACTGTCAGCAGTATGGTAGCTCACCGTACA CTTTTGGCCAGGGGACCAAGCTGGAGATCAAACGAACT GTGGCTGCACCATCTGTC | SEQ ID NO:133 |

TABLE 6-continued

Sequences of Exemplary Antibodies

| Antibody | Sequence | Identifier |
|---|---|---|
| C09 VLC Amino Acid Sequence | GVHSDTQMTQSPGTLSLSPGEPATLSCRASQSVSSTYL AWYQQKPGQAPRLLTSGASSRATGIPDRFSGSGSGTDF TLTISRLEPEDFAVYYCQQYGSSPYTFGQGTKLEIKRT VAAPSV | SEQ ID NO:134 |
| C09 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTCAGTACTTTATGAATTGGGTTCGC CAAGCTCCTGGTAAAGGTTTGGAGTGGGTTTCTTATAT TTCTGGTGGCCGTACTCCTTATGCTGACTCCGTTAAAG GTCGCTTCACTATCTCTAGAGACAACTCTAAGAATACT CTCTACTTGCAGATGAACAGCTTAAGGGCTGAGGACAC TGCAGTCTACTATTGTGCGATCCTTCTGGGACCGAGCA GCTCCAATCACCCTTTCCTGGGGCCCTGGGGCCAGGGA ACCCTGGTCACCGTCTCAAGCGCCTCCACCAAGGGCCC ATCGCTCTTCCCGCTAGCGCCC | SEQ ID NO:135 |
| C09 VHC Amino Acid Sequence | EVQLLESGGGLVQPGGSLRLSCAASGFTFSQYFMNWVR QAPGKGLEWVSYISGGRTPYADSVKGRFTISRDNSKNT LYLQMNSLPAEDTAVYYCAILLGPSSSNHPFLGPWGQG TLVTVSSASTKGPSVFPLAP | SEQ ID NO:136 |
| C10 VLC Nucleic Acid Sequence | GGCGTGCACTCACAGAGCGAATTGACTCAGCCTGCCTC CGTGTCTGGGTCTCCTGGACAGTCGATCACCATCTCCT GCACTGGAACCAGCAGTGATGTTGGGAGTTATAACCTT GTCTCCTGGTACCAACAGCACCCAGGCAAAGCCCCCAA ACTCATGATTTATGAGGGCAGTAAGCGGCCCTCAGGGG TTTCTAATCGCTTCTCTGGCTCCAAGTCTGGCAACACG GCCTCCCTGACAATCTCTGGGCTCCAGGCTGAGGACGA GGCTGATTATTACTGCTGCTCATATGCAGGTAGTAGCA CTTATGTCTTCGGAACTGGGACCAAGGTCACCGTCCTA GGTCAGCCCAAGGCCAACCCCACT | SEQ ID NO:137 |
| C10 VLC Amino Acid Sequence | GVHSQSELTQPASVSGSPGQSITISCTGTSSDVGSYNL VSWYQQHPGKAPKLMIYEGSKRPSGVSNRFSGSKSGNT ASLTISGLQAEDEADYYCCSYAGSSTYVFGTGTKVTVL GQPKANPT | SEQ ID NO:138 |
| C10 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTGTTTACGTTATGATGTGGGTTCGC CAAGCTCCTGGTAAAGGTTTGGAGTGGGTTTCTGGTAT CGTTCCTTCTGGTGGCAAGACTCATTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGAGACCGGACTACG GTGGTAATTCGCGCCCCCTTGAGTACTGGGGCCAGGGA ACCCTGGTCACCGTCTCAAGCGCCTCCACCAAGGGCCC ATCGGTCTTCCCG | SEQ ID NO:139 |
| C10 VHC Amino Acid Sequence | EVQLLESGGGLVQPGGSLRLSCAASGFTFSVYVMMWVR QAPGKGLEWVSGIVPSGGKTHYADSVKGRFTISRDNSK NTLYLQMNSLRAEDTAVYYCARPDYGGNSRPLEYWGQG TLVTVSSASTKGPSVFP | SEQ ID NO:140 |
| C11 VLC Nucleic Acid Sequence | GGCGTGCACTCACAGAGCGAATTGACTCAGCCTCCCTC CGCGTCCGGGTCTCCTGGACAGTCAGTCACCATCTCCT GCACTGGAACCAGCAGTGACGTTGGTGGTTATAACTAT GTCTCCTGGTATCAACAACACCCAGACAAAGCCCCCAA ACTCCTGATTTATGAGGTCACTCAGCGGCCCTCAGGGG TCCCTGATCGCTTCTCTGGCTCCAGGTCTGGCAACACG GCCTCCCTGACCGTCTCTGGGCTCCAGGCTGAGGATGA GGCTGATTATTACTGCAGCTCATATGCAGGCAGGAACA ATCTTTATGTCTTCGGACCTGGGACCAAGGTCACCGTC CTAGGTCAGCCCAAGGCCAACCCCACT | SEQ ID NO:141 |
| C11 VLC Amino Acid Sequence | GVHSQSELTQPPSASGSPGQSVTISCTGTSSDVGGYNY VSWYQQHPDKAPKLLIYEVTQRPSGVPDRFSGSRSGNT ASLTVSGLQAEDEADYYCSSYAGRNNLYVFGPGTKVTV LGQPKANPT | SEQ ID NO:142 |
| C11 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTGAGTACCCTATGGGTGGGTTCGC CAAGCTCCTGGTAAAGGTTTGGAGTGGGTTTCTTGGAT | SEQ ID NO:143 |

TABLE 6-continued

Sequences of Exemplary Antibodies

| Antibody | Sequence | Identifier |
|---|---|---|
| | CTATCCTTCTGGTGGCAATACTGATTATGCTGACTCCG<br>TTAAAGGTCGCTTCACTATCTCTAGAGACAACTCTAAG<br>AATACTCTCTACTTGCAGATGAACAGCTTAAGGGCTGA<br>GGACACTGCAGTCTACTATTGTGCGATTCCCTATTGTA<br>GTAGTTCCAGCTGCCCCCTACACTGGGGCCAGGGAACC<br>CTGGTCACCGTCTCAAGCGCCTCCACCAAGGGCCCATC<br>GGTCTTCCCG | |
| C11 VHC Amino Acid Sequence | EVQLLESGGGLVQPGGSLRLSCAASGFTFSEYPMWWVR<br>QAPGKGLEWVSWTYPSGGNTDYADSVKGRFTISRDNSK<br>NTLYLQMNSLPAEDTAVYYCAIPYCSSSSCPLHWGQGT<br>LVTVSSASTKGPSVFP | SEQ ID NO:144 |
| C12 VLC Nucleic Acid Sequence | GGCGTGCACTCACAGAGCGAATTGACTCAGCCACCCTC<br>AGTGTCCGTGTCCCCAGCACAGACAGCCAGCATCACCT<br>GCTCTGGAGATAAATTGGGGGATAAATATGCTTGCTGG<br>TATCAGCAGAAGCCAGGCCAGTCCCCTGTACTGGTCAT<br>CTATGAAGATACCAAGCGGCCCTCAGGGATCCCTGAGC<br>GATTCTCTGGCTCCAATTCTGGGAACACAGCCACTCTG<br>ACCATCAGCGGGACCCAGGTTATGGATGAGGCTGACTA<br>TTACTGTCAGGTGTGGGACAGCAGCACTGCGGTATTCG<br>GCGGAGGGACCAAGCTGACCGTCCTGGGTCAGCCCAAG<br>GCTGCCCCCTCG | SEQ ID NO:145 |
| C12 VLC Amino Acid Sequence | GVHSQSELTQPPSVSVSPAQTASITCSGDKLGDKYACW<br>YQQKPGQSPVLVIYEDTKRPSGTPERFSGSNSGNTATL<br>TISGTQVMDEADYYCQVWDSSTAVFGGGTKLTVLGQPK<br>AAPS | SEQ ID NO:146 |
| D02 VLC Nucleic Acid Sequence | GGCGTGCACTCTGACATCCAGATGACCCAGTCTCCATC<br>CTTCCTGTCTGCATCTGTAGGAGACAGAGTCACCATCA<br>CTTGCCGGGCCAGTCAGGGCATTAGCACTTATTTAGCC<br>TGGTATCAGCAAAAACCAGCGAAAGCCCCTAAGGTCCT<br>CATCTATACTGCATCCACTTTGCAAAGTGGGGTCCCAT<br>CAAGGTTCAGCGGCAGTGGATCTGGGACAGAATTCACT<br>CTCACAATCAGCAGCCTGCAGCCTGAAGATTTTGCAAC<br>TTACTACTGTCAACAGAGTTACATTACCCCTCCGGAGG<br>TCACTTTCGGCCCTGGGACCAAAGTGGATATCAAACGA<br>ACTGTGGCTGCACCATCTGTC | SEQ ID NO:153 |
| D02 VLC Amino Acid Sequence | GVHSDIQMTQSPSFLSASVGDRVTTTCPASQGISTYLA<br>WYQQKPGKAPKVLIYTASTLQSGVPSRFSGSGSGTEFT<br>LTISSLQPEDFATYYCQQSYITPPEVTFGPGTKVDIKR<br>TVAAPSV | SEQ ID NO:154 |
| D02 VHC Nucleic Acid Sequence | GAAGTTCAATTGTTAGAGTCTGGTGGCGGTCTTGTTCA<br>GCCTGGTGGTTCTTTACGTCTTTCTTGCGCTGCTTCCG<br>GATTCACTTTCTCTTGGTACGATATGGCTTGGGTTCGC<br>CAAGCTCCTGGTAAAGGTTTGGAGTGGGTTTCTCGTAT<br>CGTTCCTTCTGGTGGCCATACTTCTTATGCTGACTCCG<br>TTAAAGGTCGCTTCACTATCTCTAGAGACAACTTTAAG<br>AATACTCTCTACTTGCAGATGAACAGCTTAAGGGCTGA<br>GGACACTGCAGTCTACTATTGTGCGAGAAGGGCAAGTC<br>GTCCTGAGTTTTTTGACTACTGGGGCCAGGGAGCCCTG<br>GTCACCGTCTCAAGCGCCTCCACCAAGGGCCCATCGGT<br>CTTCCCG | SEQ ID NO:155 |
| D02 VHC Amino Acid Sequence | EVQLLESGGGLVQPGGSLRLSCAASGFTFSWYDMAWVR<br>QAPGKGLEWVSRTVPSGGHTSYADSVKGRFTISRDNFK<br>NTLYLQMNSLPAEDTAVYYCARRASRPEFFDYWGQGAL<br>VTVSSASTKGPSVFP | SEQ ID NO:156 |
| D03 VLC Nucleic Acid Sequence | GGCGTGCACTCTGACATCCAGATGACCCAGTCTCCATC<br>TGCCATGTCTGCATCTGTCGGAGACAGAGTCACCATCA<br>CTTGTCGGGCGAGTCAGGTCATGATCAATTATATAGCC<br>TGGTTTCGGCAGAAACCAGGGAAAGTCCCTGAGCGCCT<br>GATCTATGCAGCATCCACTCTGCAAAATGGGGTCCCAT<br>CAAGGTTCAGCGGCAGTGGGTCTGGGACAGACTTCACT<br>CTCACCATCAGCAGACTAGAACCTGAGGATTTTGCAGT<br>TTATTACTGTCAGCACCGTATCACCTGGCCTCCGGCGC<br>TCACTTTCGGCGGAGGGACCACGGTGGAGATCAAACGA<br>ACTGTGGCTGCACCATCTGTC | SEQ ID NO:157 |

TABLE 6-continued

Sequences of Exemplary Antibodies

| Antibody | Sequence | Identifier |
|---|---|---|
| D03 VLC Amino Acid Sequence | GVHSDIQMTQSPSAMSASVGDRVTITCPASQVMINYTA WFRQKPGKVPERLIYAASTLQNGVPSRFSGSGSGTDFT LTISRLEPEDFAVYYCQHRITWPPALTFGGGTTVETKR TVAAPSV | SEQ ID NO:158 |
| D03 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTTGGTACCGTATGGATTGGGTTCGC CAAGCTCCTGGTAAAGGTTTGGAGTGGGTTTCTGTTAT CGGTTCTTCTGGTGGCATGACTTATTATGCTGACTCCG TTAAAGGTCGCTTCACTATCTCTAGAGACAACTCTAAG AATACTCTCTACTTGCAGATGAACAGCTTAAGGGCTGA GGACACTGCAGTCTACTATTGTGCGAGACGGGTAGTCG GGGGCGCCGGTATGGACGTCTGGGGCCAAGGGACCACG GTCACCGTCTCAAGCGCCTCCACCAAGGGCCCATCGGT CTTCCCG | SEQ ID NO:159 |
| D03 VHC Amino Acid Sequence | EVQLLESGGGLVQPGGSLRLSCAASGFTFSWYRMDWVR QAPGKGLEWVSVIGSSGGMTYYADSVKGRFTTSRDNSK NTLYLQMNSLPAEDTAVYYCARRVVGGAGMDVWGQGTT VTVSSASTKGPSVFP | SEQ ID NO:160 |
| D04 VLC Nucleic Acid Sequence | GGCGTGCACTCTGACATCCAGATGACCCAGTCTCCATC CTCCCTGTCTGCATCTGTGGGAGACAGAGTCGCCATCA CTTGCCGCGCAAGTCAGAGCATCGACACCTATTTAAAT TGGTATCAGCAGAAACCAGGGAAAGCCCCTAAACTCCT GATCTATGCTGCATCCAAGTTGGAAGACGGGGTCCCAT CAAGATTCAGTGGCAGTGGAACTGGGACAGATTTCACT CTCACCATCAGAAGTCTGCAACCTGAAGATTTTGCAAG TTATTTCTGTCAACAGAGCTACTCTAGTCCAGGGATCA CTTTCGGCCCTGGGACCAAGGTGGAGATCAAACGAACT GTGGCTGCACCATCTGTC | SEQ ID NO:161 |
| D04 VLC Amino Acid Sequence | GVHSDIQMTQSPSSLSASVGDRVAITCRASQSIDTYLN WYQQKPGKAPKLLIYAASKLEDGVPSRFSGSGTGTDFT LTIRSLQPEDFASYFCQQSYSSPGITFGPGTKVEIKRT VAAPSV | SEQ ID NO:162 |
| D04 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTGATTACCAGATGATGTGGGTTCGC CAAGCTCCTGGTAAAGGTTTGGAGTGGGTTTCTCGTAT CTCTCCTTCTGGTGGCATGACTCGTTATGCTGACTCCG TTAAAGGTCGCTTCACTATCTCTAGAGACAACTCTAAG AATACTCTCTACTTGCCGATGAACAGCTTAAGGGCTGA GGACACTGCAGTCTACTATTGTGCGAGATCGGGGCCGT ACTACTTTGACTACTGGGGCCAGGGAACCCTGGTCACC GTCTCAAGCGCCTCCACCAAGGGCCCATCGGTCTTCCC G | SEQ ID NO:163 |
| D04 VHC Amino Acid Sequence | EVQLLESGGGLVQPGGSLRLSCAASGFTFSDYQMMWVR QAPGKGLEWVSRISPSGGMTRYADSVKGRFTISRDNSK NTLYLPMNSLRAEDTAVYYCARSGPYYFDYWGQGTLVT VSSASTKGPSVFP | SEQ ID NO:164 |
| D05 VLC Nucleic Acid Sequence | GGCGTGCACTCACAGAGCGTCTTGACTCAGCCTGACTC CGTGTCTGGGTCTCCTGGGCAGTCGATCACCATCTCCT GCACTGGCAGCAGTCATGACATTGGTTCCTATGACTAT GTCTCCTGGTATCAGCACCACCCAGGGAAAGCCCCCAA ATTCATACTTTATGATGTCTATAATCGGCCCTCAGGTG TTTCTGATCGCTTCTCTGGCTCCAAGTCTGGCAACACG GCCTCCCTGACTATCTCTGGGCTCCAGCCTGACGACGA GGCTGACTATTTTGTATGTCCTATACAATCACAACGC TTCTCTTCGGAACTGGGACCAGGGTCACCGTCCTGAGT CAGCCCAAGGCCAACCCCACT | SEQ ID NO:165 |
| D05 VLC Amino Acid Sequence | GVHSQSVLTQPDSVGSPGQSITISCTGSSHDIGSYDY VSWYQHHPGKAPKFILYDVYNRPSGVSDRFSGSKSGNT ASLTISGLQPDDEADYFCMSYTITTLLFGTGTRVTVLS QPKANPT | SEQ ID NO:166 |
| D05 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTCATTACAATATGGCTTGGGTTCGC | SEQ ID NO:167 |

TABLE 6-continued

Sequences of Exemplary Antibodies

| Antibody | Sequence | Identifier |
|---|---|---|
| Sequence | CAAGCTCCTGGTAAAGGTTTGGAGTGGCTTTCTCGTAT<br>CCGTTCTTCTGGTGGCCTTACTGTTTATGCTGACTCCG<br>TTAAAGGTCGCTTCACTATCTCTAGAGACAACTCTAAG<br>AATACTCTCTACTTGCAGATGAACAGCTTAAGGGCTGA<br>GGACACTGCAGTCTACTATTGTGCGAGAGTGGCTGGCC<br>CTGGGTACTGGGGCCAGGGAACCCTGGTCACCGTCTCA<br>AGCGCCTCCACCAAGGGCCCATCGGTCTTCCCG | |
| D05 VHC<br>Amino<br>Acid<br>Sequence | EVQLLESGGGLVQPGGSLRLSCAASGFTFSHYNMAWVR<br>QAPGKGLEWVSRIRSSGGLTVYADSVKGRFTISRDNSK<br>NTLYLQMNSLPAEDTAVYYCARVAGPGYWGQGTLVTVS<br>SASTKGPSVFP | SEQ ID NO:168 |
| D06 VLC<br>Nucleic<br>Acid<br>Sequence | GGCGTGCACTCTGACATCCAGATGACCCAGTCTCCATC<br>CTCCCTGTCTGCATCTGTAGGAGACAGAGTCACTATCA<br>CTTGCCGGACAAGTCAAATCATTAACACCTATTTAAAT<br>TGGTATCAACAAAAACCGGGAAAAGCCCCTAAACTCCT<br>GATCTATGCTGCCTCCACTTTACAGGGTGGGGTCCCGT<br>CAAGATTCAGTGGCAGTGGATCCGGGACAGACTTCACT<br>CTCACCATCAAGAGTCTGCAACCTGACGACTTTGCAAC<br>TTACTATTGTCAACAGAGTTATACTTCCCCGCGAACAT<br>TCGGCCAAGGGACCAAGGTGGAAATCAAACGAACTGTG<br>GCTGCACCATCTGTC | SEQ ID NO:169 |
| D06 VLC<br>Amino<br>Acid<br>Sequence | GVHSDTQMTQSPSSLSASVGDRVTITCRTSQIINTYLN<br>WYQQKPGKAPKLLIYAASTLQGGVPSRFSGSGSGTDFT<br>LTIKSLQPDDFATYYCQQSYTSPRTFGQGTKVEIKRTV<br>AAPSV | SEQ ID NO:170 |
| D06 VHC<br>Nucleic<br>Acid<br>Sequence | GAAGTTCAATTGTTAGAGTCTGGTGGCGGTCTTGTTCA<br>GCCTGGTGGTTCTTTACGTCTTTCTTGCGCTGCTTCCG<br>GATTCACTTTCTCTGGTTACATTATGGAGTGGGTTCGC<br>CAAGCTCCTGGTAAAGGTTTGGAGTGGGTTTCTGTTAT<br>CGTTTCTTCTGGTGGCTTTACTATGTATGCTGACTCCG<br>TTAAAGGTCGCTTCACTATCTCTAGAGACAACTCTAAG<br>AATACTCTCTACTTGCAGATGAACAGCTTAAGGGCTGA<br>GGACACTGCAGTCTACTATTGTGCGAGAGTTGGGGATT<br>CCAAGGGCGGGTACTACCTTGACTACTGGGGCCAGGGA<br>ACCCTGGTCACCGTCTCAAGCGCCTCCACCAAGGGCCC<br>ATCGGTCTTCCCGCTAGCGCCC | SEQ ID NO:171 |
| D06 VHC<br>Amino<br>Acid<br>Sequence | EVQLLESGGGLVQPGGSLRLSCAASGFTFSGYIMEWVR<br>QAPGKGLEWVSVIVSSGGFTMYADSVKGRFTISRDNSK<br>NTLYLQMNSLRAEDTAVYYCARVGDSKGGYYLDYWQG<br>TLVTVSSASTKGPSVFPLAP | SEQ ID NO:172 |
| D07 VLC<br>Nucleic<br>Acid<br>Sequence | GGCGTGCACTCACAGAGCGAATTGACTCAGCCTGCCTC<br>CGTGTCTGGGTCTCCTGGACAGTCGATCACCATCTCCT<br>GCACTGGACCAACAGTGACATTGGTGGTTATAATTAT<br>GTCTCCTGGTACCAACAACACCCGGGCAAAGTCCCCAA<br>ACTCTTGATTTTTGAGGTCAATAATCGGCCCTCAGGGG<br>TTTCTAGTCGCTTCTCTGGCTCCAAGTCTGGCGACACG<br>GCCTCCCTGACCATCTCTGGGCTCCAACCTGAGGACGA<br>GGCTGTTTATTACTGCGGCTCATTTACAGTCAGCGTCA<br>CCTATGTCTTCGGAACTGGGACCAAGGTCACCGTCCTG<br>GGTCAGCCCAAGGCCAACCCCACT | SEQ ID NO:173 |
| D07 VLC<br>Amino<br>Acid<br>Sequence | GVHSQSELTQPASVSGSPGQSITISCTGTNSDIGGYNY<br>VSWYQQHPGKVPKLLIFEVNNRPSGVSSRFSGSKSGDT<br>ASLTISGLQPEDEAVYYCGSFTVSVTYVFGTGTKVTVL<br>GQPKANPT | SEQ ID NO:174 |
| D07 VHC<br>Nucleic<br>Acid<br>Sequence | GAAGTTCAATTGTTAGAGTCTGGTGGCGGTCTTGTTCA<br>GCCTGGTGGTTCTTTACGTCTTTCTTGCGCTGCTTCCG<br>GATTCACTTTCTCTGAGTACAATATGTTTTGGGTTCGC<br>CAAGCTCCTGGTAAAGGTTTGGAGTGGGTTTCTTATAT<br>CTATTCTTCTGGTGGCTCTACTGATTATGCTGACTCCG<br>TTAAAGGTCGCTTCACTATCTCTAGAGACAACTCTAAG<br>AATACTCTCTACTTGCAGATGAACAGCTTAAGGGCTGA<br>GGACACTGCAGTCTACTATTGTGCGAGAGTAGGTATAG<br>CAGCTCGTCCGTTCGACCCCTGGGGCAGGGAACCCTG<br>GTCACCGTCTCAAGCGCCTCCACCAAGGGCCCATCGGT<br>CTTCCCGCTAGCGCCCTG | SEQ ID NO:175 |

TABLE 6-continued

Sequences of Exemplary Antibodies

| Antibody | Sequence | Identifier |
|---|---|---|
| D07 VHC Amino Acid Sequence | EVQLLESGGGLVQPGGSLRLSCAASGFTFSEYNMFWVR QAPGKGLEWVSYIYSSGGSTDYADSVKGRFTISRDNSK NTLYLQMNSLRAEDTAVYYCARVGIAARPFDPWGQGTL VTVSSASTKGPSVFPLAP | SEQ ID NO:176 |
| D08 VLC Nucleic Acid Sequence | GGCGTGCACTCTGACATCCAGATGACCCAGTCTCCATC CTCCCTGTCTGCATCTGTAGGAGACAGAGTCACCATCA CTTGCCGGGCAAGTCAGAGCATTAGCGACTATTTAAAT TGGTATCAGCAGAAACCAGGGAAAGCCCCTGACCTCCT GATCTATGCTGCATCCAGTTTGCAAAGTGGGGTCCCAT CAAGGTTCAGTGGCAGTGGATCTGGGACAGATTTCACT CTCACCGTCAGCAGTCTGCAACCTGAAGATTTTGCAAC TTACTTCTGTCAACAGAGTTACTCTATTCCTCTCACTT TCGGCGGCGGGACCAAGGTTGAGATCACTCGAACTGTG GCTGCACCATCTGTC | SEQ ID NO:177 |
| D08 VLC Amino Acid Sequence | GVHSDIQMTQSPSSLSASVGDRVTITCRASQSISDYLN WYQQKPGKAPDLLIYAASSLQSGVPSRFSGSGSGTDFT LTVSSLQPEDFATYFCQQSYSIPLTFGGGTKVEITRTV AAPSV | SEQ ID NO:178 |
| D08 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTTTTTACGCTATGTGGTGGGTTCGC CAAGCTCCTGGTAAAGGTTTGGAGTGGGTTTCTCGTAT CTATTCTTCTGGTGGCAAGACTTGGTATGCTGACTCCG TTAAAGGTCGCTTCACTATCTCTAGAGACAACTCTAAG AATACTCTACTTGCAGATGAACAGCTTAAGGGCTGA GGACACTGCAGTCTACTATTGTGCGAGAGTGGGGATGT CCACCTATGCTTTTGATATCTGGGGCCAAGGGACAATG GTCACCGTCTCAAGCGCCTCCACCAAGGGCCCATCGGT CTTCCCG | SEQ ID NO:179 |
| D08 VHC Amino Acid Sequence | EVQLLESGGGLVQPGGSLRLSCAASGFTFSFYAMWWVR QAPGKGLEWVSRIYSSGGKTWYADSVKGRFTISRDNSK NTLYLQMNSLRAEDTAVYYCARVGMSTYAFDIWGQGTM VTVSSASTKGPSVFP | SEQ ID NO:180 |
| D09 VLC Nucleic Acid Sequence | GGCGTGCACTCACAGAGCGAATTGACTCAGCCACCCTC AGTGTCCGTGTCCCCAGGACAGACAGCCAGCATCACCT GCTCTGGAGATAAATTGGGGGATAAATATGCTTGCTGG TATCAGCAGAAGCCAGGCCAGTCCCCTGTGCTGGTCAT CTATCAAGATAGCAAGCGGCCCTCAGGGATCCTGAGC GATTCTCTGGCTCCAACTCTGGGAACACAGCCACTCTG ACCATCAGCGGGACCCAGGCTATGGATGAGGCTGACTA TTACTGTCAGGCGTGGGACAGCAGCGCTGTGGTATTCG GCGGAGGGACCAAGCTGACCGTCCTAGGTCAGCCCAAG GCTGCCCCCTCG | SEQ ID NO:181 |
| D09 VLC Amino Acid Sequence | GVHSQSELTQPPSVSVSPGQTASITCSGDKLGDKYACW YQQKPGQSPVLVIYQDSKRPSGIPERFSGSNSGNTATL TISGTQAMDEADYYCQAWDSSAVVFGGGTKLTVLGQPK AAPS | SEQ ID NO:182 |
| D09 VHC Nucleic Acid Sequence | GAAGTTCAATTGTTAGAGTCTGGTGGCGGTCTTGTTCA GCCTGGTGGTTCTTTACGTCTTTCTTGCGCTGCTTCCG GATTCACTTTCTCTCATTACAATATGCATTGGGTTCGC CAAGCTCCTGGTAAAGGTTTGGAGTGGGTTTCTGGTAT CGTTTCTTCTGGTGGCAATACTGGTTATGCTGACTCCG TTAAAGGTCGCTTCACTATCTCTAGAGACAACTCTAAG AATACTCTACTTGCAGATGAACAGCTTAAGGGCTGA GGACACTGCAGTCGACTATTGTGCGAGAGTGGTACGGT ATAGCAGTGGCTGGTACTACTGGTTCGACCCCTGGGGC CAGGGAACCCTGGTCACCGTCTCAAGCGCCTCCACCAA GGGCCCATCGGTCTTCCCG | SEQ ID NO:183 |
| D09 VHC Amino Acid Sequence | EVQLLESGGGLVQPGGSLRLSCAASGFTFSHYNNHWVR QAPGKGLEWVSGIVSSGGNTGYADSVKGRFTISRDNSK NTLYLQMNSLRAEDTAVDYCARVVRYSSGWYYWFDPWG QGTLVTVSSASTKGPSVFP | SEQ ID NO:184 |

A sequence analysis of the CDRs of the light and heavy chain variable regions has identified a number of consensus motifs amongst the MMP-26-antibodies. We have separated these clones into two groups: Group I ("Inhibitory Fab's"): Fab's that bind MMP-26 and inhibit invasion of JEG-3 cells through MATRIGEL™ basement membrane matrix; and Group II ("Non-inhibitory Fab's"): Fab's that bind MMP-26 but do not substantially inhibit invasion of JEG-3 cells through MATRIGEL™ basement membrane matrix.

At least some members of Group I HC can include one of the following sequences in the region of CDR2:

R-I-X-(SP)-S-G-G-X-T, (SEQ ID NO:264)

R-I-X-(SP)-S-G-G-X-T-X-Y-A-D-S-V-K-G, (SEQ ID NO:185)

TABLE 7

Group I (Inhibitors) HC

| HCs Name | | Column 1 CDR1 | Column 2 CDR2 | Column 3 CDR3 | 4 Type |
|---|---|---|---|---|---|
| a01 | (SEQ ID NO:16) | AYNMF | GIGSSGGIAPYADSVKG | AAYEVENWFDP | H |
| a04 | (SEQ ID NO:24) | EYNMA | RIGSSGGKTKYADSVKG | DEAPDYGDDAEAFDI | H |
| a11 | (SEQ ID NO:52) | WYTMM | RISPSGGHTLYADSVKG | DTWDDYYDSSGYYNDFDY | H |
| b04 | (SEQ ID NO:74) | FYWMM | GISSSGGFTKYADSVKG | ETSRRAFDI | H |
| b06 | (SEQ ID NO:80) | QYFMK | SISPSGGLTQYADSVKG | GGIEAPGSPSDY | H |
| b10 | (SEQ ID NO:92) | SYAMM | WIVPSGGTTFYADSVKG | GLYR | H |
| c01 | (SEQ ID NO:104) | NYGMS | VIGPSGGITMYADSVKG | GSSSGWYPNFDY | H |
| c04 | (SEQ ID NO:116) | MYFMV | WIGSSGGETPYADSVKG | GYSSGWYVMGDY | H |
| c05 | (SEQ ID NO:120) | SYQMD | RIVPSGGDTTYADSVKG | HVYYDSSDYFPNPFDY | H |
| c08 | (SEQ ID NO:132) | YYEMM | SISPSGGPTMYADSVKG | KMGRVGYCSSTSCYRDDYYGMDV | H |
| c11 | (SEQ ID NQ:144) | EYPMW | WIYPSGGNTDYADSVKG | PYCSSSSCPLH | H |
| c12 | (SEQ ID NO:148) | AYNMM | RIYPSGGYTLYADSVKG | QKLMIRAVRPFDY | H |
| d02 | (SEQ ID NO:156) | WYDMA | RIVPSGGHTSYADSVKG | RASRPEFFDY | H |
| d04 | (SEQ ID NO:164) | DYQMM | RISPSGGMTRYADSVKG | SGPYYFDY | H |
| d06 | (SEQ ID NO:172) | GYIME | VIVSSGGFTMYADSVKG | VGDSKGGYYLDY | H |
| d07 | (SEQ ID NO:176) | EYNMF | YIYSSGGSTDYADSVKG | VGIAARPFDP | H |
| d08 | (SEQ ID NO:180) | FYAMW | RIYSSGGKTWYADSVKG | VGMSTYAFDI | H |
| A1-orig | (SEQ ID NO:4) | YYRMS | SIGPSGGDTLYADSVKG | SFSSGPYYFDY | H |
| D6-orig | (SEQ ID NO:8) | MYSMR | SIYPSGGSTEYADSVKG | EGGENDY | H |
| H6-orig | (SEQ ID NO:12) | QYWMN | GIGPSGGITYYADSVKG | GEEDGYNSDY | H |

At least some members of Group I HC can include the following sequence in the region of CDR1:

$X_1$-Y-$X_3$-M-M, (SEQ ID NO:236)

or (ASMYWFEQ)-Y-(AWFNQ)-M-(ASMWF), (SEQ ID NO:237)

where "(ASMYWFEQ)" means that, in one embodiment, $X_1$ could be any of the amino-acid types given; "(AWFNQ)" means that $X_3$ could be any of the types listed; and "(ASMWF)" means that the final position of CDR1 could be any of Ala, Ser, Met, Trp, or Phe.

(GSVWR)-I-(GSVY)-(SP)-S-G-G-(SIFKDH)-T-(LMKDP), (SEQ ID NO:265)

or (GSVWR)-I-(GSVY)-(SP)-S-G-G-(SIFKDH)-T-(LMKDP)-Y-A-D-S-V-K-G. (SEQ ID NO:186)

At least some members of Group I HC can include the following sequence in the region of CDR3: F-D-I, e.g., A-F-D-I (SEQ ID NO:253). The CDR3 region can also include a di tyrosine, e.g., in addition to the tripeptide F-D-I.

TABLE 8

Group I (Inhibitors) LC

| Name | | CDR1 (column 1) | CDR2 (column 2) | CDR3 (column 3) | Type |
|---|---|---|---|---|---|
| a01 | (SEQ ID NO:14) | RASQIVRSTYLA | GTSSRAT | QRYGDSPPIT | K |
| b04 | (SEQ ID NO:22) | RASQGISKSLA | GAFSLES | QQANSFPLT | K |
| b06 | (SEQ ID NO:78) | RASQGISSYLA | AASTLQS | QESYSTPFFT | K |
| b10 | (SEQ ID NO:90) | RTSQNVNRYLN | GATILQS | QQTYSPPLT | K |
| c01 | (SEQ ID NO:102) | RASQSIGNWLA | QASSLEG | QQYNSYSYT | K |
| c08 | (SEQ ID NO:130) | RASQSISRYVN | AASIVEN | QQTYSTPLT | K |
| d02 | (SEQ ID NQ:154) | RASQGISTYLA | TASTLQS | QQSYITPPEVT | K |
| d04 | (SEQ ID NO:162) | RASQSIDTYLN | AASKLED | QQSYSSPGIT | K |
| d06 | (SEQ ID NO:170) | RTSQIINTYLN | AASTLQG | QQSYTSPRT | K |
| d08 | (SEQ ID NO:178) | RASQSISDYLN | AASSLQS | QQSYSIPLT | K |
| D6-orig | (SEQ ID NO:6) | RASQSIDTYLN | AASKLED | QQSYSSPGIT | K |
| a04 | (SEQ ID NO:22) | SGGYSNMGSNYAH | NNNQRPS | AAWDENLSGPV | L |
| a11 | (SEQ ID NO:50) | GGNNIGTKSVH | DDSDRPS | QVWDSGSDHQV | L |
| c05 | (SEQ ID NO:118) | SGSSSNIGSEYVY | RNDQRPS | TTWDDSLSGPV | L |
| c04 | (SEQ ID NO:114) | SGTSSNIGSHYVF | RNDERPS | ATWDDNLNGPV | K |
| c11 | (SEQ ID NO:142) | TGTSSDVGGYNYVS | EVTQRPS | SSYAGRNNLYV | L |
| c12 | (SEQ ID NO:146) | SGDKLGDKYAC | EDTKRPS | QVWDSSTAV | L |
| d07 | (SEQ ID NO:174) | TGTNSDIGGYNYVS | EVNNRPS | GSFTVSVTYV | L |
| A1-orig | (SEQ ID NO:2) | SGSSSNIGSHYVH | RNGQRPS | ATWDDSVL | L |
| H6-orig | (SEQ ID NO:10) | TGTSSDVGAYNYVS | EVNKRPS | NSYAGSNSLI | L |

(CDRs sequences are from corresponding sequences for the variable domain provided with sequence identifiers in Table 6 above)

At least some members of Group I LC κ sequences can include one of the following sequences in the region of CDR1:

(SEQ ID NO:187)
R-(AT)-S-Q-(GSI)-(IV)-(SDN)-(STR)-Y-L-(AN)-X, (SEQ ID NO:188)
R-(AT)-S-Q-(GSIN)-(IV)-(GSRDN)-(STRKDN)-(STYW)-(LVY)-(ALN)-A, (SEQ ID NO:189)
R-A-S-Q-(GS)-I-(SD)-(ST)-Y-L-(AN)-X, (SEQ ID NO:190)
R-A-S-Q-X-I-X-X-Y-L-N-X,
or (SEQ ID NO:191)
R-A-S-Q-(GSI)-(IV)-(GSRD)-(STRKDN)-(STYW)-(LVY)-(ALN)-A.

At least some members of Group I LC κ sequences can include one of the following sequences in the region of CDR2:

(SEQ ID NO:238)
(AG)-A-S-(STIK)-L-(EQ)-(GSD), (SEQ ID NO:239)
(AGTQ)-(AT)-(STF)-(STIK)-(LVR)-(AEQ)-(GSTDN),
or (SEQ ID NO:192)
A-A-S-X-L-(EDNQ).

At least some members of Group I LC κ sequences can include one of the following sequences in the region of CDR3:

(SEQ ID NO:193)
Q-Q-(STY)-(YN)-S-(ST)-P-(GLP)-(TI)-T,
or (SEQ ID NO:194)
Q-(REQ)-(ASTY)-(GYN)-(STID)-(STIYFP)-(SP)-(GLYFRP)-(TIFE)-(TV)-T.

At least some members of Group I LC λ sequences can include one of the following sequences in the region of CDR1:

S-G-X-S-S-X-X-G-S, (SEQ ID NO:195)
or

T-G-T-(SN)-S-D-(IV)-G-(AG)-Y-N-Y-V-S (SEQ ID NO:196)

At least some members of Group I LC λ sequences can include one of the following sequences in the region of CDR2:

(RDNE)-(VDN)-(GSTDN)-(KDNEQ)-R-P-S, (SEQ ID NO:240)
or (RE)-(VDN)-(TDN)-(KQ)-R-P-S. (SEQ ID NO:241)

At least some members of Group I LC λ sequences can include one of the following sequences in the region of CDR3:

(AQ)-(STV)-(YW)-(AD)-(GSD)-(SN)-(LVN)-(SN)-(GL)-P-V, (SEQ ID NO:242)
or

W-D-X-S-X-X-X-V. (SEQ ID NO:197)

TABLE 9

Group II HC

| HCs Name | | 1 CDR1 | 2 CDR2 | 3 CDR3 | 4 Type |
|---|---|---|---|---|---|
| a02 | (SEQ ID NO:296,297) | PYFMF | SIGSSGGDTSYADSVKG | GLYR | H |
| a03 | (SEQ ID NO:20) | IYSMD | SIYSSGGATRYADSVKG | CSWLQLVPMHP | H |
| a05 | (SEQ ID NO:28) | VYSMN | YIVPSGGNTPYADSVKG | DGAATVDLDY | H |
| a06 | (SEQ ID NO:32) | PYHMG | GIYPSGGWTNYADSVKG | DGYSSGWFRY | H |
| a07 | (SEQ ID NO:36) | EYNMM | VISPSGGGTLYADSVKG | DLNNSSPPDSNDAFDI | H |
| a08 | (SEQ ID NO:40) | VYDMP | VIYPSGGFTRYADSVKG | DPTIQLWAYYYGMDV | H |
| a09 | (SEQ ID NO:44) | WYDMY | SIYSSGGYTAYADSVKG | DRDPCSRTTCYNWFDP | H |
| a10 | (SEQ ID NO:48) | AYRMF | SIWPSGGTTSYADSVKG | DRGYDSSGYFDY | H |
| a12 | (SEQ ID NO:56) | AYWMD | VIYPSGGSTNYADSVKG | EGIAAAAPMDV | H |
| b01 | (SEQ ID NO:60) | TYDML | SISPSGGSTSYADSVKG | EKASDLSGTYSEALDH | H |
| b02 | (SEQ ID NO:64) | DYFMK | SIYPSGGPTKYADSVKG | ERSSGWYGYYYYGMDV | H |
| b03 | (SEQ ID NO:68) | PYEMQ | GIGSSGGDSVKG | ERVDCSGGGCGSYFDY | H |
| b05 | (SEQ ID NO:76) | EYWMP | RIYPSGGVTTYADSVKG | GGDYDFWSVQYYYYYMDV | H |
| b07 | (SEQ ID NO:84) | QYQMI | VIVPSGGITNYADSVKG | GGVEAVDSSSPDY | H |
| b08 | (SEQ ID NO:88) | RYMMN | VIWSSGGKTLYADSVKG | GGYNNYYYSMDV | H |
| b09 | (SEQ ID NO:298,297) | PYFMF | SIGSSGGDTSYADSVKG | GLYR | H |
| b11 | (SEQ ID NO:96) | PYFMF | SIGSSGGDTSYADSVKG | GLYR | H |
| b12 | (SEQ ID NO:100) | LYVMY | YISSSGGITHYADSVKG | GSIVVVPAAIRSNNWFDP | H |
| c02 | (SEQ ID NO:108) | HYSMR | YIVPSGGFTQYADSVKG | GTHLPGVDY | H |
| c03 | (SEQ ID NO:112) | LYMMK | VISSSGGYTQYADSVKG | GWDV | H |
| c06 | (SEQ ID NO:123) | FYFMF | YIGPSGGPTNYADSVKG | HYPREYQLPGSFDP | H |
| c07 | (SEQ ID NO:128) | YYVMM | VIRPSGGITTYADSVKG | IDYGGNSFYFDY | H |
| c09 | (SEQ ID NO:136) | QYFMN | YISGGRTPYADSVKG | LLGPSSSNHPFLGP | H |
| c10 | (SEQ ID NO:140) | VYVMM | GIVPSGGKTHYADSVKG | PDYGGNSRPLEY | H |
| d01 | (SEQ ID NO:152) | MYLMF | VISSSGGETSYADSVKG | QVSDWTRLYSFDY | H |
| d03 | (SEQ ID NO:160) | WYRMD | VIGSSGGMTYYADSVKG | RVVGGAGMDV | H |

TABLE 9-continued

| | Group II HC | | | |
|---|---|---|---|---|
| HCs Name | 1 CDR1 | 2 CDR2 | 3 CDR3 | 4 Type |
| d05 (SEQ ID NO:168) | HYNMA | RIRSSGGLTVYADSVKG | VAGPGY | H |
| d09 (SEQ ID NO:184) | HYNMH | GIVSSGGNTGYADSVKG | VVRYSSGWYYWFDP | H |

(CDRs sequences are from corresponding sequences for the variable domain provided with sequence identifiers in Table 6 above)

At least some members of Group II HC sequences can include one of the following sequences in the region of CDR1:

P-Y-F-M-F,                  (SEQ ID NO:202)
or
(ALVEP)-Y-(SMWFD)-M-(YFKDNP).  (SEQ ID NO:243)

At least some members of Group II HC sequences can include one of the following sequences in the region of CDR2:

(SV)-I-Y-(SP)-S-G-G-X-T-X-Y-A-D-S-V-K-G,  (SEQ ID NO:203)
or (GSVY)-I-(GSVYW)-(SP)-S-G-G-(SIYFD)-T-(SLRNQ)-Y-A-D-S-V-K-G.  (SEQ ID NO:204)

TABLE 10

| | Group II (LC) | | | |
|---|---|---|---|---|
| Kappas Name | 1 CDR1 | 2 CDR2 | 3 CDR3 | 4 type |
| a05 (SEQ ID NO:26) | RASQSVSSYLA | DASNRAT | QQRSNWPRT | K |
| a06 (SEQ ID NO:30) | RASQSISSYLN | AASSLQS | QQSYSTPPENT | K |
| a12 (SEQ ID NO:54) | RASQSVSRSYLG | GASNRAT | QQYGISPLT | K |
| b01 (SEQ ID NO:58) | RASQSVSSSYFA | DASSRAT | QQYGSSPPMYT | K |
| b02 (SEQ ID NO:62) | RASQSIDTYLN | AASKLED | QQSYSSPGIT | K |
| b03 (SEQ ID NO:66) | RASQGIRDFLG | AASILQS | QQLNGYRA | K |
| b05 (SEQ ID NO:74) | RASQSVSSSYLA | GASSRAT | QQYGSSPEIT | K |
| b07 (SEQ ID NO:82) | RASQSVSSYLA | DASNRAT | QQRSNWPRT | K |
| b12 (SEQ ID NO:98) | GGDNIDTKNVQ | DNSDRPS | QVFDGRSDHPV | K |
| c02 (SEQ ID NO:106) | RASQTISTYLV | GASTLQS | QQSYTSPRT | K |
| c06 (SEQ ID NO:122) | RASQGISNYLA | PASTLQS | QQADSFPPT | K |
| c07 (SEQ ID NO:126) | RASQSISNYLN | AASSLER | QQSYSPPPLT | K |
| c09 (SEQ ID NO:134) | RASQSVSSTYLA | GASSRAT | QQYGSSPYT | K |
| d03 (SEQ ID NO:158) | RASQVMINYIA | AASTLQN | QHRITWPPALT | K |
| a02 (SEQ ID NO:295) | GGNNIGTKSVH | DDSDRPS | QVWDSGSDHQV | L |
| a03 (SEQ ID NO:18) | SGGSSNIGSNFVY | RNYQRPS | AAWDDNVGGV | L |
| a07 (SEQ ID NO:34) | TGTSSDVGGYNYVS | EVTQRPS | SSYAGRNNLYV | L |
| a08 (SEQ ID NO:38) | SGGYPNMGSNYAH | NDNQRPS | AAWDDSLSGPV | L |
| a09 (SEQ ID NO:42) | SGGSSNIGSNFVY | RNYQRPS | AAWDDNVGGV | L |
| a10 (SEQ ID NO:46) | SGGSSNIGSNYVS | NNNQRPS | AAWDDSLSSAV | L |
| b08 (SEQ ID NO:86) | TRSSGSIAGNYVQ | EDNKRPS | HSYDTSNQV | L |

TABLE 10-continued

Group II (LC)

| Kappas Name | 1 CDR1 | 2 CDR2 | 3 CDR3 | 4 type |
|---|---|---|---|---|
| b09 (SEQ ID NO:299) | GGNNIGTKSVH | DDSDRPS | QVWDSGSDHQV | L |
| b11 (SEQ ID NO:94) | GGNNIGTKSVH | DDSDRPS | QVWDSGSDHQV | L |
| c03 (SEQ ID NO:110) | SGSNSNIGGNIVI | DVSDRPS | AAWDDSLNGWV | L |
| c10 (SEQ ID NO:138) | TGTSSDVGSYNLVS | EGSKRPS | CSYAGSSTYV | L |
| d01 (SEQ ID NO:150) | SGSSSNIGSNYVY | RNDQRPS | ASWDDSLSGVV | L |
| d05 (SEQ ID NO:166) | TGSSHDIGSYDYVS | YDVYNRPS | MSYTITTLL | L |
| d09 (SEQ ID ND:182) | SGDKLGDKYAC | QDSKRPS | QAWDSSAVV | L |

(CDRs sequences are from corresponding sequences for the variable domain provided with sequence identifiers in Table 6 above)

At least some members of Group II LC κ sequences can include one of the following sequences in the region of CDR1:

(SEQ ID NO:205)
R-A-S-Q-S-(IV)-S-(SN)-(SY)-(LY)-(ALN)-A,;

(SEQ ID NO:206)
R-A-S-Q-(GS)-(IV)-S-(STN)-(SY)-(LY)-(ALN)-A,;

(SEQ ID NO:207)
R-A-S-Q-S-(IV)-S-S-Y-L,;
or (SEQ ID NO:208)
R-A-S-Q,.

At least some members of Group II LC κ sequences can include one of the following sequences in the region of CDR2:

(SEQ ID NO:256)
(AGDP)-(AN)-S-(STIKDN)-(LR)-(AEPQ)-(STRDN), (SEQ ID NO:257)
(AGD)-A-S-(STN)-(LR)-(AEQ)-(ST), (SEQ ID NO:258)
(AGD)-A-S-(STN)-(LR)-(AQ)-(ST),
or (SEQ ID NO:259)
(AGD)-A-S-S-(LR)-(AQ)-(ST).

At least some members of Group II LC κ sequences can include one of the following sequences in the region of CDR3:

(SEQ ID NO:266)
Q-Q-X-X-X-X-P, (SEQ ID NO:267)
Q-Q-(SYR)-(GSYD)-(GSTN)-(SW)-P-(RP)-(TI)-T-T, (SEQ ID NO:268)
Q-Q-(SYR)-(GSY)-(SN)-(SW)-P-(RP)-(TI)-T-T,
or

-continued (SEQ ID NO:269)
Q-Q-(ASLYR)-(GSYDN)-(GSTIN)-(STYWFP)-(RP)-(AGLYREP)-(TILME)-(TYN)-T.

At least some members of Group II LC λ sequences can include one of the following sequences in the region of CDR1:

(SEQ ID NO:209)
S-G-X-S-S-N-I-G-S-N-X-V-X-X,;

(SEQ ID NO:233)
(GST)-G-(GSTN)-(SN)-(SI)-(GDN)-(TIV)-(GK)-(GS)-(VYN)-(YFNH)-(VY)-(VY)-S;

(SEQ ID NO:210)
(ST)-G-(GST)-S-S-(DN)-(IV)-G-(GS)-(YN)-(YFN)-(VY)-(VY)-S,;

(SEQ ID NO:234)
G-G-(SN)-(SN)-(ID)-(GI)-(GT)-(SK)-(SYN)-V-H,;
or (SEQ ID NO:235)
G-(GST)-(SN)-(SN)-(IDN)-(GIV)-(GST)-(SKN)-(SYN)-(VFN)-(VYH).

At least some members of Group II LC λ sequences can include one of the following sequences in the region of CDR2:

D-(DN)-S-(DQ)-R-P-S-X,; or (SEQ ID NO:233)

(RDNE)-(VDN)-(SYN)-(KDQ)-R-P-S-X. (SEQ ID NO:247)

Group II LC (e.g., κ or λ) can include one or more of the following sequences in the region of CDR2:

(SEQ ID NO:230)
D-(AD)-S-X-(LR)-(AP)-(ST), (SEQ ID NO:231)
(AD)-(ADN)-S-(SKDNQ)-(LR)-(APQ)-(ST),
or

-continued (AGRD)-(ADN)-(SYN)-(SKDNQ)-(LR)-(APQ)-(ST) (SEQ ID NO:232)

At least some members of Group II LC λ sequences can include one of the following sequences in the region of CDR3:

A-A-W-D-D-(SN)-(LV),; (SEQ ID NO:234)

(QA)-X-W-D-(SDT)-(GSN); (SEQ ID NO:248)
or (AQ)-(ASV)-(YW)-(AD)-(GSID)-(GSN)-(STLVN)-(GSDN)-(GSLVH)-(VQ)-V. (SEQ ID NO:249)

Fab's from Group I can be classified as described below:
Set 1: a04(lambda) and b04(kappa).
Set 2 includes a11, c05, A1-orig, d02, and d04.
Set 3 includes b10, c01, c08, d04, and d06.
Set 4 includes c11 and d07
Some features that may be present in inhibitors include:
Cons: I-G-P-S-G-G-I-T-X-Y-A-D-S-V-K-G (SEQ ID NO:294)

Where two or more antibodies share the property of inhibiting MMP-26 and have recognizable similarity in amino-acid sequence, particularly where the similarity occurs in more than one CDR, it is likely that the two antibodies bind related epitopes, e.g., they bind at essentially the same site. In this case it can be useful to recombine the sequences within a set.

Since a04 and b04 appear to have similar HCs, antibodies that include features of HC-a04/LC-b04 and HC-b04/LC-a04 are likely to also be inhibitors of MMP-26 and may have useful functional properties (e.g., match or surpass either or both parents in binding ability).

Since a11, c05, A1-orig, d02, and d04 have similarities, combinations involving one of these HCs with of these LCs, or combinations of features thereof, are likely to be inhibitors of MMP-26. Since a11, c05, and A1-orig all have lambda LCs, new light chains having the common lambda framework and all recombinations of the lambda CDRs coupled to each of the HCs are likely to give additional MMP-26 inhibitory antibodies, some of which may have useful functional properties. For example, a light chain comprising FR1(a11)-CDR1(a11)-FR2(a11)-CDR2(c05)-FR3(a11)-CDR3(A1-orig)-FR4(a11) could be combined with all of the HC of Set 2. Similarly, d02 and d04 show similarity in HC CDR2, HC CDR3, and kappa CDR1, new LCs having the kappa CDRs mixed between d02 and d04 when combined with any of the HC of Set 2 are likely to give antibodies that inhibit MMP-26. One can also exchange the HC CDRs to make additional antibodies that are likely to inhibit MMP-26.

Set 3 comprises b10, c01, c08, d04, and d06, all having kappa LCs. Combining each of these kappa chains with each of the HCs in set 3 will give new antibodies that are likely to inhibit MMP-26, some of which may have useful functional properties. One can make additional antibodies by exchanging the CDRs of the LC and HC within set 3.

Set 4 comprises c11 and d07 which have highly similar lambda chains. Exchanging LC and HCs gives two new antibodies that are likely to inhibit MMP-26. Exchanging CDRs gives rise to a further set of 120 antibodies which are likely to inhibit MMP-26.

EXAMPLE

With respect to each example below, there are related antibody variable domains whose amino acid sequence is encoded by a germline gene (e.g., the germline-encoded amino acid sequence aligned in the example or a related germline-encoded amino acid sequence) that can include one or more of the above mutations (e.g., at least 30, 50, 70, 75, 80, 85, 90, or 95% of the above mutations), e.g., one or more of the above mutations (e.g., at least 30, 50, 70, 75, 80, 85, 90, or 95%) of the mutations that are located in the CDRs.

The germline-encoded amino acid sequences referred to below are provided as:

| Name | SEQ ID NO: |
| --- | --- |
| A27 | 270 |
| V2-A14 | 271 |
| V2-A17 | 272 |
| L6 | 273 |
| O2 | 274 |
| V1-2 | 275 |
| L5 | 276 |
| V1-22 | 277 |
| L12 | 278 |
| V1-12 | 279 |
| V1-16 | 280 |
| A20 | 281 |
| V1-17 | 282 |
| L8 | 283 |
| L14 | 284 |
| V1-4 | 285 |
| V2-1 | 286 |
| V3-23 | 287 |

Name: A27 is related to VKIII

| Mutation | Location |
| --- | --- |
| E1D, V3Q, L4M | FR1 |
| S28I, S30R, S31aT | CDR1 |
| A51T | CDR2 |
| I58V, R77G, V85L | FR3 |
| Q90R, S93D | CDR3 |
| K107T | FR4 |

This is relative to the A27 VKIII germline sequence (SEQ ID NO:270).

Name: A02 (Same as A1 1) is related to V2-14 (VL2).

The sequence of the A02 light chain variable domain includes:

GVHSQSELTQ PPSVSLAPGQ TARITCGGNN IGTKSVHWYQ QKPGQAPVLV (SEQ ID NO:295)

VYDDSDRPSG IPERFSGSNS GNTATLTISR VEAGDEADYY CQVWDSGSDH

QVFGGGTKLT VLGQPKAAPS

| Mutation | Location |
|---|---|
| S1Q, Y2S, V3A, V13L | FR1 |
| S31aT | CDR1 |
| | FR2 |
| | CDR2 |
| | FR3 |
| S94G | CDR3 |
| | FR4 GLG for Q96 could be P or V |

Name: A03 is related to VI-17 (VL1).

| Mutation | Location |
|---|---|
| V3A | FR1 |
| S26G, Y32F | CDR1 |
| Q37R | FR2 |
| S50N, N52Y | CDR2 |
| R79L | FR3 |
| S95aG | CDR3 |
| T100S | FR4 G96 is GLG if from VL, but Y96G if from JL1 |

V97 is GLG if from JL1, but P97V if from VL

Name: A04 is related to V1-17.

| Mutation | Location |
|---|---|
| V3A | FR1 |
| S26G, S27Y, I30M, V33A, Y34H | CDR1 |
| L39V | FR2 |
| S50N | CDR2 |
| | FR3 |
| D93E, S94N | CDR3 |
| | FR4 |

P96 is GLG if from V1-17, but Y96P if from JL1.

Name: A05 is related to L6 (VKIII).

| Mutation | Location |
|---|---|
| E1D, V3Q, L4M, A9S, T10S | FR1 |
| | CDR1 |
| | FR2 |
| | CDR2 |
| | FR3 |
| | CDR3 |
| L96R | FR4 |

Name: A06 is related to O2 (VK1)

| Mutation | Location |
|---|---|
| | FR1 |
| | CDR1 |
| | FR2 |
| | CDR2 |
| | FR3 |
| | CDR3 |
| Y96N | FR4 |

Name: A07 is related to V1-2 (VL1).

| Mutation | Location |
|---|---|
| A3E | FR1 |
| | CDR1 |
| G41D, M47L | FR2 |
| S52T, K53Q | CDR2 |
| K66R | FR3 |
| S94R | CDR3 |
| T100P | FR4 |

Name: A08 is related to V1-17 (VL1).

| Mutation | Location |
|---|---|
| A11V | FR1 |
| S26G, S27Y, S28P, I30M, V33A, Y34H | CDR1 |
| | FR2 |
| S50N, N51D | CDR2 |
| | FR3 |
| | CDR3 |
| | FR4 P96 is GLG if from V1-17, P96 is V96P if from JL2 |

Name: A09 is related to V1-17 (VL1).

| Mutation | Location |
|---|---|
| V3E | FR1 |
| S26G, Y32F | CDR1 |
| Q37R | FR2 |
| S50R, N51aY | CDR2 |
| R79L | FR3 |
| S95aG | CDR3 |
| T100S | FR4 |

G96 is GLG if from V1-17, but G96 is Y96G if from JL1.

Name: A10 is related to V1-17 (VL1).

| Mutation | Location |
|---|---|
| V3E | FR1 |
| S26G, Y34S | CDR1 |
| S50N | CDR2 |
| G95bS | CDR3 |

P95cA is a mutation only if this came from VL, but A is GLG if this came from JL7.

Name: A11 is related to V2-14 (VL2).

| Mutation | Location |
|---|---|
| S1Q, Y2S, V3A, V13L | FR1 |
| S31aT | CDR1 |
| | FR2 |
| | CDR2 |
| | FR3 |
| S94G | CDR3 |
| | FR4 |

GLG for Q96 could be P or V.

Name: A12 is related to A27 (VKIII).

| Mutation | Location |
|---|---|
| E1D, V3Q, L4M | FR1 |
| S31R, A34G | CDR1 |
|  | FR2 |
| S53N | CDR2 |
|  | FR3 |
| S93I | CDR3 |
| F96L | FR4 |

Name: A1-O (same as a1-orig) is related to V1-17.

| Mutation | Location |
|---|---|
| T20I | FR1 |
| N31bH | CDR1 |
| Y34H |  |
| L39V | FR2 |
| S50R | CDR2 |
| N52G |  |
| S65F | FR3 |
| D85N |  |
| A90T | CDR3 |
| L95aV |  |
| S95bL |  |
| S95c |  |
| S95d |  |
| V96 | FR4 |
| V97 |  |

Name: B01 is related to A27.

| Mutation | Location |
|---|---|
| E1D | FR1 |
| V3Q |  |
| L4M |  |
| L33F | CDR1 |
|  | FR2 |
| G50D | CDR2 |
|  | FR3 |
|  | CDR3 |
|  | FR4 |

Name: B10 is related to O2.

| Mutation | Location |
|---|---|
| T22A | FR1 |
| A25T | CDR1 |
| S28N |  |
| I29V |  |
| S30N |  |
| S31R |  |
| Q38H | FR2 |
| P40L |  |
| K42Q |  |
| A50G | CDR2 |
| S52T |  |
| S53I |  |
| S63R | FR3 |
| T72I |  |

-continued

| Mutation | Location |
|---|---|
| S76T |  |
| S77N |  |
| T85V |  |
| S91T | CDR3 |
| T94P |  |
| -95aP |  |
| -95bL |  |
| W96- | FR4 |
| V104A |  |
| I106F |  |

Name: B11 is related to V2-14.

| Mutation | Location |
|---|---|
| 1SQ | FR1 |
| Y2S |  |
| V3E |  |
| V13L |  |
| S31aT | CDR1 |
|  | FR2 |
|  | CDR2 |
|  | FR3 |
|  | CDR3 |
| S94G |  |
| P95cQ |  |
| V96- | FR4 |

Name: B12 is related to V2-14.

| Mutation | Location |
|---|---|
| S1Q | FR1 |
| Y2S |  |
| V3A |  |
| T22S |  |
| N28D | CDR1 |
| G31D |  |
| S31aT |  |
| S32N |  |
| H33Q |  |
| K39R | FR2 |
| I48V |  |
| D51aN | CDR2 |
| G57A | FR3 |
| W91F | CDR3 |
| S93G |  |
| S94R |  |
| V96P | FR4 |

Name: B02 is related to O2.

| Mutation | Location |
|---|---|
| T20A | FR1 |
| S30D |  |
| S31T |  |
|  | CDR1 |
|  | FR2 |
| S53K | CDR2 |
| Q55E |  |
| S56D |  |
| S67T | FR3 |
| S76R |  |

-continued

| Mutation | Location |
|---|---|
| T85S | |
| Y87F | |
| T94S | CDR3 |
| .95aG | |
| F96I | FR4 |
| D105E | |

Name: B03 is related to L8.

| Mutation | Location |
|---|---|
| L4M | FR1 |
| S30R | CDR1 |
| S31D | |
| Y32F | |
| A34G | |
| K45N | FR2 |
| L46Q | |
| T53I | CDR2 |
| E70D | FR3 |
| S76T | |
| Y87F | |
| S93G | CDR3 |
| P95R | |
| .95aA | |
| I96. | FR4 |
| T97. | |

Name: B04 is related to L5.

| Mutation | Location |
|---|---|
| | FR1 |
| S31K | CDR1 |
| W32S | |
| I48V | FR2 |
| A50G | CDR2 |
| S52F | |
| Q55E | |
| S65T | FR3 |
| S67A | |
| T72I | |
| S77R | |
| | CDR3 |
| | FR4 |

Name: B05 is related to A27.

| Mutation | Location |
|---|---|
| E1D | FR1 |
| V3Q | |
| L4M | |
| | CDR1 |
| | FR2 |
| | CDR2 |
| | FR3 |
| .95aE | CDR3 |
| | FR4 |

Name: B06 is related to L8.

| Mutation | Location |
|---|---|
| L4M | FR1 |
| | CDR1 |
| | FR2 |
| | CDR2 |
| E70D | FR3 |
| Q79E | |
| Q90E | CDR3 |
| L91S | |
| N92Y | |
| Y94T | |
| .95aF | |
| K107R | FR4 |

Name: B07 is related to L6.

| Mutation | Location |
|---|---|
| E1D | FR1 |
| V3Q | |
| L4M | |
| | CDR1 |
| | FR2 |
| | CDR2 |
| | FR3 |
| | CDR3 |
| L96. | FR4 |

Name: B08 is related to V1-22.

| Mutation | Location |
|---|---|
| N1Q | FR1 |
| F2S | |
| M3E | |
| E13G | |
| S31aG | CDR1 |
| | FR2 |
| Q53KT | CDR2 |
| T74I | FR3 |
| Q89H | CDR3 |
| V96Q | FR4 |

Name: B09 is related to V2-14.

The B09 light chain variable domain can include:

```
GVHSQSELTQ PPSVSLAPGQ TARITCGGNN IGTKSVHWYQ QKPGQAPVLV   (SEQ ID NO:299)
VYDDSDRPSG IPERFSGSNS GNTATLTISR VEAGDEADYY CQVWDSGSDH
QVFGGGTKLT VLGQPKAAPS
```

| Mutation | Location |
|---|---|
| S1Q | FR1 |
| Y2S | |
| V3E | |
| V13L | |
| S31aT | CDR1 |
| | FR2 |
| | CDR2 |
| | FR3 |
| S94G | CDR3 |
| P95cQ | |
| V96. | FR4 |

Name: C01 is related to L12.

| Mutation | Location |
|---|---|
| | FR1 |
| S30G | CDR1 |
| S31N | |
| K42E | FR2 |
| K45H | |
| D50Q | CDR2 |
| S56G | |
| E70K | FR3 |
| T74N | |
| | CDR3 |
| E105D | FR4 |

Name: C10 is related to V1-7.

| Mutation | Location |
|---|---|
| A3E | FR1 |
| | CDR1 |
| | FR2 |
| | CDR2 |
| | FR3 |
| F95b. | CDR3 |
| | FR4 |

Name: C11 is related to V1-2.

| Mutation | Location |
|---|---|
| A3E | FR1 |
| | CDR1 |
| G41D | FR2 |
| M47L | |
| S52T | CDR2 |
| K53Q | |
| K66R | FR3 |

-continued

| Mutation | Location |
|---|---|
| S94R | CDR3 |
| F95bL | |
| T100P | FR4 |

Name: C12 is related to V2-1.

| Mutation | Location |
|---|---|
| S1Q | FR1 |
| Y2S | |
| G16A | |
| | CDR1 |
| | FR2 |
| Q50E | CDR2 |
| S52T | |
| A80V | FR3 |
| A90V | CDR3 |
| V96. | FR4 |

Name: C03 is related to V1-16.

| Mutation | Location |
|---|---|
| V3A | FR1 |
| S27N | CDR1 |
| S31aG | |
| T32I | |
| N34I | |
| Y36L | FR2 |
| L47M | |
| S50D | CDR2 |
| N51V | |
| N52S | |
| Q53D | FR3 |
| P96cW | CDR3 |
| V96. | FR4 |

Name: C04 is related to V1-17.

| Mutation | Location |
|---|---|
| V3A | FR1 |
| S26T | CDR1 |
| N31bH | |
| Y34F | |
| Y49H | FR2 |
| S50R | CDR2 |
| N52D | |
| Q53E | |
| R79Q | FR3 |

-continued

| Mutation | Location |
|---|---|
| A90T | CDR3 |
| S94N | |
| S95aN | |
| V96. | FR4 |
| V106G | |
| L107P | |

Name: C05 is related to VI-17.

| Mutation | Location |
|---|---|
| V3E | FR1 |
| A11V | |
| N31bE | CDR1 |
| Y36F | FR2 |
| K45R | |
| S50R | CDR2 |
| N52D | |
| A84T | FR3 |
| A89T | CDR3 |
| A90T | |
| V96. | FR4 |

Name: C06 is related to A20.

| Mutation | Location |
|---|---|
| | FR1 |
| | CDR1 |
| | FR2 |
| A50P | CDR2 |
| V83F | FR3 |
| K90Q | CDR3 |
| Y91A | |
| N92D | |
| A94F | |
| .95aP | |
| L96. | FR4 |
| K107R | |

Name: C07 is related to O2.

| Mutation | Location |
|---|---|
| | FR1 |
| S31N | CDR1 |
| K39R | FR2 |
| Q55E | CDR2 |
| S56R | |
| P80S | FR3 |
| T94P | CDR3 |
| .95aP | |
| | FR4 |

Name: C08 is related to O2.

| Mutation | Location |
|---|---|
| S9P | FR1 |
| S14L | |

-continued

| Mutation | Location |
|---|---|
| S31R | CDR1 |
| L33N | |
| L46V | FR2 |
| S53I | CDR2 |
| L54V | |
| Q55E | |
| S56N | |
| T72S | FR3 |
| S91T | CDR3 |
| E105A | FR4 |

Name: C09 is related to A27.

| Mutation | Location |
|---|---|
| E1D | FR1 |
| V3Q | |
| L4M | |
| S31aT | CDR1 |
| Y49S | FR2 |
| | CDR2 |
| | FR3 |
| | CDR3 |
| | FR4 |

Name: D01 is related to V1-17.

| Mutation | Location |
|---|---|
| V3E | FR1 |
| V19I | |
| | CDR1 |
| L39F | FR2 |
| G41E | |
| Y49S | |
| S50R | CDR2 |
| N52D | |
| | FR3 |
| A90S | CDR3 |
| P95a. | |
| | FR4 |

Name: D02 is related to L8.

| Mutation | Location |
|---|---|
| L4M | FR1 |
| S31T | CDR1 |
| L46V | FR2 |
| A50T | CDR2 |
| | FR3 |
| L91S | CDR3 |
| N92Y | |
| S93I | |
| Y94T | |
| .95aP | |
| .95bE | |
| F96V | |
| | FR4 |

Name: D03 is related to L14.

| Mutation | Location |
|---|---|
| N1D | FR1 |
| R26S | CDR1 |
| G28V | |
| I29M | |
| S30I | |
| L33I | |
| Q37R | FR2 |
| K45E | |
| H46R | |
| S53T | CDR2 |
| S56N | |
| E70D | FR3 |
| S77R | |
| Q79E | |
| T85V | |
| L89Q | CDR3 |
| Q90H | |
| H91R | |
| N92I | |
| S93T | |
| Y94W | |
| .95aP | |
| .95bA | |
| K103T | FR4 |

Name: D04 is related to O2.

| Mutation | Location |
|---|---|
| T20A | FR1 |
| S30D | CDR1 |
| S31T | |
| | FR2 |
| S53K | CDR2 |
| Q55E | |
| S56D | |
| S67T | FR3 |
| S76R | |
| T85S | |
| Y87F | |
| T94S | |
| .95aG | CDR3 |
| F96I | |
| D105E | FR4 |

Name: D05 is related to V1-4.

| Mutation | Location |
|---|---|
| A3V | FR1 |
| A9D | |
| T26S | CDR1 |
| S28H | |
| V30I | |
| G31aS | |
| N31cD | |
| Q38H | FR2 |
| L46F | |
| M47I | |
| I48L | |
| E50D | CDR2 |
| S52Y | |
| N60D | FR3 |
| A81P | |
| E82D | |
| Y87F | |
| S89M | CDR3 |

-continued

| Mutation | Location |
|---|---|
| S93I | |
| S94T | |
| S95T | |
| T95aL | |
| Y96. | FR4 |
| V97L | |
| K103R | |

Name: D06 is related to O2.

| Mutation | Location |
|---|---|
| | FR1 |
| A25T | CDR1 |
| S28I | |
| S30N | |
| S31T | |
| | FR2 |
| S53T | CDR2 |
| S56G | |
| S76K | FR3 |
| E81D | |
| S93T | CDR3 |
| T94S | |
| W96R | FR4 |

Name: D6-O is related to O2.

| Mutation | Location |
|---|---|
| S9L | FR1 |
| T20A | |
| S30D | CDR1 |
| S31T | |
| | FR2 |
| S53K | CDR2 |
| Q55E | |
| S56D | |
| S67T | FR3 |
| S76R | |
| T85S | |
| Y87F | |
| T94S | CDR3 |
| .95aG | |
| F96I | FR4 |
| D105E | |

Name: D07 is related to V1-4.

| Mutation | Location |
|---|---|
| A3E | FR1 |
| S27N | CDR1 |
| V30I | |
| A43V | FR2 |
| M47L | |
| Y49F | |
| S52N | CDR2 |
| N60D | FR3 |
| A80P | |
| D85V | |

-continued

| Mutation | Location |
|---|---|
| S89G | CDR3 |
| Y91F | |
| S93V | |
| S95V | |
| L95b. | |
| | FR4 |

Name: D07 is related to V1-4.

| Mutation | Location |
|---|---|
| | FR1 |
| | CDR1 |
| | FR2 |
| | CDR2 |
| | FR3 |
| | CDR3 |
| | FR4 |

Name: D08 is related to O2.

| Mutation | Location |
|---|---|
| | FR1 |
| S31D | CDR1 |
| K45D | FR2 |
| | CDR2 |
| Y87F | FR3 |
| T94I | CDR3 |
| K107T | FR4 |

Name: D09 is related to V2-1.

| Mutation | Location |
|---|---|
| S1Q | FR1 |
| Y2S | |
| | CDR1 |
| | FR2 |
| | CDR2 |
| | FR3 |
| T95A | CDR3 |
| A95a. | |
| | FR4 |

Name: H6-O is related to V1-2.

| Mutation | Location |
|---|---|
| A3E | FR1 |
| G29A | CDR1 |
| M47I | FR2 |
| S51aN | CDR2 |
| G64A | FR3 |
| | CDR3 |
| N97S, F98L | FR4 |

EXAMPLE

This example includes an analysis of HC germline differences In each example the isolate name is written under the GLG.

The AA sequence encoded by the synthetic DNA up to Cys-92. The germ-line gene (GLG) for 3-23 is shown in SEQ ID NO:287. The AA sequences of the six human JH segments are shown below:

AA sequences of human JHs

```
JH1   ---AEYFQHWGQGTLVTVSS    (SEQ ID NO:288)
JH2   ---YWYFDLWGRGTLVTVSS    (SEQ ID NO:289)
JH3   -----AFDIWGQGTMVTVSS    (SEQ ID NO:290)
JH4   -----YFDYWGQGTLVTVSS    (SEQ ID NO:291)
JH5   ----NWFDPWGQGTLVTVSS    (SEQ ID NO:292)
JH6   YYYYYGMDVWGQGTTVTVSS    (SEQ ID NO:293)
```

The following analysis of the 48 isolates. For each isolate the entry shows: the name, 2) and the mutations written as if from GLG (SEQ ID NO:287) to the isolate. With respect to each example, there are related antibody variable domains whose amino acid sequence is encoded by a germline gene (e.g., the germline-encoded amino acid sequence aligned in the example or a related germline-encoded amino acid sequence) that can include one or more of the above mutations (e.g., at least 30, 50, 70, 75, 80, 85, 90, or 95% of the above mutations), e.g., one or more of the above mutations (e.g., at least 30, 50, 70, 75, 80, 85, 90, or 95%) of the mutations that are located in the CDRs.

Below the listing of muations is a description of which JH matched best and an alignment of the best JH with all the isolate AA sequence after C92.

Isolate: A01
S31A, A33N, S35F, A50G, S51aG, G52S, S56I, T57A, Y58P
JH is 5

Isolate: A02
S31P, A33F, S35F, A50S, S51aG, G52S, S56D, Y58S
JH is 4

The A02 heavy chain variable domain can include:

```
EVQLLESGGG LVQPGGSLRL SCAASGFTFS PYFMFWVRQA PGKGLEWVSS (SEQ ID NO:296)
IGSSGGDTSY ADSVKGRFTI SRDNSKNTLY LQMNSLPAED TAVYYC
``` and a CDR3 that includes GLYR (SEQ ID NO:297).

Isolate: A03
S31I, A33S, S35D, A50S, S51aY, G52S, S56A, Y58R
JH is 4

Isolate: a04
S31E, A33N, S35A, A50R, S51aG, G52S, S56K, Y58K
JH is 3

Isolate: a05
S31V, A33S, S35N, A50Y, S51aV, G52P, S56N, Y58P
JH is 4

Isolate: a06
S31P, A33H, S35G, A50G, S51aY, G52P, S56W, Y58N
JH is 4

Isolate: a07
S31E, A33N, S35M, A50V, G52P, S56G, Y58L
JH is 3

Isolate: a08
S31V, A33D, S35P, A50V, S51aY, G52P, S56F, Y58R
JH is 6

Isolate: a09
S31W, A33D, S35Y, A50S, S51aY, G52S, S56Y, Y58A
JH is 5

Isolate: a10
S31A, A33R, S35F, A50S, S51aW, G52P, S56T, Y58S
JH is 4

Isolate: a11
S31W, A33T, S35M, A50R, G52P, S56H, Y58L, K75z
JH is 4

Isolate: a12
S31A, A33W, S35D, A50V, S51aY, G52P, Y58N
JH is 3

Isolate: b01
S31T, A33D, S35L, A50S, G52P, Y58S, M82L
JH is 3

Isolate: b02
S31D, A33F, S35K, A50S, S51aY, G52P, S56P, Y58K
JH is 6

Isolate: b03
S31P, A33E, S35Q, A50G, S51aG, G52S, S56-, T57-, Y58-, Y59-, A60-N.B. 5 AA deletion in CDR2.
JH is 4

Isolate: b04
S31F, A33W, S35M, A50G, G52S, S56F, Y58K
JH is 3

Isolate: b05
S31E, A33W, S35P, A50R, S51aY, G52P, S56V, Y58T
JH is 6

Isolate: b06
S31Q, A33F, S35K, A50S, G52P, S56L, Y58Q
JH is 4

Isolate: b07
S31Q, A33Q, S35I, A50V, S51aV, G52P, S56I, Y58N
JH is 4

Isolate: b08
S31R, A33M, S35N, A50V, S51aW, G52S, S56K, Y58L, N82aK
JH is 6

Isolate: b09
S31P, A33F, S35F, A50S, S51aG, G52S, S56D, Y58S
JH is 4

The b09 heavy chain variable domain can include:

```
EVQLLESGGG LVQPGGSLRL SCAASGFTFS PYFMFWVRQA PGKGLEWVSS (SEQ ID NO:298)
IGSSGGDTSY ADSVKGRFTI SRDNSKNTLY LQMNSLRAED TAVYYC
``` and a CDR3 that includes GLYR (SEQ ID NO:297).

Isolate: b10
S35M, A50W, S51aV, G52P, S56T, Y58F
JH is 4

Isolate: b11
S31P, A33F, S35F, A50S, S51aG, G52S, S56D, Y58S, K75z
JH is 4

Isolate: 12
S31L, A33V, S35Y, A50Y, G52S, S56I, Y58H
JH is 5

Isolate: c01
S31N, A33G, A50V, S51aG, G52P, S56I, Y58M
JH is 4

Isolate: c02
S31H, A33S, S35R, A50Y, S51aV, G52P, S56F, Y58Q
JH is 4

Isolate: c03
S31L, A33M, S35K, A50V, G52S, S56Y, Y58Q, S82bN
JH is 3

Isolate: c04
S31M, A33F, S35V, A50W, S51aG, G52S, S56E, Y58P
JH is 4

Isolate: c05
A33Q, S35D, A50R, S51aV, G52P, S56D, Y58T
JH is 4

Isolate: c06
S31F, A33F, S35F, A50Y, S51aG, G52P, S56P, Y58N
JH is 4

Isolate: c07
S31Y, A33V, S35M, A50V, S51aR, G52P, S56I, Y58T, M82T
JH is 4

Isolate: c08
S31Y, A33E, S35M, A50S, G52P, S56P, Y58M, A88G
JH is 6

Isolate: c09
S31Q, A33F, S35N, A50Y, G52-, S53-, S56R, Y58P N.B. 2 AA deletion in CDR2.
JH is 4

Isolate: c10
S31V, A33V, S35M, A50G, S51aV, G52P, S56K, Y58H
JH is 4

Isolate: c11
S31E, A33P, S35W, A50W, S51aY, G52P, S56N, Y58D
JH is 4

Isolate: c12
S31A, A33N, S35M, A50R, S51aY, G52P, S56Y, Y58L
JH is 4

Isolate: d01
S31M, A33L, S35F, A50V, G52S, S56E, Y58S
JH is 4

Isolate: d02
S31W, A33D, S35A, A50R, S51aV, G52P, S56H, Y58S, S74F
JH is 4

Isolate: d03
S31W, A33R, S35D, A50V, S51aG, G52S, S56M
JH is 3

Isolate: d04
S31D, A33Q, S35M, A50R, G52P, S56M, Y58R, Q81P
JH is 4

Isolate: d05
S31H, A33N, S35A, A50R, S51aR, G52S, S56L, Y58V
JH is 4

Isolate: d06
S31G, A33I, S35E, A50V, S51aV, G52S, S56F, Y58M
JH is 4

Isolate: d07
S31E, A33N, S35F, A50Y, S51aY, G52S, Y58D
JH is 4

Isolate: d08
S31F, S35W, A50R, S51aY, G52S, S56K, Y58W
JH is 3

Isolate: d09
S31H, A33N, S35H, A50G, S51aV, G52S, S56N, Y58G, Y90D
JH is 5

A1-orig
S31Y, A33R, A50S, S51aG, G52P, S56D, Y58L
JH is 4

D6-orig
S31M, A33S, S35R, A50S, S51aY, G52P, Y58E
JH is 4

H6-orig
S31Q, A33W, S35N, A50G, S51aG, G52P, S56I
JH is 4

Other embodiments of the invention are within the following claims.

---

What is claimed:

1. An isolated protein which binds to matrix metalloproteinase 26 (MMP-26), said protein comprising a heavy chain immunoglobulin variable domain (HC) sequence and a light chain immunoglobulin variable domain (LC) sequence, wherein
   (a) the HC comprises CDR1, CDR2, and CDR3 of SEQ ID NO:4 and the LC comprises CDR1, CDR2, and CDR3 of SEQ ID NO:2;
   (b) the HC comprises CDR1, CDR2, and CDR3 of SEQ ID NO:8 and the LC comprises CDR1, CDR2, and CDR3 of SEQ ID NO:6;
   (c) the HC comprises CDR1, CDR2, and CDR3 of SEQ ID NO:12 and the LC comprises CDR1, CDR2, and CDR3 of SEQ ID NO:10;
   (d) the HC comprises CDR1, CDR2, and CDR3 of SEQ ID NO:16 and the LC comprises CDR1, CDR2, and CDR3 of SEQ ID NO:14;
   (e) the HC comprises CDR1, CDR2, and CDR3 of SEQ ID NO:52 and the LC comprises CDR1, CDR2, and CDR3 of SEQ ID NO:50;
   (f) the HC comprises CDR1, CDR2, and CDR3 of SEQ ID NO:104 and the LC comprises CDR1, CDR2, and CDR3 of SEQ ID NO:102;
   (g) the HC comprises CDR1, CDR2, and CDR3 of SEQ ID NO:132 and the LC comprises CDR1, CDR2, and CDR3 of SEQ ID NO:130;
   (h) the HC comprises CDR1, CDR2, and CDR3 of SEQ ID NO:148 and the LC comprises CDR1, CDR2, and CDR3 of SEQ ID NO:146;
   (i) the HC comprises CDR1, CDR2, and CDR3 of SEQ ID NO:164 and the LC comprises CDR1, CDR2, and CDR3 of SEQ ID NO:162; or
   (j) the HC comprises CDR1, CDR2, and CDR3 of SEQ ID NO:180 and the LC comprises CDR1, CDR2, and CDR3 of SEQ ID NO:178.

2. The protein of claim 1 wherein the protein is capable of reducing cell invasion by JEG-3 choriocarcinoma cells in an in vitro model of cell invasion.

3. The protein of claim 1 wherein the protein comprises two independent polypeptide chains, a first chain comprising the LC sequence and the second chain comprising the HC sequence, and each chain comprising a constant immunoglobulin domain.

4. The protein of claim 1 wherein the protein comprises CL, CH1, CH2, and CH3 domains.

5. The protein of claim 1, wherein
   (a) the HC sequence comprises SEQ ID NO:4 and the LC sequence comprises SEQ ID NO:2;
   (b) the HC sequence comprises SEQ ID NO:8 and the LC sequence comprises SEQ ID NO:6;
   (c) the HC sequence comprises SEQ ID NO:12 and the LC sequence comprises SEQ ID NO:10;
   (d) the HC sequence comprises SEQ ID NO:16 and the LC sequence comprises SEQ ID NO:14;
   (e) the HC sequence comprises SEQ ID NO:52 and the LC sequence comprises SEQ ID NO:50;
   (f) the HC sequence comprises SEQ ID NO:104 and the LC sequence comprises SEQ ID NO:102;
   (g) the HC sequence comprises SEQ ID NO:132 and the LC sequence comprises SEQ ID NO:130;
   (h) the HC sequence comprises SEQ ID NO:148 and the LC sequence comprises SEQ ID NO:146;
   (i) the HC sequence comprises SEQ ID NO:164 and the LC sequence comprises SEQ ID NO:162, or
   (j) the HC sequence comprises SEQ ID NO:180 and the LC sequence comprises SEQ ID NO:178.

6. The protein of claim 5, wherein the HC sequence comprises SEQ ID NO:4 and the LC sequence comprises SEQ ID NO:2.

7. The protein of claim 1, wherein the HC comprises CDR1, CDR2, and CDR3 of SEQ ID NO:4 and the LC comprises CDR1, CDR2, and CDR3 of SEQ ID NO:2.

8. The protein of claim 1, wherein the HC comprises CDR1, CDR2, and CDR3 of SEQ ID NO:52 and the LC comprises CDR1, CDR2, and CDR3 of SEQ ID NO:50.

9. The protein of claim 8, wherein the protein inhibits MMP-26 proteolytic activity.

10. The protein of claim 5, wherein the HC sequence comprises SEQ ID NO:52 and the LC sequence comprises SEQ ID NO:50.

11. The protein of claim 10, wherein the protein inhibits MMP-26 proteolytic activity.

12. The protein of claim 7, wherein the protein inhibits MMP-26 proteolytic activity.

13. The protein of claim 6, wherein the protein inhibits MMP-26 proteolytic activity.

* * * * *

SEQUENCE LISTING

<160> NUMBER OF SEQ ID NOS: 299

<210> SEQ ID NO 1
<211> LENGTH: 354
<212> TYPE: DNA
<213> ORGANISM: Homo sapiens

<400> SEQUENCE: 1

```
ggcgtgcact cacagagcgt cttgactcag ccaccctcag cgtctgggac ccccgggcag    60
agggtcatca tctcttgttc tggaagcagc tccaacatcg gaagtcatta tgtacactgg   120
taccaacagg tcccaggaac ggcccccaaa ctcctcattt ataggaatgg tcagcggccc   180 tcagggtcc ctgaccgatt ctctggcttc aagtctggca cctcagcctc cctggccatc   240
agtgggctcc ggtccgagga tgaggctaat tattactgtg caacatggga tgacagtgtc   300
ctattcggcg gagggaccac gctgaccgtc ctaggtcagc ccaaggctgc cccc         354
```

<210> SEQ ID NO 2
<211> LENGTH: 118
<212> TYPE: PRT
<213> ORGANISM: Homo sapiens

<400> SEQUENCE: 2

```
Gly Val His Ser Gln Ser Val Leu Thr Gln Pro Pro Ser Ala Ser Gly
 1               5                  10                  15

Thr Pro Gly Gln Arg Val Ile Ile Ser Cys Ser Gly Ser Ser Ser Asn
            20                  25                  30
```

Ile Gly Ser His Tyr Val His Trp Tyr Gln Gln Val Pro Gly Thr Ala
            35                  40                  45

Pro Lys Leu Leu Ile Tyr Arg Asn Gly Gln Arg Pro Ser Gly Val Pro
    50                  55                  60

Asp Arg Phe Ser Gly Phe Lys Ser Gly Thr Ser Ala Ser Leu Ala Ile
65                  70                  75                  80

Ser Gly Leu Arg Ser Glu Asp Glu Ala Asn Tyr Tyr Cys Ala Thr Trp
                85                  90                  95

Asp Asp Ser Val Leu Phe Gly Gly Gly Thr Thr Leu Thr Val Leu Gly
                100                 105                 110

Gln Pro Lys Ala Ala Pro
            115

<210> SEQ ID NO 3
<211> LENGTH: 399
<212> TYPE: DNA
<213> ORGANISM: Homo sapiens

<400> SEQUENCE: 3
gaagttcaat tgttagagtc tggtggcggt cttgttcagc ctggtggttc tttacgtctt      60
tcttgcgctg cttccggatt cactttctct tattaccgta tgtcttgggt tcgccaagct     120
cctggtaaag gtttggagtg gtttcttcta tcggtccctt ctggtggcga tactctttat    180
gctgactccg ttaaaggtcg cttcactatc tctagagaca actctaagaa tactctctac    240
ttgcagatga acagcttaag ggctgaggac actgcagtct actattgtgc gagatctttc    300
agcagtggcc cgtactactt tgactactgg ggccagggaa ccctggtcac cgtctcaagc    360
gcctccacca agggcccatc ggtcttcccg ctagcgccc                            399

<210> SEQ ID NO 4
<211> LENGTH: 133
<212> TYPE: PRT
<213> ORGANISM: Homo sapiens

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Arg Met Ser Trp Val Arg Gln Ala Pro Gly Lys Gly Leu Glu Trp Val
        35                  40                  45

Ser Ser Ile Gly Pro Ser Gly Gly Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Phe Ser Ser Gly Pro Tyr Tyr Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro
        130

<210> SEQ ID NO 5
<211> LENGTH: 354

```
<212> TYPE: DNA
<213> ORGANISM: Homo sapiens

<400> SEQUENCE: 5
ggcgtgcact ctgacatcca gatgacccag tctccactct ccctgtctgc atctgtggga      60
gacagagtcg ccatcacttg ccgcgcaagt cagagcatcg acacctattt aaattggtat     120
cagcagaaac cagggaaagc ccctaaactc ctgatctatg ctgcatccaa gttggaagac     180
ggggtcccat caagattcag tggcagtgga actgggacag atttcactct caccatcaga     240
agtctgcaac tgaagatttt gcaagttatt tctgtcaac agagctactc tagtccaggg      300
atcactttcg gccctgggac caaggtggag atcaaacgaa ctgtggctgc acca           354

<210> SEQ ID NO 6
<211> LENGTH: 118
<212> TYPE: PRT
<213> ORGANISM: Homo sapiens

<400> SEQUENCE: 6

Gly Val His Ser Asp Ile Gln Met Thr Gln Ser Pro Leu Ser Leu Ser
1               5                   10                  15

Ala Ser Val Gly Asp Arg Val Ala Ile Thr Cys Arg Ala Ser Gln Ser
            20                  25                  30

Ile Asp Thr Tyr Leu Asn Trp Tyr Gln Gln Lys Pro Gly Lys Ala Pro
        35                  40                  45

Lys Leu Leu Ile Tyr Ala Ala Ser Lys Leu Glu Asp Gly Val Pro Ser
    50                  55                  60

Arg Phe Ser Gly Ser Gly Thr Gly Thr Asp Phe Thr Leu Thr Ile Arg
65                  70                  75                  80

Ser Leu Gln Pro Glu Asp Phe Ala Ser Tyr Phe Cys Gln Gln Ser Tyr
                85                  90                  95

Ser Ser Pro Gly Ile Thr Phe Gly Pro Gly Thr Lys Val Glu Ile Lys
            100                 105                 110

Arg Thr Val Ala Ala Pro
        115

<210> SEQ ID NO 7
<211> LENGTH: 387
<212> TYPE: DNA
<213> ORGANISM: Homo sapiens

<400> SEQUENCE: 7
gaagttcaat tgttagagtc tggtggcggt cttgttcagc ctggtggttc tttacgtctt      60
tcttgcgctg cttccggatt cacttttctct atgtactcta tgcgttgggt tcgccaagct    120
cctggtaaag gtttggagtg ggtttcttct atctatcctt ctggtggctc tactgagtat    180
gctgactccg ttaaaggtcg cttcactatc tctagagaca actctaagaa tactctctac    240
ttgcagatga acagcttaag ggctgaggac actgcagtct actattgtgc gagagagggc    300
ggggagaacg actactgggg ccagggaacc ctggtcaccg tctcaagcgc ctccaccaag    360
ggcccatcgg tcttcccgct agcgccc                                         387

<210> SEQ ID NO 8
<211> LENGTH: 129
<212> TYPE: PRT
<213> ORGANISM: Homo sapiens

<400> SEQUENCE: 8
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Ser Met Arg Trp Val Arg Gln Ala Pro Gly Lys Gly Leu Glu Trp Val
        35                  40                  45

Ser Ser Ile Tyr Pro Ser Gly Gly Ser Thr Glu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Glu Asn Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro

<210> SEQ ID NO 9
<211> LENGTH: 363
<212> TYPE: DNA
<213> ORGANISM: Homo sapiens

<400> SEQUENCE: 9
ggcgtgcact cacagagcga attgactcag cctccctccg cgtccgggtc tcctggacag      60
tcagtcacca tctcctgcac tggaaccagc agtgacgttg gtgcttataa ctatgtctcc     120
tggtaccaac aacacccagg caaagccccc aaactcataa tctatgaagt caataagcgg     180
ccctcagggg tccctgatcg cttctctgcc tccaagtctg gcaacacggc ctccctgacc     240
gtctctgggc tccaggctga agatgaggct gattattact gcaactcata tgcaggcagc     300
aacagtttga tattcggcgg agggaccaaa ctgaccgtct taggtcagcc caaggctgcc     360
ccc                                                                   363

<210> SEQ ID NO 10
<211> LENGTH: 121
<212> TYPE: PRT
<213> ORGANISM: Homo sapiens

<400> SEQUENCE: 10

Gly Val His Ser Gln Ser Glu Leu Thr Gln Pro Pro Ser Ala Ser Gly
1               5                   10                  15

Ser Pro Gly Gln Ser Val Thr Ile Ser Cys Thr Gly Thr Ser Ser Asp
            20                  25                  30

Val Gly Ala Tyr Asn Tyr Val Ser Trp Tyr Gln Gln His Pro Gly Lys
        35                  40                  45

Ala Pro Lys Leu Ile Ile Tyr Glu Val Asn Lys Arg Pro Ser Gly Val
50                  55                  60

Pro Asp Arg Phe Ser Ala Ser Lys Ser Gly Asn Thr Ala Ser Leu Thr
65                  70                  75                  80

Val Ser Gly Leu Gln Ala Glu Asp Glu Ala Asp Tyr Tyr Cys Asn Ser
                85                  90                  95

Tyr Ala Gly Ser Asn Ser Leu Ile Phe Gly Gly Thr Lys Leu Thr
            100                 105                 110

Val Leu Gly Gln Pro Lys Ala Ala Pro
        115                 120

<210> SEQ ID NO 11
<211> LENGTH: 396
<212> TYPE: DNA
<213> ORGANISM: Homo sapiens

<400> SEQUENCE: 11

```
gaagttcaat tgttagagtc tggtggcggt cttgttcagc ctggtggttc tttacgtctt    60
tcttgcgctg cttccggatt cactttctct cagtactgga tgaattgggt tcgccaagct   120
cctggtaaag gtttggagtg gtttctggt atcggtcctt ctggtggcat tacttattat    180
gctgactccg ttaaaggtcg cttcactatc tctagagaca actctaagaa tactctctac   240
ttgcagatga acagcttaag ggctgaggac actgcagtct actattgtgc gagaggtgag   300
gaagatggct acaattctga ctactgggggc cagggaaccc tggtcaccgt ctcaagcgcc   360
tccaccaagg gcccatcggt cttcccgcta gcgccc                              396
```

<210> SEQ ID NO 12
<211> LENGTH: 132
<212> TYPE: PRT
<213> ORGANISM: Homo sapiens

<400> SEQUENCE: 12

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Gln Tyr
             20                  25                  30

Trp Met Asn Trp Val Arg Gln Ala Pro Gly Lys Gly Leu Glu Trp Val
         35                  40                  45

Ser Gly Ile Gly Pro Ser Gly Gly Ile Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Glu Glu Asp Gly Tyr Asn Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro
    130
```

<210> SEQ ID NO 13
<211> LENGTH: 363
<212> TYPE: DNA
<213> ORGANISM: Homo sapiens

<400> SEQUENCE: 13

```
ggcgtgcact ctgacatcca gatgacccag tctccaggca ccctgtcttt gtctccaggg    60
gaaagagcca ccctctcctg cagggccagt cagattgttc gcagcaccta cttagcctgg   120
tatcagcaga aacctggcca ggctcccagg ctcctcatct atggtacatc cagcagggcc   180
actggcgtcc cagacaggtt cagtggcagt gggtctggga cagacttcac tctcaccatc   240
agcggactgg agcctgaaga ttttgcacta tactactgtc agcggtatgg tgactcacct   300
ccgatcacct tcggccaagg gacacgactg gagattacac gaactgtggc tgcaccatct   360
gtc                                                                  363
```

<210> SEQ ID NO 14
<211> LENGTH: 121
<212> TYPE: PRT
<213> ORGANISM: Homo sapiens

<400> SEQUENCE: 14

```
Gly Val His Ser Asp Ile Gln Met Thr Gln Ser Pro Gly Thr Leu Ser
1               5                   10                  15

Leu Ser Pro Gly Glu Arg Ala Thr Leu Ser Cys Arg Ala Ser Gln Ile
            20                  25                  30

Val Arg Ser Thr Tyr Leu Ala Trp Tyr Gln Gln Lys Pro Gly Gln Ala
        35                  40                  45

Pro Arg Leu Leu Ile Tyr Gly Thr Ser Arg Ala Thr Gly Val Pro
    50                  55                  60

Asp Arg Phe Ser Gly Ser Gly Ser Gly Thr Asp Phe Thr Leu Thr Ile
65                  70                  75                  80

Ser Gly Leu Glu Pro Glu Asp Phe Ala Leu Tyr Tyr Cys Gln Arg Tyr
                85                  90                  95

Gly Asp Ser Pro Pro Ile Thr Phe Gly Gln Gly Thr Arg Leu Glu Ile
            100                 105                 110

Thr Arg Thr Val Ala Ala Pro Ser Val
        115                 120
```

<210> SEQ ID NO 15
<211> LENGTH: 390
<212> TYPE: DNA
<213> ORGANISM: Homo sapiens

<400> SEQUENCE: 15

```
gaagttcaat tgttagagtc tggtggcggt cttgttcagc ctggtggttc tttacgtctt    60
tcttgcgctg cttccggatt cactttctct gcttacaata tgttttgggt tcgccaagct   120
cctggtaaag gtttggagtg ggtttctggt atcggttctt ctggtggcat tgctccttat   180
gctgactccg ttaaaggtcg cttcactatc tctagagaca actctaagaa tactctctac   240
ttgcagatga acagcttaag ggctgaggac actgcagtct actattgtgc gagagccgcg   300
tacgaggtgg agaactggtt cgaccccctgg ggccagggaa ccctggtcac cgtctcaagc   360
gcctccacca agggcccatc ggtcttcccg                                    390
```

<210> SEQ ID NO 16
<211> LENGTH: 130
<212> TYPE: PRT
<213> ORGANISM: Homo sapiens

<400> SEQUENCE: 16

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Asn Met Phe Trp Val Arg Gln Ala Pro Gly Lys Gly Leu Glu Trp Val
        35                  40                  45

Ser Gly Ile Gly Ser Ser Gly Gly Ile Ala Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Ala Arg Ala Ala Tyr Glu Val Glu Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro
    130

<210> SEQ ID NO 17
<211> LENGTH: 363
<212> TYPE: DNA
<213> ORGANISM: Homo sapiens

<400> SEQUENCE: 17
ggcgtgcact cacagagcgc tttgactcag ccaccctcag cgtctgggac ccccgggcag     60
agggtcacca tctcttgttc tggaggcagc tccaacatcg aagtaatttt tgtttactgg    120
taccggcagc tcccaggaac ggcccccaaa ctcctcatct ataggaatta tcagcggccc    180 tcagggggtcc ctgaccgatt ctcgggttcc aagtctggca cctcagcctc cctggccatc   240
agtgggctcc tgtccgaaga tgaggctgat tattactgcg cagcatggga tgacaacgtg    300
ggtggggtct tcggatctgg gaccaaggtc accgtcctgg gtcagcccaa ggccaacccc    360
act                                                                  363

<210> SEQ ID NO 18
<211> LENGTH: 121
<212> TYPE: PRT
<213> ORGANISM: Homo sapiens

<400> SEQUENCE: 18

Gly Val His Ser Gln Ser Ala Leu Thr Gln Pro Pro Ser Ala Ser Gly
1               5                   10                  15

Thr Pro Gly Gln Arg Val Thr Ile Ser Cys Ser Gly Gly Ser Ser Asn
            20                  25                  30

Ile Gly Ser Asn Phe Val Tyr Trp Tyr Arg Gln Leu Pro Gly Thr Ala
        35                  40                  45

Pro Lys Leu Leu Ile Tyr Arg Asn Tyr Gln Arg Pro Ser Gly Val Pro
    50                  55                  60

Asp Arg Phe Ser Gly Ser Lys Ser Gly Thr Ser Ala Ser Leu Ala Ile
65                  70                  75                  80

Ser Gly Leu Leu Ser Glu Asp Glu Ala Asp Tyr Tyr Cys Ala Ala Trp
                85                  90                  95

Asp Asp Asn Val Gly Gly Val Phe Gly Ser Gly Thr Lys Val Thr Val
            100                 105                 110

Leu Gly Gln Pro Lys Ala Asn Pro Thr
        115                 120

<210> SEQ ID NO 19
<211> LENGTH: 390
<212> TYPE: DNA
<213> ORGANISM: Homo sapiens

<400> SEQUENCE: 19
gaagttcaat tgttagagtc tggtggcggt cttgttcagc ctggtggttc tttacgtctt     60
tcttgcgctg cttccggatt cactttctct atttactcta tggattgggt tcgccaagct    120
cctggtaaag gtttggagtg ggtttcttct atctattctt ctggtggcgc tactcgttat    180
```

```
gctgactccg ttaaaggtcg cttcactatc tctagagaca actctaagaa tactctctac    240
ttgcagatga acagcttaag ggctgaggac actgcagtct actattgtgc gaggtgtagc    300
tggctacaat tagtaccgat gcaccctgg ggccagggaa ccctggtcac cgtctcaagc     360
gcctccacca agggcccatc ggtcttcccg                                     390
```

<210> SEQ ID NO 20
<211> LENGTH: 130
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ser Met Asp Trp Val Arg Gln Ala Pro Gly Lys Gly Leu Glu Trp Val
        35                  40                  45

Ser Ser Ile Tyr Ser Ser Gly Gly Ala Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Cys Ser Trp Leu Gln Leu Val Pro Met His Pro Trp Gly Gln
            100                 105                 110

Gly Thr Leu Val Thr Val Ser Ser Ala Ser Thr Lys Gly Pro Ser Val
        115                 120                 125

Phe Pro
    130

<210> SEQ ID NO 21
<211> LENGTH: 366
<212> TYPE: DNA
<213> ORGANISM: Homo sapiens

<400> SEQUENCE: 21

```
ggcgtgcact cacagagcgc tttgactcag ccaccctcag cgtctgggac ccccgggcag    60
agggtcacca tctcttgttc tggaggctac tccaacatgg gaagcaatta tgcacactgg    120
taccagcagg tcccaggaac ggcccccaaa ctcctcatct ataacaataa tcagaggccc    180 tcagggtgtcc ctgaccgatt ctctggctcc aagtctggca cctcagcctc cctagccatc    240
agtgggctcc ggtccgagga tgaggctgat tattactgtg cagcatggga tgaaaacctg    300
agtggtccgg tcttcggaac tgggaccaag gtcaccgtcc taggtcagcc caaggccaac    360
cccact                                                               366
```

<210> SEQ ID NO 22
<211> LENGTH: 122
<212> TYPE: PRT
<213> ORGANISM: Homo sapiens

<400> SEQUENCE: 22

Gly Val His Ser Gln Ser Ala Leu Thr Gln Pro Pro Ser Ala Ser Gly
1               5                   10                  15

Thr Pro Gly Gln Arg Val Thr Ile Ser Cys Ser Gly Gly Tyr Ser Asn
            20                  25                  30

```
Met Gly Ser Asn Tyr Ala His Trp Tyr Gln Gln Val Pro Gly Thr Ala
            35                  40                  45

Pro Lys Leu Leu Ile Tyr Asn Asn Asn Gln Arg Pro Ser Gly Val Pro
        50                  55                  60

Asp Arg Phe Ser Gly Ser Lys Ser Gly Thr Ser Ala Ser Leu Ala Ile
65                  70                  75                  80

Ser Gly Leu Arg Ser Glu Asp Glu Ala Asp Tyr Tyr Cys Ala Ala Trp
                85                  90                  95

Asp Glu Asn Leu Ser Gly Pro Val Phe Gly Thr Gly Thr Lys Val Thr
            100                 105                 110

Val Leu Gly Gln Pro Lys Ala Asn Pro Thr
            115                 120
```

<210> SEQ ID NO 23
<211> LENGTH: 402
<212> TYPE: DNA
<213> ORGANISM: Homo sapiens

<400> SEQUENCE: 23

```
gaagttcaat tgttagagtc tggtggcggt cttgttcagc ctggtggttc tttacgtctt    60
tcttgcgctg cttccggatt cactttctct gagtacaata tggcttgggt tcgccaagct   120
cctggtaaag gtttggagtg gtttctcgt atcggttctt ctggtggcaa gactaagtat   180
gctgactccg ttaaaggtcg cttcactatc tctagagaca actctaagaa tactctctac   240
ttgcagatga acagcttaag ggctgaggac actgcagtct actattgtgc gagagatgaa   300
gcccccgact acggtgacga cgcggaagct tttgatatct ggggccaagg acaatggtc   360
accgtctcaa gcgcctccac caagggccca tcggtcttcc cg                      402
```

<210> SEQ ID NO 24
<211> LENGTH: 134
<212> TYPE: PRT
<213> ORGANISM: Homo sapiens

<400> SEQUENCE: 24

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Asn Met Ala Trp Val Arg Gln Ala Pro Gly Lys Gly Leu Glu Trp Val
        35                  40                  45

Ser Arg Ile Gly Ser Ser Gly Gly Lys Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Ala Pro Asp Tyr Gly Asp Asp Ala Glu Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro
    130
```

<210> SEQ ID NO 25
<211> LENGTH: 357
<212> TYPE: DNA

<213> ORGANISM: Homo sapiens

<400> SEQUENCE: 25

```
ggcgtgcact ctgacatcca gatgacccag tctccatcct ccctgtcttt gtctccaggg      60
gaaagagcca ccctctcctg cagggccagt cagagtgtta gcagctactt agcctggtac     120
caacagaaac ctggccaggc tcccaggctc ctcatctatg atgcatccaa cagggccact     180
ggcatcccag ccaggttcag tggcagtggg tctgggacag acttcactct caccatcagc     240
agcctagagc ctgaagattt tgcagtttat tactgtcagc agcgtagcaa ctggcctcgg     300
actttcggcg agggaccaa ggtggagatc aaacgaactg tggctgcacc atctgtc        357
```

<210> SEQ ID NO 26
<211> LENGTH: 119
<212> TYPE: PRT
<213> ORGANISM: Homo sapiens

<400> SEQUENCE: 26

Gly Val His Ser Asp Ile Gln Met Thr Gln Ser Pro Ser Ser Leu Ser
1               5                  10                  15

Leu Ser Pro Gly Glu Arg Ala Thr Leu Ser Cys Arg Ala Ser Gln Ser
            20                  25                  30

Val Ser Ser Tyr Leu Ala Trp Tyr Gln Gln Lys Pro Gly Gln Ala Pro
        35                  40                  45

Arg Leu Leu Ile Tyr Asp Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Arg Ser
                85                  90                  95

Asn Trp Pro Arg Thr Phe Gly Gly Thr Lys Val Glu Ile Lys Arg
            100                 105                 110

Thr Val Ala Ala Pro Ser Val
        115

<210> SEQ ID NO 27
<211> LENGTH: 387
<212> TYPE: DNA
<213> ORGANISM: Homo sapiens

<400> SEQUENCE: 27

```
gaagttcaat tgttagagtc tggtggcggt cttgttcagc ctggtggttc tttacgtctt      60
tcttgcgctg cttccggatt cactttctct gtttactcta tgaattgggt tcgccaagct     120
cctggtaaag gtttggagtg gtttcttat atcgttcctt ctggtggcaa tactccttat     180
gctgactccg ttaaaggtcg cttcactatc tctagagaca actctaagaa tactctctac     240
ttgcagatga acagcttaag ggctgaggac actgcagtct actattgtgc aagagatggg     300
gcggctacgg tggacttaga ctactggggc cagggaaccc tggtcaccgt ctcaagcgcc     360
tccaccaagg gcccatcggt cttcccg                                          387
```

<210> SEQ ID NO 28
<211> LENGTH: 129
<212> TYPE: PRT
<213> ORGANISM: Homo sapiens

<400> SEQUENCE: 28

Glu Val Gln Leu Leu Glu Ser Gly Gly Gly Leu Val Gln Pro Gly Gly

```
                    1               5                   10                  15
Ser Leu Arg Leu Ser Cys Ala Ala Ser Gly Phe Thr Phe Ser Val Tyr
                20                  25                  30

Ser Met Asn Trp Val Arg Gln Ala Pro Gly Lys Gly Leu Glu Trp Val
                35                  40                  45

Ser Tyr Ile Val Pro Ser Gly Gly Asn Thr Pro Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ala Ala Thr Val Asp Leu Asp Tyr Trp Gly Gln Gly
                100                 105                 110

Thr Leu Val Thr Val Ser Ser Ala Ser Thr Lys Gly Pro Ser Val Phe
                115                 120                 125

Pro
```

<210> SEQ ID NO 29
<211> LENGTH: 363
<212> TYPE: DNA
<213> ORGANISM: Homo sapiens

<400> SEQUENCE: 29

```
ggcgtgcact ctgacatcca gatgacccag tctccatcct ccctgtctgc atctgtagga      60
gacagagtca ccatcacttg ccgggcaagt cagagcatta gcagctattt aaattggtat     120
cagcagaaac cagggaaagc ccctaagctc ctgatctatg ctgcatccag tttgcaaagt     180
ggggtcccat caaggttcag tggcagtgga tctgggacag atttcactct caccatcagc     240
agtctgcaac tgaagatttt gcaacttac tactgtcaac agagttacag taccccctccg     300 gagaacactt ttggccaggg gaccaagctg gagatcaaac gaactgtggc tgcaccatct     360
gtc                                                                   363
```

<210> SEQ ID NO 30
<211> LENGTH: 121
<212> TYPE: PRT
<213> ORGANISM: Homo sapiens

<400> SEQUENCE: 30

```
Gly Val His Ser Asp Ile Gln Met Thr Gln Ser Pro Ser Ser Leu Ser
1               5                   10                  15

Ala Ser Val Gly Asp Arg Val Thr Ile Thr Cys Arg Ala Ser Gln Ser
                20                  25                  30

Ile Ser Ser Tyr Leu Asn Trp Tyr Gln Gln Lys Pro Gly Lys Ala Pro
                35                  40                  45

Lys Leu Leu Ile Tyr Ala Ala Ser Ser Leu Gln Ser Gly Val Pro Ser
                50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Tyr
                85                  90                  95

Ser Thr Pro Pro Glu Asn Thr Phe Gly Gln Gly Thr Lys Leu Glu Ile
                100                 105                 110

Lys Arg Thr Val Ala Ala Pro Ser Val
                115                 120
```

<210> SEQ ID NO 31
<211> LENGTH: 387
<212> TYPE: DNA
<213> ORGANISM: Homo sapiens

<400> SEQUENCE: 31

```
gaagttcaat tgttagagtc tggtggcggt cttgttcagc ctggtggttc tttacgtctt      60
tcttgcgctg cttccggatt cactttctct ccttaccata tgggttgggt tcgccaagct     120
cctggtaaag gtttggagtg ggtttctggt atctatcctt ctggtggctg gactaattat     180
gctgactccg ttaaaggtcg cttcactatc tctagagaca actctaagaa tactctctac     240
ttgcagatga acagcttaag ggctgaggac actgcagtct actattgtgc gagagatggg     300
tatagcagtg gctggttccg gtactggggc caggaaccc tggtcaccgt ctcaagcgcc      360
tccaccaagg gcccatcggt cttcccg                                         387
```

<210> SEQ ID NO 32
<211> LENGTH: 129
<212> TYPE: PRT
<213> ORGANISM: Homo sapiens

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

His Met Gly Trp Val Arg Gln Ala Pro Gly Lys Gly Leu Glu Trp Val
        35                  40                  45

Ser Gly Ile Tyr Pro Ser Gly Gly Trp Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Ser Ser Gly Trp Phe Arg Tyr Trp Gly Gln Gly
            100                 105                 110

Thr Leu Val Thr Val Ser Ser Ala Ser Thr Lys Gly Pro Ser Val Phe
        115                 120                 125

Pro

<210> SEQ ID NO 33
<211> LENGTH: 369
<212> TYPE: DNA
<213> ORGANISM: Homo sapiens

<400> SEQUENCE: 33

```
ggcgtgcact cacagagcga attgactcag cctccctccg cgtccgggtc tcctggacag      60
tcagtcacca tctcctgcac tggaaccagc agtgacgttg gtggttataa ctatgtctcc     120
tggtatcaac aacacccaga caaagccccc aaactcctga tttatgaggt cactcagcgg     180
ccctcagggg tccctgatcg cttctctggc tccaggtctg gcaacacggc ctccctgacc     240
gtctctgggc tccaggctga ggatgaggct gattattact gcagctcata tgcaggcagg     300
aacaatcttt atgtcttcgg acctgggacc aaggtcaccg tcctaggtca gcccaaggcc     360
aaccccact                                                            369
```

<210> SEQ ID NO 34
<211> LENGTH: 123
<212> TYPE: PRT
<213> ORGANISM: Homo sapiens

<400> SEQUENCE: 34

Gly Val His Ser Gln Ser Glu Leu Thr Gln Pro Pro Ser Ala Ser Gly
1               5                   10                  15

Ser Pro Gly Gln Ser Val Thr Ile Ser Cys Thr Gly Thr Ser Ser Asp
            20                  25                  30

Val Gly Gly Tyr Asn Tyr Val Ser Trp Tyr Gln Gln His Pro Asp Lys
        35                  40                  45

Ala Pro Lys Leu Leu Ile Tyr Glu Val Thr Gln Arg Pro Ser Gly Val
    50                  55                  60

Pro Asp Arg Phe Ser Gly Ser Arg Ser Gly Asn Thr Ala Ser Leu Thr
65                  70                  75                  80

Val Ser Gly Leu Gln Ala Glu Asp Glu Ala Asp Tyr Tyr Cys Ser Ser
                85                  90                  95

Tyr Ala Gly Arg Asn Asn Leu Tyr Val Phe Gly Pro Gly Thr Lys Val
            100                 105                 110

Thr Val Leu Gly Gln Pro Lys Ala Asn Pro Thr
        115                 120

<210> SEQ ID NO 35
<211> LENGTH: 405
<212> TYPE: DNA
<213> ORGANISM: Homo sapiens

<400> SEQUENCE: 35
gaagttcaat tgttagagtc tggtggcggt cttgttcagc ctggtggttc tttacgtctt      60
tcttgcgctg cttccggatt cactttctct gagtacaata tgatgtgggt tcgccaagct     120
cctggtaaag gtttggagtg ggtttctgtt atctctcctt ctggtggcgg tactcttat     180 gctgactccg ttaaaggtcg cttcactatc tctagagaca actctaagaa tactctctac     240
ttgcagatga acagcttaag ggctgaggac actgcagtct actattgtgc gagagatcta     300
aataacagct cgcccccgga ttccaatgat gcttttgata tctggggccg aggacaatg      360 gtcaccgtct caagcgcctc caccaagggc ccatcggtct cccg                       405

<210> SEQ ID NO 36
<211> LENGTH: 135
<212> TYPE: PRT
<213> ORGANISM: Homo sapiens

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Asn Met Met Trp Val Arg Gln Ala Pro Gly Lys Gly Leu Glu Trp Val
        35                  40                  45

Ser Val Ile Ser Pro Ser Gly Gly Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Asn Asn Ser Ser Pro Pro Asp Ser Asn Asp Ala Phe
            100                 105                 110

Asp Ile Trp Gly Arg Gly Thr Met Val Thr Val Ser Ser Ala Ser Thr
            115                 120                 125

Lys Gly Pro Ser Val Phe Pro
        130             135

<210> SEQ ID NO 37
<211> LENGTH: 366
<212> TYPE: DNA
<213> ORGANISM: Homo sapiens

<400> SEQUENCE: 37
ggcgtgcact cacagagcgt cttgactcag ccaccctcag tgtctgggac ccccggacag     60
agggtcacca tctcttgttc tggaggctac cccaacatgg gaagcaatta tgcacactgg    120
taccagcaac tcccaggaac ggcccccaaa ctcctcatct ataacgataa tcagcggccc    180
tcagggrtcc ctgaccgatt ctctggctcc aagtctggca cctcagcctc cctggccatc    240
agtgggctcc ggtccgagga tgaggctgat tattactgtg cagcatggga tgacagcctg    300
agtggtccgg tgttcggcgg agggaccaag ctgaccgtcc taggtcagcc caaggctgcc    360
ccctcg                                                                366

<210> SEQ ID NO 38
<211> LENGTH: 122
<212> TYPE: PRT
<213> ORGANISM: Homo sapiens

<400> SEQUENCE: 38

Gly Val His Ser Gln Ser Val Leu Thr Gln Pro Pro Ser Val Ser Gly
1               5                   10                  15

Thr Pro Gly Gln Arg Val Thr Ile Ser Cys Ser Gly Gly Tyr Pro Asn
            20                  25                  30

Met Gly Ser Asn Tyr Ala His Trp Tyr Gln Gln Leu Pro Gly Thr Ala
        35                  40                  45

Pro Lys Leu Leu Ile Tyr Asn Asp Asn Gln Arg Pro Ser Gly Val Pro
    50                  55                  60

Asp Arg Phe Ser Gly Ser Lys Ser Gly Thr Ser Ala Ser Leu Ala Ile
65                  70                  75                  80

Ser Gly Leu Arg Ser Glu Asp Glu Ala Asp Tyr Tyr Cys Ala Ala Trp
                85                  90                  95

Asp Asp Ser Leu Ser Gly Pro Val Phe Gly Gly Gly Thr Lys Leu Thr
            100                 105                 110

Val Leu Gly Gln Pro Lys Ala Ala Pro Ser
        115                 120

<210> SEQ ID NO 39
<211> LENGTH: 402
<212> TYPE: DNA
<213> ORGANISM: Homo sapiens

<400> SEQUENCE: 39
gaagttcaat tgttagagtc tggtggcggt cttgttcagc ctggtggttc tttacgtctt     60
tcttgcgctg cttccggatt cacttctctg tttacgata tgcctgggt tcgccaagct    120 cctggtaaag gtttgagtg ggtttctgtt atctatcctt ctggtggctt tactcgttat    180
gctgactccg ttaaaggtcg cttcactatc tctagagaca actctaagaa tactctctac    240

```
ttgcagatga acagcttaag ggctgaggac actgcagtct actattgtgc ggcagatccg      300
acgatacagc tatgggccta ctactacggt atggacgtct ggggccaagg gaccacggtc      360
accgtctcaa gcgcctccac caagggccca tcggtcttcc cg                         402
```

```
<210> SEQ ID NO 40
<211> LENGTH: 134
<212> TYPE: PRT
<213> ORGANISM: Homo sapiens

<400> SEQUENCE: 40
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Asp Met Pro Trp Val Arg Gln Ala Pro Gly Lys Gly Leu Glu Trp Val
        35                  40                  45

Ser Val Ile Tyr Pro Ser Gly Gly Phe Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Pro Thr Ile Gln Leu Trp Ala Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro
    130

```
<210> SEQ ID NO 41
<211> LENGTH: 363
<212> TYPE: DNA
<213> ORGANISM: Homo sapiens

<400> SEQUENCE: 41
ggcgtgcact cacagagcga attgactcag ccaccctcag cgtctgggac ccccgggcag      60
agggtcacca tctcttgttc tggaggcagc tccaacatcg gaagtaattt tgtttactgg     120
taccggcagc tcccaggaac ggccccccaaa ctcctcatct ataggaatta tcagcggccc    180
tcaggggtcc ctgaccgatt ctcgggttcc aagtctggca cctcagcctc cctggccatc     240
agtgggctcc gtccgaaga tgaggctgat tattactgcg cagcatggga tgacaacgtg      300 ggtgggggtct tcggatctgg gaccaaggtc accgtcctgg gtcagcccaa ggccaacccc    360
act                                                                   363
```

```
<210> SEQ ID NO 42
<211> LENGTH: 121
<212> TYPE: PRT
<213> ORGANISM: Homo sapiens

<400> SEQUENCE: 42
```

Gly Val His Ser Gln Ser Glu Leu Thr Gln Pro Pro Ser Ala Ser Gly
1               5                   10                  15

Thr Pro Gly Gln Arg Val Thr Ile Ser Cys Ser Gly Gly Ser Ser Asn
            20                  25                  30

Ile Gly Ser Asn Phe Val Tyr Trp Tyr Arg Gln Leu Pro Gly Thr Ala
        35                  40                  45

```
Pro Lys Leu Leu Ile Tyr Arg Asn Tyr Gln Arg Pro Ser Gly Val Pro
        50                  55                  60

Asp Arg Phe Ser Gly Ser Lys Ser Gly Thr Ser Ala Ser Leu Ala Ile
 65              70                  75                  80

Ser Gly Leu Leu Ser Glu Asp Glu Ala Asp Tyr Tyr Cys Ala Ala Trp
                85                  90                  95

Asp Asp Asn Val Gly Gly Val Phe Gly Ser Gly Thr Lys Val Thr Val
            100                 105                 110

Leu Gly Gln Pro Lys Ala Asn Pro Thr
        115                 120

<210> SEQ ID NO 43
<211> LENGTH: 405
<212> TYPE: DNA
<213> ORGANISM: Homo sapiens

<400> SEQUENCE: 43
gaagttcaat tgttagagtc tggtggcggt cttgttcagc ctggtggttc tttacgtctt      60
tcttgcgctg cttccggatt cactttctct tggtacgata tgtattgggt cgccaagct     120
cctggtaaag gtttggagtg ggtttcttct atctattctt ctggtggcta tactgcttat     180
gctgactccg ttaaaggtcg cttcactatc tctagagaca actctaagaa tactctctac     240
ttgcagatga acagcttaag gctgaggac actgcagtct actattgtgc gaaagatcgt      300
gatccttgta gtagaaccac ctgctataac tggttcgacc cctggggcca gggaaccctg     360
gtcaccgtct caagcgcctc caccaagggc ccatcggtct tcccg                     405

<210> SEQ ID NO 44
<211> LENGTH: 135
<212> TYPE: PRT
<213> ORGANISM: Homo sapiens

<400> SEQUENCE: 44

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
            20                  25                  30

Asp Met Tyr Trp Val Arg Gln Ala Pro Gly Lys Gly Leu Glu Trp Val
        35                  40                  45

Ser Ser Ile Tyr Ser Ser Gly Gly Tyr Thr Ala Tyr Ala Asp Ser Val
    50                  55                  60

Lys Gly Arg Phe Thr Ile Ser Arg Asp Asn Ser Lys Asn Thr Leu Tyr
 65              70                  75                  80

Leu Gln Met Asn Ser Leu Arg Ala Glu Asp Thr Ala Val Tyr Tyr Cys
                85                  90                  95

Ala Lys Asp Arg Asp Pro Cys Ser Arg Thr Thr Cys Tyr Asn Trp Phe
            100                 105                 110

Asp Pro Trp Gly Gln Gly Thr Leu Val Thr Val Ser Ser Ala Ser Thr
        115                 120                 125

Lys Gly Pro Ser Val Phe Pro
    130                 135

<210> SEQ ID NO 45
<211> LENGTH: 366
<212> TYPE: DNA
<213> ORGANISM: Homo sapiens
```

```
<400> SEQUENCE: 45
ggcgtgcact cacagagcga attgactcag ccaccctcag cgtctgggac ccccgggcag      60
agggtcacca tctcttgttc tggaggcagc tccaacatcg aagtaatta tgtctcctgg      120 taccagcagc tcccaggaac ggcccccaaa ctcctcatct ataataataa tcagcggccc    180 tcagggtcc ctgaccgatt ctctggctcc aagtctggca cctcagcctc cctggccatc      240
agtgggctcc ggtccgagga tgaggctgat tattactgtg cagcatggga tgacagcctg    300
agttctgctg tgttcggagg aggcacccag ctgaccgtcc tcggtcagcc caaggctgcc    360
ccctcg                                                                366

<210> SEQ ID NO 46
<211> LENGTH: 122
<212> TYPE: PRT
<213> ORGANISM: Homo sapiens

<400> SEQUENCE: 46

Gly Val His Ser Gln Ser Glu Leu Thr Gln Pro Pro Ser Ala Ser Gly
1               5                   10                  15

Thr Pro Gly Gln Arg Val Thr Ile Ser Cys Ser Gly Ser Ser Asn
            20                  25                  30

Ile Gly Ser Asn Tyr Val Ser Trp Tyr Gln Gln Leu Pro Gly Thr Ala
        35                  40                  45

Pro Lys Leu Leu Ile Tyr Asn Asn Asn Gln Arg Pro Ser Gly Val Pro
    50                  55                  60

Asp Arg Phe Ser Gly Ser Lys Ser Gly Thr Ser Ala Ser Leu Ala Ile
65                  70                  75                  80

Ser Gly Leu Arg Ser Glu Asp Glu Ala Asp Tyr Tyr Cys Ala Ala Trp
                85                  90                  95

Asp Asp Ser Leu Ser Ser Ala Val Phe Gly Gly Gly Thr Gln Leu Thr
            100                 105                 110

Val Leu Gly Gln Pro Lys Ala Ala Pro Ser
        115                 120

<210> SEQ ID NO 47
<211> LENGTH: 393
<212> TYPE: DNA
<213> ORGANISM: Homo sapiens

<400> SEQUENCE: 47
gaagttcaat tgttagagtc tggtggcggt cttgttcagc ctggtggttc tttacgtctt    60
tcttgcgctg cttccggatt cactttctct gcttaccgta tgttttgggt cgccaagct     120 cctggtaaag gtttggagtg ggtttcttct atctggcctt ctggtggcac tacttcttat    180
gctgactccg ttaaaggtcg cttcactatc tctagagaca actctaagaa tactctctac    240
ttgcagatga acagcttaag ggctgaggac actgcagtct actattgtgc gagagatcgg   300
ggctatgata gtagtggtta ttttgactac tggggccagg gaaccctggt caccgtctca    360
agcgcctcca ccaagggccc atcggtcttc ccg                                  393

<210> SEQ ID NO 48
<211> LENGTH: 131
<212> TYPE: PRT
<213> ORGANISM: Homo sapiens

<400> SEQUENCE: 48

Glu Val Gln Leu Leu Glu Ser Gly Gly Gly Leu Val Gln Pro Gly Gly
```

```
                1               5                  10                 15
Ser Leu Arg Leu Ser Cys Ala Ala Ser Gly Phe Thr Phe Ser Ala Tyr
                20                 25                 30

Arg Met Phe Trp Val Arg Gln Ala Pro Gly Lys Gly Leu Glu Trp Val
                35                 40                 45

Ser Ser Ile Trp Pro Ser Gly Gly Thr Thr Ser Tyr Ala Asp Ser Val
                50                 55                 60

Lys Gly Arg Phe Thr Ile Ser Arg Asp Asn Ser Lys Asn Thr Leu Tyr
65                     70                 75                 80

Leu Gln Met Asn Ser Leu Arg Ala Glu Asp Thr Ala Val Tyr Tyr Cys
                    85                 90                 95

Ala Arg Asp Arg Gly Tyr Asp Ser Ser Gly Tyr Phe Asp Tyr Trp Gly
                100                105                110

Gln Gly Thr Leu Val Thr Val Ser Ser Ala Ser Thr Lys Gly Pro Ser
                115                120                125

Val Phe Pro
        130

<210> SEQ ID NO 49
<211> LENGTH: 360
<212> TYPE: DNA
<213> ORGANISM: Homo sapiens

<400> SEQUENCE: 49
ggcgtgcact cacagagcgc tttgactcag ccaccctcgg tgtcactggc cccaggacag      60
acggccagga ttacctgtgg gggaaacaac attggaacta aaagtgttca ctggtaccag     120
cagaagccag gccaggcccc tgtgctggtc gtctatgatg acagcgaccg gccctcaggg     180
atccctgagc gattctctgg ctccaattct gggaacacgg ccaccctgac catcagcagg     240
gtcgaagccg gggatgaggc cgactattat tgtcaggtgt gggatagtgg tagtgatcat     300
caggtcttcg gcggagggac caagctgacc gtcctaggtc agcccaaggc tgccccctcg     360

<210> SEQ ID NO 50
<211> LENGTH: 120
<212> TYPE: PRT
<213> ORGANISM: Homo sapiens

<400> SEQUENCE: 50

Gly Val His Ser Gln Ser Ala Leu Thr Gln Pro Pro Ser Val Ser Leu
1               5                  10                 15

Ala Pro Gly Gln Thr Ala Arg Ile Thr Cys Gly Gly Asn Asn Ile Gly
                20                 25                 30

Thr Lys Ser Val His Trp Tyr Gln Gln Lys Pro Gly Gln Ala Pro Val
                35                 40                 45

Leu Val Val Tyr Asp Asp Ser Asp Arg Pro Ser Gly Ile Pro Glu Arg
                50                 55                 60

Phe Ser Gly Ser Asn Ser Gly Asn Thr Ala Thr Leu Thr Ile Ser Arg
65                     70                 75                 80

Val Glu Ala Gly Asp Glu Ala Asp Tyr Tyr Cys Gln Val Trp Asp Ser
                    85                 90                 95

Gly Ser Asp His Gln Val Phe Gly Gly Gly Thr Lys Leu Thr Val Leu
                100                105                110

Gly Gln Pro Lys Ala Ala Pro Ser
                115                120
```

<210> SEQ ID NO 51
<211> LENGTH: 422
<212> TYPE: DNA
<213> ORGANISM: Homo sapiens
<220> FEATURE:
<221> NAME/KEY: misc_feature
<222> LOCATION: (226)..(226)
<223> OTHER INFORMATION: n is a, c, g, or t

<400> SEQUENCE: 51

```
gaagttcaat tgttagagtc tggtggcggt cttgttcagc ctggtggttc tttacgtctt    60
tcttgcgctg cttccggatt cactttctct tggtacacta tgatgtgggt tcgccaagct   120
cctggtaaag gtttggagtg ggtttctcgt atctctcctt ctggtggcca tactctttat   180
gctgactccg ttaaaggtcg cttcactatc tctagagaca actctnagaa tactctctac   240
ttgcagatga acagcttaag ggctgaggac actgcagtct actattgtgc gagagacact   300
tgggacgatt actatgatag tagtggttat acaacgatt tgactactg ggccaggga   360
accctggtca ccgtctcaag cgcctccacc aagggcccat cggtcttccc gctagcgccc   420
tg                                                                  422
```

<210> SEQ ID NO 52
<211> LENGTH: 140
<212> TYPE: PRT
<213> ORGANISM: Homo sapiens

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Thr Met Met Trp Val Arg Gln Ala Pro Gly Lys Gly Leu Glu Trp Val
        35                  40                  45

Ser Arg Ile Ser Pro Ser Gly Gly His Thr Leu Tyr Ala Asp Ser Val
    50                  55                  60

Lys Gly Arg Phe Thr Ile Ser Arg Asp Asn Ser Glx Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Trp Asp Asp Tyr Tyr Asp Ser Ser Gly Tyr Tyr Asn
            100                 105                 110

Asp Phe Asp Tyr Trp Gly Gln Gly Thr Leu Val Thr Val Ser Ser Ala
        115                 120                 125

Ser Thr Lys Gly Pro Ser Val Phe Pro Leu Ala Pro
    130                 135                 140

<210> SEQ ID NO 53
<211> LENGTH: 360
<212> TYPE: DNA
<213> ORGANISM: Homo sapiens

<400> SEQUENCE: 53

```
ggcgtgcact ctgacatcca gatgacccag tctccaggca ccctgtcttt gtctccaggg    60
gaaagagcca ccctctcctg cagggccagt cagagtgtta gtcgtagcta cttaggctgg   120
taccagcaga aacctggcca ggctcccagg ctcctcatct atggtgcatc caacagggcc   180
actggcatcc cagacaggtt cagtggcagt gggtctggga cagacttcac tctcaccatc   240
agcagactgg agcctgaaga ttttgcagtg tattactgtc agcagtacgg tatctcaccc   300
```
ctcaccttcg gccctgggac caaagtggat atcaaacgaa ctgtggctgc accatctgtc    360

<210> SEQ ID NO 54
<211> LENGTH: 120
<212> TYPE: PRT
<213> ORGANISM: Homo sapiens

<400> SEQUENCE: 54

Gly Val His Ser Asp Ile Gln Met Thr Gln Ser Pro Gly Thr Leu Ser
1               5                   10                  15

Leu Ser Pro Gly Glu Arg Ala Thr Leu Ser Cys Arg Ala Ser Gln Ser
            20                  25                  30

Val Ser Arg Ser Tyr Leu Gly Trp Tyr Gln Gln Lys Pro Gly Gln Ala
        35                  40                  45

Pro Arg Leu Leu Ile Tyr Gly Ala Ser Asn Arg Ala Thr Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Gln Gln Tyr
                85                  90                  95

Gly Ile Ser Pro Leu Thr Phe Gly Pro Gly Thr Lys Val Asp Ile Lys
            100                 105                 110

Arg Thr Val Ala Ala Pro Ser Val
        115                 120

<210> SEQ ID NO 55
<211> LENGTH: 390
<212> TYPE: DNA
<213> ORGANISM: Homo sapiens

<400> SEQUENCE: 55
gaagttcaat tgttagagtc tggtggcggt cttgttcagc ctggtggttc tttacgtctt     60
tcttgcgctg cttccggatt cactttctct gcttactgga tggattgggt tcgccaagct    120
cctggtaaag gtttggagtg gtttctgtt atctatcctt ctggtggctc tactaattat     180
gctgactccg ttaaaggtcg cttcactatc tctagagaca actctaagaa tactctctac    240
ttgcagatga acagcttaag ggctgaggac actgcagtct actattgtgc gagagagggg    300
atagccgcag cagcaccaat ggacgtctgg ggcaaaggga ccacggtcac cgtctcaagc    360
gcctccacca agggcccatc ggtcttcccg                                      390

<210> SEQ ID NO 56
<211> LENGTH: 130
<212> TYPE: PRT
<213> ORGANISM: Homo sapiens

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Trp Met Asp Trp Val Arg Gln Ala Pro Gly Lys Gly Leu Glu Trp Val
        35                  40                  45

Ser Val Ile Tyr Pro Ser Gly Gly Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Glu Gly Ile Ala Ala Ala Pro Met Asp Val Trp Gly Lys
                100             105                 110

Gly Thr Thr Val Thr Val Ser Ser Ala Ser Thr Lys Gly Pro Ser Val
            115                 120                 125

Phe Pro
    130

<210> SEQ ID NO 57
<211> LENGTH: 366
<212> TYPE: DNA
<213> ORGANISM: Homo sapiens

<400> SEQUENCE: 57
ggcgtgcact ctgacatcca gatgacccag tctccaggca ccctgtcttt gtctccaggg     60
gaaagagcca ccctctcctg cagggccagt cagagtgtta gcagcagcta ctttgcctgg    120
taccagcaga aacctggcca ggctcccagg ctcctcatct atgatgcatc cagcagggcc    180
actggcatcc cagacaggtt cagtggcagt gggtctggga cagacttcac tctcaccatc    240
agcagactgg agcctgaaga ttttgcagtg tattactgtc agcagtatgg tagctcacct    300
ccgatgtaca cttttggcca ggggaccaag ctggagatca aacgaactgt ggctgcacca    360
tctgtc                                                               366

<210> SEQ ID NO 58
<211> LENGTH: 122
<212> TYPE: PRT
<213> ORGANISM: Homo sapiens

<400> SEQUENCE: 58

Gly Val His Ser Asp Ile Gln Met Thr Gln Ser Pro Gly Thr Leu Ser
1               5                   10                  15

Leu Ser Pro Gly Glu Arg Ala Thr Leu Ser Cys Arg Ala Ser Gln Ser
            20                  25                  30

Val Ser Ser Ser Tyr Phe Ala Trp Tyr Gln Gln Lys Pro Gly Gln Ala
        35                  40                  45

Pro Arg Leu Leu Ile Tyr Asp Ala Ser Ser Arg Ala Thr Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Gln Gln Tyr
                85                  90                  95

Gly Ser Ser Pro Pro Met Tyr Thr Phe Gly Gln Gly Thr Lys Leu Glu
                100                 105                 110

Ile Lys Arg Thr Val Ala Ala Pro Ser Val
            115                 120

<210> SEQ ID NO 59
<211> LENGTH: 405
<212> TYPE: DNA
<213> ORGANISM: Homo sapiens

<400> SEQUENCE: 59
gaagttcaat tgttagagtc tggtggcggt cttgttcagc ctggtggttc tttacgtctt     60
tcttgcgctg cttccggatt cactttctct acttacgata tgcttgggt tcgccaagct    120

```
cctggtaaag gtttggagtg ggtttcttct atctctcctt ctggtggctc tacttcttat    180
gctgactccg ttaaaggtcg cttcactatc tctagagaca actctaagaa tactctctac    240
ttgcagctga acagcttaag ggctgaggac actgcagtct actattgtgc gagagagaaa    300
gcgtcggatc tttcggggac ttactctgag gcccttgacc actggggcca gggaaccctg    360
gtcaccgtct caagcgcctc caccaagggc ccatcggtct cccg                     405
```

<210> SEQ ID NO 60
<211> LENGTH: 135
<212> TYPE: PRT
<213> ORGANISM: Homo sapiens

<400> SEQUENCE: 60

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Thr Tyr
            20                  25                  30
Asp Met Leu Trp Val Arg Gln Ala Pro Gly Lys Gly Leu Glu Trp Val
        35                  40                  45
Ser Ser Ile Ser Pro Ser Gly Gly Ser Thr Ser Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Leu Asn Ser Leu Arg Ala Glu Asp Thr Ala Val Tyr Tyr Cys
                85                  90                  95
Ala Arg Glu Lys Ala Ser Asp Leu Ser Gly Thr Tyr Ser Glu Ala Leu
            100                 105                 110
Asp His Trp Gly Gln Gly Thr Leu Val Thr Val Ser Ser Ala Ser Thr
        115                 120                 125
Lys Gly Pro Ser Val Phe Pro
    130                 135

<210> SEQ ID NO 61
<211> LENGTH: 360
<212> TYPE: DNA
<213> ORGANISM: Homo sapiens

<400> SEQUENCE: 61

```
ggcgtgcact ctgacatcca gatgacccag tctccatcct ccctgtctgc atctgtggga    60
gacagagtcg ccatcacttg ccgtgcaagt cagagcatcg acacctattt aaattggtat    120
cagcagaaac cagggaaagc ccctaaactc ctgatctatg ctgcatccaa gttggaagac    180
ggggtcccat caagattcag tggcagtgga actgggacag atttcactct caccatcaga    240
agtctgcaac tgaagatttt gcaagttat ttctgtcaac agagctactc tagtccaggg    300
atcactttcg gccctgggac caaggtggag atcaaacgaa ctgtggctgc accatctgtc    360
```

<210> SEQ ID NO 62
<211> LENGTH: 120
<212> TYPE: PRT
<213> ORGANISM: Homo sapiens

<400> SEQUENCE: 62

Gly Val His Ser Asp Ile Gln Met Thr Gln Ser Pro Ser Ser Leu Ser
1               5                   10                  15
Ala Ser Val Gly Asp Arg Val Ala Ile Thr Cys Arg Ala Ser Gln Ser
            20                  25                  30

```
Ile Asp Thr Tyr Leu Asn Trp Tyr Gln Gln Lys Pro Gly Lys Ala Pro
         35                  40                  45

Lys Leu Leu Ile Tyr Ala Ala Ser Lys Leu Glu Asp Gly Val Pro Ser
     50                  55                  60

Arg Phe Ser Gly Ser Gly Thr Gly Thr Asp Phe Thr Leu Thr Ile Arg
65                  70                  75                  80

Ser Leu Gln Pro Glu Asp Phe Ala Ser Tyr Phe Cys Gln Gln Ser Tyr
                 85                  90                  95

Ser Ser Pro Gly Ile Thr Phe Gly Pro Gly Thr Lys Val Glu Ile Lys
             100                 105                 110

Arg Thr Val Ala Ala Pro Ser Val
             115                 120
```

<210> SEQ ID NO 63
<211> LENGTH: 405
<212> TYPE: DNA
<213> ORGANISM: Homo sapiens

<400> SEQUENCE: 63

```
gaagttcaat tgttagagtc tggtggcggt cttgttcagc ctggtggttc tttacgtctt      60
tcttgcgctg cttccggatt cactttctct gattacttta tgaagtgggt tcgccaagct     120
cctggtaaag gtttggagtg gtttcttct atctatcctt ctggtggccc tactaagtat      180
gctgactccg ttaaaggtcg cttcactatc tctagagaca actctaagaa tactctctac     240
ttgcagatga acagcttaag ggctgaggac actgcagtct actattgtgc gagagagcgt     300
agcagtggct ggtacggtta ctactactac ggtatggacg tctggggcca agggaccacg     360
gtcaccgtct caagcgcctc caccaagggc ccatcggtct tcccg                      405
```

<210> SEQ ID NO 64
<211> LENGTH: 135
<212> TYPE: PRT
<213> ORGANISM: Homo sapiens

<400> SEQUENCE: 64

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
             20                  25                  30

Phe Met Lys Trp Val Arg Gln Ala Pro Gly Lys Gly Leu Glu Trp Val
         35                  40                  45

Ser Ser Ile Tyr Pro Ser Gly Gly Pro Thr Lys Tyr Ala Asp Ser Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Glu Arg Ser Ser Gly Trp Tyr Gly Tyr Tyr Tyr Tyr Gly Met
             100                 105                 110

Asp Val Trp Gly Gln Gly Thr Thr Val Thr Val Ser Ser Ala Ser Thr
         115                 120                 125

Lys Gly Pro Ser Val Phe Pro
         130                 135
```

<210> SEQ ID NO 65
<211> LENGTH: 354
<212> TYPE: DNA

<213> ORGANISM: Homo sapiens

<400> SEQUENCE: 65

```
ggcgtgcact ctgacatcca gatgacccag tctccatcct tcctgtctgc ttctgtaggg    60
gacagagtca ccatcacttg ccgggccagt cagggcatta gggattttt aggctggtat    120
caacaaaaac cagggaaagc ccctaatcaa ctgatctatg ctgcatccat tttgcaaagt    180
ggggtcccat caaggttcag cggcagtgga tctgggacag atttcactct cacgatcacc    240
agcctgcagc ctgaggattt tgcaacttat ttctgtcaac agcttaatgg ctaccgcgcc    300
ttcggccaag ggacacgact ggaaataaag cgaactgtgg ctgcaccatc tgtc          354
```

<210> SEQ ID NO 66
<211> LENGTH: 118
<212> TYPE: PRT
<213> ORGANISM: Homo sapiens

<400> SEQUENCE: 66

```
Gly Val His Ser Asp Ile Gln Met Thr Gln Ser Pro Ser Phe Leu Ser
1               5                   10                  15
Ala Ser Val Gly Asp Arg Val Thr Ile Thr Cys Arg Ala Ser Gln Gly
            20                  25                  30
Ile Arg Asp Phe Leu Gly Trp Tyr Gln Gln Lys Pro Gly Lys Ala Pro
        35                  40                  45
Asn Gln Leu Ile Tyr Ala Ala Ser Ile Leu Gln Ser Gly Val Pro Ser
    50                  55                  60
Arg Phe Ser Gly Ser Gly Ser Gly Thr Asp Phe Thr Leu Thr Ile Thr
65                  70                  75                  80
Ser Leu Gln Pro Glu Asp Phe Ala Thr Tyr Phe Cys Gln Gln Leu Asn
                85                  90                  95
Gly Tyr Arg Ala Phe Gly Gln Gly Thr Arg Leu Glu Ile Lys Arg Thr
            100                 105                 110
Val Ala Ala Pro Ser Val
        115
```

<210> SEQ ID NO 67
<211> LENGTH: 390
<212> TYPE: DNA
<213> ORGANISM: Homo sapiens

<400> SEQUENCE: 67

```
gaagttcaat tgttagagtc tggtggcggt cttgttcagc ctggtggttc tttacgtctt    60
tcttgcgctg cttccggatt cactttctct ccttacgaga tgcagtgggt tcgccaagct    120
cctggtaaag gtttggagtg ggtttctggt atcggttctt ctggtggtga ctccgttaaa    180
ggtcgcttca ctatctctag agacaactct aagaatactc tctacttgca gatgaacagc    240
ttaagggctg aggacactgc agtctactat tgtgcgagag agggtagatt gtagtggt    300
ggtggctgcg ggagctactt tgactactgg ggccagggaa ccctggtcac cgtctcaagc    360
gcctccacca agggcccatc ggtcttcccg                                     390
```

<210> SEQ ID NO 68
<211> LENGTH: 130
<212> TYPE: PRT
<213> ORGANISM: Homo sapiens

<400> SEQUENCE: 68

```
Glu Val Gln Leu Leu Glu Ser Gly Gly Gly Leu Val Gln Pro Gly Gly
```

```
                1               5                   10                  15
Ser Leu Arg Leu Ser Cys Ala Ala Ser Gly Phe Thr Phe Ser Pro Tyr
                    20                  25                  30

Glu Met Gln Trp Val Arg Gln Ala Pro Gly Lys Gly Leu Glu Trp Val
            35                  40                  45

Ser Gly Ile Gly Ser Ser Gly Gly Asp Ser Val Lys Gly Arg Phe Thr
    50                  55                  60

Ile Ser Arg Asp Asn Ser Lys Asn Thr Leu Tyr Leu Gln Met Asn Ser
65                  70                  75                  80

Leu Arg Ala Glu Asp Thr Ala Val Tyr Tyr Cys Ala Arg Glu Arg Val
                85                  90                  95

Asp Cys Ser Gly Gly Cys Gly Ser Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro
    130
```

<210> SEQ ID NO 69
<211> LENGTH: 357
<212> TYPE: DNA
<213> ORGANISM: Homo sapiens

<400> SEQUENCE: 69

```
ggcgtgcact ctgacatcca gatgacccag tctccatctt ccgtgtctgc atctgtagga      60
gacagagtca cgatcacttg tcgggcgagt cagggtatta gcaagagctt agcctggtat     120
cagcagaaac cagggaaagc ccctaaactc ctggtctatg gtgcattcag tttggaaagt     180
ggggtcccat caagattcag cggcactgga gctgggacag atttcattct caccatcagc     240
aggctgcagc ctgaagactt tgcaacttat tattgtcaac aggctaacag tttcccgctc     300
actttcggcg gagggaccaa ggtggagatc aaacgaactg tggctgcacc atctgtc       357
```

<210> SEQ ID NO 70
<211> LENGTH: 119
<212> TYPE: PRT
<213> ORGANISM: Homo sapiens

<400> SEQUENCE: 70

```
Gly Val His Ser Asp Ile Gln Met Thr Gln Ser Pro Ser Ser Val Ser
1               5                   10                  15

Ala Ser Val Gly Asp Arg Val Thr Ile Thr Cys Arg Ala Ser Gln Gly
            20                  25                  30

Ile Ser Lys Ser Leu Ala Trp Tyr Gln Gln Lys Pro Gly Lys Ala Pro
        35                  40                  45

Lys Leu Leu Val Tyr Gly Ala Phe Ser Leu Glu Ser Gly Val Pro Ser
    50                  55                  60

Arg Phe Ser Gly Thr Gly Ala Gly Thr Asp Phe Ile Leu Thr Ile Ser
65                  70                  75                  80

Arg Leu Gln Pro Glu Asp Phe Ala Thr Tyr Tyr Cys Gln Gln Ala Asn
                85                  90                  95

Ser Phe Pro Leu Thr Phe Gly Gly Gly Thr Lys Val Glu Ile Lys Arg
            100                 105                 110

Thr Val Ala Ala Pro Ser Val
        115
```

<210> SEQ ID NO 71
<211> LENGTH: 384
<212> TYPE: DNA
<213> ORGANISM: Homo sapiens

<400> SEQUENCE: 71

```
gaagttcaat tgttagagtc tggtggcggt cttgttcagc ctggtggttc tttacgtctt      60
tcttgcgctg cttccggatt cactttctct ttttactgga tgatgtgggt tcgccaagct     120
cctggtaaag gtttggagtg ggtttctggt atctcttctt ctggtggctt tactaagtat     180
gctgactccg ttaaaggtcg cttcactatc tctagagaca actccaagaa tactctctac     240
ttgcagatga acagcttaag ggctgaggac actgcagtct actattgtgc gagggagacc     300
agccggaggg cttttgatat ctggggccaa gggacaatgg tcaccgtctc aagcgcctcc     360
accaagggcc catcggtctt cccg                                             384
```

<210> SEQ ID NO 72
<211> LENGTH: 128
<212> TYPE: PRT
<213> ORGANISM: Homo sapiens

<400> SEQUENCE: 72

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Trp Met Met Trp Val Arg Gln Ala Pro Gly Lys Gly Leu Glu Trp Val
        35                  40                  45

Ser Gly Ile Ser Ser Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Ser Arg Arg Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125
```

<210> SEQ ID NO 73
<211> LENGTH: 363
<212> TYPE: DNA
<213> ORGANISM: Homo sapiens

<400> SEQUENCE: 73

```
ggcgtgcact ctgacatcca gatgacccag tctccaggca ccctgtcttt gtctccaggg      60
gaaagagcca ccctctcctg cagggccagt cagagtgtta gcagcagcta cttagcctgg     120
taccagcaga aacctggcca ggctcccagg ctcctcatct atggtgcatc cagcagggcc     180
actggcatcc cagacaggtt cagtggcagt gggtctggga cagacttcac tctcaccatc     240
agcagactgg agcctgaaga ttttgcagtg tattactgtc agcagtatgg tagctcacct     300
gagatcacct tcggccaagg gacacgactg gagattaaac gaactgtggc tgcaccatct     360
gtc                                                                    363
```

<210> SEQ ID NO 74
<211> LENGTH: 121
<212> TYPE: PRT

<213> ORGANISM: Homo sapiens

<400> SEQUENCE: 74

Gly Val His Ser Asp Ile Gln Met Thr Gln Ser Pro Gly Thr Leu Ser
1               5                   10                  15

Leu Ser Pro Gly Glu Arg Ala Thr Leu Ser Cys Arg Ala Ser Gln Ser
            20                  25                  30

Val Ser Ser Ser Tyr Leu Ala Trp Tyr Gln Gln Lys Pro Gly Gln Ala
        35                  40                  45

Pro Arg Leu Leu Ile Tyr Gly Ala Ser Ser Arg Ala Thr Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Gln Gln Tyr
                85                  90                  95

Gly Ser Ser Pro Glu Ile Thr Phe Gly Gln Gly Thr Arg Leu Glu Ile
            100                 105                 110

Lys Arg Thr Val Ala Ala Pro Ser Val
            115                 120

<210> SEQ ID NO 75
<211> LENGTH: 411
<212> TYPE: DNA
<213> ORGANISM: Homo sapiens

<400> SEQUENCE: 75
gaagttcaat tgttagagtc tggtggcggt cttgttcagc ctggtggttc tttacgtctt     60
tcttgcgctg cttccggatt cactttctct gagtactgga tgccttgggt tcgccaagct    120
cctggtaaag gtttggagtg ggtttctcgt atctatcctt ctggtggcgt tactacttat    180
gctgactccg ttaaaggtcg cttcactatc tctagagaca actctaagaa tactctctac    240
ttgcagatga acagcttaag ggctgaggac actgcagtct actattgtgc gagagggggg    300
gattacgatt tttggagtgt acaatactac tactactaca tggacgtctg gggcaaaggg    360
accacggtca ccgtctcaag cgcctccacc aagggcccat cggtcttccc g             411

<210> SEQ ID NO 76
<211> LENGTH: 137
<212> TYPE: PRT
<213> ORGANISM: Homo sapiens

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Trp Met Pro Trp Val Arg Gln Ala Pro Gly Lys Gly Leu Glu Trp Val
        35                  40                  45

Ser Arg Ile Tyr Pro Ser Gly Gly Val Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Tyr Asp Phe Trp Ser Val Gln Tyr Tyr Tyr Tyr
            100                 105                 110

```
Tyr Met Asp Val Trp Gly Lys Gly Thr Thr Val Thr Val Ser Ser Ala
            115                 120                 125
Ser Thr Lys Gly Pro Ser Val Phe Pro
        130                 135

<210> SEQ ID NO 77
<211> LENGTH: 360
<212> TYPE: DNA
<213> ORGANISM: Homo sapiens

<400> SEQUENCE: 77
ggcgtgcact ctgacatcca gatgacccag tctccatcct tcctgtctgc atctgtagga    60
gacagagtca ccatcacttg ccgggccagt cagggcatta gcagttattt agcctggtat   120
cagcaaaaac cagggaaagc ccctaagctc ctgatctatg ctgcatccac tttgcaaagt   180
ggggtcccat caaggttcag cggcagtgga tctggaacag atttcactct caccatcagc   240
agtctggaac tgaagatttt gcaacttac tactgtcaag agagttacag tacccccttc    300
tttactttcg gccctgggac caaagtggat atcagacgaa ctgtggctgc accatctgtc   360

<210> SEQ ID NO 78
<211> LENGTH: 120
<212> TYPE: PRT
<213> ORGANISM: Homo sapiens

<400> SEQUENCE: 78

Gly Val His Ser Asp Ile Gln Met Thr Gln Ser Pro Ser Phe Leu Ser
1               5                   10                  15
Ala Ser Val Gly Asp Arg Val Thr Ile Thr Cys Arg Ala Ser Gln Gly
            20                  25                  30
Ile Ser Ser Tyr Leu Ala Trp Tyr Gln Gln Lys Pro Gly Lys Ala Pro
        35                  40                  45
Lys Leu Leu Ile Tyr Ala Ala Ser Thr Leu Gln Ser Gly Val Pro Ser
    50                  55                  60
Arg Phe Ser Gly Ser Gly Ser Gly Thr Asp Phe Thr Leu Thr Ile Ser
65                  70                  75                  80
Ser Leu Glu Pro Glu Asp Phe Ala Thr Tyr Tyr Cys Gln Glu Ser Tyr
                85                  90                  95
Ser Thr Pro Phe Phe Thr Phe Gly Pro Gly Thr Lys Val Asp Ile Arg
            100                 105                 110
Arg Thr Val Ala Ala Pro Ser Val
        115                 120

<210> SEQ ID NO 79
<211> LENGTH: 393
<212> TYPE: DNA
<213> ORGANISM: Homo sapiens

<400> SEQUENCE: 79
gaagttcaat tgttagagtc tggtggcggt cttgttcagc ctggtggttc tttacgtctt    60
tcttgcgctg cttccggatt cactttctct cagtacttta tgaagtgggt cgccaagct   120 cctggtaaag gtttggagtg ggtttcttct atctctcctt ctggtggcct tactcagtat   180
gctgactccg ttaaaggtcg cttcactatc tctagagaca actctaagaa tactctctac   240
ttgcagatga acagcttaag ggctgaggac actgcagtct actattgtgc gagaggtggt   300
atagaagcac ctgggtcccc ctctgactac tgggccagg gaaccctggt caccgtctca    360
agcgcctcca ccaagggccc atcggtcttc ccg                                393
```

<210> SEQ ID NO 80
<211> LENGTH: 131
<212> TYPE: PRT
<213> ORGANISM: Homo sapiens

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Phe Met Lys Trp Val Arg Gln Ala Pro Gly Lys Gly Leu Glu Trp Val
        35                  40                  45

Ser Ser Ile Ser Pro Ser Gly Gly Leu Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ile Glu Ala Pro Gly Ser Pro Ser Tyr Trp Gly
            100                 105                 110

Gln Gly Thr Leu Val Thr Val Ser Ser Ala Ser Thr Lys Gly Pro Ser
        115                 120                 125

Val Phe Pro
    130

<210> SEQ ID NO 81
<211> LENGTH: 357
<212> TYPE: DNA
<213> ORGANISM: Homo sapiens

<400> SEQUENCE: 81
ggcgtgcact ctgacatcca gatgacccag tctccagcca ccctgtcttt gtctccaggg      60
gaaagagcca ccctctcctg cagggccagt cagagtgtta gcagctactt agcctggtac     120
caacagaaac ctggccaggc tcccaggctc ctcatctatg atgcatccaa cagggccact     180
ggcatcccag ccaggttcag tggcagtggg tctgggacag acttcactct caccatcagc     240
agcctagagc ctgaagattt tgcagtttat tactgtcagc agcgtagcaa ctggcctcgg     300
actttcggcg gagggaccaa ggtggagatc aaacgaactg tggctgcacc atctgtc       357

<210> SEQ ID NO 82
<211> LENGTH: 119
<212> TYPE: PRT
<213> ORGANISM: Homo sapiens

<400> SEQUENCE: 82

Gly Val His Ser Asp Ile Gln Met Thr Gln Ser Pro Ala Thr Leu Ser
1               5                   10                  15

Leu Ser Pro Gly Glu Arg Ala Thr Leu Ser Cys Arg Ala Ser Gln Ser
            20                  25                  30

Val Ser Ser Tyr Leu Ala Trp Tyr Gln Gln Lys Pro Gly Gln Ala Pro
        35                  40                  45

Arg Leu Leu Ile Tyr Asp Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Arg Ser
            85                  90                  95

Asn Trp Pro Arg Thr Phe Gly Gly Thr Lys Val Glu Ile Lys Arg
            100                 105                 110

Thr Val Ala Ala Pro Ser Val
            115

<210> SEQ ID NO 83
<211> LENGTH: 396
<212> TYPE: DNA
<213> ORGANISM: Homo sapiens

<400> SEQUENCE: 83
gaagttcaat tgttagagtc tggtggcggt cttgttcagc ctggtggttc tttacgtctt     60
tcttgcgctg cttccggatt cactttctct cagtaccaga tgatttgggt tcgccaagct    120
cctggtaaag gtttggagtg gtttctgtt atcgttcctt ctggtggcat tactaattat    180
gctgactccg ttaaaggtcg cttcactatc tctagagaca actctaagaa tactctctac    240
ttgcagatga acagcttaag ggctgaggac actgcagtct actattgtgc gagaggtggg    300
gtagaggcag tggatagttc gtcgcctgac tactggggcc agggaaccct ggtcaccgtc    360
tcaagcgcct ccaccaaggg cccatcggtc ttcccg                              396

<210> SEQ ID NO 84
<211> LENGTH: 132
<212> TYPE: PRT
<213> ORGANISM: Homo sapiens

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Gln Met Ile Trp Val Arg Gln Ala Pro Gly Lys Gly Leu Glu Trp Val
            35                  40                  45

Ser Val Ile Val Pro Ser Gly Gly Ile Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Gly Val Glu Ala Val Asp Ser Ser Pro Asp Tyr Trp
            100                 105                 110

Gly Gln Gly Thr Leu Val Thr Val Ser Ser Ala Ser Thr Lys Gly Pro
            115                 120                 125

Ser Val Phe Pro
    130

<210> SEQ ID NO 85
<211> LENGTH: 366
<212> TYPE: DNA
<213> ORGANISM: Homo sapiens

<400> SEQUENCE: 85
ggcgtgcact cacagagcga attgactcag ccccactctg tgtcggggtc tccggggaag     60
acggtaacca tctcctgcac ccgcagcagt ggcagcattg ccggcaacta tgtgcagtgg    120
taccagcagc gcccgggcag ttccccccacc actgtgatct atgaggataa caaaagaccc    180

```
tctggggtcc ctgatcggtt ctctggctcc atcgacagct cctccaactc tgcctccctc    240
atcatctctg gactgaagac tgaggacgag gctgactact actgtcattc ttatgatacc    300
agcaatcagg tattcggcgg agggaccaaa ctgaccgtcc taggtcagcc caaggctgcc    360
ccctcg                                                               366
```

```
<210> SEQ ID NO 86
<211> LENGTH: 122
<212> TYPE: PRT
<213> ORGANISM: Homo sapiens

<400> SEQUENCE: 86
```

Gly Val His Ser Gln Ser Glu Leu Thr Gln Pro His Ser Val Ser Gly
1               5                   10                  15

Ser Pro Gly Lys Thr Val Thr Ile Ser Cys Thr Arg Ser Ser Gly Ser
            20                  25                  30

Ile Ala Gly Asn Tyr Val Gln Trp Tyr Gln Gln Arg Pro Gly Ser Ser
        35                  40                  45

Pro Thr Thr Val Ile Tyr Glu Asp Asn Lys Arg Pro Ser Gly Val Pro
    50                  55                  60

Asp Arg Phe Ser Gly Ser Ile Asp Ser Ser Asn Ser Ala Ser Leu
65                  70                  75                  80

Ile Ile Ser Gly Leu Lys Thr Glu Asp Glu Ala Asp Tyr Tyr Cys His
                85                  90                  95

Ser Tyr Asp Thr Ser Asn Gln Val Phe Gly Gly Gly Thr Lys Leu Thr
            100                 105                 110

Val Leu Gly Gln Pro Lys Ala Ala Pro Ser
        115                 120

```
<210> SEQ ID NO 87
<211> LENGTH: 393
<212> TYPE: DNA
<213> ORGANISM: Homo sapiens

<400> SEQUENCE: 87
```

```
gaagttcaat tgttagagtc tggtggcggt cttgttcagc ctggtggttc tttacgtctt    60
tcttgcgctg cttccggatt cactttctct cgttacatga tgaattgggt tcgccaagct    120
cctggtaaag gtttggagtg ggtttctgtt atctggtctt ctggtggcaa gactctttat    180
gctgactccg ttaaaggtcg cttcactatc tctagagaca actctaagaa tactctctac    240
ttgcagatga gagcttaag ggctgaggac actgcagtct actattgtgc gagggtggt     300 tacaacaact actactactc tatggacgtc tggggccaag ggaccacggt caccgtctca    360
agcgcctcca ccaagggccc atcggtcttc ccg                                 393
```

```
<210> SEQ ID NO 88
<211> LENGTH: 131
<212> TYPE: PRT
<213> ORGANISM: Homo sapiens

<400> SEQUENCE: 88
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Met Met Asn Trp Val Arg Gln Ala Pro Gly Lys Gly Leu Glu Trp Val
        35                  40                  45

```
Ser Val Ile Trp Ser Ser Gly Lys Thr Leu Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Lys Ser Leu Arg Ala Glu Asp Thr Ala Val Tyr Tyr Cys
                 85                  90                  95

Ala Arg Gly Gly Tyr Asn Asn Tyr Tyr Tyr Ser Met Asp Val Trp Gly
            100                 105                 110

Gln Gly Thr Thr Val Thr Val Ser Ser Ala Ser Thr Lys Gly Pro Ser
            115                 120                 125

Val Phe Pro
    130
```

<210> SEQ ID NO 89
<211> LENGTH: 357
<212> TYPE: DNA
<213> ORGANISM: Homo sapiens

<400> SEQUENCE: 89

```
ggcgtgcact ctgacatcca gatgacccag tctccttcct ccctgtctgc ctctgtagga      60
gacagagtca ccatcgcgtg ccggacaagt cagaacgtta ataggtacct gaattggtat     120
caacataaac tcggccaggc ccctaaactc ctgatctacg gtgcaaccat tttgcagagt     180
ggggtcccat caaggttccg tggcagtgga tctgggacag atttcatcct caccatcacc     240
aatctgcaac ctgaagattt tgcagtttac tactgtcaac agacttacag tccccccactg    300 acgttcggcc aagggaccaa ggcggaattt aaaggaactg tggctgcacc atctgtc        357
```

<210> SEQ ID NO 90
<211> LENGTH: 119
<212> TYPE: PRT
<213> ORGANISM: Homo sapiens

<400> SEQUENCE: 90

```
Gly Val His Ser Asp Ile Gln Met Thr Gln Ser Pro Ser Ser Leu Ser
  1               5                  10                  15

Ala Ser Val Gly Asp Arg Val Thr Ile Ala Cys Arg Thr Ser Gln Asn
             20                  25                  30

Val Asn Arg Tyr Leu Asn Trp Tyr Gln His Lys Leu Gly Gln Ala Pro
         35                  40                  45

Lys Leu Leu Ile Tyr Gly Ala Thr Ile Leu Gln Ser Gly Val Pro Ser
     50                  55                  60

Arg Phe Arg Gly Ser Gly Ser Gly Thr Asp Phe Ile Leu Thr Ile Thr
 65                  70                  75                  80

Asn Leu Gln Pro Glu Asp Phe Ala Val Tyr Tyr Cys Gln Gln Thr Tyr
                 85                  90                  95

Ser Pro Pro Leu Thr Phe Gly Gln Gly Thr Lys Ala Glu Phe Lys Gly
            100                 105                 110

Thr Val Ala Ala Pro Ser Val
            115
```

<210> SEQ ID NO 91
<211> LENGTH: 369
<212> TYPE: DNA
<213> ORGANISM: Homo sapiens

<400> SEQUENCE: 91

```
gaagttcaat tgttagagtc tggtggcggt cttgttcagc ctggtggttc tttacgtctt      60
tcttgcgctg cttccggatt cactttctct tcttacgcta tgatgtgggt tcgccaagct     120
cctggtaaag gtttggagtg gtttcttgg atcgttcctt ctggtggcac tactttttat     180
gctgactccg ttaaaggtcg cttcactatc tctagagaca actctaagaa tactctctac     240
ttgcagatga acagcttaag ggctgaggac actgcagtct actattgtgc gagaggcctg     300
taccggtggg gccagggaac cctggtcacc gtctcaagcg cctccaccaa gggcccatcg     360
gtcttcccg                                                             369
```

<210> SEQ ID NO 92
<211> LENGTH: 123
<212> TYPE: PRT
<213> ORGANISM: Homo sapiens

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Met Trp Val Arg Gln Ala Pro Gly Lys Gly Leu Glu Trp Val
        35                  40                  45

Ser Trp Ile Val Pro Ser Gly Gly Thr Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Tyr Arg Trp Gly Gln Gly Thr Leu Val Thr Val Ser
            100                 105                 110

Ser Ala Ser Thr Lys Gly Pro Ser Val Phe Pro
            115                 120

<210> SEQ ID NO 93
<211> LENGTH: 360
<212> TYPE: DNA
<213> ORGANISM: Homo sapiens

<400> SEQUENCE: 93

```
ggcgtgcact cacagagcga attgactcag ccaccctcgg tgtcactggc cccaggacag      60
acggccagga ttacctgtgg gggaaacaac attggaacta aaagtgttca ctggtaccag     120
cagaagccag gccaggcccc tgtgctggtc gtctatgatg acagcgaccg gccctcaggg     180
atccctgagc gattctctgg ctccaattct gggaacacgg ccaccctgac catcagcagg     240
gtcgaagccg gggatgaggc cgactattat tgtcaggtgt gggatagtgg tagtgatcat     300
caggtcttcg gcggagggac caagctgacc gtcctaggtc agcccaaggt tgcccctcg     360
```

<210> SEQ ID NO 94
<211> LENGTH: 120
<212> TYPE: PRT
<213> ORGANISM: Homo sapiens

<400> SEQUENCE: 94

Gly Val His Ser Gln Ser Glu Leu Thr Gln Pro Pro Ser Val Ser Leu
1               5                   10                  15

Ala Pro Gly Gln Thr Ala Arg Ile Thr Cys Gly Gly Asn Asn Ile Gly
            20                  25                  30

Thr Lys Ser Val His Trp Tyr Gln Gln Lys Pro Gly Gln Ala Pro Val
            35                  40                  45

Leu Val Val Tyr Asp Asp Ser Asp Arg Pro Ser Gly Ile Pro Glu Arg
        50                  55                  60

Phe Ser Gly Ser Asn Ser Gly Asn Thr Ala Thr Leu Thr Ile Ser Arg
65                  70                  75                  80

Val Glu Ala Gly Asp Glu Ala Asp Tyr Tyr Cys Gln Val Trp Asp Ser
                85                  90                  95

Gly Ser Asp His Gln Val Phe Gly Gly Gly Thr Lys Leu Thr Val Leu
            100                 105                 110

Gly Gln Pro Lys Val Ala Pro Ser
            115                 120

<210> SEQ ID NO 95
<211> LENGTH: 378
<212> TYPE: DNA
<213> ORGANISM: Homo sapiens
<220> FEATURE:
<221> NAME/KEY: misc_feature
<222> LOCATION: (226)..(226)
<223> OTHER INFORMATION: n is a, c, g, or t

<400> SEQUENCE: 95
gaagttcaat tgttagagtc tggtggcggt cttgttcagc ctggtggttc tttacgtctt      60
tcttgcgctg cttccggatt cactttctct ccttacttta tgttttgggt tcgccaagct     120
cctggtaaag gtttggagtg gtttcttct atcggttctt ctggtggcga tacttcttat     180
gctgactccg ttaaaggtcg cttcactatc tctagagaca actctnagaa tactctctac     240
ttgcagatga acagcttaag ggctgaggac actgcagtct actattgtgc gagaggcctg     300
taccggtggg gccagggaac cctggtcacc gtctcaagcg cctccaccaa gggcccatcg     360 gtcttccccgc tagcgccc                                                   378

<210> SEQ ID NO 96
<211> LENGTH: 126
<212> TYPE: PRT
<213> ORGANISM: Homo sapiens

<400> SEQUENCE: 96

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Phe Met Phe Trp Val Arg Gln Ala Pro Gly Lys Gly Leu Glu Trp Val
        35                  40                  45

Ser Ser Ile Gly Ser Ser Gly Gly Asp Thr Ser Tyr Ala Asp Ser Val
    50                  55                  60

Lys Gly Arg Phe Thr Ile Ser Arg Asp Asn Ser Glx Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Tyr Arg Trp Gly Gln Gly Thr Leu Val Thr Val Ser
            100                 105                 110

Ser Ala Ser Thr Lys Gly Pro Ser Val Phe Pro Leu Ala Pro
        115                 120                 125

<210> SEQ ID NO 97

<211> LENGTH: 360
<212> TYPE: DNA
<213> ORGANISM: Homo sapiens

<400> SEQUENCE: 97

```
ggcgtgcact cacagagcgc tttgactcag ccaccctcgg tgtcagtggc cccaggacag      60
acggccagga tttcctgtgg gggcgacaac attgacacta aaaatgtaca gtggtaccag     120
cagaggccag gccaggcccc tgtgctggtc gtctatgata tagcgaccg gccctcagcg      180
atccctgagc gattctctgg ctccaactct ggaccacgg ccaccctgac catcagcagg      240
gtcgaggccg gggatgaggc cgactattac tgtcaggtgt tgatggtag gagtgatcat      300
ccggtgttcg gcggagggac caagctgacc gttcctgggt cagcccaagg ctgcccctc      360
```

<210> SEQ ID NO 98
<211> LENGTH: 120
<212> TYPE: PRT
<213> ORGANISM: Homo sapiens

<400> SEQUENCE: 98

```
Gly Val His Ser Gln Ser Ala Leu Thr Gln Pro Pro Ser Val Ser Val
  1               5                  10                  15

Ala Pro Gly Gln Thr Ala Arg Ile Ser Cys Gly Gly Asp Asn Ile Asp
             20                  25                  30

Thr Lys Asn Val Gln Trp Tyr Gln Gln Arg Pro Gly Gln Ala Pro Val
         35                  40                  45

Leu Val Val Tyr Asp Asn Ser Asp Arg Pro Ser Ala Ile Pro Glu Arg
     50                  55                  60

Phe Ser Gly Ser Asn Ser Gly Thr Thr Ala Thr Leu Thr Ile Ser Arg
 65                  70                  75                  80

Val Glu Ala Gly Asp Glu Ala Asp Tyr Tyr Cys Gln Val Phe Asp Gly
                 85                  90                  95

Arg Ser Asp His Pro Val Phe Gly Gly Gly Thr Lys Leu Thr Val Pro
            100                 105                 110

Gly Ser Ala Gln Gly Cys Pro Leu
        115                 120
```

<210> SEQ ID NO 99
<211> LENGTH: 411
<212> TYPE: DNA
<213> ORGANISM: Homo sapiens

<400> SEQUENCE: 99

```
gaagttcaat tgttagagtc tggtggcggt cttgttcagc ctggtggttc tttacgtctt      60
tcttgcgctg cttccggatt cactttctct ctttacgtta tgtattgggt cgccaagct     120
cctggtaaag gtttggagtg ggtttcttat atctcttctt ctggtggcat tactcattat     180
gctgactccg ttaaaggtcg cttcactatc tctagagaca actctaagaa tactctctac     240
ttgcagatga acagcttaag ggctgaggac actgcagtct actattgtgc gagaggctct     300
attgtagtag taccagctgc tatacggagc aacaactggt tcgaccctg gggccaggga     360
accctggtca ccgtctcaag cgcctccacc aagggcccat cggtcttccc g             411
```

<210> SEQ ID NO 100
<211> LENGTH: 137
<212> TYPE: PRT
<213> ORGANISM: Homo sapiens

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Val Met Tyr Trp Val Arg Gln Ala Pro Gly Lys Gly Leu Glu Trp Val
        35                  40                  45

Ser Tyr Ile Ser Ser Ser Gly Gly Ile Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ile Val Val Pro Ala Ala Ile Arg Ser Asn Asn
            100                 105                 110

Trp Phe Asp Pro Trp Gly Gln Gly Thr Leu Val Thr Val Ser Ser Ala
            115                 120                 125

Ser Thr Lys Gly Pro Ser Val Phe Pro
        130                 135

<210> SEQ ID NO 101
<211> LENGTH: 357
<212> TYPE: DNA
<213> ORGANISM: Homo sapiens

<400> SEQUENCE: 101
ggcgtgcact ctgacatcca gatgacccag tctccttcca ccctgtctgc atctgtagga      60
gacagagtca ccatcacttg ccgggccagt cagagtattg gaaactggtt ggcctggtat     120
cagcagaaac aggggaagc ccctcacctc ctgatctatc aggcgtctag tttagaaggt      180
ggggtcccat caaggttcag cggcagtggg tctgggacaa aattcactct caacatcagc     240
agcctgcagc ctgatgactt tgcaacttat tactgccaac agtataattc ttattcgtac     300
acttttggcc aggggaccaa gctggacatc aaacgaactg tggctgcacc atctgtc       357

<210> SEQ ID NO 102
<211> LENGTH: 119
<212> TYPE: PRT
<213> ORGANISM: Homo sapiens

<400> SEQUENCE: 102

Gly Val His Ser Asp Ile Gln Met Thr Gln Ser Pro Ser Thr Leu Ser
1               5                   10                  15

Ala Ser Val Gly Asp Arg Val Thr Ile Thr Cys Arg Ala Ser Gln Ser
            20                  25                  30

Ile Gly Asn Trp Leu Ala Trp Tyr Gln Gln Lys Pro Gly Glu Ala Pro
        35                  40                  45

His Leu Leu Ile Tyr Gln Ala Ser Ser Leu Glu Gly Gly Val Pro Ser
    50                  55                  60

Arg Phe Ser Gly Ser Gly Ser Gly Thr Lys Phe Thr Leu Asn Ile Ser
65                  70                  75                  80

Ser Leu Gln Pro Asp Asp Phe Ala Thr Tyr Tyr Cys Gln Gln Tyr Asn
                85                  90                  95

Ser Tyr Ser Tyr Thr Phe Gly Gln Gly Thr Lys Leu Asp Ile Lys Arg
            100                 105                 110

Thr Val Ala Ala Pro Ser Val
            115

<210> SEQ ID NO 103
<211> LENGTH: 393
<212> TYPE: DNA
<213> ORGANISM: Homo sapiens

<400> SEQUENCE: 103

| | | | | | |
|---|---|---|---|---|---|
| gaagttcaat | tgttagagtc | tggtggcggt | cttgttcagc | ctggtggttc | tttacgtctt | 60 |
| tcttgcgctg | cttccggatt | cactttctct | aattacggta | tgtcttgggt | tcgccaagct | 120 |
| cctggtaaag | gtttggagtg | ggtttctgtt | atcggtcctt | ctggtggcat | tactatgtat | 180 |
| gctgactccg | ttaaaggtcg | cttcactatc | tctagagaca | actctaagaa | tactctctac | 240 |
| ttgcagatga | acagcttaag | ggctgaggac | actgcagtct | actattgtgc | gacegggtct | 300 |
| agcagtggct | ggtaccctaa | ctttgactac | tggggccagg | gaaccctggt | caccgtctca | 360 |
| agcgcctcca | ccaagggccc | atcggtcttc | ccg | | | 393 |

<210> SEQ ID NO 104
<211> LENGTH: 131
<212> TYPE: PRT
<213> ORGANISM: Homo sapiens

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ser Val Ile Gly Pro Ser Gly Gly Ile Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Ser Ser Ser Gly Trp Tyr Pro Asn Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro
    130

<210> SEQ ID NO 105
<211> LENGTH: 366
<212> TYPE: DNA
<213> ORGANISM: Homo sapiens

<400> SEQUENCE: 105

| | | | | | |
|---|---|---|---|---|---|
| ttctattctc | acagtgcaca | agacatccag | atgacccagt | ctccatcctc | cctgtctgca | 60 |
| tctgtaggag | atagagtcac | catcacttgc | cgggcaagtc | agaccattag | cacctattta | 120 |
| gtttggtatc | agcagaaacc | cgagaaagcc | cctacgctcc | tgatctccgg | tgcatccact | 180 |
| ttgcaaagtg | ggtcccaaa | caggttcaga | ggcagtggat | ctgggacaga | cttcactctc | 240 |
| gccatctcca | gtcttcaacc | tgaagatttt | gcaacttact | actgtcaaca | gagttacact | 300 |
| tcccctagaa | cgttcggcca | agggaccaag | gtggaaatca | aacgaactgt | ggctgcacca | 360 |
| tctgtc | | | | | | 366 |

<210> SEQ ID NO 106
<211> LENGTH: 122
<212> TYPE: PRT
<213> ORGANISM: Homo sapiens

<400> SEQUENCE: 106

Phe Tyr Ser His Ser Ala Gln Asp Ile Gln Met Thr Gln Ser Pro Ser
1               5                   10                  15

Ser Leu Ser Ala Ser Val Gly Asp Arg Val Thr Ile Thr Cys Arg Ala
            20                  25                  30

Ser Gln Thr Ile Ser Thr Tyr Leu Val Trp Tyr Gln Gln Lys Pro Glu
        35                  40                  45

Lys Ala Pro Thr Leu Leu Ile Ser Gly Ala Ser Thr Leu Gln Ser Gly
    50                  55                  60

Val Pro Asn Arg Phe Arg Gly Ser Gly Ser Gly Thr Asp Phe Thr Leu
65                  70                  75                  80

Ala Ile Ser Ser Leu Gln Pro Glu Asp Phe Ala Thr Tyr Tyr Cys Gln
                85                  90                  95

Gln Ser Tyr Thr Ser Pro Arg Thr Phe Gly Gly Gly Thr Lys Val Glu
            100                 105                 110

Ile Lys Arg Thr Val Ala Ala Pro Ser Val
        115                 120

<210> SEQ ID NO 107
<211> LENGTH: 384
<212> TYPE: DNA
<213> ORGANISM: Homo sapiens

<400> SEQUENCE: 107
gaagttcaat tgttagagtc tggtggcggt cttgttcagc ctggtggttc tttacgtctt      60
tcttgcgctg cttccggatt cactttctct cattactcta tgcgttgggt tcgccaagct     120
cctggtaaag gtttggagtg ggtttcttat atcgttcctt ctggtggctt tactcagtat     180
gctgactccg ttaaaggtcg cttcactatc tctagagaca actctaagaa tactctctac     240
ttgcagatga acagcttaag ggctgaggac actgcagtct actattgtgc gagaggcacg     300 cacctccccgg gggttgacta ctggggccag ggaaccctgg tcaccgtctc aagcgcctcc     360
accaagggcc catcggtctt cccg                                            384

<210> SEQ ID NO 108
<211> LENGTH: 128
<212> TYPE: PRT
<213> ORGANISM: Homo sapiens

<400> SEQUENCE: 108

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ser Met Arg Trp Val Arg Gln Ala Pro Gly Lys Gly Leu Glu Trp Val
        35                  40                  45

Ser Tyr Ile Val Pro Ser Gly Gly Phe Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                    85                  90                  95
Ala Arg Gly Thr His Leu Pro Gly Val Asp Tyr Trp Gly Gln Gly Thr
                100                 105                 110

Leu Val Thr Val Ser Ser Ala Ser Thr Lys Gly Pro Ser Val Phe Pro
        115                 120                 125

<210> SEQ ID NO 109
<211> LENGTH: 366
<212> TYPE: DNA
<213> ORGANISM: Homo sapiens

<400> SEQUENCE: 109
ggcgtgcact cacagagcgc tttgactcag ccaccctcag cgtctgggac ccccgggcag        60
agggtcacca tctcttgttc tggaagcaac tccaacatcg aggtaatat tgtaatctgg       120 ctccagcagc tcccaggaac ggcccccaaa ctcatgattt atgatgtcag tgatcggccc       180
tcaggggtcc ctgaccgatt ctctggctcc aagtctggca cctcagcctc cctggccatc       240
agtgggctcc agtctgagga tgaggccgat tattattgtg cagcctggga tgacagcctg       300
aatggttggg tgttcggcgg agggaccaag ctgaccgtcc taagtcagcc caaggctgcc       360
ccctcg                                                                  366

<210> SEQ ID NO 110
<211> LENGTH: 122
<212> TYPE: PRT
<213> ORGANISM: Homo sapiens

<400> SEQUENCE: 110

Gly Val His Ser Gln Ser Ala Leu Thr Gln Pro Pro Ser Ala Ser Gly
1               5                   10                  15

Thr Pro Gly Gln Arg Val Thr Ile Ser Cys Ser Gly Ser Asn Ser Asn
            20                  25                  30

Ile Gly Gly Asn Ile Val Ile Trp Leu Gln Gln Leu Pro Gly Thr Ala
        35                  40                  45

Pro Lys Leu Met Ile Tyr Asp Val Ser Asp Arg Pro Ser Gly Val Pro
    50                  55                  60

Asp Arg Phe Ser Gly Ser Lys Ser Gly Thr Ser Ala Ser Leu Ala Ile
65                  70                  75                  80

Ser Gly Leu Gln Ser Glu Asp Glu Ala Asp Tyr Tyr Cys Ala Ala Trp
                85                  90                  95

Asp Asp Ser Leu Asn Gly Trp Val Phe Gly Gly Gly Thr Lys Leu Thr
            100                 105                 110

Val Leu Ser Gln Pro Lys Ala Ala Pro Ser
        115                 120

<210> SEQ ID NO 111
<211> LENGTH: 369
<212> TYPE: DNA
<213> ORGANISM: Homo sapiens

<400> SEQUENCE: 111
gaagttcaat tgttagagtc tggtggcggt cttgttcagc ctggtggttc tttacgtctt        60
tcttgcgctg cttccggatt cactttctct ctttacatga tgaagtgggt tgccaagct       120 cctggtaaag gtttggagtg ggtttctgtt atctcttctt ctggtggcta tactcagtat       180
gctgactccg ttaaaggtcg cttcactatc tctagagaca actctaagaa tactctctac       240
ttgcagatga caacttaag ggctgaggac actgcagtct actattgtgc gagagggtgg       300
```

```
gacgtctggg gcaaagggac cacggtcacc gtctcaagcg cctccaccaa gggcccatcg    360
gtcttcccg                                                             369
```

<210> SEQ ID NO 112
<211> LENGTH: 123
<212> TYPE: PRT
<213> ORGANISM: Homo sapiens

<400> SEQUENCE: 112

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Met Met Lys Trp Val Arg Gln Ala Pro Gly Lys Gly Leu Glu Trp Val
        35                  40                  45

Ser Val Ile Ser Ser Gly Gly Tyr Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Arg Gly Trp Asp Val Trp Gly Lys Gly Thr Thr Val Thr Val Ser
            100                 105                 110

Ser Ala Ser Thr Lys Gly Pro Ser Val Phe Pro
        115                 120
```

<210> SEQ ID NO 113
<211> LENGTH: 366
<212> TYPE: DNA
<213> ORGANISM: Homo sapiens

<400> SEQUENCE: 113

```
ggcgtgcact cacagagcgc tttgactcag ccaccctcag cgtctgggac cccgggcag     60 agggtcacca tctcctgttc tggaaccagc tccaacatcg gaagtcatta tgtattctgg   120
tatcagcagc tcccaggaac ggccccccaaa ctcctcatcc ataggaatga tgagcggccc  180
tcaggggtcc ctgaccgctt ctctggctcc aagtctggca cctccgcctc cctggccatc   240
agtggcctcc agtctgagga tgaggctgat tattactgtg ctacgtggga tgacaaccta   300
aatggtccgg tattcggcgg agggaccaag ctgaccggcc ctgggtcagc ccaaggctgc   360
cccctc                                                              366
```

<210> SEQ ID NO 114
<211> LENGTH: 122
<212> TYPE: PRT
<213> ORGANISM: Homo sapiens

<400> SEQUENCE: 114

```
Gly Val His Ser Gln Ser Ala Leu Thr Gln Pro Pro Ser Ala Ser Gly
1               5                   10                  15

Thr Pro Gly Gln Arg Val Thr Ile Ser Cys Ser Gly Thr Ser Ser Asn
            20                  25                  30

Ile Gly Ser His Tyr Val Phe Trp Tyr Gln Gln Leu Pro Gly Thr Ala
        35                  40                  45

Pro Lys Leu Leu Ile His Arg Asn Asp Glu Arg Pro Ser Gly Val Pro
    50                  55                  60
```

```
Asp Arg Phe Ser Gly Ser Lys Ser Gly Thr Ser Ala Ser Leu Ala Ile
 65                  70                  75                  80

Ser Gly Leu Gln Ser Glu Asp Glu Ala Asp Tyr Tyr Cys Ala Thr Trp
                 85                  90                  95

Asp Asp Asn Leu Asn Gly Pro Val Phe Gly Gly Gly Thr Lys Leu Thr
            100                 105                 110

Gly Pro Gly Ser Ala Gln Gly Cys Pro Leu
        115                 120
```

<210> SEQ ID NO 115
<211> LENGTH: 393
<212> TYPE: DNA
<213> ORGANISM: Homo sapiens

<400> SEQUENCE: 115

```
gaagttcaat tgttagagtc tggtggcggt cttgttcagc ctggtggttc tttacgtctt    60
tcttgcgctg cttccggatt cactttctct atgtacttta tggtttgggt tcgccaagct   120
cctggtaaag gtttggagtg gtttcttgg atcggttctt ctggtggcga gactccttat    180
gctgactccg ttaaaggtcg cttcactatc tctagagaca actctaagaa tactctctac   240
ttgcagatga acagcttaag gctgaggac actgcagtct actattgtgc aagagggtac    300
agcagtggct ggtatgtaat gggagactac tggggccagg gaaccctggt caccgtctca   360
agcgcctcca ccaagggccc atcggtcttc ccg                                393
```

<210> SEQ ID NO 116
<211> LENGTH: 131
<212> TYPE: PRT
<213> ORGANISM: Homo sapiens

<400> SEQUENCE: 116

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Met Tyr
             20                  25                  30

Phe Met Val Trp Val Arg Gln Ala Pro Gly Lys Gly Leu Glu Trp Val
         35                  40                  45

Ser Trp Ile Gly Ser Ser Gly Gly Glu Thr Pro Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Ser Ser Gly Trp Tyr Val Met Gly Asp Tyr Trp Gly
            100                 105                 110

Gln Gly Thr Leu Val Thr Val Ser Ser Ala Ser Thr Lys Gly Pro Ser
        115                 120                 125

Val Phe Pro
        130
```

<210> SEQ ID NO 117
<211> LENGTH: 366
<212> TYPE: DNA
<213> ORGANISM: Homo sapiens

<400> SEQUENCE: 117

```
ggcgtgcact cacagagcga attgactcag ccaccctcag tgtctgggac ccccgggcag    60
```

```
agggtcacca tctcttgttc tggaagcagt tccaacatcg aagtgagta tgtgtactgg    120 ttccagcagc tcccaggaac ggcccccaga ctcctcatct ataggaatga tcagcggccc    180 tcagggtcc ctgaccgatt ctctggctcc aagtctggca cctcagcctc cctggccatc    240
agtgggctcc ggtccgagga tgagactgat tattactgta caacatggga tgacagcctg    300
agtggtccgg tgttcggcgg agggaccaag ctgaccgtcc taggtcagcc caaggctgcc    360
ccctcg                                                                366
```

<210> SEQ ID NO 118
<211> LENGTH: 122
<212> TYPE: PRT
<213> ORGANISM: Homo sapiens

<400> SEQUENCE: 118

```
Gly Val His Ser Gln Ser Glu Leu Thr Gln Pro Pro Ser Val Ser Gly
1               5                   10                  15

Thr Pro Gly Gln Arg Val Thr Ile Ser Cys Ser Gly Ser Ser Ser Asn
            20                  25                  30

Ile Gly Ser Glu Tyr Val Tyr Trp Phe Gln Gln Leu Pro Gly Thr Ala
        35                  40                  45

Pro Arg Leu Leu Ile Tyr Arg Asn Asp Gln Arg Pro Ser Gly Val Pro
    50                  55                  60

Asp Arg Phe Ser Gly Ser Lys Ser Gly Thr Ser Ala Ser Leu Ala Ile
65                  70                  75                  80

Ser Gly Leu Arg Ser Glu Asp Glu Thr Asp Tyr Tyr Cys Thr Thr Trp
                85                  90                  95

Asp Asp Ser Leu Ser Gly Pro Val Phe Gly Gly Gly Thr Lys Leu Thr
            100                 105                 110

Val Leu Gly Gln Pro Lys Ala Ala Pro Ser
        115                 120
```

<210> SEQ ID NO 119
<211> LENGTH: 405
<212> TYPE: DNA
<213> ORGANISM: Homo sapiens

<400> SEQUENCE: 119

```
gaagttcaat tgttagagtc tggtggcggt cttgttcagc tggtggttc tttacgtctt    60 tcttgcgctg cttccggatt cactttctct tcttaccaga tggattgggt tcgccaagct    120
cctggtaaag gtttggagtg ggtttctcgt atcgttcctt ctggtggcga tactactat    180 gctgactccg ttaaaggtcg cttcactatc tctagagaca actctaagaa tactctctac    240
ttgcagatga acagcttaag ggctgaggac actgcagtct actattgtgc gagacatgtc    300
tactatgata gtagtgatta tttccccaac ccgtttgact actggggcca gggaaccctg    360
gtcaccgtct caagcgcctc caccaagggc ccatcggtct tcccg                    405
```

<210> SEQ ID NO 120
<211> LENGTH: 135
<212> TYPE: PRT
<213> ORGANISM: Homo sapiens

<400> SEQUENCE: 120

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Gln Met Asp Trp Val Arg Gln Ala Pro Gly Lys Gly Leu Glu Trp Val
             35                  40                  45

Ser Arg Ile Val Pro Ser Gly Gly Asp Thr Thr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg His Val Tyr Tyr Asp Ser Ser Asp Tyr Phe Pro Asn Pro Phe
             100                 105                 110

Asp Tyr Trp Gly Gln Gly Thr Leu Val Thr Val Ser Ser Ala Ser Thr
         115                 120                 125

Lys Gly Pro Ser Val Phe Pro
        130                 135

<210> SEQ ID NO 121
<211> LENGTH: 357
<212> TYPE: DNA
<213> ORGANISM: Homo sapiens

<400> SEQUENCE: 121
ggcgtgcact ctgacatcca gatgacccag tctccatcct ccctgtctgc gtctgtagga    60
gacagagtca ccatcacttg ccgggcgagt cagggcatta gcaattattt agcctggtat   120
cagcagaaac cagggaaagt tcctaagctc ctgatctatc ctgcatccac tttgcaaagt   180
ggggtcccat caaggttcag cggcagtgga tctgggacag atttcactct caccatcagc   240
agcctgcagc ctgaagattt tgcaacttat tattgtcaac aggctgacag tttcccgccc   300
accttcggcg agggaccac ggtggagatc agacgaactg tggctgcacc atctgtc      357

<210> SEQ ID NO 122
<211> LENGTH: 119
<212> TYPE: PRT
<213> ORGANISM: Homo sapiens

<400> SEQUENCE: 122

Gly Val His Ser Asp Ile Gln Met Thr Gln Ser Pro Ser Ser Leu Ser
1               5                  10                  15

Ala Ser Val Gly Asp Arg Val Thr Ile Thr Cys Arg Ala Ser Gln Gly
             20                  25                  30

Ile Ser Asn Tyr Leu Ala Trp Tyr Gln Gln Lys Pro Gly Lys Val Pro
         35                  40                  45

Lys Leu Leu Ile Tyr Pro Ala Ser Thr Leu Gln Ser Gly Val Pro Ser
 50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ala Asp
                 85                  90                  95

Ser Phe Pro Pro Thr Phe Gly Gly Gly Thr Thr Val Glu Ile Arg Arg
             100                 105                 110

Thr Val Ala Ala Pro Ser Val
         115

<210> SEQ ID NO 123
<211> LENGTH: 399
<212> TYPE: DNA
<213> ORGANISM: Homo sapiens

<400> SEQUENCE: 123

```
gaagttcaat tgttagagtc tggtggcggt cttgttcagc ctggtggttc tttacgtctt      60
tcttgcgctg cttccggatt cactttctct ttttacttta tgttttgggt tcgccaagct     120
cctggtaaag gtttggagtg ggtttcttat atcggtcctt ctggtggccc tactaattat     180
gctgactccg ttaaaggtcg cttcactatc tctagagaca actctaagaa tactctctac     240
ttgcagatga acagcttaag ggctgaggac actgcagtct actattgtgc gagacattac     300
cccagggagt accagctgcc cgggtcgttc gacccctggg gccagggaac cctggtcacc     360
gtctcaagcg cctccaccaa gggcccatcg gtcttcccg                            399
```

<210> SEQ ID NO 124
<211> LENGTH: 133
<212> TYPE: PRT
<213> ORGANISM: Homo sapiens

<400> SEQUENCE: 124

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Phe Tyr
             20                  25                  30

Phe Met Phe Trp Val Arg Gln Ala Pro Gly Lys Gly Leu Glu Trp Val
         35                  40                  45

Ser Tyr Ile Gly Pro Ser Gly Gly Pro Thr Asn Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Tyr Pro Arg Glu Tyr Gln Leu Pro Gly Ser Phe Asp Pro
            100                 105                 110

Trp Gly Gln Gly Thr Leu Val Thr Val Ser Ser Ala Ser Thr Lys Gly
        115                 120                 125

Pro Ser Val Phe Pro
    130
```

<210> SEQ ID NO 125
<211> LENGTH: 360
<212> TYPE: DNA
<213> ORGANISM: Homo sapiens

<400> SEQUENCE: 125

```
ggcgtgcact ctgacatcca gatgacccag tctccatctt ccctgtctgc atctgtagga      60
gacagagtca ccatcacttg ccgggcaagt cagagtatta gtaactattt aaattggtat     120
cagcagagac agggaaggc ccctaagctc ctgatctatg ctgcatccag tttggaaaga     180
ggggtcccat caaggttcag tggcagtgga tctgggacag atttcactct caccatcagc     240
agtctgcaat ctgaagattt tgcaacttac tactgtcaac agagttacag tccccctcct     300
ctcactttcg gcggagggac caaactagag atcaaacgaa ctgtggctgc accatctgtc     360
```

<210> SEQ ID NO 126
<211> LENGTH: 120
<212> TYPE: PRT
<213> ORGANISM: Homo sapiens

<400> SEQUENCE: 126

```
Gly Val His Ser Asp Ile Gln Met Thr Gln Ser Pro Ser Ser Leu Ser
1               5                   10                  15

Ala Ser Val Gly Asp Arg Val Thr Ile Thr Cys Arg Ala Ser Gln Ser
            20                  25                  30

Ile Ser Asn Tyr Leu Asn Trp Tyr Gln Gln Arg Pro Gly Lys Ala Pro
        35                  40                  45

Lys Leu Leu Ile Tyr Ala Ala Ser Ser Leu Glu Arg Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Ser Glu Asp Phe Ala Thr Tyr Tyr Cys Gln Gln Ser Tyr
                85                  90                  95

Ser Pro Pro Pro Leu Thr Phe Gly Gly Thr Lys Leu Glu Ile Lys
                100                 105                 110

Arg Thr Val Ala Ala Pro Ser Val
            115                 120

<210> SEQ ID NO 127
<211> LENGTH: 393
<212> TYPE: DNA
<213> ORGANISM: Homo sapiens

<400> SEQUENCE: 127
gaagttcaat tgttagagtc tggtggcggt cttgttcagc ctggtggttc tttacgtctt    60
tcttgcgctg cttccggatt cactttctct tattacgtta tgatgtgggt tcgccaagct   120
cctggtaaag gtttggagtg ggtttctgtt atccgtcctt ctggtggcat tactacttat   180
gctgactccg ttaaaggtcg cttcactatc tctagagaca actctaagaa tactctctac   240
ttgcagacga acagcttaag ggctgaggac actgcagtct actattgtgc gaaaatcgac   300
tacggtggta actcgttcta ctttgactac tggggccagg gaaccctggt caccgtctca   360
agcgcctcca ccaagggccc atcggtcttc ccg                                393

<210> SEQ ID NO 128
<211> LENGTH: 131
<212> TYPE: PRT
<213> ORGANISM: Homo sapiens

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Val Met Met Trp Val Arg Gln Ala Pro Gly Lys Gly Leu Glu Trp Val
        35                  40                  45

Ser Val Ile Arg Pro Ser Gly Gly Ile Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Thr Asn Ser Leu Arg Ala Glu Asp Thr Ala Val Tyr Tyr Cys
                85                  90                  95

Ala Lys Ile Asp Tyr Gly Gly Asn Ser Phe Tyr Phe Asp Tyr Trp Gly
                100                 105                 110

Gln Gly Thr Leu Val Thr Val Ser Ser Ala Ser Thr Lys Gly Pro Ser
            115                 120                 125
```

Val Phe Pro
    130

<210> SEQ ID NO 129
<211> LENGTH: 357
<212> TYPE: DNA
<213> ORGANISM: Homo sapiens

<400> SEQUENCE: 129

```
ggcgtgcact ctgacatcca gatgacccag tctccaccct ccctgtctgc attagtaggg     60
gacagagtca ccatcacttg ccgggcaagt cagagcataa gcagatatgt gaattggtat    120
cagcagaaac cagggaaagc ccctaaggtc ctgatctatg ctgcatccat agtagaaaat    180
ggggtcccat ctaggttcag tggcagtgga tctgggacag atttcagtct caccatcagc    240
agtctgcaac tgaagatttt gcaacttac tactgtcaac aaacttacag tactccgctc    300
actttcggcg gagggaccaa gctggcgatc aaacgaactg tggctgcacc atctgtc      357
```

<210> SEQ ID NO 130
<211> LENGTH: 119
<212> TYPE: PRT
<213> ORGANISM: Homo sapiens

<400> SEQUENCE: 130

Gly Val His Ser Asp Ile Gln Met Thr Gln Ser Pro Pro Ser Leu Ser
1               5                   10                  15

Ala Leu Val Gly Asp Arg Val Thr Ile Thr Cys Arg Ala Ser Gln Ser
            20                  25                  30

Ile Ser Arg Tyr Val Asn Trp Tyr Gln Gln Lys Pro Gly Lys Ala Pro
        35                  40                  45

Lys Val Leu Ile Tyr Ala Ala Ser Ile Val Glu Asn Gly Val Pro Ser
    50                  55                  60

Arg Phe Ser Gly Ser Gly Ser Gly Thr Asp Phe Ser Leu Thr Ile Ser
65                  70                  75                  80

Ser Leu Gln Pro Glu Asp Phe Ala Thr Tyr Tyr Cys Gln Gln Thr Tyr
                85                  90                  95

Ser Thr Pro Leu Thr Phe Gly Gly Gly Thr Lys Leu Ala Ile Lys Arg
            100                 105                 110

Thr Val Ala Ala Pro Ser Val
            115

<210> SEQ ID NO 131
<211> LENGTH: 426
<212> TYPE: DNA
<213> ORGANISM: Homo sapiens

<400> SEQUENCE: 131

```
gaagttcaat tgttagagtc tggtggcggt cttgttcagc ctggtggttc tttacgtctt     60
tcttgcgctg cttccggatt cactttctct tattacgaga tgatgtgggt tcgccaagct    120
cctggtaaag gtttggagtg gtttcttct atctctcctt ctggtggccc tactatgtat    180
gctgactccg ttaaaggtcg cttcactatc tctagagaca actctaagaa tactctctac    240
ttgcagatga acagcttaag ggctgaggac actggagtct actattgtgc gagaaagatg    300
gggcgtgtag atattgtag tagtaccagc tgctatcggg atgactacta cggtatggac    360
gtctggggcc aagggaccac ggtcaccgtc tcagcgcct ccaccaaggg cccatcggtc    420
ttcccg                                                             426
```

<210> SEQ ID NO 132
<211> LENGTH: 142
<212> TYPE: PRT
<213> ORGANISM: Homo sapiens

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Glu Met Met Trp Val Arg Gln Ala Pro Gly Lys Gly Leu Glu Trp Val
        35                  40                  45

Ser Ser Ile Ser Pro Ser Gly Gly Pro Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Gly Val Tyr Tyr Cys
                85                  90                  95

Ala Arg Lys Met Gly Arg Val Gly Tyr Cys Ser Ser Thr Ser Cys Tyr
            100                 105                 110

Arg Asp Asp Tyr Tyr Gly Met Asp Val Trp Gly Gln Gly Thr Thr Val
        115                 120                 125

Thr Val Ser Ser Ala Ser Thr Lys Gly Pro Ser Val Phe Pro
    130                 135                 140

<210> SEQ ID NO 133
<211> LENGTH: 360
<212> TYPE: DNA
<213> ORGANISM: Homo sapiens

<400> SEQUENCE: 133
ggcgtgcact ctgacatcca gatgacccag tctccaggca ccctgtcttt gtctccaggg      60
gaaagagcaa ccctctcctg cagggccagt cagagtgtta gcagcaccta tttagcctgg     120
taccagcaga aacctggcca ggctcccagg ctcctcatct ctggtgcatc cagcagggcc     180
actggcatcc cagacaggtt cagtggcagt gggtctggga cagacttcac tctcaccatc     240
agcagactgg agcctgaaga ttttgcagtg tattactgtc agcagtatgg tagctcaccg     300 tacactttg gccaggggac caagctggag atcaaacgaa ctgtggctgc accatctgtc     360

<210> SEQ ID NO 134
<211> LENGTH: 120
<212> TYPE: PRT
<213> ORGANISM: Homo sapiens

<400> SEQUENCE: 134

Gly Val His Ser Asp Ile Gln Met Thr Gln Ser Pro Gly Thr Leu Ser
1               5                   10                  15

Leu Ser Pro Gly Glu Arg Ala Thr Leu Ser Cys Arg Ala Ser Gln Ser
            20                  25                  30

Val Ser Ser Thr Tyr Leu Ala Trp Tyr Gln Gln Lys Pro Gly Gln Ala
        35                  40                  45

Pro Arg Leu Leu Ile Ser Gly Ala Ser Ser Arg Ala Thr Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Gln Gln Tyr 85                  90                  95
Gly Ser Ser Pro Tyr Thr Phe Gly Gln Gly Thr Lys Leu Glu Ile Lys
                100                 105                 110

Arg Thr Val Ala Ala Pro Ser Val
        115                 120

<210> SEQ ID NO 135
<211> LENGTH: 402
<212> TYPE: DNA
<213> ORGANISM: Homo sapiens

<400> SEQUENCE: 135
gaagttcaat tgttagagtc tggtggcggt cttgttcagc ctggtggttc tttacgtctt    60
tcttgcgctg cttccggatt cactttctct cagtacttta tgaattgggt tcgccaagct   120
cctggtaaag gtttggagtg ggtttcttat atttctggtg gccgtactcc ttatgctgac   180
tccgttaaag gtcgcttcac tatctctaga gacaactcta agaatactct ctacttgcag   240
atgaacagct aagggctga ggacactgca gtctactatt gtgcgatcct tctgggaccg   300
agcagctcca atcacccttt cctggggccc tggggccagg gaaccctggt caccgtctca   360
agcgcctcca ccaagggccc atcggtcttc ccgctagcgc cc                      402

<210> SEQ ID NO 136
<211> LENGTH: 134
<212> TYPE: PRT
<213> ORGANISM: Homo sapiens

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Phe Met Asn Trp Val Arg Gln Ala Pro Gly Lys Gly Leu Glu Trp Val
        35                  40                  45

Ser Tyr Ile Ser Gly Gly Arg Thr Pro Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Ile
                85                  90                  95

Leu Leu Gly Pro Ser Ser Asn His Pro Phe Leu Gly Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro
    130

<210> SEQ ID NO 137
<211> LENGTH: 366
<212> TYPE: DNA
<213> ORGANISM: Homo sapiens

<400> SEQUENCE: 137
ggcgtgcact cacagagcga attgactcag cctgcctccg tgtctgggtc tcctggacag    60
tcgatcacca tctcctgcac tggaaccagc agtgatgttg ggagttataa ccttgtctcc   120
tggtaccaac agcacccagg caaagccccc aaactcatga tttatgaggg cagtaagcgg   180

```
ccctcagggg tttctaatcg cttctctggc tccaagtctg gcaacacggc ctccctgaca      240
atctctgggc tccaggctga ggacgaggct gattattact gctgctcata tgcaggtagt      300
agcacttatg tcttcggaac tgggaccaag gtcaccgtcc taggtcagcc caaggccaac      360
cccact                                                                366
```

<210> SEQ ID NO 138
<211> LENGTH: 122
<212> TYPE: PRT
<213> ORGANISM: Homo sapiens

<400> SEQUENCE: 138

```
Gly Val His Ser Gln Ser Glu Leu Thr Gln Pro Ala Ser Val Ser Gly
1               5                   10                  15

Ser Pro Gly Gln Ser Ile Thr Ile Ser Cys Thr Gly Thr Ser Ser Asp
            20                  25                  30

Val Gly Ser Tyr Asn Leu Val Ser Trp Tyr Gln Gln His Pro Gly Lys
        35                  40                  45

Ala Pro Lys Leu Met Ile Tyr Glu Gly Ser Lys Arg Pro Ser Gly Val
    50                  55                  60

Ser Asn Arg Phe Ser Gly Ser Lys Ser Gly Asn Thr Ala Ser Leu Thr
65                  70                  75                  80

Ile Ser Gly Leu Gln Ala Glu Asp Glu Ala Asp Tyr Tyr Cys Cys Ser
                85                  90                  95

Tyr Ala Gly Ser Ser Thr Tyr Val Phe Gly Thr Gly Thr Lys Val Thr
            100                 105                 110

Val Leu Gly Gln Pro Lys Ala Asn Pro Thr
        115                 120
```

<210> SEQ ID NO 139
<211> LENGTH: 393
<212> TYPE: DNA
<213> ORGANISM: Homo sapiens

<400> SEQUENCE: 139

```
gaagttcaat tgttagagtc tggtggcggt cttgttcagc ctggtggttc tttacgtctt       60
tcttgcgctg cttccggatt cacttttctct gtttacgtta tgatgtgggt tcgccaagct      120
cctggtaaag gtttggagtg gtttctggt atcgttcctt ctggtggcaa gactcattat       180
gctgactccg ttaaaggtcg cttcactatc tctagagaca actctaagaa tactctctac      240
ttgcagatga acagcttaag ggctgaggac actgcagtct actattgtgc gagaccggac      300
tacggtggta attcgcgccc ccttgagtac tggggccagg gaaccctggt caccgtctca      360
agcgcctcca ccaagggccc atcggtcttc ccg                                  393
```

<210> SEQ ID NO 140
<211> LENGTH: 131
<212> TYPE: PRT
<213> ORGANISM: Homo sapiens

<400> SEQUENCE: 140

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Val Met Met Trp Val Arg Gln Ala Pro Gly Lys Gly Leu Glu Trp Val
        35                  40                  45
```

```
Ser Gly Ile Val Pro Ser Gly Lys Thr His Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Pro Asp Tyr Gly Gly Asn Ser Arg Pro Leu Glu Tyr Trp Gly
            100                 105                 110

Gln Gly Thr Leu Val Thr Val Ser Ser Ala Ser Thr Lys Gly Pro Ser
        115                 120                 125

Val Phe Pro
    130

<210> SEQ ID NO 141
<211> LENGTH: 369
<212> TYPE: DNA
<213> ORGANISM: Homo sapiens

<400> SEQUENCE: 141
ggcgtgcact cacagagcga attgactcag cctccctccg cgtccgggtc tcctggacag      60
tcagtcacca tctcctgcac tggaaccagc agtgacgttg gtggttataa ctatgtctcc     120
tggtatcaac aacacccaga caaagccccc aaactcctga tttatgaggt cactcagcgg     180
ccctcagggg tccctgatcg cttctctggc tccaggtctg gcaacacggc ctccctgacc     240
gtctctgggc tccaggctga ggatgaggct gattattact gcagctcata tgcaggcagg     300
aacaatcttt atgtcttcgg acctgggacc aaggtcaccg tcctaggtca gcccaaggcc     360
aaccccact                                                            369

<210> SEQ ID NO 142
<211> LENGTH: 123
<212> TYPE: PRT
<213> ORGANISM: Homo sapiens

<400> SEQUENCE: 142

Gly Val His Ser Gln Ser Glu Leu Thr Gln Pro Pro Ser Ala Ser Gly
 1               5                  10                  15

Ser Pro Gly Gln Ser Val Thr Ile Ser Cys Thr Gly Thr Ser Ser Asp
             20                  25                  30

Val Gly Gly Tyr Asn Tyr Val Ser Trp Tyr Gln Gln His Pro Asp Lys
         35                  40                  45

Ala Pro Lys Leu Leu Ile Tyr Glu Val Thr Gln Arg Pro Ser Gly Val
     50                  55                  60

Pro Asp Arg Phe Ser Gly Ser Arg Ser Gly Asn Thr Ala Ser Leu Thr
 65                  70                  75                  80

Val Ser Gly Leu Gln Ala Glu Asp Glu Ala Asp Tyr Tyr Cys Ser Ser
                 85                  90                  95

Tyr Ala Gly Arg Asn Asn Leu Tyr Val Phe Gly Pro Gly Thr Lys Val
            100                 105                 110

Thr Val Leu Gly Gln Pro Lys Ala Asn Pro Thr
        115                 120

<210> SEQ ID NO 143
<211> LENGTH: 390
<212> TYPE: DNA
<213> ORGANISM: Homo sapiens

<400> SEQUENCE: 143
```

```
gaagttcaat tgttagagtc tggtggcggt cttgttcagc ctggtggttc tttacgtctt    60
tcttgcgctg cttccggatt cactttctct gagtaccta tgtggtgggt tcgccaagct   120
cctggtaaag gtttggagtg gtttcttgg atctatcctt ctggtggcaa tactgattat   180
gctgactccg ttaaaggtcg cttcactatc tctagagaca actctaagaa tactctctac   240
ttgcagatga acagcttaag ggctgaggac actgcagtct actattgtgc gattccctat   300
tgtagtagtt ccagctgccc cctacactgg ggccagggaa ccctggtcac cgtctcaagc   360
gcctccacca agggcccatc ggtcttcccg                                    390
```

<210> SEQ ID NO 144
<211> LENGTH: 130
<212> TYPE: PRT
<213> ORGANISM: Homo sapiens

<400> SEQUENCE: 144

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Pro Met Trp Trp Val Arg Gln Ala Pro Gly Lys Gly Leu Glu Trp Val
        35                  40                  45

Ser Trp Ile Tyr Pro Ser Gly Gly Asn Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Pro Tyr Cys Ser Ser Ser Cys Pro Leu His Trp Gly Gln
            100                 105                 110

Gly Thr Leu Val Thr Val Ser Ser Ala Ser Thr Lys Gly Pro Ser Val
            115                 120                 125

Phe Pro
    130

<210> SEQ ID NO 145
<211> LENGTH: 354
<212> TYPE: DNA
<213> ORGANISM: Homo sapiens

<400> SEQUENCE: 145

```
ggcgtgcact cacagagcga attgactcag ccaccctcag tgtccgtgtc cccagcacag    60
acagccagca tcacctgctc tggagataaa ttgggggata aatatgcttg ctggtatcag   120
cagaagccag gccagtcccc tgtactggtc atctatgaag ataccaagcg gccctcaggg   180
atccctgagc gattctctgg ctccaattct gggaacacag ccactctgac catcagcggg   240
acccaggtta tggatgaggc tgactattac tgtcaggtgt gggacagcag cactgcggta   300
ttcggcggag ggaccaagct gaccgtcctg ggtcagccca aggctgcccc ctcg           354
```

<210> SEQ ID NO 146
<211> LENGTH: 118
<212> TYPE: PRT
<213> ORGANISM: Homo sapiens

<400> SEQUENCE: 146

Gly Val His Ser Gln Ser Glu Leu Thr Gln Pro Pro Ser Val Ser Val

```
                1               5                  10                 15
Ser Pro Ala Gln Thr Ala Ser Ile Thr Cys Ser Gly Asp Lys Leu Gly
                20                 25                 30

Asp Lys Tyr Ala Cys Trp Tyr Gln Gln Lys Pro Gly Gln Ser Pro Val
                35                 40                 45

Leu Val Ile Tyr Glu Asp Thr Lys Arg Pro Ser Gly Ile Pro Glu Arg
                50                 55                 60

Phe Ser Gly Ser Asn Ser Gly Asn Thr Ala Thr Leu Thr Ile Ser Gly
65                  70                 75                 80

Thr Gln Val Met Asp Glu Ala Asp Tyr Tyr Cys Gln Val Trp Asp Ser
                85                 90                 95

Ser Thr Ala Val Phe Gly Gly Gly Thr Lys Leu Thr Val Leu Gly Gln
                100                105                110

Pro Lys Ala Ala Pro Ser
        115

<210> SEQ ID NO 147
<211> LENGTH: 396
<212> TYPE: DNA
<213> ORGANISM: Homo sapiens

<400> SEQUENCE: 147
gaagttcaat tgttagagtc tggtggcggt cttgttcagc ctggtggttc tttacgtctt     60
tcttgcgctg cttccggatt cactttctct gcttacaata tgatgtgggt tcgccaagct    120
cctggtaaag gtttggagtg gtttctcgt atctatcctt ctggtggcta tactctttat     180
gctgactcgg ttaaaggtcg cttcactatc tctagagaca actctaagaa tactctctac    240
ttgcagatga acagcttaag ggctgaggac actgcagtct actattgtgc gagacaaaaa    300
cttatgattc gggcagttcg cccgtttgac tactggggcc agggaaccct ggtcaccgtc    360
tcaagcgcct ccaccaaggg cccatcggtc ttcccg                              396

<210> SEQ ID NO 148
<211> LENGTH: 132
<212> TYPE: PRT
<213> ORGANISM: Homo sapiens

<400> SEQUENCE: 148

Glu Val Gln Leu Leu Glu Ser Gly Gly Gly Leu Val Gln Pro Gly Gly
1               5                  10                 15

Ser Leu Arg Leu Ser Cys Ala Ala Ser Gly Phe Thr Phe Ser Ala Tyr
                20                 25                 30

Asn Met Met Trp Val Arg Gln Ala Pro Gly Lys Gly Leu Glu Trp Val
                35                 40                 45

Ser Arg Ile Tyr Pro Ser Gly Gly Tyr Thr Leu Tyr Ala Asp Ser Val
                50                 55                 60

Lys Gly Arg Phe Thr Ile Ser Arg Asp Asn Ser Lys Asn Thr Leu Tyr
65                  70                 75                 80

Leu Gln Met Asn Ser Leu Arg Ala Glu Asp Thr Ala Val Tyr Tyr Cys
                85                 90                 95

Ala Arg Gln Lys Leu Met Ile Arg Ala Val Arg Pro Phe Asp Tyr Trp
                100                105                110

Gly Gln Gly Thr Leu Val Thr Val Ser Ser Ala Ser Thr Lys Gly Pro
                115                120                125

Ser Val Phe Pro
        130
```

<210> SEQ ID NO 149
<211> LENGTH: 366
<212> TYPE: DNA
<213> ORGANISM: Homo sapiens

<400> SEQUENCE: 149

| | | | | | |
|---|---|---|---|---|---|
| ggcgtgcact | cacagagcga | attgactcag | ccaccgtcag | cgtccgggac | ccccgggcag | 60 |
| aggatcacca | tctcttgttc | tggaagcagc | tccaacatcg | gaagtaatta | tgtatactgg | 120 |
| taccaacagt | tcccagagac | ggccccccaaa | ctcctcatct | ctagaaatga | tcagcggccc | 180 |
| tcagggtcc | ctgaccgatt | ctctggctcc | aagtctggca | cctcagcctc | cctggccatc | 240 |
| agtgggctcc | ggtccgaaga | tgaggctgat | tattactgtg | catcatggga | tgacagcctg | 300 |
| agtggtgtgg | ttttcggcgg | agggaccaag | ctgaccgtcc | taggtcagcc | caaggctgcc | 360 |
| ccctcg | | | | | | 366 |

<210> SEQ ID NO 150
<211> LENGTH: 122
<212> TYPE: PRT
<213> ORGANISM: Homo sapiens

<400> SEQUENCE: 150

Gly Val His Ser Gln Ser Glu Leu Thr Gln Pro Pro Ser Ala Ser Gly
1               5                   10                  15

Thr Pro Gly Gln Arg Ile Thr Ile Ser Cys Ser Gly Ser Ser Ser Asn
            20                  25                  30

Ile Gly Ser Asn Tyr Val Tyr Trp Tyr Gln Gln Phe Pro Glu Thr Ala
        35                  40                  45

Pro Lys Leu Leu Ile Ser Arg Asn Asp Gln Arg Pro Ser Gly Val Pro
    50                  55                  60

Asp Arg Phe Ser Gly Ser Lys Ser Gly Thr Ser Ala Ser Leu Ala Ile
65                  70                  75                  80

Ser Gly Leu Arg Ser Glu Asp Glu Ala Asp Tyr Tyr Cys Ala Ser Trp
                85                  90                  95

Asp Asp Ser Leu Ser Gly Val Val Phe Gly Gly Thr Lys Leu Thr
            100                 105                 110

Val Leu Gly Gln Pro Lys Ala Ala Pro Ser
        115                 120

<210> SEQ ID NO 151
<211> LENGTH: 396
<212> TYPE: DNA
<213> ORGANISM: Homo sapiens

<400> SEQUENCE: 151

| | | | | | |
|---|---|---|---|---|---|
| gaagttcaat | tgttagagtc | tggtggcggt | cttgttcagc | ctggtggttc | tttacgtctt | 60 |
| tcttgcgctg | cttccggatt | cactttctct | atgtaccta | tgttttgggt | tcgccaagct | 120 |
| cctggtaaag | gtttggagtg | ggtttctgtt | atctcttctt | ctggtggcga | gacttcttat | 180 |
| gctgactccg | ttaaaggtcg | cttcactatc | tctagagaca | actctaagaa | tactctctac | 240 |
| ttgcagatga | acagcttaag | ggctgaggac | actgcagtct | actattgtgc | gagacaggtc | 300 |
| agtgactgga | cgcgcctcta | ctcctttgac | tactggggcc | agggaaccct | ggtcaccgtc | 360 |
| tcaagcgcct | ccaccaaggg | cccatcggtc | ttcccg | | | 396 |

<210> SEQ ID NO 152

<211> LENGTH: 132
<212> TYPE: PRT
<213> ORGANISM: Homo sapiens

<400> SEQUENCE: 152

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Leu Met Phe Trp Val Arg Gln Ala Pro Gly Lys Gly Leu Glu Trp Val
        35                  40                  45

Ser Val Ile Ser Ser Ser Gly Gly Glu Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Val Ser Asp Trp Thr Arg Leu Tyr Ser Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro
    130

<210> SEQ ID NO 153
<211> LENGTH: 363
<212> TYPE: DNA
<213> ORGANISM: Homo sapiens

<400> SEQUENCE: 153
ggcgtgcact ctgacatcca gatgacccag tctccatcct tcctgtctgc atctgtagga    60
gacagagtca ccatcacttg ccgggccagt cagggcatta gcacttattt agcctggtat   120
cagcaaaaac cagggaaagc ccctaaggtc ctcatctata ctgcatccac tttgcaaagt   180
ggggtcccat caaggttcag cggcagtgga tctgggacag aattcactct cacaatcagc   240
agcctgcagc ctgaagattt tgcaacttac tactgtcaac agagttacat taccctccg    300 gaggtcactt tcggccctgg gaccaaagtg gatatcaaac gaactgtggc tgcaccatct   360
gtc                                                                 363

<210> SEQ ID NO 154
<211> LENGTH: 121
<212> TYPE: PRT
<213> ORGANISM: Homo sapiens

<400> SEQUENCE: 154

Gly Val His Ser Asp Ile Gln Met Thr Gln Ser Pro Ser Phe Leu Ser
1               5                   10                  15

Ala Ser Val Gly Asp Arg Val Thr Ile Thr Cys Arg Ala Ser Gln Gly
            20                  25                  30

Ile Ser Thr Tyr Leu Ala Trp Tyr Gln Gln Lys Pro Gly Lys Ala Pro
        35                  40                  45

Lys Val Leu Ile Tyr Thr Ala Ser Thr Leu Gln Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Glu Asp Phe Ala Thr Tyr Tyr Cys Gln Gln Ser Tyr

```
                85                  90                  95
Ile Thr Pro Pro Glu Val Thr Phe Gly Pro Gly Thr Lys Val Asp Ile
            100                 105                 110
Lys Arg Thr Val Ala Ala Pro Ser Val
        115                 120

<210> SEQ ID NO 155
<211> LENGTH: 387
<212> TYPE: DNA
<213> ORGANISM: Homo sapiens

<400> SEQUENCE: 155
gaagttcaat tgttagagtc tggtggcggt cttgttcagc ctggtggttc tttacgtctt     60
tcttgcgctg cttccggatt cactttctct tggtacgata tggcttgggt cgccaagct    120 cctggtaaag gtttggagtg ggtttctcgt atcgttcctt ctggtggcca tacttcttat    180
gctgactccg ttaaaggtcg cttcactatc tctagagaca actttaagaa tactctctac    240
ttgcagatga acagcttaag ggctgaggac actgcagtct actattgtgc gagaagggca    300
agtcgtcctg agttttttga ctactggggc caggagcccc tggtcaccgt ctcaagcgcc    360
tccaccaagg gcccatcggt cttcccg                                        387

<210> SEQ ID NO 156
<211> LENGTH: 129
<212> TYPE: PRT
<213> ORGANISM: Homo sapiens

<400> SEQUENCE: 156

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Asp Met Ala Trp Val Arg Gln Ala Pro Gly Lys Gly Leu Glu Trp Val
        35                  40                  45

Ser Arg Ile Val Pro Ser Gly Gly His Thr Ser Tyr Ala Asp Ser Val
    50                  55                  60

Lys Gly Arg Phe Thr Ile Ser Arg Asp Asn Phe Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Ser Arg Pro Glu Phe Phe Asp Tyr Trp Gly Gln Gly
            100                 105                 110

Ala Leu Val Thr Val Ser Ser Ala Ser Thr Lys Gly Pro Ser Val Phe
        115                 120                 125

Pro

<210> SEQ ID NO 157
<211> LENGTH: 363
<212> TYPE: DNA
<213> ORGANISM: Homo sapiens

<400> SEQUENCE: 157
ggcgtgcact ctgacatcca gatgacccag tctccatctg ccatgtctgc atctgtcgga     60
gacagagtca ccatcacttg tcgggcgagt caggtcatga tcaattatat agcctggttt    120
cggcagaaac cagggaaagt ccctgagcgc ctgatctatg cagcatccac tctgcaaaat    180
ggggtcccat caaggttcag cggcagtggg tctgggacag acttcactct caccatcagc    240
```

```
agactagaaac ctgaggattt tgcagtttat tactgtcagc accgtatcac ctggcctccg    300
gcgctcactt tcggcggagg gaccacggtg gagatcaaac gaactgtggc tgcaccatct    360
gtc                                                                   363
```

<210> SEQ ID NO 158
<211> LENGTH: 121
<212> TYPE: PRT
<213> ORGANISM: Homo sapiens

<400> SEQUENCE: 158

```
Gly Val His Ser Asp Ile Gln Met Thr Gln Ser Pro Ser Ala Met Ser
1               5                   10                  15

Ala Ser Val Gly Asp Arg Val Thr Ile Thr Cys Arg Ala Ser Gln Val
            20                  25                  30

Met Ile Asn Tyr Ile Ala Trp Phe Arg Gln Lys Pro Gly Lys Val Pro
        35                  40                  45

Glu Arg Leu Ile Tyr Ala Ala Ser Thr Leu Gln Asn Gly Val Pro Ser
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln His Arg Ile
                85                  90                  95

Thr Trp Pro Pro Ala Leu Thr Phe Gly Gly Gly Thr Thr Val Glu Ile
            100                 105                 110

Lys Arg Thr Val Ala Ala Pro Ser Val
        115                 120
```

<210> SEQ ID NO 159
<211> LENGTH: 387
<212> TYPE: DNA
<213> ORGANISM: Homo sapiens

<400> SEQUENCE: 159

```
gaagttcaat tgttagagtc tggtggcggt cttgttcagc ctggtggttc tttacgtctt     60
tcttgcgctg cttccggatt cactttctct tggtaccgta tggattgggt tcgccaagct    120
cctggtaaag gtttggagtg gtttctgtt atcggttctt ctggtggcat gacttattat    180
gctgactccg ttaaaggtcg cttcactatc tctagagaca actctaagaa tactctctac    240
ttgcagatga acagcttaag ggctgaggac actgcagtct actattgtgc gagacgggta    300
gtcgggggcg ccggtatgga cgtctgggc aagggaccca cggtcaccgt ctcaagcgcc    360
tccaccaagg gcccatcggt cttcccg                                         387
```

<210> SEQ ID NO 160
<211> LENGTH: 129
<212> TYPE: PRT
<213> ORGANISM: Homo sapiens

<400> SEQUENCE: 160

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Arg Met Asp Trp Val Arg Gln Ala Pro Gly Lys Gly Leu Glu Trp Val
        35                  40                  45

Ser Val Ile Gly Ser Ser Gly Gly Met Thr Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Val Val Gly Gly Ala Gly Met Asp Val Trp Gly Gln Gly
                100                 105                 110

Thr Thr Val Thr Val Ser Ser Ala Ser Thr Lys Gly Pro Ser Val Phe
            115                 120                 125

Pro

<210> SEQ ID NO 161
<211> LENGTH: 360
<212> TYPE: DNA
<213> ORGANISM: Homo sapiens

<400> SEQUENCE: 161
ggcgtgcact ctgacatcca gatgacccag tctccatcct ccctgtctgc atctgtggga    60
gacagagtcg ccatcacttg ccgcgcaagt cagagcatcg acacctattt aaattggtat   120
cagcagaaac cagggaaagc ccctaaactc ctgatctatg ctgcatccaa gttggaagac   180
ggggtcccat caagattcag tggcagtgga actgggacag attcactctc accatcaga   240 agtctgcaac tgaagatttt gcaagttatt tctgtcaac agagctactc tagtccaggg   300
atcactttcg gccctgggac caaggtggag atcaaacgaa ctgtggctgc accatctgtc   360

<210> SEQ ID NO 162
<211> LENGTH: 120
<212> TYPE: PRT
<213> ORGANISM: Homo sapiens

<400> SEQUENCE: 162

Gly Val His Ser Asp Ile Gln Met Thr Gln Ser Pro Ser Ser Leu Ser
 1               5                  10                  15

Ala Ser Val Gly Asp Arg Val Ala Ile Thr Cys Arg Ala Ser Gln Ser
                20                  25                  30

Ile Asp Thr Tyr Leu Asn Trp Tyr Gln Gln Lys Pro Gly Lys Ala Pro
            35                  40                  45

Lys Leu Leu Ile Tyr Ala Ala Ser Lys Leu Glu Asp Gly Val Pro Ser
 50                  55                  60

Arg Phe Ser Gly Ser Gly Thr Gly Thr Asp Phe Thr Leu Thr Ile Arg
 65                  70                  75                  80

Ser Leu Gln Pro Glu Asp Phe Ala Ser Tyr Phe Cys Gln Gln Ser Tyr
                 85                  90                  95

Ser Ser Pro Gly Ile Thr Phe Gly Pro Gly Thr Lys Val Glu Ile Lys
                100                 105                 110

Arg Thr Val Ala Ala Pro Ser Val
            115                 120

<210> SEQ ID NO 163
<211> LENGTH: 381
<212> TYPE: DNA
<213> ORGANISM: Homo sapiens

<400> SEQUENCE: 163
gaagttcaat tgttagagtc tggtggcggt cttgttcagc ctggtggttc tttacgtctt    60
tcttgcgctg cttccggatt cactttctct gattaccaga tgatgtgggt tcgccaagct   120
```

```
cctggtaaag gtttggagtg ggtttctcgt atctctcctt ctggtggcat gactcgttat      180
gctgactccg ttaaaggtcg cttcactatc tctagagaca actctaagaa tactctctac      240
ttgccgatga acagcttaag ggctgaggac actgcagtct actattgtgc gagatcgggg      300
ccgtactact ttgactactg gggccaggga accctggtca ccgtctcaag cgcctccacc      360
aagggcccat cggtcttccc g                                                381
```

<210> SEQ ID NO 164
<211> LENGTH: 127
<212> TYPE: PRT
<213> ORGANISM: Homo sapiens
<400> SEQUENCE: 164

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Met Trp Val Arg Gln Ala Pro Gly Lys Gly Leu Glu Trp Val
        35                  40                  45

Ser Arg Ile Ser Pro Ser Gly Gly Met Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Pro Met Asn Ser Leu Arg Ala Glu Asp Thr Ala Val Tyr Tyr Cys
                85                  90                  95

Ala Arg Ser Gly Pro Tyr Tyr Phe Asp Tyr Trp Gly Gln Gly Thr Leu
            100                 105                 110

Val Thr Val Ser Ser Ala Ser Thr Lys Gly Pro Ser Val Phe Pro
        115                 120                 125
```

<210> SEQ ID NO 165
<211> LENGTH: 363
<212> TYPE: DNA
<213> ORGANISM: Homo sapiens
<400> SEQUENCE: 165

```
ggcgtgcact cacagagcgt cttgactcag cctgactccg tgtctgggtc tcctgggcag      60
tcgatcacca tctcctgcac tggcagcagt catgacattg gttcctatga ctatgtctcc      120
tggtatcagc accacccagg gaaagccccc aaattcatac tttatgatgt ctataatcgg      180
ccctcaggtg tttctgatcg cttctctggc tccaagtctg caacacggc ctccctgact       240 atctctgggc tccagcctga cgacgaggct gactattttt gtatgtccta tacaatcaca      300
acgcttctct tcggaactgg gaccagggtc accgtcctga gtcagcccaa ggccaacccc      360
act                                                                    363
```

<210> SEQ ID NO 166
<211> LENGTH: 121
<212> TYPE: PRT
<213> ORGANISM: Homo sapiens
<400> SEQUENCE: 166

```
Gly Val His Ser Gln Ser Val Leu Thr Gln Pro Asp Ser Val Ser Gly
1               5                   10                  15

Ser Pro Gly Gln Ser Ile Thr Ile Ser Cys Thr Gly Ser Ser His Asp
            20                  25                  30
```

```
Ile Gly Ser Tyr Asp Tyr Val Ser Trp Tyr Gln His Pro Gly Lys
        35                  40                  45

Ala Pro Lys Phe Ile Leu Tyr Asp Val Tyr Asn Arg Pro Ser Gly Val
 50                  55                  60

Ser Asp Arg Phe Ser Gly Ser Lys Ser Gly Asn Thr Ala Ser Leu Thr
 65                  70                  75                  80

Ile Ser Gly Leu Gln Pro Asp Asp Glu Ala Asp Tyr Phe Cys Met Ser
                85                  90                  95

Tyr Thr Ile Thr Thr Leu Leu Phe Gly Thr Gly Thr Arg Val Thr Val
            100                 105                 110

Leu Ser Gln Pro Lys Ala Asn Pro Thr
            115                 120

<210> SEQ ID NO 167
<211> LENGTH: 375
<212> TYPE: DNA
<213> ORGANISM: Homo sapiens

<400> SEQUENCE: 167
gaagttcaat tgttagagtc tggtggcggt cttgttcagc ctggtggttc tttacgtctt      60
tcttgcgctg cttccggatt cactttctct cattacaata tggcttgggt tcgccaagct     120
cctggtaaag gtttggagtg gtttctcgt atccgttctt ctggtggcct tactgtttat      180
gctgactccg ttaaaggtcg cttcactatc tctagagaca actctaagaa tactctctac     240
ttgcagatga acagcttaag ggctgaggac actgcagtct actattgtgc gagagtggct     300
ggccctgggt actggggcca gggaaccctg gtcaccgtct caagcgcctc caccaagggc     360
ccatcggtct tcccg                                                      375

<210> SEQ ID NO 168
<211> LENGTH: 125
<212> TYPE: PRT
<213> ORGANISM: Homo sapiens

<400> SEQUENCE: 168

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
            20                  25                  30

Asn Met Ala Trp Val Arg Gln Ala Pro Gly Lys Gly Leu Glu Trp Val
        35                  40                  45

Ser Arg Ile Arg Ser Ser Gly Gly Leu Thr Val Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Val Ala Gly Pro Gly Tyr Trp Gly Gln Gly Thr Leu Val Thr
            100                 105                 110

Val Ser Ser Ala Ser Thr Lys Gly Pro Ser Val Phe Pro
            115                 120                 125

<210> SEQ ID NO 169
<211> LENGTH: 357
<212> TYPE: DNA
<213> ORGANISM: Homo sapiens

<400> SEQUENCE: 169
```

```
ggcgtgcact ctgacatcca gatgacccag tctccatcct ccctgtctgc atctgtagga      60
gacagagtca ctatcacttg ccggacaagt caaatcatta acacctattt aaattggtat     120
caacaaaaac cgggaaaagc ccctaaactc ctgatctatg ctgcctccac tttacagggt     180
ggggtcccgt caagattcag tggcagtgga tccgggacag acttcactct caccatcaag     240
agtctgcaac tgacgactt tgcaacttac tattgtcaac agagttatac ttccccgcga      300
acattcggcc aagggaccaa ggtggaaatc aaacgaactg tggctgcacc atctgtc        357
```

<210> SEQ ID NO 170
<211> LENGTH: 119
<212> TYPE: PRT
<213> ORGANISM: Homo sapiens

<400> SEQUENCE: 170

Gly Val His Ser Asp Ile Gln Met Thr Gln Ser Pro Ser Ser Leu Ser
1               5                   10                  15

Ala Ser Val Gly Asp Arg Val Thr Ile Thr Cys Arg Thr Ser Gln Ile
            20                  25                  30

Ile Asn Thr Tyr Leu Asn Trp Tyr Gln Gln Lys Pro Gly Lys Ala Pro
        35                  40                  45

Lys Leu Leu Ile Tyr Ala Ala Ser Thr Leu Gln Gly Gly Val Pro Ser
    50                  55                  60

Arg Phe Ser Gly Ser Gly Ser Gly Thr Asp Phe Thr Leu Thr Ile Lys
65                  70                  75                  80

Ser Leu Gln Pro Asp Asp Phe Ala Thr Tyr Tyr Cys Gln Gln Ser Tyr
                85                  90                  95

Thr Ser Pro Arg Thr Phe Gly Gln Gly Thr Lys Val Glu Ile Lys Arg
            100                 105                 110

Thr Val Ala Ala Pro Ser Val
        115

<210> SEQ ID NO 171
<211> LENGTH: 402
<212> TYPE: DNA
<213> ORGANISM: Homo sapiens

<400> SEQUENCE: 171

```
gaagttcaat tgttagagtc tggtggcggt cttgttcagc ctggtggttc tttacgtctt      60
tcttgcgctg cttccggatt cacttttctct ggttacatta tggagtgggt tcgccaagct    120
cctggtaaag gtttggagtg ggtttctgtt atcgtttctt ctggtggctt tactatgtat     180
gctgactccg ttaaaggtcg cttcactatc tctagagaca actctaagaa tactctctac     240
ttgcagatga acagcttaag gctgaggac actgcagtct actattgtgc gagagttggg      300
gattccaagg gcgggtacta ccttgactac tggggccagg gaaccctggt caccgtctca     360
agcgcctcca ccaagggccc atcggtcttc ccgctagcgc cc                        402
```

<210> SEQ ID NO 172
<211> LENGTH: 134
<212> TYPE: PRT
<213> ORGANISM: Homo sapiens

<400> SEQUENCE: 172

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr

```
                   20                  25                  30
Ile Met Glu Trp Val Arg Gln Ala Pro Gly Lys Gly Leu Glu Trp Val
            35                  40                  45
Ser Val Ile Val Ser Ser Gly Gly Phe Thr Met Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Val Gly Asp Ser Lys Gly Tyr Tyr Leu Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro
        130

<210> SEQ ID NO 173
<211> LENGTH: 366
<212> TYPE: DNA
<213> ORGANISM: Homo sapiens

<400> SEQUENCE: 173
ggcgtgcact cacagagcga attgactcag cctgcctccg tgtctgggtc tcctggacag      60
tcgatcacca tctcctgcac tggaaccaac agtgacattg gtggttataa ttatgtctcc     120
tggtaccaac aacacccggg caaagtcccc aaactcttga ttttttgaggt caataatcgg     180 ccctcagggg tttctagtcg cttctctggc tccaagtctg gcgacacggc ctccctgacc     240
atctctgggc tccaacctga ggacgaggct gtttattact gcggctcatt tacagtcagc     300
gtcacctatg tcttcggaac tgggaccaag gtcaccgtcc tgggtcagcc caaggccaac     360
cccact                                                                366

<210> SEQ ID NO 174
<211> LENGTH: 122
<212> TYPE: PRT
<213> ORGANISM: Homo sapiens

<400> SEQUENCE: 174

Gly Val His Ser Gln Ser Glu Leu Thr Gln Pro Ala Ser Val Ser Gly
1               5                   10                  15
Ser Pro Gly Gln Ser Ile Thr Ile Ser Cys Thr Gly Thr Asn Ser Asp
            20                  25                  30
Ile Gly Gly Tyr Asn Tyr Val Ser Trp Tyr Gln Gln His Pro Gly Lys
        35                  40                  45
Val Pro Lys Leu Leu Ile Phe Glu Val Asn Asn Arg Pro Ser Gly Val
    50                  55                  60
Ser Ser Arg Phe Ser Gly Ser Lys Ser Gly Asp Thr Ala Ser Leu Thr
65                  70                  75                  80
Ile Ser Gly Leu Gln Pro Glu Asp Glu Ala Val Tyr Tyr Cys Gly Ser
                85                  90                  95
Phe Thr Val Ser Val Thr Tyr Val Phe Gly Thr Gly Thr Lys Val Thr
            100                 105                 110
Val Leu Gly Gln Pro Lys Ala Asn Pro Thr
        115                 120

<210> SEQ ID NO 175
```

```
<211> LENGTH: 398
<212> TYPE: DNA
<213> ORGANISM: Homo sapiens

<400> SEQUENCE: 175
gaagttcaat tgttagagtc tggtggcggt cttgttcagc ctggtggttc tttacgtctt      60
tcttgcgctg cttccggatt cactttctct gagtacaata tgttttgggt tcgccaagct     120
cctggtaaag gtttggagtg ggtttcttat atctattctt ctggtggctc tactgattat     180
gctgactccg ttaaaggtcg cttcactatc tctagagaca actctaagaa tactctctac     240
ttgcagatga acagcttaag ggctgaggac actgcagtct actattgtgc gagagtaggt     300
atagcagctc gtccgttcga cccctggggc cagggaaccc tggtcaccgt ctcaagcgcc     360
tccaccaagg gcccatcggt cttcccgcta gcgccctg                             398

<210> SEQ ID NO 176
<211> LENGTH: 132
<212> TYPE: PRT
<213> ORGANISM: Homo sapiens

<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Asn Met Phe Trp Val Arg Gln Ala Pro Gly Lys Gly Leu Glu Trp Val
        35                  40                  45

Ser Tyr Ile Tyr Ser Ser Gly Gly Ser Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Ile Ala Ala Arg Pro Phe Asp Pro Trp Gly Gln Gly
            100                 105                 110

Thr Leu Val Thr Val Ser Ser Ala Ser Thr Lys Gly Pro Ser Val Phe
        115                 120                 125

Pro Leu Ala Pro
    130

<210> SEQ ID NO 177
<211> LENGTH: 357
<212> TYPE: DNA
<213> ORGANISM: Homo sapiens

<400> SEQUENCE: 177
ggcgtgcact ctgacatcca gatgacccag tctccatcct ccctgtctgc atctgtagga      60
gacagagtca ccatcacttg ccgggcaagt cagagcatta gcgactattt aaattggtat     120
cagcagaaac cagggaaagc ccctgaccte ctgatctatg ctgcatccag tttgcaaagt     180
ggggtcccat caaggttcag tggcagtgga tctgggacag atttcactct caccgtcagc     240
agtctgcaac tgaagatttt gcaacttac ttctgtcaac agagttactc tattcctctc     300
actttcggcg gcgggaccaa ggttgagatc actcgaactg tggctgcacc atctgtc       357

<210> SEQ ID NO 178
<211> LENGTH: 119
<212> TYPE: PRT
```

<213> ORGANISM: Homo sapiens

<400> SEQUENCE: 178

Gly Val His Ser Asp Ile Gln Met Thr Gln Ser Pro Ser Ser Leu Ser
1               5                   10                  15

Ala Ser Val Gly Asp Arg Val Thr Ile Thr Cys Arg Ala Ser Gln Ser
            20                  25                  30

Ile Ser Asp Tyr Leu Asn Trp Tyr Gln Gln Lys Pro Gly Lys Ala Pro
        35                  40                  45

Asp Leu Leu Ile Tyr Ala Ala Ser Ser Leu Gln Ser Gly Val Pro Ser
    50                  55                  60

Arg Phe Ser Gly Ser Gly Ser Gly Thr Asp Phe Thr Leu Thr Val Ser
65                  70                  75                  80

Ser Leu Gln Pro Glu Asp Phe Ala Thr Tyr Phe Cys Gln Gln Ser Tyr
                85                  90                  95

Ser Ile Pro Leu Thr Phe Gly Gly Gly Thr Lys Val Glu Ile Thr Arg
            100                 105                 110

Thr Val Ala Ala Pro Ser Val
        115

<210> SEQ ID NO 179
<211> LENGTH: 387
<212> TYPE: DNA
<213> ORGANISM: Homo sapiens

<400> SEQUENCE: 179
gaagttcaat tgttagagtc tggtggcggt cttgttcagc ctggtggttc tttacgtctt      60
tcttgcgctg cttccggatt cactttctct ttttacgcta tgtggtgggt tcgccaagct     120
cctggtaaag gtttggagtg ggtttctcgt atctattctt ctggtggcaa gacttggtat     180
gctgactccg ttaaaggtcg cttcactatc tctagagaca actctaagaa tactctctac     240
ttgcagatga acagcttaag ggctgaggac actgcagtct actattgtgc gagagtgggg     300
atgtccacct atgcttttga tatctggggc caagggacaa tggtcaccgt ctcaagcgcc     360
tccaccaagg gcccatcggt cttcccg                                         387

<210> SEQ ID NO 180
<211> LENGTH: 129
<212> TYPE: PRT
<213> ORGANISM: Homo sapiens

<400> SEQUENCE: 180

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Ala Met Trp Trp Val Arg Gln Ala Pro Gly Lys Gly Leu Glu Trp Val
        35                  40                  45

Ser Arg Ile Tyr Ser Ser Gly Gly Lys Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Met Ser Thr Tyr Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro

<210> SEQ ID NO 181
<211> LENGTH: 354
<212> TYPE: DNA
<213> ORGANISM: Homo sapiens

<400> SEQUENCE: 181
ggcgtgcact cacagagcga attgactcag ccaccctcag tgtccgtgtc cccaggacag      60
acagccagca tcacctgctc tggagataaa ttgggggata atatgcttg ctggtatcag     120 cagaagccag gccagtcccc tgtgctggtc atctatcaag atagcaagcg gccctcaggg     180
atccctgagc gattctctgg ctccaactct gggaacacag ccactctgac catcagcggg     240
acccaggcta tggatgaggc tgactattac tgtcaggcgt gggacagcag cgctgtggta     300
ttcggcggag ggaccaagct gaccgtccta ggtcagccca aggctgcccc ctcg           354

<210> SEQ ID NO 182
<211> LENGTH: 118
<212> TYPE: PRT
<213> ORGANISM: Homo sapiens

<400> SEQUENCE: 182

Gly Val His Ser Gln Ser Glu Leu Thr Gln Pro Pro Ser Val Ser Val
1               5                   10                  15

Ser Pro Gly Gln Thr Ala Ser Ile Thr Cys Ser Gly Asp Lys Leu Gly
            20                  25                  30

Asp Lys Tyr Ala Cys Trp Tyr Gln Gln Lys Pro Gly Gln Ser Pro Val
        35                  40                  45

Leu Val Ile Tyr Gln Asp Ser Lys Arg Pro Ser Gly Ile Pro Glu Arg
    50                  55                  60

Phe Ser Gly Ser Asn Ser Gly Asn Thr Ala Thr Leu Thr Ile Ser Gly
65                  70                  75                  80

Thr Gln Ala Met Asp Glu Ala Asp Tyr Tyr Cys Gln Ala Trp Asp Ser
                85                  90                  95

Ser Ala Val Val Phe Gly Gly Gly Thr Lys Leu Thr Val Leu Gly Gln
            100                 105                 110

Pro Lys Ala Ala Pro Ser
        115

<210> SEQ ID NO 183
<211> LENGTH: 399
<212> TYPE: DNA
<213> ORGANISM: Homo sapiens

<400> SEQUENCE: 183
gaagttcaat tgttagagtc tggtggcggt cttgttcagc ctggtggttc tttacgtctt      60
tcttgcgctg cttccggatt cacttttctct cattacaata tgcattgggt tcgccaagct     120
cctggtaaag gtttggagtg gtttctggt atcgtttctt ctggtggcaa tactggttat      180
gctgactccg ttaaaggtcg cttcactatc tctagagaca actctaagaa tactctctac     240
ttgcagatga acagcttaag ggctgaggac actgcagtcg actattgtgc gagagtggta     300
cggtatagca gtggctggta ctactggttc gaccccctggg gccagggaac cctggtcacc     360
gtctcaagcg cctccaccaa gggcccatcg gtcttcccg                            399

```
<210> SEQ ID NO 184
<211> LENGTH: 133
<212> TYPE: PRT
<213> ORGANISM: Homo sapiens

<400> SEQUENCE: 184

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Asn Met His Trp Val Arg Gln Ala Pro Gly Lys Gly Leu Glu Trp Val
        35                  40                  45

Ser Gly Ile Val Ser Ser Gly Gly Asn Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Asp Tyr Cys
                85                  90                  95

Ala Arg Val Val Arg Tyr Ser Ser Gly Trp Tyr Tyr Trp Phe Asp Pro
            100                 105                 110

Trp Gly Gln Gly Thr Leu Val Thr Val Ser Ser Ala Ser Thr Lys Gly
        115                 120                 125

Pro Ser Val Phe Pro
    130

<210> SEQ ID NO 185
<211> LENGTH: 4
<212> TYPE: PRT
<213> ORGANISM: Homo sapiens

<400> SEQUENCE: 185

Ala Ser Asp Phe
1

<210> SEQ ID NO 186
<211> LENGTH: 4
<212> TYPE: PRT
<213> ORGANISM: Homo sapiens

<400> SEQUENCE: 186

Ala Ser Asp Phe
1

<210> SEQ ID NO 187
<211> LENGTH: 4
<212> TYPE: PRT
<213> ORGANISM: Homo sapiens

<400> SEQUENCE: 187

Ala Ser Asp Phe
1

<210> SEQ ID NO 188
<211> LENGTH: 4
<212> TYPE: PRT
<213> ORGANISM: Homo sapiens

<400> SEQUENCE: 188

Ala Ser Asp Phe
1
```

```
<210> SEQ ID NO 189
<211> LENGTH: 4
<212> TYPE: PRT
<213> ORGANISM: Homo sapiens

<400> SEQUENCE: 189

Ala Ser Asp Phe
1

<210> SEQ ID NO 190
<211> LENGTH: 4
<212> TYPE: PRT
<213> ORGANISM: Homo sapiens

<400> SEQUENCE: 190

Ala Ser Asp Phe
1

<210> SEQ ID NO 191
<211> LENGTH: 4
<212> TYPE: PRT
<213> ORGANISM: Homo sapiens

<400> SEQUENCE: 191

Ala Ser Asp Phe
1

<210> SEQ ID NO 192
<211> LENGTH: 4
<212> TYPE: PRT
<213> ORGANISM: Homo sapiens

<400> SEQUENCE: 192

Ala Ser Asp Phe
1

<210> SEQ ID NO 193
<211> LENGTH: 4
<212> TYPE: PRT
<213> ORGANISM: Homo sapiens

<400> SEQUENCE: 193

Ala Ser Asp Phe
1

<210> SEQ ID NO 194
<211> LENGTH: 4
<212> TYPE: PRT
<213> ORGANISM: Homo sapiens

<400> SEQUENCE: 194

Ala Ser Asp Phe
1

<210> SEQ ID NO 195
<211> LENGTH: 4
<212> TYPE: PRT
<213> ORGANISM: Homo sapiens

<400> SEQUENCE: 195

Ala Ser Asp Phe
1

<210> SEQ ID NO 196
```

```
<211> LENGTH: 4
<212> TYPE: PRT
<213> ORGANISM: Homo sapiens

<400> SEQUENCE: 196

Ala Ser Asp Phe
1

<210> SEQ ID NO 197
<211> LENGTH: 4
<212> TYPE: PRT
<213> ORGANISM: Homo sapiens

<400> SEQUENCE: 197

Ala Ser Asp Phe
1

<210> SEQ ID NO 198
<211> LENGTH: 4
<212> TYPE: PRT
<213> ORGANISM: Homo sapiens

<400> SEQUENCE: 198

Ala Ser Asp Phe
1

<210> SEQ ID NO 199
<211> LENGTH: 4
<212> TYPE: PRT
<213> ORGANISM: Homo sapiens

<400> SEQUENCE: 199

Ala Ser Asp Phe
1

<210> SEQ ID NO 200
<211> LENGTH: 4
<212> TYPE: PRT
<213> ORGANISM: Homo sapiens

<400> SEQUENCE: 200

Ala Ser Asp Phe
1

<210> SEQ ID NO 201
<211> LENGTH: 4
<212> TYPE: PRT
<213> ORGANISM: Homo sapiens

<400> SEQUENCE: 201

Ala Ser Asp Phe
1

<210> SEQ ID NO 202
<211> LENGTH: 4
<212> TYPE: PRT
<213> ORGANISM: Homo sapiens

<400> SEQUENCE: 202

Ala Ser Asp Phe
1

<210> SEQ ID NO 203
<211> LENGTH: 4
<212> TYPE: PRT
```

<213> ORGANISM: Homo sapiens

<400> SEQUENCE: 203

Ala Ser Asp Phe
1

<210> SEQ ID NO 204
<211> LENGTH: 4
<212> TYPE: PRT
<213> ORGANISM: Homo sapiens

<400> SEQUENCE: 204

Ala Ser Asp Phe
1

<210> SEQ ID NO 205
<211> LENGTH: 4
<212> TYPE: PRT
<213> ORGANISM: Homo sapiens

<400> SEQUENCE: 205

Ala Ser Asp Phe
1

<210> SEQ ID NO 206
<211> LENGTH: 4
<212> TYPE: PRT
<213> ORGANISM: Homo sapiens

<400> SEQUENCE: 206

Ala Ser Asp Phe
1

<210> SEQ ID NO 207
<211> LENGTH: 4
<212> TYPE: PRT
<213> ORGANISM: Homo sapiens

<400> SEQUENCE: 207

Ala Ser Asp Phe
1

<210> SEQ ID NO 208
<211> LENGTH: 4
<212> TYPE: PRT
<213> ORGANISM: Homo sapiens

<400> SEQUENCE: 208

Ala Ser Asp Phe
1

<210> SEQ ID NO 209
<211> LENGTH: 4
<212> TYPE: PRT
<213> ORGANISM: Homo sapiens

<400> SEQUENCE: 209

Ala Ser Asp Phe
1

<210> SEQ ID NO 210
<211> LENGTH: 4
<212> TYPE: PRT
<213> ORGANISM: Homo sapiens

```
<400> SEQUENCE: 210

Ala Ser Asp Phe
1

<210> SEQ ID NO 211
<211> LENGTH: 4
<212> TYPE: PRT
<213> ORGANISM: Homo sapiens

<400> SEQUENCE: 211

Ala Ser Asp Phe
1

<210> SEQ ID NO 212
<211> LENGTH: 4
<212> TYPE: PRT
<213> ORGANISM: Homo sapiens

<400> SEQUENCE: 212

Ala Ser Asp Phe
1

<210> SEQ ID NO 213
<211> LENGTH: 4
<212> TYPE: PRT
<213> ORGANISM: Homo sapiens

<400> SEQUENCE: 213

Ala Ser Asp Phe
1

<210> SEQ ID NO 214
<211> LENGTH: 4
<212> TYPE: PRT
<213> ORGANISM: Homo sapiens

<400> SEQUENCE: 214

Ala Ser Asp Phe
1

<210> SEQ ID NO 215
<211> LENGTH: 4
<212> TYPE: PRT
<213> ORGANISM: Homo sapiens

<400> SEQUENCE: 215

Ala Ser Asp Phe
1

<210> SEQ ID NO 216
<211> LENGTH: 4
<212> TYPE: PRT
<213> ORGANISM: Homo sapiens

<400> SEQUENCE: 216

Ala Ser Asp Phe
1

<210> SEQ ID NO 217
<211> LENGTH: 4
<212> TYPE: PRT
<213> ORGANISM: Homo sapiens

<400> SEQUENCE: 217
```

Ala Ser Asp Phe
1

<210> SEQ ID NO 218
<211> LENGTH: 4
<212> TYPE: PRT
<213> ORGANISM: Homo sapiens

<400> SEQUENCE: 218

Ala Ser Asp Phe
1

<210> SEQ ID NO 219
<211> LENGTH: 4
<212> TYPE: PRT
<213> ORGANISM: Homo sapiens

<400> SEQUENCE: 219

Ala Ser Asp Phe
1

<210> SEQ ID NO 220
<211> LENGTH: 4
<212> TYPE: PRT
<213> ORGANISM: Homo sapiens

<400> SEQUENCE: 220

Ala Ser Asp Phe
1

<210> SEQ ID NO 221
<211> LENGTH: 4
<212> TYPE: PRT
<213> ORGANISM: Homo sapiens

<400> SEQUENCE: 221

Ala Ser Asp Phe
1

<210> SEQ ID NO 222
<211> LENGTH: 4
<212> TYPE: PRT
<213> ORGANISM: Homo sapiens

<400> SEQUENCE: 222

Ala Ser Asp Phe
1

<210> SEQ ID NO 223
<211> LENGTH: 4
<212> TYPE: PRT
<213> ORGANISM: Homo sapiens

<400> SEQUENCE: 223

Ala Ser Asp Phe
1

<210> SEQ ID NO 224
<211> LENGTH: 4
<212> TYPE: PRT
<213> ORGANISM: Homo sapiens

<400> SEQUENCE: 224

Ala Ser Asp Phe
1

```
<210> SEQ ID NO 225
<211> LENGTH: 4
<212> TYPE: PRT
<213> ORGANISM: Homo sapiens

<400> SEQUENCE: 225

Ala Ser Asp Phe
1

<210> SEQ ID NO 226
<211> LENGTH: 4
<212> TYPE: PRT
<213> ORGANISM: Homo sapiens

<400> SEQUENCE: 226

Ala Ser Asp Phe
1

<210> SEQ ID NO 227
<211> LENGTH: 4
<212> TYPE: PRT
<213> ORGANISM: Homo sapiens

<400> SEQUENCE: 227

Ala Ser Asp Phe
1

<210> SEQ ID NO 228
<211> LENGTH: 4
<212> TYPE: PRT
<213> ORGANISM: Homo sapiens

<400> SEQUENCE: 228

Ala Ser Asp Phe
1

<210> SEQ ID NO 229
<211> LENGTH: 4
<212> TYPE: PRT
<213> ORGANISM: Homo sapiens

<400> SEQUENCE: 229

Ala Ser Asp Phe
1

<210> SEQ ID NO 230
<211> LENGTH: 4
<212> TYPE: PRT
<213> ORGANISM: Homo sapiens

<400> SEQUENCE: 230

Ala Ser Asp Phe
1

<210> SEQ ID NO 231
<211> LENGTH: 4
<212> TYPE: PRT
<213> ORGANISM: Homo sapiens

<400> SEQUENCE: 231

Ala Ser Asp Phe
1
```

```
<210> SEQ ID NO 232
<211> LENGTH: 4
<212> TYPE: PRT
<213> ORGANISM: Homo sapiens

<400> SEQUENCE: 232

Ala Ser Asp Phe
1

<210> SEQ ID NO 233
<211> LENGTH: 4
<212> TYPE: PRT
<213> ORGANISM: Homo sapiens

<400> SEQUENCE: 233

Ala Ser Asp Phe
1

<210> SEQ ID NO 234
<211> LENGTH: 4
<212> TYPE: PRT
<213> ORGANISM: Homo sapiens

<400> SEQUENCE: 234

Ala Ser Asp Phe
1

<210> SEQ ID NO 235
<211> LENGTH: 4
<212> TYPE: PRT
<213> ORGANISM: Homo sapiens

<400> SEQUENCE: 235

Ala Ser Asp Phe
1

<210> SEQ ID NO 236
<211> LENGTH: 4
<212> TYPE: PRT
<213> ORGANISM: Homo sapiens

<400> SEQUENCE: 236

Ala Ser Asp Phe
1

<210> SEQ ID NO 237
<211> LENGTH: 4
<212> TYPE: PRT
<213> ORGANISM: Homo sapiens

<400> SEQUENCE: 237

Ala Ser Asp Phe
1

<210> SEQ ID NO 238
<211> LENGTH: 4
<212> TYPE: PRT
<213> ORGANISM: Homo sapiens

<400> SEQUENCE: 238

Ala Ser Asp Phe
1

<210> SEQ ID NO 239
<211> LENGTH: 4
```

```
<212> TYPE: PRT
<213> ORGANISM: Homo sapiens

<400> SEQUENCE: 239

Ala Ser Asp Phe
1

<210> SEQ ID NO 240
<211> LENGTH: 4
<212> TYPE: PRT
<213> ORGANISM: Homo sapiens

<400> SEQUENCE: 240

Ala Ser Asp Phe
1

<210> SEQ ID NO 241
<211> LENGTH: 4
<212> TYPE: PRT
<213> ORGANISM: Homo sapiens

<400> SEQUENCE: 241

Ala Ser Asp Phe
1

<210> SEQ ID NO 242
<211> LENGTH: 4
<212> TYPE: PRT
<213> ORGANISM: Homo sapiens

<400> SEQUENCE: 242

Ala Ser Asp Phe
1

<210> SEQ ID NO 243
<211> LENGTH: 4
<212> TYPE: PRT
<213> ORGANISM: Homo sapiens

<400> SEQUENCE: 243

Ala Ser Asp Phe
1

<210> SEQ ID NO 244
<211> LENGTH: 4
<212> TYPE: PRT
<213> ORGANISM: Homo sapiens

<400> SEQUENCE: 244

Ala Ser Asp Phe
1

<210> SEQ ID NO 245
<211> LENGTH: 4
<212> TYPE: PRT
<213> ORGANISM: Homo sapiens

<400> SEQUENCE: 245

Ala Ser Asp Phe
1

<210> SEQ ID NO 246
<211> LENGTH: 4
<212> TYPE: PRT
<213> ORGANISM: Homo sapiens
```

```
<400> SEQUENCE: 246

Ala Ser Asp Phe
1

<210> SEQ ID NO 247
<211> LENGTH: 4
<212> TYPE: PRT
<213> ORGANISM: Homo sapiens

<400> SEQUENCE: 247

Ala Ser Asp Phe
1

<210> SEQ ID NO 248
<211> LENGTH: 4
<212> TYPE: PRT
<213> ORGANISM: Homo sapiens

<400> SEQUENCE: 248

Ala Ser Asp Phe
1

<210> SEQ ID NO 249
<211> LENGTH: 4
<212> TYPE: PRT
<213> ORGANISM: Homo sapiens

<400> SEQUENCE: 249

Ala Ser Asp Phe
1

<210> SEQ ID NO 250
<211> LENGTH: 4
<212> TYPE: PRT
<213> ORGANISM: Homo sapiens

<400> SEQUENCE: 250

Ala Ser Asp Phe
1

<210> SEQ ID NO 251
<211> LENGTH: 4
<212> TYPE: PRT
<213> ORGANISM: Homo sapiens

<400> SEQUENCE: 251

Ala Ser Asp Phe
1

<210> SEQ ID NO 252
<211> LENGTH: 4
<212> TYPE: PRT
<213> ORGANISM: Homo sapiens

<400> SEQUENCE: 252

Ala Ser Asp Phe
1

<210> SEQ ID NO 253
<211> LENGTH: 4
<212> TYPE: PRT
<213> ORGANISM: Homo sapiens

<400> SEQUENCE: 253
```

Ala Ser Asp Phe
1

<210> SEQ ID NO 254
<211> LENGTH: 4
<212> TYPE: PRT
<213> ORGANISM: Homo sapiens

<400> SEQUENCE: 254

Ala Ser Asp Phe
1

<210> SEQ ID NO 255
<211> LENGTH: 4
<212> TYPE: PRT
<213> ORGANISM: Homo sapiens

<400> SEQUENCE: 255

Ala Ser Asp Phe
1

<210> SEQ ID NO 256
<211> LENGTH: 4
<212> TYPE: PRT
<213> ORGANISM: Homo sapiens

<400> SEQUENCE: 256

Ala Ser Asp Phe
1

<210> SEQ ID NO 257
<211> LENGTH: 4
<212> TYPE: PRT
<213> ORGANISM: Homo sapiens

<400> SEQUENCE: 257

Ala Ser Asp Phe
1

<210> SEQ ID NO 258
<211> LENGTH: 4
<212> TYPE: PRT
<213> ORGANISM: Homo sapiens

<400> SEQUENCE: 258

Ala Ser Asp Phe
1

<210> SEQ ID NO 259
<211> LENGTH: 4
<212> TYPE: PRT
<213> ORGANISM: Homo sapiens

<400> SEQUENCE: 259

Ala Ser Asp Phe
1

<210> SEQ ID NO 260
<211> LENGTH: 4
<212> TYPE: PRT
<213> ORGANISM: Homo sapiens

<400> SEQUENCE: 260

Ala Ser Asp Phe

```
<210> SEQ ID NO 261
<211> LENGTH: 4
<212> TYPE: PRT
<213> ORGANISM: Homo sapiens

<400> SEQUENCE: 261

Ala Ser Asp Phe
1

<210> SEQ ID NO 262
<211> LENGTH: 4
<212> TYPE: PRT
<213> ORGANISM: Homo sapiens

<400> SEQUENCE: 262

Ala Ser Asp Phe
1

<210> SEQ ID NO 263
<211> LENGTH: 4
<212> TYPE: PRT
<213> ORGANISM: Homo sapiens

<400> SEQUENCE: 263

Ala Ser Asp Phe
1

<210> SEQ ID NO 264
<211> LENGTH: 4
<212> TYPE: PRT
<213> ORGANISM: Homo sapiens

<400> SEQUENCE: 264

Ala Ser Asp Phe
1

<210> SEQ ID NO 265
<211> LENGTH: 4
<212> TYPE: PRT
<213> ORGANISM: Homo sapiens

<400> SEQUENCE: 265

Ala Ser Asp Phe
1

<210> SEQ ID NO 266
<211> LENGTH: 4
<212> TYPE: PRT
<213> ORGANISM: Homo sapiens

<400> SEQUENCE: 266

Ala Ser Asp Phe
1

<210> SEQ ID NO 267
<211> LENGTH: 4
<212> TYPE: PRT
<213> ORGANISM: Homo sapiens

<400> SEQUENCE: 267

Ala Ser Asp Phe
1
```

<210> SEQ ID NO 268
<211> LENGTH: 4
<212> TYPE: PRT
<213> ORGANISM: Homo sapiens

<400> SEQUENCE: 268

Ala Ser Asp Phe
1

<210> SEQ ID NO 269
<211> LENGTH: 4
<212> TYPE: PRT
<213> ORGANISM: Homo sapiens

<400> SEQUENCE: 269

Ala Ser Asp Phe
1

<210> SEQ ID NO 270
<211> LENGTH: 96
<212> TYPE: PRT
<213> ORGANISM: Homo sapiens

<400> SEQUENCE: 270

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 271
<211> LENGTH: 96
<212> TYPE: PRT
<213> ORGANISM: Homo sapiens

<400> SEQUENCE: 271

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

<210> SEQ ID NO 272
<211> LENGTH: 96
<212> TYPE: PRT
<213> ORGANISM: Homo sapiens

```
<400> SEQUENCE: 272

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95
```

<210> SEQ ID NO 273
<211> LENGTH: 95
<212> TYPE: PRT
<213> ORGANISM: Homo sapiens

```
<400> SEQUENCE: 273

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95
```

<210> SEQ ID NO 274
<211> LENGTH: 95
<212> TYPE: PRT
<213> ORGANISM: Homo sapiens

```
<400> SEQUENCE: 274

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95
```

<210> SEQ ID NO 275
<211> LENGTH: 96
<212> TYPE: PRT
<213> ORGANISM: Homo sapiens

```
<400> SEQUENCE: 275

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

<210> SEQ ID NO 276
<211> LENGTH: 95
<212> TYPE: PRT
<213> ORGANISM: Homo sapiens

<400> SEQUENCE: 276

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
                85                  90                  95

<210> SEQ ID NO 277
<211> LENGTH: 96
<212> TYPE: PRT
<213> ORGANISM: Homo sapiens

<400> SEQUENCE: 277

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

<210> SEQ ID NO 278
<211> LENGTH: 95
<212> TYPE: PRT
<213> ORGANISM: Homo sapiens

<400> SEQUENCE: 278
```

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65              70                  75                  80

Asp Asp Phe Ala Thr Tyr Tyr Cys Gln Gln Tyr Asn Ser Tyr Ser
                85                  90                  95
```

<210> SEQ ID NO 279
<211> LENGTH: 96
<212> TYPE: PRT
<213> ORGANISM: Homo sapiens

<400> SEQUENCE: 279

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
50                  55                  60

Ser Gly Ser Lys Ser Gly Asn Thr Ala Ser Leu Thr Val Ser Gly Leu
65              70                  75                  80

Gln Ala Glu Asp Glu Ala Asp Tyr Tyr Cys Ser Ser Tyr Ala Gly Ser
                85                  90                  95
```

<210> SEQ ID NO 280
<211> LENGTH: 96
<212> TYPE: PRT
<213> ORGANISM: Homo sapiens

<400> SEQUENCE: 280

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65              70                  75                  80

Ser Glu Asp Glu Ala Asp Tyr Tyr Cys Ala Ala Trp Asp Asp Ser Leu
                85                  90                  95
```

<210> SEQ ID NO 281
<211> LENGTH: 95
<212> TYPE: PRT
<213> ORGANISM: Homo sapiens

<400> SEQUENCE: 281

```
Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
            85                  90                  95
```

<210> SEQ ID NO 282
<211> LENGTH: 96
<212> TYPE: PRT
<213> ORGANISM: Homo sapiens

<400> SEQUENCE: 282

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
            85                  90                  95
```

<210> SEQ ID NO 283
<211> LENGTH: 95
<212> TYPE: PRT
<213> ORGANISM: Homo sapiens

<400> SEQUENCE: 283

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
            85                  90                  95
```

<210> SEQ ID NO 284
<211> LENGTH: 95
<212> TYPE: PRT
<213> ORGANISM: Homo sapiens

<400> SEQUENCE: 284

```
Asn Ile Gln Met Thr Gln Ser Pro Ser Ala Met Ser Ala Ser Val Gly
```

```
                1               5                   10                  15
Asp Arg Val Thr Ile Thr Cys Arg Ala Arg Gln Gly Ile Ser Asn Tyr
                    20                  25                  30

Leu Ala Trp Phe Gln Gln Lys Pro Gly Lys Val Pro Lys His Leu Ile
                35                  40                  45

Tyr Ala Ala Ser Ser Leu Gln Ser Gly Val Pro Ser Arg Phe Ser Gly
            50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                    85                  90                  95
```

<210> SEQ ID NO 285
<211> LENGTH: 96
<212> TYPE: PRT
<213> ORGANISM: Homo sapiens

<400> SEQUENCE: 285

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                    20                  25                  30

Asn Tyr Val Ser Trp Tyr Gln Gln His Pro Gly Lys Ala Pro Lys Leu
                35                  40                  45

Met Ile Tyr Glu Val Ser Asn Arg Pro Ser Gly Val Ser Asn Arg Phe
            50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                    85                  90                  95
```

<210> SEQ ID NO 286
<211> LENGTH: 95
<212> TYPE: PRT
<213> ORGANISM: Homo sapiens

<400> SEQUENCE: 286

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
                    20                  25                  30

Cys Trp Tyr Gln Gln Lys Pro Gly Gln Ser Pro Val Leu Val Ile Tyr
                35                  40                  45

Gln Asp Ser Lys Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala
                    85                  90                  95
```

<210> SEQ ID NO 287
<211> LENGTH: 96
<212> TYPE: PRT
<213> ORGANISM: Homo sapiens

<400> SEQUENCE: 287

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
        20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

<210> SEQ ID NO 288
<211> LENGTH: 17
<212> TYPE: PRT
<213> ORGANISM: Homo sapiens

<400> SEQUENCE: 288

```
Ala Glu Tyr Phe Gln His Trp Gly Gln Gly Thr Leu Val Thr Val Ser
 1               5                  10                  15

Ser
```

<210> SEQ ID NO 289
<211> LENGTH: 17
<212> TYPE: PRT
<213> ORGANISM: Homo sapiens

<400> SEQUENCE: 289

```
Tyr Trp Tyr Phe Asp Leu Trp Gly Arg Gly Thr Leu Val Thr Val Ser
 1               5                  10                  15

Ser
```

<210> SEQ ID NO 290
<211> LENGTH: 15
<212> TYPE: PRT
<213> ORGANISM: Homo sapiens

<400> SEQUENCE: 290

```
Ala Phe Asp Ile Trp Gly Gln Gly Thr Met Val Thr Val Ser Ser
 1               5                  10                  15
```

<210> SEQ ID NO 291
<211> LENGTH: 15
<212> TYPE: PRT
<213> ORGANISM: Homo sapiens

<400> SEQUENCE: 291

```
Tyr Phe Asp Tyr Trp Gly Gln Gly Thr Leu Val Thr Val Ser Ser
 1               5                  10                  15
```

<210> SEQ ID NO 292
<211> LENGTH: 16
<212> TYPE: PRT
<213> ORGANISM: Homo sapiens

<400> SEQUENCE: 292

```
Asn Trp Phe Asp Pro Trp Gly Gln Gly Thr Leu Val Thr Val Ser Ser
 1               5                  10                  15
```

<210> SEQ ID NO 293
<211> LENGTH: 20
<212> TYPE: PRT

```
<213> ORGANISM: Homo sapiens

<400> SEQUENCE: 293

Tyr Tyr Tyr Tyr Tyr Gly Met Asp Val Trp Gly Gln Gly Thr Thr Val
1               5                   10                  15

Thr Val Ser Ser
            20

<210> SEQ ID NO 294
<211> LENGTH: 4
<212> TYPE: PRT
<213> ORGANISM: Homo sapiens

<400> SEQUENCE: 294

Ala Ser Asp Phe
1

<210> SEQ ID NO 295
<211> LENGTH: 120
<212> TYPE: PRT
<213> ORGANISM: Homo sapiens

<400> SEQUENCE: 295

Gly Val His Ser Gln Ser Glu Leu Thr Gln Pro Ser Val Ser Leu
1               5                   10                  15

Ala Pro Gly Gln Thr Ala Arg Ile Thr Cys Gly Gly Asn Asn Ile Gly
                20                  25                  30

Thr Lys Ser Val His Trp Tyr Gln Gln Lys Pro Gly Gln Ala Pro Val
            35                  40                  45

Leu Val Val Tyr Asp Asp Ser Asp Arg Pro Ser Gly Ile Pro Glu Arg
        50                  55                  60

Phe Ser Gly Ser Asn Ser Gly Asn Thr Ala Thr Leu Thr Ile Ser Arg
65                  70                  75                  80

Val Glu Ala Gly Asp Glu Ala Asp Tyr Tyr Cys Gln Val Trp Asp Ser
                85                  90                  95

Gly Ser Asp His Gln Val Phe Gly Gly Gly Thr Lys Leu Thr Val Leu
            100                 105                 110

Gly Gln Pro Lys Ala Ala Pro Ser
        115                 120

<210> SEQ ID NO 296
<211> LENGTH: 96
<212> TYPE: PRT
<213> ORGANISM: Homo sapiens

<400> SEQUENCE: 296

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
                20                  25                  30

Phe Met Phe Trp Val Arg Gln Ala Pro Gly Lys Gly Leu Glu Trp Val
            35                  40                  45

Ser Ser Ile Gly Ser Ser Gly Gly Asp Thr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

<210> SEQ ID NO 297
<211> LENGTH: 4
<212> TYPE: PRT
<213> ORGANISM: Homo sapiens

<400> SEQUENCE: 297

Gly Leu Tyr Arg
1

<210> SEQ ID NO 298
<211> LENGTH: 96
<212> TYPE: PRT
<213> ORGANISM: Homo sapiens

<400> SEQUENCE: 298

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Phe Met Phe Trp Val Arg Gln Ala Pro Gly Lys Gly Leu Glu Trp Val
        35                  40                  45

Ser Ser Ile Gly Ser Ser Gly Gly Asp Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

<210> SEQ ID NO 299
<211> LENGTH: 120
<212> TYPE: PRT
<213> ORGANISM: Homo sapiens

<400> SEQUENCE: 299

Gly Val His Ser Gln Ser Glu Leu Thr Gln Pro Pro Ser Val Ser Leu
1               5                   10                  15

Ala Pro Gly Gln Thr Ala Arg Ile Thr Cys Gly Gly Asn Asn Ile Gly
            20                  25                  30

Thr Lys Ser Val His Trp Tyr Gln Gln Lys Pro Gly Gln Ala Pro Val
        35                  40                  45

Leu Val Val Tyr Asp Asp Ser Asp Arg Pro Ser Gly Ile Pro Glu Arg
    50                  55                  60

Phe Ser Gly Ser Asn Ser Gly Asn Thr Ala Thr Leu Thr Ile Ser Arg
65                  70                  75                  80

Val Glu Ala Gly Asp Glu Ala Asp Tyr Tyr Cys Gln Val Trp Asp Ser
                85                  90                  95

Gly Ser Asp His Gln Val Phe Gly Gly Gly Thr Lys Leu Thr Val Leu
                100                 105                 110

Gly Gln Pro Lys Ala Ala Pro Ser
            115                 120